(12) United States Patent
DiPierro et al.

(10) Patent No.: US 10,258,738 B2
(45) Date of Patent: Apr. 16, 2019

(54) BIOSYNCHRONOUS TRANSDERMAL DRUG DELIVERY FOR LONGEVITY, ANTI-AGING, FATIGUE MANAGEMENT, OBESITY, WEIGHT LOSS, WEIGHT MANAGEMENT, DELIVERY OF NUTRACEUTICALS, AND THE TREATMENT OF HYPERGLYCEMIA, ALZHEIMER'S DISEASE, SLEEP DISORDERS, PARKINSON'S DISEASE, AIDS, EPILEPSY, ATTENTION DEFICIT DISORDER, NICOTINE ADDICTION, CANCER, HEADACHE AND PAIN CONTROL, ASTHMA, ANGINA, HYPERTENSION, DEPRESSION, COLD, FLU AND THE LIKE

(71) Applicant: CHRONO THERAPEUTICS INC., Hayward, CA (US)

(72) Inventors: Guy DiPierro, San Francisco, CA (US); Steven A. Giannos, Quincy, MA (US)

(73) Assignee: Chrono Therapeutics Inc., Hayward, CA (US)

( * ) Notice: Subject to any disclaimer, the term of this patent is extended or adjusted under 35 U.S.C. 154(b) by 0 days.

(21) Appl. No.: 15/494,392

(22) Filed: Apr. 21, 2017

(65) Prior Publication Data
US 2017/0224911 A1    Aug. 10, 2017

Related U.S. Application Data

(60) Division of application No. 14/268,725, filed on May 2, 2014, now Pat. No. 9,669,199, which is a
(Continued)

(51) Int. Cl.
*A61M 35/00* (2006.01)
*A61M 5/142* (2006.01)
(Continued)

(52) U.S. Cl.
CPC ....... *A61M 5/14248* (2013.01); *A61K 9/0014* (2013.01); *A61K 9/7023* (2013.01);
(Continued)

(58) Field of Classification Search
None
See application file for complete search history.

(56) References Cited

U.S. PATENT DOCUMENTS 2,183,482 A    12/1939 Kurkjian
3,845,217 A    10/1974 Ferno et al.
(Continued)

FOREIGN PATENT DOCUMENTS

AU    662877 B    9/1995
BE    899037 A    6/1984
(Continued)

OTHER PUBLICATIONS

Quik et al., Mov. Disorders, 2008, 23(12), pp. 1641-1652 (Year: 2008).*
(Continued)

*Primary Examiner* — Brian Gulledge
(74) *Attorney, Agent, or Firm* — Shay Glenn LLP

(57) ABSTRACT

Systems and methods for longevity, anti-aging, fatigue management, obesity, weight loss, weight management, delivery of nutraceuticals, and treating hyperglycemia, Alzheimer's disease, sleep disorders, Parkinson's disease, Attention Deficit Disorder and nicotine addiction involve synchronizing and tailoring the administration of nutraceuticals, medications and other substances in accordance with the body's natural circadian rhythms, meal times and other factors. Improved control of blood glucose levels, extended alertness, and weight control, and counteracting of disease symptoms when they are at their worst are possible. An automated, pre-programmable transdermal administration
(Continued)

system is used to provide pulsed doses of medications, pharmaceuticals, hormones, neuropeptides, anorexigens, pro-drugs, stimulants, nutraceuticals, phytochemicals, phytonutrients, enzymes, antioxidants, essential oils, fatty acids, minerals, vitamins, amino acids, coenzymes, or other physiological active ingredient or precursor. The system can utilize a pump, pressurized reservoir, a system for removing depleted carrier solution, or other modulated dispensing actuator, in conjunction with porous membranes or microfabricated structures.

27 Claims, 57 Drawing Sheets

Related U.S. Application Data continuation of application No. 13/488,195, filed on Jun. 4, 2012, now Pat. No. 8,741,336, which is a division of application No. 11/981,672, filed on Oct. 31, 2007, now Pat. No. 8,252,321, which is a continuation-in-part of application No. 11/162,525, filed on Sep. 13, 2005, now Pat. No. 7,780,981.

(60) Provisional application No. 60/863,666, filed on Oct. 31, 2006, provisional application No. 60/863,654, filed on Oct. 31, 2006, provisional application No. 60/863,640, filed on Oct. 31, 2006, provisional application No. 60/863,671, filed on Oct. 31, 2006, provisional application No. 60/863,613, filed on Oct. 31, 2006, provisional application No. 60/863,607, filed on Oct. 31, 2006, provisional application No. 60/863,677, filed on Oct. 31, 2006, provisional application No. 60/863,618, filed on Oct. 31, 2006, provisional application No. 60/863,686, filed on Oct. 31, 2006, provisional application No. 60/863,608, filed on Oct. 31, 2006, provisional application No. 60/609,418, filed on Sep. 13, 2004.

(51) Int. Cl.

| | |
|---|---|
| A61K 31/135 | (2006.01) |
| A61K 31/17 | (2006.01) |
| A61K 31/192 | (2006.01) |
| A61K 31/27 | (2006.01) |
| A61K 31/4164 | (2006.01) |
| A61K 31/42 | (2006.01) |
| A61K 31/428 | (2006.01) |
| A61K 31/435 | (2006.01) |
| A61K 31/4436 | (2006.01) |
| A61K 31/445 | (2006.01) |
| A61K 31/47 | (2006.01) |
| A61K 31/498 | (2006.01) |
| A61K 31/505 | (2006.01) |
| A61K 31/55 | (2006.01) |
| A61K 31/704 | (2006.01) |
| A61M 37/00 | (2006.01) |
| A61N 1/30 | (2006.01) |
| A61K 31/137 | (2006.01) |
| A61K 31/155 | (2006.01) |
| A61K 31/165 | (2006.01) |
| A61K 31/415 | (2006.01) |
| A61K 31/4439 | (2006.01) |
| A61K 31/473 | (2006.01) |
| A61K 31/4965 | (2006.01) |
| A61K 31/7072 | (2006.01) |
| A61K 31/708 | (2006.01) |
| A61K 9/00 | (2006.01) |
| A61K 9/70 | (2006.01) |
| A61K 31/4468 | (2006.01) |
| A61M 39/22 | (2006.01) |
| A61K 31/04 | (2006.01) |
| A61K 31/13 | (2006.01) |
| A61K 31/18 | (2006.01) |
| A61K 31/195 | (2006.01) |
| A61K 31/198 | (2006.01) |
| A61K 31/216 | (2006.01) |
| A61K 31/404 | (2006.01) |
| A61K 31/405 | (2006.01) |
| A61K 31/4168 | (2006.01) |
| A61K 31/421 | (2006.01) |
| A61K 31/4453 | (2006.01) |
| A61K 31/4458 | (2006.01) |
| A61K 31/465 | (2006.01) |
| A61K 31/485 | (2006.01) |
| A61K 31/4985 | (2006.01) |

(52) U.S. Cl.
CPC ............ *A61K 9/7084* (2013.01); *A61K 31/04* (2013.01); *A61K 31/13* (2013.01); *A61K 31/135* (2013.01); *A61K 31/137* (2013.01); *A61K 31/155* (2013.01); *A61K 31/165* (2013.01); *A61K 31/17* (2013.01); *A61K 31/18* (2013.01); *A61K 31/192* (2013.01); *A61K 31/195* (2013.01); *A61K 31/198* (2013.01); *A61K 31/216* (2013.01); *A61K 31/27* (2013.01); *A61K 31/404* (2013.01); *A61K 31/405* (2013.01); *A61K 31/415* (2013.01); *A61K 31/4164* (2013.01); *A61K 31/4168* (2013.01); *A61K 31/42* (2013.01); *A61K 31/421* (2013.01); *A61K 31/428* (2013.01); *A61K 31/435* (2013.01); *A61K 31/445* (2013.01); *A61K 31/4436* (2013.01); *A61K 31/4439* (2013.01); *A61K 31/4453* (2013.01); *A61K 31/4458* (2013.01); *A61K 31/4468* (2013.01); *A61K 31/465* (2013.01); *A61K 31/47* (2013.01); *A61K 31/473* (2013.01); *A61K 31/485* (2013.01); *A61K 31/498* (2013.01); *A61K 31/4965* (2013.01); *A61K 31/4985* (2013.01); *A61K 31/505* (2013.01); *A61K 31/55* (2013.01); *A61K 31/704* (2013.01); *A61K 31/708* (2013.01); *A61K 31/7072* (2013.01); *A61M 35/00* (2013.01); *A61M 37/00* (2013.01); *A61M 37/0015* (2013.01); *A61M 37/0092* (2013.01); *A61M 39/22* (2013.01); *A61N 1/30* (2013.01); *A61M 2005/14268* (2013.01); *A61M 2037/0007* (2013.01); *A61M 2037/0023* (2013.01); *A61M 2205/3337* (2013.01); *A61M 2205/3368* (2013.01); *A61M 2205/50* (2013.01); *A61M 2205/502* (2013.01); *A61M 2205/8206* (2013.01)

(56) References Cited

U.S. PATENT DOCUMENTS

| | | |
|---|---|---|
| 4,321,387 A | 3/1982 | Chavdarian et al. |
| 4,327,725 A | 5/1982 | Cortese et al. |
| 4,332,945 A | 6/1982 | Edwards |
| 4,379,454 A | 4/1983 | Campbell et al. |
| 4,545,990 A | 10/1985 | Le Foyer de Costil et al. |
| 4,579,858 A | 4/1986 | Ferno et al. |
| 4,590,278 A | 5/1986 | Edwards |
| 4,708,716 A | 11/1987 | Sibalis |

(56) References Cited

U.S. PATENT DOCUMENTS

| | | |
|---|---|---|
| 4,772,263 A | 9/1988 | Dorman et al. |
| 4,806,356 A | 2/1989 | Shaw |
| 4,853,854 A | 8/1989 | Behar et al. |
| 4,885,154 A | 12/1989 | Cormier et al. |
| 4,908,213 A | 3/1990 | Govil et al. |
| 4,917,676 A | 4/1990 | Heiber et al. |
| 4,917,895 A | 4/1990 | Lee et al. |
| 4,920,989 A | 5/1990 | Rose et al. |
| 4,952,928 A | 8/1990 | Carroll et al. |
| 4,953,572 A | 9/1990 | Rose et al. |
| 5,000,956 A | 3/1991 | Amkraut et al. |
| 5,013,293 A | 5/1991 | Sibalis |
| 5,049,387 A | 9/1991 | Amkraut |
| 5,069,904 A | 12/1991 | Masterson |
| 5,097,834 A | 3/1992 | Skrabal |
| 5,120,545 A | 6/1992 | Ledger et al. |
| 5,130,139 A | 7/1992 | Cormier et al. |
| 5,149,538 A | 9/1992 | Granger et al. |
| 5,149,719 A | 9/1992 | Ferber et al. |
| 5,212,188 A | 5/1993 | Caldwell et al. |
| 5,221,254 A | 6/1993 | Phipps |
| 5,227,391 A | 7/1993 | Caldwell et al. |
| 5,232,704 A | 8/1993 | Franz et al. |
| 5,232,933 A | 8/1993 | Lippiello et al. |
| 5,236,714 A | 8/1993 | Lee et al. |
| 5,242,934 A | 9/1993 | Lippiello et al. |
| 5,242,941 A | 9/1993 | Lewy et al. |
| 5,248,690 A | 9/1993 | Caldwel et al. |
| 5,252,604 A | 10/1993 | Nagy et al. |
| 5,262,165 A | 11/1993 | Govil et al. |
| 5,273,755 A | 12/1993 | Venkatraman et al. |
| 5,273,756 A | 12/1993 | Fallon et al. |
| 5,304,739 A | 4/1994 | Klug et al. |
| 5,352,456 A | 10/1994 | Fallon et al. |
| 5,364,630 A | 11/1994 | Osborne et al. |
| 5,370,635 A | 12/1994 | Strausak et al. |
| 5,388,571 A * | 2/1995 | Roberts ............... A61M 16/16 128/200.18 |
| 5,389,679 A | 2/1995 | Alliger |
| 5,393,526 A | 2/1995 | Castro |
| 5,405,614 A | 4/1995 | D'Angelo et al. |
| 5,415,629 A | 5/1995 | Henley |
| 5,445,609 A | 8/1995 | Lattin et al. |
| 5,451,407 A | 9/1995 | Cormier et al. |
| 5,464,387 A | 11/1995 | Haak et al. |
| 5,472,946 A | 12/1995 | Peck et al. |
| 5,501,697 A | 3/1996 | Fisher |
| 5,505,958 A | 4/1996 | Bello et al. |
| 5,512,306 A | 4/1996 | Carlsson et al. |
| 5,516,793 A | 5/1996 | Duffy |
| 5,525,351 A | 6/1996 | Dam |
| 5,545,407 A | 8/1996 | Hall et al. |
| 5,596,994 A | 1/1997 | Bro |
| 5,601,839 A | 2/1997 | Quan et al. |
| 5,616,332 A | 4/1997 | Herstein |
| 5,618,557 A | 4/1997 | Wille et al. |
| 5,653,682 A | 8/1997 | Sibalis |
| 5,656,255 A | 8/1997 | Jones |
| 5,662,920 A | 9/1997 | Santus |
| 5,686,100 A | 11/1997 | Wille et al. |
| 5,688,232 A | 11/1997 | Flower |
| 5,697,896 A | 12/1997 | McNichols et al. |
| 5,716,987 A | 2/1998 | Wille |
| 5,722,418 A | 3/1998 | Bro |
| 5,733,259 A | 3/1998 | Valcke et al. |
| 5,785,688 A | 7/1998 | Joshi et al. |
| 5,797,867 A | 8/1998 | Guerrera et al. |
| 5,820,875 A | 10/1998 | Fallon et al. |
| 5,833,466 A | 11/1998 | Borg |
| 5,843,979 A | 12/1998 | Wille et al. |
| 5,865,786 A | 2/1999 | Sibalis et al. |
| 5,876,368 A | 3/1999 | Flower |
| 5,879,292 A | 3/1999 | Sternberg et al. |
| 5,879,322 A | 3/1999 | Lattin et al. |
| 5,882,676 A | 3/1999 | Lee et al. |
| 5,908,301 A | 6/1999 | Lutz |
| 5,919,156 A | 7/1999 | Stropkay et al. |
| 5,932,240 A | 8/1999 | D'Angelo et al. |
| 5,945,123 A | 8/1999 | Hermelin |
| 5,967,789 A | 10/1999 | Segel et al. |
| 5,972,389 A | 10/1999 | Shell et al. |
| 5,993,435 A | 11/1999 | Haak et al. |
| 5,997,501 A | 12/1999 | Gross et al. |
| 6,018,679 A | 1/2000 | Dinh et al. |
| 6,019,997 A | 2/2000 | Scholz et al. |
| 6,024,981 A | 2/2000 | Khankari et al. |
| 6,034,079 A | 3/2000 | Sanberg et al. |
| 6,059,736 A | 5/2000 | Tapper |
| 6,059,753 A | 5/2000 | Faust et al. |
| 6,068,853 A | 5/2000 | Giannos et al. |
| 6,081,734 A | 6/2000 | Batz |
| 6,090,404 A | 7/2000 | Meconi et al. |
| 6,093,419 A | 7/2000 | Rolf |
| 6,120,803 A | 9/2000 | Wong et al. |
| 6,129,702 A | 10/2000 | Woias et al. |
| 6,165,155 A | 12/2000 | Jacobsen et al. |
| 6,211,194 B1 | 4/2001 | Westman et al. |
| 6,211,296 B1 | 4/2001 | Frate et al. |
| 6,238,689 B1 | 5/2001 | Rhodes et al. |
| 6,274,606 B1 | 8/2001 | Caldwell et al. |
| 6,310,102 B1 | 10/2001 | Dull et al. |
| 6,365,182 B1 | 4/2002 | Khankari et al. |
| 6,368,625 B1 | 4/2002 | Siebert et al. |
| 6,374,136 B1 | 4/2002 | Murdock |
| 6,416,471 B1 | 7/2002 | Kumar et al. |
| 6,417,359 B1 | 7/2002 | Crooks et al. |
| 6,423,747 B1 | 7/2002 | Lanzendörfer et al. |
| 6,436,078 B1 | 8/2002 | Svedman |
| 6,437,004 B1 | 8/2002 | Perricone |
| 6,454,708 B1 | 9/2002 | Ferguson et al. |
| 6,492,399 B1 | 12/2002 | Dull et al. |
| 6,539,250 B1 | 3/2003 | Bellinger |
| 6,567,785 B2 | 5/2003 | Clendenon |
| 6,569,449 B1 | 5/2003 | Stinchcomb et al. |
| 6,569,866 B2 | 5/2003 | Simon |
| 6,576,269 B1 | 6/2003 | Korneyev |
| 6,579,865 B2 | 6/2003 | Mak et al. |
| 6,589,229 B1 | 7/2003 | Connelly et al. |
| 6,595,956 B1 | 7/2003 | Gross et al. |
| 6,638,528 B1 | 10/2003 | Kanios |
| 6,638,543 B2 | 10/2003 | Kang et al. |
| 6,660,295 B2 | 12/2003 | Watanabe et al. |
| 6,689,380 B1 | 2/2004 | Marchitto et al. |
| 6,723,086 B2 | 4/2004 | Bassuk et al. |
| 6,723,340 B2 | 4/2004 | Gusler et al. |
| 6,746,688 B1 | 6/2004 | Kushnir et al. |
| 6,791,003 B1 | 9/2004 | Choi et al. |
| 6,799,576 B2 | 10/2004 | Farr |
| 6,849,645 B2 | 2/2005 | Majeed et al. |
| 6,861,066 B2 | 3/2005 | Van de Casteele |
| 6,867,342 B2 | 3/2005 | Johnston et al. |
| 6,887,202 B2 | 5/2005 | Currie et al. |
| 6,893,655 B2 | 5/2005 | Flanigan et al. |
| 6,900,202 B2 | 5/2005 | Imoto et al. |
| 6,911,475 B1 | 6/2005 | Villafane et al. |
| 6,998,176 B2 | 2/2006 | Morita et al. |
| 7,011,843 B2 | 3/2006 | Becher et al. |
| 7,019,622 B2 | 3/2006 | Orr et al. |
| 7,064,143 B1 | 6/2006 | Gurley et al. |
| 7,182,955 B2 | 2/2007 | Hart et al. |
| 7,196,619 B2 | 3/2007 | Perlman et al. |
| 7,229,641 B2 | 6/2007 | Cherukuri |
| 7,282,217 B1 | 10/2007 | Grimshaw et al. |
| 7,332,182 B2 | 2/2008 | Sackler |
| 7,376,700 B1 | 5/2008 | Clark et al. |
| 7,384,651 B2 | 6/2008 | Hille et al. |
| 7,384,653 B2 | 6/2008 | Wright et al. |
| 7,579,019 B2 | 8/2009 | Tapolsky et al. |
| 7,598,275 B2 | 10/2009 | Cooke et al. |
| 7,718,677 B2 | 5/2010 | Quik et al. |
| 7,780,981 B2 | 8/2010 | DiPierro et al. |
| 7,988,660 B2 | 8/2011 | Byland et al. |
| 8,021,334 B2 | 9/2011 | Shekalim |
| 8,192,756 B2 | 6/2012 | Berner et al. |

(56) References Cited

U.S. PATENT DOCUMENTS

| | | | |
|---|---|---|---|
| 8,252,321 B2* | 8/2012 | DiPierro | A61K 31/135 424/449 |
| 8,262,394 B2 | 9/2012 | Walker et al. | |
| 8,268,475 B2 | 9/2012 | Tucholski | |
| 8,309,568 B2 | 11/2012 | Stinchcomb et al. | |
| 8,372,040 B2 | 2/2013 | Huang et al. | |
| 8,414,532 B2 | 4/2013 | Brandt et al. | |
| 8,440,220 B2 | 5/2013 | Gale et al. | |
| 8,440,221 B2 | 5/2013 | Zumbrunn et al. | |
| 8,441,411 B2 | 5/2013 | Tucholski et al. | |
| 8,445,010 B2 | 5/2013 | Anderson et al. | |
| 8,449,471 B2 | 5/2013 | Tran | |
| 8,545,445 B2 | 10/2013 | Kamen et al. | |
| 8,574,188 B2 | 11/2013 | Potter et al. | |
| 8,586,079 B2 | 11/2013 | Hansted et al. | |
| 8,589,174 B2 | 11/2013 | Nelson et al. | |
| 8,614,278 B2 | 12/2013 | Loubert et al. | |
| 8,673,346 B2 | 3/2014 | Zumbrunn et al. | |
| 8,684,922 B2 | 4/2014 | Tran | |
| 8,688,189 B2 | 4/2014 | Shennib | |
| 8,690,827 B2 | 4/2014 | Edwards et al. | |
| 8,703,175 B2 | 4/2014 | Kanios et al. | |
| 8,722,233 B2 | 5/2014 | Tucholski | |
| 8,727,745 B2 | 5/2014 | Rush et al. | |
| 8,741,336 B2 | 6/2014 | DiPierro et al. | |
| 8,747,348 B2 | 6/2014 | Yodfat et al. | |
| 8,814,822 B2 | 8/2014 | Yodfat et al. | |
| 8,865,207 B2 | 10/2014 | Kanios et al. | |
| 8,956,644 B2 | 2/2015 | Yum et al. | |
| 8,999,356 B1 | 4/2015 | Ramirez et al. | |
| 9,023,392 B2 | 5/2015 | Koo et al. | |
| 9,050,348 B2 | 6/2015 | Kydonieus et al. | |
| 9,078,833 B2 | 7/2015 | Audett | |
| 9,114,240 B2 | 8/2015 | Horstmann et al. | |
| 9,155,712 B2 | 10/2015 | Kanios et al. | |
| 9,238,001 B2 | 1/2016 | Weyer et al. | |
| 9,238,108 B2 | 1/2016 | Edwards et al. | |
| 9,248,104 B2 | 2/2016 | Valia et al. | |
| 9,289,397 B2 | 3/2016 | Wright | |
| 9,308,202 B2 | 4/2016 | Hille et al. | |
| RE46,217 E | 11/2016 | Huang et al. | |
| 9,555,226 B2 | 1/2017 | Zumbrunn et al. | |
| 9,555,227 B2 | 1/2017 | Dipierro | |
| 9,655,843 B2* | 5/2017 | Finn et al. | |
| 9,669,199 B2* | 6/2017 | DiPierro | A61K 31/135 |
| 9,717,698 B2 | 8/2017 | Horstmann et al. | |
| 9,795,681 B2 | 10/2017 | Abreu | |
| 10,034,841 B2 | 7/2018 | Müller et al. | |
| 2001/0022978 A1 | 9/2001 | Lacharriere et al. | |
| 2001/0026788 A1 | 10/2001 | Piskorz | |
| 2002/0002189 A1 | 1/2002 | Smith et al. | |
| 2002/0106329 A1 | 8/2002 | Leslie | |
| 2002/0127256 A1 | 9/2002 | Murad | |
| 2002/0165170 A1 | 11/2002 | Wilson et al. | |
| 2002/0169439 A1 | 11/2002 | Flaherty | |
| 2002/0182238 A1 | 12/2002 | Creton | |
| 2003/0004187 A1 | 1/2003 | Bedard et al. | |
| 2003/0065294 A1* | 4/2003 | Pickup | A01K 11/005 604/304 |
| 2003/0065924 A1 | 4/2003 | Wuidart et al. | |
| 2003/0083645 A1 | 5/2003 | Angel et al. | |
| 2003/0087937 A1 | 5/2003 | Lindberg | |
| 2003/0119879 A1 | 6/2003 | Landh et al. | |
| 2003/0159702 A1 | 8/2003 | Lindell et al. | |
| 2004/0019321 A1 | 1/2004 | Sage et al. | |
| 2004/0034068 A1 | 2/2004 | Warchol et al. | |
| 2004/0037879 A1 | 2/2004 | Adusumilli et al. | |
| 2004/0052843 A1 | 3/2004 | Lerner et al. | |
| 2004/0062802 A1 | 4/2004 | Hermelin | |
| 2004/0138074 A1 | 7/2004 | Ahmad et al. | |
| 2004/0166159 A1 | 8/2004 | Han et al. | |
| 2004/0191322 A1 | 9/2004 | Hansson | |
| 2004/0194793 A1 | 10/2004 | Lindell et al. | |
| 2004/0229908 A1 | 11/2004 | Nelson | |
| 2004/0241218 A1 | 12/2004 | Tavares et al. | |
| 2004/0253249 A1 | 12/2004 | Rudnic et al. | |
| 2004/0259816 A1 | 12/2004 | Pandol et al. | |
| 2005/0002806 A1 | 1/2005 | Fuechslin et al. | |
| 2005/0014779 A1 | 1/2005 | Papke | |
| 2005/0021092 A1 | 1/2005 | Yun et al. | |
| 2005/0034842 A1 | 2/2005 | Huber et al. | |
| 2005/0048020 A1 | 3/2005 | Wille | |
| 2005/0053665 A1 | 3/2005 | Ek et al. | |
| 2005/0113452 A1 | 5/2005 | Flashner Barak et al. | |
| 2005/0141346 A1 | 6/2005 | Rawls et al. | |
| 2005/0151110 A1 | 7/2005 | Minor et al. | |
| 2005/0159419 A1 | 7/2005 | Stephenson et al. | |
| 2006/0024358 A1 | 2/2006 | Santini et al. | |
| 2006/0036209 A1 | 2/2006 | Subramony et al. | |
| 2006/0122577 A1 | 6/2006 | Poulsen et al. | |
| 2006/0167039 A1 | 7/2006 | Nguyen et al. | |
| 2006/0184093 A1 | 8/2006 | Phipps et al. | |
| 2006/0188859 A1 | 8/2006 | Yakobi | |
| 2006/0206054 A1 | 9/2006 | Shekalim | |
| 2007/0026054 A1 | 2/2007 | Theobald et al. | |
| 2007/0042026 A1 | 2/2007 | Wille | |
| 2007/0065365 A1 | 3/2007 | Kugelmann et al. | |
| 2007/0086275 A1 | 4/2007 | Robinson et al. | |
| 2007/0088338 A1* | 4/2007 | Ehwald | A61M 5/14526 604/892.1 |
| 2007/0149952 A1 | 6/2007 | Bland et al. | |
| 2007/0168501 A1 | 7/2007 | Cobb et al. | |
| 2007/0179172 A1 | 8/2007 | Becker et al. | |
| 2007/0191815 A1 | 8/2007 | DiPierro | |
| 2007/0250018 A1 | 10/2007 | Adachi et al. | |
| 2007/0256684 A1 | 11/2007 | Kelliher et al. | |
| 2007/0260491 A1 | 11/2007 | Palmer et al. | |
| 2007/0279217 A1 | 12/2007 | Venkatraman et al. | |
| 2007/0299401 A1 | 12/2007 | Alferness et al. | |
| 2008/0008747 A1 | 1/2008 | Royds | |
| 2008/0138294 A1 | 6/2008 | Gonda | |
| 2008/0138398 A1 | 6/2008 | Gonda | |
| 2008/0138399 A1 | 6/2008 | Gonda | |
| 2008/0138423 A1 | 6/2008 | Gonda | |
| 2008/0152592 A1 | 6/2008 | Rebec | |
| 2008/0195946 A1 | 8/2008 | Peri-Glass | |
| 2008/0201174 A1 | 8/2008 | Ramasubramanian et al. | |
| 2008/0233178 A1 | 9/2008 | Reidenberg et al. | |
| 2008/0274168 A1 | 11/2008 | Baker et al. | |
| 2008/0319272 A1 | 12/2008 | Patangay et al. | |
| 2009/0005009 A1 | 1/2009 | Marsili | |
| 2009/0024004 A1 | 1/2009 | Yang | |
| 2009/0062754 A1 | 3/2009 | Tang | |
| 2009/0118710 A1 | 5/2009 | Kortzeborn | |
| 2010/0068250 A1 | 3/2010 | Anderson et al. | |
| 2010/0114008 A1 | 5/2010 | Marchitto et al. | |
| 2010/0145303 A1 | 6/2010 | Yodfat et al. | |
| 2010/0179473 A1 | 7/2010 | Genosar | |
| 2010/0196463 A1 | 8/2010 | Quik et al. | |
| 2010/0280432 A1 | 11/2010 | DiPierro et al. | |
| 2011/0137255 A1 | 6/2011 | Nielsen et al. | |
| 2013/0158430 A1 | 6/2013 | Aceti et al. | |
| 2014/0073883 A1 | 3/2014 | Rao et al. | |
| 2014/0100241 A1 | 4/2014 | Slater et al. | |
| 2014/0200525 A1 | 7/2014 | DiPierro | |
| 2014/0207047 A1 | 7/2014 | DiPierro et al. | |
| 2014/0207048 A1 | 7/2014 | DiPierro et al. | |
| 2014/0228736 A1 | 8/2014 | Eppstein et al. | |
| 2016/0220798 A1 | 8/2016 | Netzel et al. | |
| 2016/0235916 A1 | 8/2016 | Edwards et al. | |
| 2017/0100572 A1 | 4/2017 | Zumbrunn et al. | |
| 2017/0100573 A1 | 4/2017 | DiPierro | |

FOREIGN PATENT DOCUMENTS

| | | |
|---|---|---|
| CA | 2142871 A1 | 3/1994 |
| CN | 1704056 A | 12/2005 |
| DE | 19958554 A1 | 1/2001 |
| DE | 10105759 C1 | 10/2001 |
| DE | 10103158 A1 | 8/2002 |
| EP | 0314528 B1 | 12/1992 |
| EP | 0354554 B1 | 1/1994 |
| EP | 0726005 A1 | 8/1996 |
| EP | 0612525 B1 | 9/2001 |

(56) References Cited

FOREIGN PATENT DOCUMENTS

| | | |
|---|---|---|
| EP | 1815784 A1 | 8/2007 |
| EP | 1977746 B1 | 7/2014 |
| EP | 1662989 B1 | 9/2014 |
| GB | 2230439 A | 10/1919 |
| GB | 1528391 A | 10/1978 |
| GB | 2030862 A | 4/1980 |
| GB | 2142822 A | 1/1985 |
| JP | 02202813 A | 8/1990 |
| JP | 09512006 A | 12/1997 |
| JP | 2002092180 A | 3/2002 |
| JP | 2005525147 A | 8/2005 |
| JP | 2009544338 A | 12/2009 |
| WO | WO86/07269 A1 | 12/1986 |
| WO | WO88/003803 A1 | 6/1988 |
| WO | WO91/14441 A1 | 10/1991 |
| WO | WO94/010987 A1 | 5/1994 |
| WO | WO95/06497 A1 | 3/1995 |
| WO | WO97/11741 A1 | 4/1997 |
| WO | WO97/18782 A1 | 5/1997 |
| WO | WO97/028801 A1 | 8/1997 |
| WO | WO97/034605 A1 | 9/1997 |
| WO | WO97/042941 A2 | 11/1997 |
| WO | WO98/46093 A1 | 10/1998 |
| WO | WO99/066916 A1 | 12/1999 |
| WO | WO00/035279 A1 | 6/2000 |
| WO | WO00/035456 A1 | 6/2000 |
| WO | WO00/74763 A2 | 12/2000 |
| WO | WO00/74933 A1 | 12/2000 |
| WO | WO01/005459 A1 | 1/2001 |
| WO | WO01/037814 A1 | 5/2001 |
| WO | WO02/076211 A1 | 10/2002 |
| WO | WO03/022349 A2 | 3/2003 |
| WO | WO03/026655 A1 | 4/2003 |
| WO | WO03/055486 A1 | 7/2003 |
| WO | WO03/061656 A1 | 7/2003 |
| WO | WO03/070191 A1 | 8/2003 |
| WO | WO03/097146 A1 | 11/2003 |
| WO | WO2004/024124 A1 | 3/2004 |
| WO | WO2004/073429 A1 | 9/2004 |
| WO | WO2005/023227 A2 | 3/2005 |
| WO | WO2005/079161 A2 | 9/2005 |
| WO | WO2006/069097 A2 | 6/2006 |
| WO | WO2007/013975 A2 | 2/2007 |
| WO | WO2007/104574 A2 | 9/2007 |
| WO | WO2007/104575 A2 | 9/2007 |
| WO | WO2007/133141 A1 | 11/2007 |
| WO | WO2008/024408 A2 | 2/2008 |
| WO | WO 2008/054788 * 5/2008 ........... A61K 9/0014 |
| WO | WO2008/069921 A2 | 6/2008 |
| WO | WO2008/069970 A2 | 6/2008 |
| WO | WO2008069972 A2 | 6/2008 |
| WO | WO2008/135283 A1 | 11/2008 |

OTHER PUBLICATIONS

Ahlskog et al.; Frequency of levodopa-related dyskinesias and motor fluctuations as estimated from the cumulative literature; Movement Disorders; 16(3); pp. 448-458; May 1, 2001.

Chen et al.; Enhanced striatal opioid receptor-mediated G-protein activation in L-DOPA-treated dyskinetic monkeys; Neuroscience; 132(2); pp. 409-420; Dec. 31, 2005.

Di Monte et al.; Relationship among nigrostriatal denervation, parkinsonism, and dyskinesias in the MPTP primate model; Movement Disorders; 15(3); pp. 459-466; May 1, 2000.

Domino et al.; Nicotine alone and in combination with L-DOPA methyl ester or the D2 agonist N-0923 in MPTP-induced chronic hemiparkinsonian monkeys; Experimental Neurology; 158(2); pp. 414-421; Aug. 31, 1999.

Ebersbach et al.; Worsening of motor performance in patients with Parkinson's disease following transdermal nicotine administration; Movement Disorders; 14(6); pp. 1011-1013; Nov. 1, 1999.

He et al; Autoradiographic analysis of N-methyl-D-aspartate receptor binding in monkey brain: Effects of 1-methyl-4-phenyl-1,2,3,6-tetrahydropyridine andleyodopa treatment; Neuroscience; 99(4); pp. 697-704; Aug. 23, 2000.

Jeyarasasingam et al.; Stimulation of non-o7 nicotinic receptors partially protects dopaminergic neurons from 1-methyl-4-phenylpyridinium-induced toxicity in culture; Neuroscience; 109(2); pp. 275-285; Jan. 28, 2002.

Jeyarasasingam et al.; Tacrine, a reversible acetylcholinesterase inhibitor, induces myopathy; Neuroreport; 11(6); pp. 1173-1176; Apr. 27, 2000.

Kelton et al.; The effects of nicotine on Parkinson's disease; Brain Cognition; 43(1-3); pp. 274-282; Jun. 2000.

Lai et al.; Selective recovery of striatal 125I-a-conotoxinMII nicotinic receptors after nigrostriatal damage in monkeys; Neuroscience; 127(2); pp. 399-408; Dec. 31, 2004.

Langston et al.; Investigating levodopa-induced dyskinesias in the parkinsonian primate; Annals of Neurology; 47(4 Suppl 1); pp. S79-S88; Apr. 2000.

McCallum et al.; Compensation in pre-synaptic dopaminergic function following nigrostriatal damage in primates; Journal of Neurochemistry; 96(4); pp. 960-972; Feb. 1, 2006.

McCallum et al.; Increases in aplha 4* but not aplha3*/alpha6* nicotinic receptor sites and function in the primate striatum following chronic oral nicotine treatment; Journal of Neurochemistry; 96(4); pp. 1028-1041; Feb. 2006.

Meredith et al.; Behavioral models of Parkinson's disease in rodents: a new look at an old problem; Movement Disorders; 21(10); pp. 1595-1606; Oct. 1, 2006.

Meshul et al.; Nicotine Affects Striatal Glutamatergic Function in 6-OHDA Lesioned Rats; Advanced in behavioural Biology. Basal Ganglia VI.; Springer, Boston, MA.; vol. 54; pp. 589-598; (year of pub. sufficiently earlier than effective US filed and any foreign priority date) 2002.

Meshul et al.; Nicotine alters striatal glutamate function and decreases the apomorphine-induced contralateral rotations in 6-OHDA-lesioned rats; Experimental Neurology; 175(1); pp. 257-274; May 31, 2002.

Olanow; The scientific basis for the current treatment of Parkinson's disease; Annu. Rev. Med.; 55; pp. 41-60; Feb. 18, 2004.

Petzinger et al.; Reliability and validity of a new global dyskinesia rating scale in the MPTP-lesioned non-human primate; Movement Disorders; 16(2); pp. 202-207; Mar. 1, 2001.

Quik et al.; Differential alterations in nicotinic receptor a6 and /33 subunit messenger RNAs in monkey substantia nigra after nigrostriatal degeneration; Neuroscience; 100(1); pp. 63-72; Sep. 7, 2000.

Quik et al.; Differential nicotinic receptor expression in monkey basal ganglia: Effects of nigrostriatal damage; Neuroscience; 112(3); pp. 619-630; Jul. 5, 2002.

Quik et al.; Expression of D3 receptor messenger RNA and binding sites in monkey striatum and substantia nigra after nigrostriatal degeneration: Effect of levodopa treatment.;Neuroscience; 98(2); pp. 263-273; Jun. 30, 2000.

Quik et al.; Increases in striatal preproenkephalin gene expression are associated with nigrostriatal damage but not L-DOPA-induced dyskinesias in the squirrel monkey; Neuroscience; 113(1); pp. 213-220; Aug. 2, 2002.

Quik et al.; Localization of nicotinic receptor subunit mRNAs in monkey brain by in situ hybridization; The Journal of Comparative Neurology; 425(1); pp. 58-69; Sep. 11, 2000.

Quik et al.; Nicotine administration reduces striatal MPP+ levels in mice; Brain Research; 917(2); pp. 219-224; Nov. 2, 2001.

Quik et al.; Nicotine neuroprotection against nigrostriatal damage: importance of the animal model; Trends in Pharmacological sciences; 28(5); pp. 229-235; May 31, 2007.

Quik et al.; Nicotinic receptors and Parkinson's disease; European Journal of Pharmacology; 393(1); pp. 223-230; Mar. 30, 2000.

Samii et al.; Parkinson's disease; The Lancet; 363(9423); pp. 1783-1793; May 29, 2004.

Schapira; Disease modification in Parkinson's disease; The Lancet Neurology; 3(6); pp. 362-368; Jun. 30, 2004.

Schneider et al.; Effects of SIB-1508Y, a novel neuronal nictonic acetylcholine receptor agonist, on motor behavior in parkinsonian monkeys; Movement Disorders; 13(4); pp. 637-642; Jul. 1, 1998.

(56) References Cited

OTHER PUBLICATIONS

Schneider et al.; Effects of the nicotinic acetylcholine receptor agonist SIB-1508Y or object retrieval performance in MPTP-treated monkeys: Comparison with levodopa treatment; Annals of Neurology; 43(3); pp. 311-317; Mar. 1, 1998.

Schober et al.; Classic toxin-induced animal models of Parkinson's disease: 6-OHDA and MPTP; Cell and Tissue Research; 318(1); pp. 215-224; Oct. 1, 2004.

Stocchi et al.; Motor fluctuations in levodopa treatment: clinical pharmacology; European Neurology; 36(Suppl 1); pp. 38-42; Jan. 1996.

Togasaki et al.; Dyskinesias in normal squirrel monkeys induced by nomifensine and levodopa; Neuropharmacology; 48(3); pp. 398-405; Mar. 31, 2005.

Togasaki et al.; Levodopa induces dyskinesias in normal squirrel monkeys; Annals of Neurology; 50(2); pp. 254-257; Aug. 1, 2001.

Togasaki et al.; The Webcam system: A simple, automated, computer-based video system for quantitative measurement of movement of nonhuman primates; Journal of Neuroscience Methods; 145(1); pp. 159-166; Jun. 30, 2005.

Vieregge et al.; Transdermal nicotine in PD: A randomized, double-blind, placebo-controlled study; Neurology; 57(6); pp. 1032-1035; Sep. 25, 2001.

Westman et al.; Oral nicotine solution for smoking cessation: a pilot tolerability study; Nicotine and Tobacco Research; 3(4); pp. 391-396; Nov. 1, 2001.

Angulo et al.; Oral nicotine in treatment of primary sclerosing cholangitis: a pilot study; Digestive diseases and sciences; 44(3); pp. 602-607; Mar. 1, 1999.

Benowitz et al.; Sources of variability in nicotine and cotinine levels with use of nicotine nasal spray, transdermal nicotine, and cigarette smoking; British Journal of Clinical Pharmacology; 43(3); pp. 259-267; Mar. 1, 1997.

Bordia et al.; Partial recovery of striatal nicotinic receptors in l-methyl-4-phenyl-1,2,3,6-tetrahydropyridine (MPTP)-lesioned monkeys with chronic oral nicotinic; The Journal of Pharmacology and Experimental Therapeutics; 319(1); pp. 285-292; Oct. 1, 2006.

Bove et al.; Toxin-induced models of Parkinson's disease; NeuroRx; 2(3); pp. 484-494; Jul. 31, 2005.

Brotchie et al.; Levodopa-induced dyskinesia in Parkinson's disease; Journal of Neural Transmission; 112(3); pp. 359-391; Mar. 1, 2005.

Damaj et al.; Antinociceptive responses to nicotinic acetylcholine receptor ligands after systemic and intrathecal administration in mice; Journal of Pharmacology and Experimental Therapeutics; 284(3); pp. 1058-1065; Mar. 1, 1998.

Davie; A review of Parkinson's disease. British Medical Bulletin 2008 86(1): 109-127; Apr. 8, 2008.

De La Fuente et al.; The placebo effect in Parkinson's disease; Trends in Neuroscience; 25(6); pp. 302-306; Jun. 1, 2002.

Fagerstrom et al.; Nicotine may relieve symptoms of Parkinson's disease; Psychopharmacology; 116(1); pp. 117-119; Sep. 16, 1994.

Food and Drug Administration; Guidance for Industry—Dissolution Testing of Immediate Release Solid Oral Dosage Forms; 17 pages; retrieved from the internet (https://www.fda.gov/downloads/drugs/guidances/ucm070237.pdf); Aug. 1997.

Gatto et al.; TC-1734: An orally active neuronal nicotinic acetylcholine receptor modulator with antidepressant, neuroprotective and long-lasting cognitive effects; CNS Drug Reviews; 10(2); pp. 147-166; Jun. 1, 2004.

Gora; Nicotine transdermal systems; The Annals of Pharmacotherapy; 27(6); pp. 742-750; Jun. 1993.

Gotti et al.; Brain nicotinic acetylcholine receptors: native subtypes and their relevance; Treands in Pharmacological Sciences; 27(9); pp. 482-491; Sep. 30, 2006.

Green et al.; An oral formulation of nicotine for release and absorption in the colon: its development and pharmacokinetics. British Journal of Clinical Pharmacology; 48(4); pp. 485-493; Oct. 1999.

He et al.; Autoradiographic analysis of dopamine receptor-stimulated [35S]GTPtS binding in rat striatum; Brain Research; 885(1); pp. 133-136; Dec. 1, 2000.

Hsu et al.; Effect of the D3 dopamine receptor partial agonist BP897 [N-[4-(4-(2-methoxyphenyl)piperazinyl) butyl]-2-napthamide] on L-3,4-dihydroxyphenylalanine-induced dyskinesias and parkinsonism in squirrel monkeys; The Journal of Pharmacology and Experimental Therapeutics. 311(2); pp. 770-777; Nov. 1, 2004.

Hukkanen et al.; Metabolism and disposition kinetics of nicotine; Pharmacological Reviews; 57(1); pp. 79-115; Mar. 1, 2005.

Ingram et al.; Preliminary observations of oral nicotine therapy for inflammatory bowel disease: an open-label phase I-II study of tolerance; Inflamm Bowel Diseases; 11(12); pp. 1092-1096; Dec. 1, 2005.

Jeyarasasingam et al.; Nitric oxide is involved in acetylcholinesterase inhibitor-induced myopathy in rats; The Journal of Pharmacology and Experimental Therapeutics; 295(1); pp. 314-320; Oct. 1, 2000.

Kulak et al.; 5-Iodo-A-85380 binds to oconotoxin Mil-sensitive nicotinic acetylcholine receptors (nAChRs) as well as o4j32* subtypes; Journal of Neurochemistry; 81(2); pp. 403-406; Apr. 1, 2002.

Kulak et al.; Declines in different pi* nicotinic receptor populations in monkey striatum after nigrostriatal damage; The Journal of Pharmacology and Experimental Therapeutics; 303(2); pp. 633-639; Nov. 1, 2002.

Kulak et al.; Loss of nicotinic receptors in monkey striatum after l-methyl-4-phenyl-1,2,3,6-tetrahydropyridine treatment is due to a decline in oconotoxin Mil sites; Molecular Pharmacology; 61(1); pp. 230-238; Jan. 1, 2002.

Lai et al.; Long-term nicotine treatment decreases striatal a6* nicotinic acetylcholine receptor sites and function in mice; Molecular Pharmacology; 67(5); pp. 1639-1647; May 1, 2005.

Lieber Man; Compressed tablets by direct compression; Pharmaceutical Dosage forms; vol. 1, 2nd ed.; Marcel Dekker Inc.; pp. 195-246; (year of pub. sufficiently earlier than effective US filing date and any foreign priority date) 1989.

Matta et al.; Guidelines on nicotine dose selection for in vivo research; Psychopharmacology (Berl.); 190(3); pp. 269-319; Feb. 1, 2007.

McCallum et al.; Decrease in alpha3*/alpha6* nicotinic receptors in monkey brain after nigrostriatal damage; Molecular Pharmacology; 68(3); pp. 737-746; Sep. 2005.

McCallum et al.; Differential regulation of mesolimbic alpha 3/alpha 6 beta 2 and aplha 4 beta 2 nicotinic acetylcholine receptor sites and function after long-term oral nicotine to monkeys; The Journal of Pharmacology and Experimental Therapeutics; 318(1); pp. 381-388; Jul. 2006.

Menzaghi et al.; Interactions between a novel cholinergic ion channel against, SIB-1765F anf L-DOPA in the reserpine model of parkinson's disease in rats; Journal of Pharmacology and Experimental Therapeutics; 280(1); pp. 393-401; Jan. 1, 1997.

National Institute of Neurological Disorders and Stroke. Parkinson's Disease: Hope Through Reasearch. 54 pages; Retrieved from the internet (https://catalog.ninds.nih.gov/pubstatic//15-139/15-139.pdf) on Jan. 15, 2018.

O'Neill et al.; The role of neuronal nicotinic acetylcholine receptors in acute and chronic neurodegeneration; Current Drug Targets-CNS and Neurological Disorders; 1(4); pp. 399-412; Aug. 1, 2002.

Parkinson Study Group; Levodopa and the progression of Parkinson's disease; N Engl J Med.; 351; pp. 2498-2508; Dec. 9, 2004.

Quik et al.; Chronic oral nicotine normalizes dopaminergic function and synaptic plasticity in l-methyl-4-phenyl-l,2,3,6-tetrahydropyridine-lesioned primates; The Journal of Neuroscience; 26(17); pp. 4681-4689; Apr. 26, 2006.

Quik et al.; Chronic oral nicotine treatment protects against striatal degeneration in MPTP-treated primates; Journal of Neurochemistry; 98(6); pp. 1866-1875; Sep. 1, 2006.

Quik et al.; Differential declines in striatal nicotinic receptor subtype function after nigrostriatal damage in mice; Molecular Pharmacology; 63(5); pp. 1169-1179; May 1, 2003.

Quik et al.; Loss of a-conotoxinMII- and A85380-sensitive nicotinic receptors in Parkinson's disease striatum; Journal of Neurochemistry; 88(3); pp. 668-679; Feb. 1, 2004.

(56) References Cited

OTHER PUBLICATIONS

Quik et al.; Striatal α6* nicotinic acetylcholine receptors: Potential targets for Parkinson's disease therapy; The Journal of Pharmacology and Experimental Therapeutics; 316(2); pp. 481-489; Feb. 1, 2006.
Quik et al.; Subunit composition of nicotinic receptors in monkey striatum: Effect of treatments with 1-methyl-4-phenyl-1,2,3,6-tetrahydropyridine or L-DOPA; Molecular Pharmacology; 67(1); pp. 32-41; Jan. 2005.
Quik et al.; Vulnerability of 125l-a-conotoxin Mil binding sites to nigrostriatal damage in monkey; The Journal of Neuroscience; 21(15); pp. 5494-5500; Aug. 1, 2001.
Rueter et al.; ABT-089: Pharmacological properties of a neuronal nicotinic acetylcholine receptor agonist for the potential treatment of cognitive disorders; CNS Drug Reviews; 10(2); pp. 167-182; Jun. 1, 2004.
Savitt et al.; Diagnosis and treatment of Parkinson disease: molecules to medicine; The Journal of Clinical Investigation; 116(7); pp. 1744-54; Jul. 3, 2006.
Darmour et al.; U.S. Appl. No. 15/551,178 entitled "Craving input and support system," filed Aug. 15, 2017.
Netzel et al.; U.S. Appl. No. 15/699,382 entitled "Drug delivery methods and systems," filed Sep. 8, 2017.
Quik et al.; U.S. Appl. No. 15/611,724 entitled "Methods and compositions for reduction of side effects of therapeutic treatments," filed Jun. 1, 2017.
Azhir et al.; U.S. Appl. No. 15/659,383 entitled "Compositions and methods for treatment of symptoms in parkinson's disease patients," Jul. 25, 2017.
Bruguerolle; Chronopharmacokinetics; Clin Pharmacokinet; 35(2); pp. 83-94; Aug. 1998.
Dockser-Marcus, A.; New research shows drugs work best at certain times; The Wall Street Journal; 6 pgs.; May 27, 2003; (http://www.wsj.com/articles/SB105397312486508700).
Domino et al.; Nicotine alone and in combination with L-DOPA methyl ester or the D(2) agonist N-0923 in MPTP-induced chronic hemiparkinsonian monkeys; Exp Neurol; 158(2); pp. 414-421; Aug. 1999.
Ethicon Endo-Surgery, Inc.; Sedasys® Computer-assisted personalized sedation system essential product information; retrieved May 12, 2015 from the internet (http://www.sedasys.com/explore-the-system/essential-product-information); 2 pgs.
Gennaro (Editor); Remington: The Science and Practice of Pharmacy; 19th Ed.; Mack Publishing Co.; Easton, PA; p. 1582-1584; Jun. 1995.
Giannos; Chapter 20: Pulsatile fSmartf Drug Delivery, in Skin Delivery Systems: Transdermals, Dermatologicals, and Cosmetic Actives; (ed.) Wille, Jr; Blackwell Pub.; Oxford, UK; pp. 327-357; Jun. 2006.
Gries et al.; Importance of Chronopharmacokinetics in Design and Evaluation of Transdermal Drug Delivery Systems; J Pharmoacol Exp Ther; 285(2); pp. 457-463; May 1998.
Guy; Current status and future prospects of transdermal drug delivery; Pharm Res; 13(12); pp. 1765-1769; Dec. 1996.
Halberg et al.; Chronomics: circadian and circaseptan timing of radiotherapy, drugs, calories, perhaps nutriceuticals and beyond; Journal of Experimental Therapeutics and Oncology; 3(5); pp. 223-260; Sep. 2003.
Hrushesky; Temporally optimizable delivery systems: sine qua non for the next therapeutic revolution; J Cont Rel; 19(1-3); pp. 363-368; Mar. 1992.
Huang et al.; Inhibitory effects of curcumin on in vitro lipoxygenase and cyclooxygenase activities in mouse epidermis; Cancer Res; 51(3); pp. 813-819; Feb. 1991.
Kalish et al.; Prevention of contact hypersensitivity to topically applied drugs by ethacrynic acid: potential application to transdermal drug delivery; J. Controll Rel; 48(1); pp. 79-87; Sep. 1997.
Kalish et al.; Sensitization of mice to topically applied drugs: albuterol, chlorpheniramine, clonidine and nadolol; Contact Dermatitis; 35(2); pp. 76-82; Aug. 1996.

Kotwal; Enhancement of intophoretic transport of diphenhydramine hydrochloride thermosensitive gel by optimization of pH, polymer concentration, electrode design, and pulse rate; AAPS PharmSciTech; 8(4); pp. 320-325; Oct. 2007.
Kydonieus et al. (Editors); Biochemical Modulation of Skin Reactions; CRC Press; Boca Ratan, FL; pp. 9-10; Dec. 1999.
Labrecque, G. et al.; Chronopharmacokinetics; Pharmaceutical News; 4 (2); pp. 17-21; 1997.
Lamberg; Chronotherapeutics: Implications for drug therapy; American Pharmacy; NS31(11); pp. 20-23; Nov. 1991.
Laser et al.; A review of micropumps; J. of Micromech. And Microeng.; 14; pp. R35-R64; Apr. 2004.
Lemay et al.; Lack of efficacy of a nicotine transdermal treatment on motor and cognitive deficits in Parkinson's disease; Prog Neuropsychopharmacol Biol Psychiatry; 28(1); pp. 31-39; Jan. 2004.
Lemmer; Clinical Chronopharmacology: The Importance of Time in Drug Treatment, in Ciba Foundation Symposium 183—Circadian Clocks and their Adjustment (eds. Chadwick and Ackrill); John Wiley & Sons, Inc.; pp. 235-253; Apr. 1995.
Lemmer; Implications of chronopharmacokinetics for drug delivery: antiasthmatics, H2-blockers and cardiovascular active drugs; Adv Drug Del Rev; 6(1); pp. 83-100; Jan./Feb. 1991.
Lemmer; The clinical relevance of chronopharmacology in therapeutics; Pharmacological Research; 33(2); pp. 107-115; Feb. 1996.
LeWitt et al.; New developments in levodopa therapy; Neurology; 62(No. 1, Suppl. 1); pp. S9-S16; Jan. 2004.
Maillefer et al.; A high-performance silicon micropump for an implantable drug delivery system; 12th IEEE Int'l Conf. on Micro Electro Mechanical Systems; MEMS '99; Orlando, FL; pp. 541-546; Jan. 1999.
Medtronic; MiniMed Paradigm® Veo(TM) System (product info.); retrieved May 12, 2015 from the internet: (http://www.medtronic.co.uk/your-health/diabetes/device/insulin-pumps/paradigm-veo-pump/); 3 pgs.
Molander et al.; Reduction of tobacco withdrawal symptoms with a sublingual nicotine tablet: A placebo controlled study; Nictonie & Tob. Res.; 2(2); pp. 187-191; May 2000.
Murphy et al.; Transdermal drug delivery systems and skin sensitivity reactions. Incidence and management; Am. J. Clin Dermatol.; 1(6); pp. 361-368; Nov./Dec. 2000.
Mutalik et al.; Glibenclamide transdermal patches: physicochemical, pharmacodynamic, and pharmacokinetic evaluation; J Pharm Sci; 93(6); pp. 1577-1594; Jun. 2004.
Mutalik et al.; Glipizide matrix transdermal systems for diabetes mellitus: preparation, in vitro and preclinical studies; Life Sci; 79(16); pp. 1568-1567; Sep. 2006.
Nakadate et al.; Effects of chalcone derivatives on lipoxygenase and cyclooxygenase activities of mouse epidermis; Prostaglandins; 30(3); pp. 357-368; Sep. 1985.
Newmark; Plant phenolics as potential cancer prevention agents; Chapter 3 in Dietary Phytochemicals in Cancer Prevention; Chap. 3; Adv. Exp. Med. Biol. 401; pp. 25-34; ©1996.
Ohdo; Changes in toxicity and effectiveness with timing of drug administration: implications for drug safety; Drug Safety; 26(14); pp. 999-1010; Dec. 2003.
Olsson et al.; A valve-less planar pump in silicon; IEEE; The 8th International Conference on Solid-State Sensors and Actuators; vol. 2; pp. 291-294, Jun. 1995.
Olsson et al.; An improved valve-less pump fabricated using deep reactive ion etching; Proc. Of the IEEE, 9th Int'l Workshop on MEMS; San Diego, CA; pp. 479-484; Feb. 11-15, 1996.
Priano et al.; Nocturnal anomalous movement reduction and sleep microstructure analysis in parkinsonian patients during 1-night transdermal apomorphine treatment; Neurol Sci.; 24(3); pp. 207-208; Oct. 2003.
Prosise et al.; Effect of abstinence from smoking on sleep and daytime sleepiness; Chest; 105(4); pp. 1136-1141; Apr. 1994.
Quik et al.; L-DOPA treatment modulates nicotinic receptors in monkey striatum; Mol Pharmacol; 64(3); pp. 619-628; Sep. 2003.
Quik et al.; Nicotine and nicotinic receptors; relevance to Parkinson's disease; Neurotoxicology; 23(4-5); pp. 581-594; Oct. 2002.

(56) References Cited

OTHER PUBLICATIONS

Quik; Smoking, nicotine and Parkinson's disease; Trends in Neurosciences; 27 (9); pp. 561-568; Sep. 2004.
Redfern et al.; Circadian rhythms, jet lag, and chronobiotics: An overview; Chronobiology International; 11(4); pp. 253-265; Aug. 1994.
Reinberg; Concepts of Circadian Chronopharmacology; Annals of the New York Academy of Sciences; 618 (Temporal Control of Drug Delivery); pp. 102-115; Feb. 1991.
Shin et al.; Enhanced bioavailability of triprolidine from the transdermal TPX matrix system in rabbits; Int. J. Pharm.; 234(1-2); pp. 67-73; Mar. 2002.
Singer et al.; Nightmares in patients with Alzheimer's disease caused by donepezil: Therapeutic effect depends on the time of intake; Nervenarzt; 76(9); pp. 1127-1129; Sep. 2005 (Article in German w/ Eng. Summary).
Star Micronics Co., Ltd; Prototype Diaphragm Micro Pump SDMP305 (specifications); retrieved May 12, 2015 from the internet archive as of Jul. 2006 (http://www.star-m.jp/eng/products/develop/de07.htm); 3 pgs.
Thiele et al. (Ed.); Oxidants and Antioxidants in Cutaneous Biology: Current Problems in Dermatology (Book 29); S. Karger; 196 pgs.; Feb. 2001.
Wille et al.; cis-urocanic Acid Induces Mast Cell Degranulation and Release of Preformed TNF-alpha: A Possible Mechanism Linking UVB and cis-urocanic Acid to Immunosuppression of Contact Hypersensitivity; Skin Pharm Appl Skin Physiol; 12(1-2); pp. 18-27; Jan. 1999.
Wille et al.; Inhibition of irritation and contact hypersensitivity by ethacrynic acid; Skin Pharm Appl Skin Physiol; 11(4-5); pp. 279-288; Jul. 1998.
Wille et al.; Inhibition of Irritation and Contact Hypersensitivity by Phenoxyacetic Acid Methyl Ester in Mice; Skin Pharm Appl Skin Physiol; 13(2); pp. 65-74; Mar. 2000.
Wille et al.; Several different ion channel modulators abrogate contact hypersensitivity in mice; Skin Pharm Appl Skin Physiol; 12(1-2); pp. 12-17; Jan. 1999.
Wille, J.; Novel topical delivery system for plant derived hydrophobic anti-irritant active (presentation abstract No. 273); 226th ACS National Meeting; New York, NY; Sep. 7-11, 2003.
Wille; In Closing: an editorial on Plant-Derived Anti-irritants. Cosmetics & Toiletries, 118 (8), Aug. 2003.
Wille; Novel plant-derived anti-irritants; (presented Dec. 5-6, 2002 at the 2002 Ann. Scientific Mtg. & Tech. Showcase); J. Cosmet. Sci.; 54; pp. 106-107; Jan./Feb. 2003.
Wille; Thixogel: Novel topical delivery system for hydrophobic plant actives; in ROSEN (Ed.) Delivery System Handbook for Personal Care and Cosmetic Products; 1st Ed.; ISBN: 978-0-8155-1504-3; pp. 762-794; Sep. 2005.
Youan; Chronopharmaceutics: gimmick or clinically relevant approach to drug delivery?; J Cont Rel; 98(3); pp. 337-353; Aug. 2004.
Yun et al.; A distributed memory MIMD multi-computer with reconfigurable custom computing capabilities; IEEE; Proc. Int'l. Conf. on Parallel and Distributed Systems; pp. 8-13; Dec. 10-13, 1997.

DiPierro et al.; U.S. Appl. No. 15/458,831 entitled "Biosynchronous transdermal drug delivery for longevity, anti-aging, fatigue management, obesity, weight loss, weight management, delivery of nutraceuticals, and the treatment of hyperglycemia, alheimer's disease, sleep disorders, parkinson's disease, aids, epilepsy, attention hypertension, depression, cold, flue and the like," filed Mar. 14, 2017.
Abood et al.; Structure-activity studies of carbamate and other esters: agonists and antagonists to nicotine; Pharmacology Biochemistry and Behavior; 30(2); pp. 403-408; Jun. 1988.
Baldessarini et al.; Preclinical studies of the pharmacology of aporphines; In: Gessa GL, Corsini GU, eds.; Apomorphine and other dopaminomi-'metics vol. 1, Basic pharmacology; New York: Raven Press; pp. 219-228; (year of pub. sufficiently earlier than effective US filed and any foreign priority date) 1981.
Jarvik et al.; Inhibition of cigarette smoking by orally administered nicotine; Clinical Pharmacology and Therapeutics; 11(4); pp. 574-576; Jul. 1, 1970.
Kiwi Drug; Buy nicorette microtabs; 3 pages; retrieved from the internet (www.kiwidrug.com/search/nicorette_microtabs); on Jul. 26, 2018.
Lieberman; Compression—coated and layer tablets; Pharmaceutical Dosage forms; vol. 1, 2nd ed.; Marcel Dekker Inc.; pp. 266-271; (year of pub. sufficiently earlier than effective US filed and any foreign priority date) 1989.
McNeil Sweden AB. Package Leaflet: information for the user. Nicorette Microtab Lemon 2mg sublingual tablets. (This leaflet was last approved in Apr. 16, 2008). retrived from ( www.lakemedelsverket.se/SPC_PIL/df/enhumpil/Nicorette%20Microtab%20Lemon%202mg%20sublingual%20tablet%20ENG.pdf.) Accessed Aug. 19, 2010.
MERCK manual of therapy and diagnosis; 17th edition. Merck Research Laboratories; pp. 1466-1471; (year of pub. sufficiently earlier than effective US filed and any foreign priority date) 1999.
Silver et al.; Transdermal nicotine and haloperidol in Tourette's disorder: a double-blind placebo-controlled study; Journal of Clinical Psychiatry; 62(9); pp. 707-714; Sep. 1, 2001.
Strong et al.; Genotype and smoking history affect risk of levodopa-induced dyskinesias in parkinson's disease; Movement Disorders; 21(5); pp. 654-659; May 1, 2006.
Tolosa et al.; Antagonism by piperidine of levodopa effects in Parkinson disease; Neurology; 27(9); pp. 875-877; Sep. 1, 1977.
Villafane et al.; Long-term nicotine administration can improve Parkinson's disease: report of a case after three years of treatment; Revista Neurologica Argentina; 27(2); pp. 95-97; (year of pub. sufficiently earlier than effective US filed and any foreign priority date) 2002.
Warburton et al.; Facilitation of learning and state dependency with nicotine; Psychoparmacology; 89(1); pp. 55-59; May 1, 1986.
Wesnes et al.; Effects of scopolamine and nicotine on human rapid information processing performance; Psychoparmacology; 82(3); pp. 147-150; Sep. 1, 1984.
Darmour et al.; U.S. Appl. No. 16/115,415 entitled "Craving input and support system," filed Aug. 28, 2018.

* cited by examiner

US 10,258,738 B2

BIOSYNCHRONOUS TRANSDERMAL DRUG DELIVERY FOR LONGEVITY, ANTI-AGING, FATIGUE MANAGEMENT, OBESITY, WEIGHT LOSS, WEIGHT MANAGEMENT, DELIVERY OF NUTRACEUTICALS, AND THE TREATMENT OF HYPERGLYCEMIA, ALZHEIMER'S DISEASE, SLEEP DISORDERS, PARKINSON'S DISEASE, AIDS, EPILEPSY, ATTENTION DEFICIT DISORDER, NICOTINE ADDICTION, CANCER, HEADACHE AND PAIN CONTROL, ASTHMA, ANGINA, HYPERTENSION, DEPRESSION, COLD, FLU AND THE LIKE

RELATED APPLICATIONS

This application is a divisional of U.S. patent application Ser. No. 14/268,725, filed May 2, 2014, which is a continuation of U.S. patent application Ser. No. 13/488,195, filed Jun. 4, 2012, now U.S. Pat. No. 8,741,336, which is a divisional of U.S. patent application Ser. No. 11/981,672, filed Oct. 31, 2007, now U.S. Pat. No. 8,252,321, which claims priority of U.S. Provisional Application Nos. 60/863,607 (Biosynchronous Transdermal Delivery of Nutraceuticals), 60/863,608 (Biosynchronous Transdermal Drug Delivery For the Treatment of Hyperglycemia), 60/863,613 (Biosynchronous Transdermal Delivery for Longevity and Anti-Aging), 60/863,618 (Biosynchronous Drug Delivery for Fatigue Management), 60/863,640 (Biosynchronous Transdermal Drug Delivery for Obesity, Weight-Loss and Weight Management), 60/863,654 (Biosynchronous Transdermal Drug Delivery for the Treatment of Alzheimer's Disease), 60/863,666 (Biosynchronous Transdermal Drug Delivery for the Treatment of Sleep Disorders), 60/863,671 (Biosynchronous Transdermal Drug Delivery for the Treatment of Parkinson's Disease (PD)), 60/863,677 (Biosynchronous Transdermal Drug Delivery for the Treatment of Attention Deficit Disorder (ADD/ADHD)) and 60/863,686 (Biosynchronous Transdermal Drug Delivery for the Treatment of Nicotine Addiction), each filed Oct. 31, 2006. The contents of all of the above listed applications are incorporated herein in their entireties by this reference. Application Ser. No. 11/981,672 is also a continuation-in-part application of U.S. Ser. No. 11/162,525 filed Sep. 13, 2005 and entitled Biosynchronous Transdermal Drug Delivery, now U.S. Pat. No. 7,780,981, which claims priority of U.S. Provisional Application No. 60/609,418 filed Sep. 13, 2004, both applications also being incorporated herein in their entireties by this reference. This application also relates to PCT Application No. PCT/IB2004/002947 entitled Transdermal Drug Delivery Method and System filed Sep. 13, 2004, published as WO 2005/039685 A1, which is incorporated herein by reference.

FIELD OF THE INVENTION

The present invention relates to transdermal devices and methods for controllable dispensing of a nutraceutical or an active substance such as a chemical substance, a medication, a drug, a stimulant or the like, to a human or other mammal for purposes of promoting longevity, for anti-aging, for fatigue management, for treating obesity, for weight loss, for weight management for, delivery of nutraceuticals, and for the treatment of hyperglycemia, alzheimer's disease, sleep disorders, parkinson's disease, aids, epilepsy, attention deficit disorder, nicotine addiction, cancer, headache and pain control, asthma, angina, hypertension, depression, cold, flu and the like.

RELEVANT BACKGROUND

Nutraceutical is a portmanteau of "nutritional" and "pharmaceutical" and refers to foods thought to have a beneficial effect on human health. It can also refer to individual chemicals which are present in common foods (and therefore may be delivered in a non-drug form). Many such nutraceuticals are phytonutrients.

Dr. Stephen DeFelice coined the term in 1989. The term has no regulatory definition, but it is commonly used in marketing. It is certainly not a new concept. Chinese medicine would be one example. Another would be Hippocrates who is quoted as saying, "Let your food be your medicine and let your medicine be your food." Nutraceuticals are often used in nutrient premixes or nutrient systems in the food and pharmaceutical industries. Nutraceuticals are sometimes called functional foods.

In contrast, medications are often closely regulated by governmental agencies. Medications may be prescribed for any of a number of purposes, including minimizing or removing symptoms, treating or irradicating disease, preventing occurrences of disease outbreaks.

Both nutraceuticals and medications provide effective treatments for a variety of illnesses. It is often preferred that a nutraceutical, active substance or medication is applied at a certain time or with a certain time pattern and in a manner that keeps the concentration of nutraceutical, active substance or medication at a certain value to achieve a desired therapeutic result most efficiently. There are some drug delivery technologies that are only able to release the active pharmaceutical ingredient (API) over a long period of time. Additionally, APIs can be partially or totally inactivated following oral ingestion due to the highly acidic environment of the stomach or by the first pass effect of the liver.

In order to overcome such problems, drugs are either administered transdermally through the skin (e.g., with a patch), or subcutaneously with an IV needle or continuous drip, these later two methods being common parenteral methods for drug delivery. For a long-term treatment, the parenteral methods may be uncomfortable for the patient because of the repeated injury by needle injections and the limited liberty of action due to intravenous drip apparatus.

Transdermal therapeutic systems (TTS) or "patches" are a form of transdermal drug delivery that is applied on the surface of the skin. Transdermal systems have gained acceptance, as a drug delivery platform, because they are portable, comfortable, and suitable for patients with drug delivery in continuous dosages over a relatively long period of time without requiring active participation of the patient.

In the last decade, portable dispensing systems have been developed to provide a more flexible, precise and complex administration of drugs. Generally, the dispensing systems comprise a reservoir for a drug, a dispensing unit, and a patch (or a membrane that is permeable to the active substance, drug, or the like but relatively impermeable to a solvent in which the active substance is mixed in the reservoir). The reservoir through the dispensing unit is interconnected to the patch. The dispensing unit controls the releasing of the drug in the reservoir to the patch. The efficiency for patch transdermal drug delivery depends mainly on the diffusion rate of the effective substances through the skin. Maintenance of the concentration of the effective substances on the patch is essential to achieve the desirable diffusion rate. However, it has proven problematic to effectively control the concentration of substances on the patch in an effective manner. Further, it has proven difficult to provide an inexpensive portable device that allows a user or patient to easily refill the reservoir and to otherwise maintain the device.

In the field of drug delivery, it is recognized that supplying the drug in a correct temporal pattern is an important attribute of any drug delivery methodology. Controlled release drug delivery systems are intended to improve the response to a drug and/or lessen side effects of a drug. The recurring interest in chronopharmacology demonstrates the fact that biological rhythms are an important aspect of clinical pharmacology and should be taken into account when evaluating drug delivery systems (Hrushesky, W. J. Cont. Rel. 19:363 (1992), Lemmer, B., Adv. Drug Del. Rev. 6:19 (1991), Redfern, P., Ed., "Chronotherapeutics," Pharmaceutical Press: London (2003), Youn, C. B. J., Cont. Rel. 98 (3) 337 (2004) and Youn, C. B. J., Ed., "Chronopharmaceutics," John Wiley & Sons, New York (In preparation)).

The onset and symptoms of diseases such as asthma attacks, coronary infarction, angina pectoris, stroke and ventricular tachycardia are circadian phase dependent. In humans, variations during the 24 h day in pharmacokinetics (chrono-pharmacokinetics) have been shown for cardiovascular active drugs (propranolol, nifedipine, verapamil, enalapril, isosorbide 5-mononitrate and digoxin), anti-asthmatics (theophylline and terbutaline), anticancer drugs, psychotropics, analgesics, local anesthetics and antibiotics, to mention but a few. Even more drugs have been shown to display significant variations in their effects throughout the day (chronopharmacodynamics and chronotoxicology) even after chronic application or constant infusion (Ohdo, S. Drug Safety 26 (14) 999-1010 (2003)). Moreover, there is clear evidence that dose/concentration-response relationships can be significantly modified based on the time of day. Thus, circadian time has to be taken into account as an important variable influencing a drug's pharmacokinetics and its effects or side-effects (Bruguerolle, B., Clin. Pharmacokinet. August 35 (2) 83-94 (1998)).

Studies indicate that the onset of certain diseases show strong circadian temporal dependency. This has led to the need for timed patterning of drug delivery as opposed to constant drug release (Lemmer B., Ciba Found. Symp. 183:235-47; discussion 247-53 (1995).

The term "controlled release" refers generally to delivery mechanisms that make an active ingredient available to the biological system of a host in a manner that supplies the drug according to a desired temporal pattern. Controlled release drug delivery systems may be implemented using: a) instantaneous release systems; b) delayed release systems, and c) sustained release systems. In most cases, controlled release systems are designed to maintain a sustained plasma level of an active ingredient in a drug within a human or animal host over a period of time.

Instantaneous release refers to systems that make the active ingredient available immediately after administration to the biosystem of the host. Instantaneous release systems include continuous or pulsed intravenous infusion or injections. Such systems provide a great deal of control because administration can be both instantaneously started and stopped and the delivery rate can be controlled with great precision. However, the administration is undesirably invasive as they involve administration via a puncture needle or catheter.

Delayed release refers to systems in which the active ingredient made available to the host at some time after administration. Such systems include oral as well as injectable drugs in which the active ingredient is coated or en-capsulated with a substance that dissolves at a known rate so as to release the active ingredient after the delay. Unfortunately, it is often difficult to control the degradation of the coating or encapsulant after administration and the actual performance will vary from patient to patient.

Sustained Release generally refers to release of active ingredient such that the level of active ingredient available to the host is maintained at some level over a period of time. Like delayed release systems, sustained release systems are difficult to control and exhibit variability from patient to patient. Due to the adsorption through the gastrointestinal tract, drug concentrations rise quickly in the body when taking a pill, but the decrease is dependent on excretion and metabolism, which cannot be controlled. In addition, the adsorption through the gastrointestinal tract in many cases leads to considerable side effects (such as bleeding and ulcers), and can severely damage the liver.

Transdermal therapeutic systems (TTS) have been developed primarily for sustained release of drugs in situations where oral sustained release systems are inadequate. In some cases, drugs cannot be effectively administered orally because the active ingredients are destroyed or altered by the gastrointestinal system. In other cases the drug may be physically or chemically incompatible with the coatings and/or chelating agents used to implement sustained release. In other cases a transdermal delivery system may provide sustained release over a period of days or weeks whereas orally administered drugs may offer sustained performance over only a few hours.

In most cases transdermal delivery systems are passive, taking the form of a patch that is attached to the skin by an adhesive. The TTS includes a quantity of the active substance, along with a suitable carrier if need be, in a reservoir, matrix or in the adhesive itself. Once applied, the active ingredient diffuses through the skin at a rate determined by the concentration of the active substance and the diffusivity of the active substance. However, a variety of physical and chemical processes at the skin/patch boundary affect the delivery rate and may eventually inhibit drug delivery altogether.

The original performance target for controlled drug delivery is to achieve a zero-order release rate of the drug, so that a constant efficacious drug concentration is maintained in the blood plasma. However, more than two decades of research in chronobiology and chronopharmacology have demonstrated the importance of biological rhythms to the dosing of medications as well as determine the influence of a patient's circadian or other biological rhythms on drug efficacy and efficiency. This research reveals that certain disease symptoms follow a daily pattern, with peak symptoms at certain times of the day. It has been widely acknowledged that hormones, neurotransmitters and other intra-body compounds are released in different amounts at different times of the day pursuant to daily patterns.

The new approach stems from a growing body of research that demonstrates that certain diseases tend to get worse at certain times of the day. By synchronizing medications with a patient's body clock, many physicians believe that the drugs will work more effectively and with fewer side effects. In some cases, the improvements have been so pronounced that doctors have been able to reduce dosages. Circadian physiologic processes have been found to alter drug absorption, distribution, metabolism, and excretion. As a result, drug doses need to be adjusted to meet the differing needs of target organs or tissues at various times of the day (see, L. Lamberg, American Pharmacy, N831 (11): 20-23 (1991)).

The continued interest in chronopharmacology shows the ever-increasing need to develop technologies to control the temporal profile in drug delivery. Research findings suggest that the onset and severity of many diseases are cyclic in nature, or follow circadian patterns. Drug tolerance adds to the need for modulation of drug dosing profiles. Additionally, skin irritation and sensitization caused by medications may require intervals during which no drug is administered. Therefore, this improved form of drug delivery will be very important to people who need medicine easily, painlessly and automatically delivered to their bodies in timed increments (see Smolensk, M. H. & Lamberg, L. Body Clock Guide to Better Health: How to Use Your Body's Natural Clock to Fight Illness and Achieve Maximum Health, Henry Holt & Company, New York (2001) and Grimes, J. et al., Pharmacol Exp Ther 285 (2): 457-463 (1998)).

Active transdermal delivery systems have been developed to help regulate the delivery rate by providing mechanisms to improve drug delivery over time by "pumping" the active ingredient. One such system, (U.S. Pat. No. 5,370,635), describes a system for delivering a medicament and dispensing it to an organism for a relatively long period of time, for example at least a few days. The device can be adapted for positioning on the surface of the skin of a human or possibly an animal body in order to apply a medicament thereto from the outer side thereof. Conventional transdermal systems circumvent the disadvantages of the adsorption through the gastrointestinal tract, but they do not optimize or tailor the dosing regiment to offset peak symptoms. In addition the constant transdermal delivery of a drug can lead to severe side effects, including debilitating sleep disorders and ever increasing tolerance.

A simple type of pulsed transdermal chronotherapy is a biphasic profile, in which the drug concentration changes from a high to a low level (or vice versa) over time. Although the system can be physically applied or removed to alter the drug level, patient compliance With this procedure may be difficult, particularly during inconvenient hours. To generate a biphasic profile, the delivery system may utilize an external regulator, as described in Fallon et al. (U.S. Pat. No. 5,352,456) which illustrates a device for drug administration through intact skin that provides an initial pulse in the flux of the drug through the skin followed by a substantially lower flux of drug through the skin. Additionally, Fallon et al. (U.S. Pat. No. 5,820,875) later describe a device for the administration of a drug through an area of intact skin over a period of time in which the flux of the drug through the skin varies temporally in a controlled manner. The device is such that the skin flux of the drug varies in a controlled manner over the period of administration, typically from a high flux in the initial stage of administration to a lower flux in the later stage of administration.

Transdermal temporally controlled drug delivery systems, proposed by Giannos et al. (U.S. Pat. No. 6,068,853) coupled pH oscillators with membrane diffusion in order to generate a periodic release of a drug or active ingredient transdermally, without external power sources and/or electronic controllers. The intent was to address chronotherapy with a pulsatile transdermal system. The strategy was based on the observation that a drug may be rendered charged or uncharged relative to its pKa value. Since only the uncharged form of a drug can permeate across lipophilic membranes, including the skin, a periodic delivery profile may be obtained by oscillating the pH of the drug solution (see Giannos, S. A., "Pulsatile Delivery of Drugs and Topical Actives," in "Skin Delivery Systems; Transdermal, Dermatologicals and Cosmetic Actives", Edited by John. J. Wille, Jr.: Blackwell Publishing, Oxford UK (2006)).

Recently, an orally administered drug for arthritis treatment has suggested a chronotherapeutic approach using a delay release system. The delay is scheduled to release the active ingredient at the beginning of an interleukin 6 cascade that is believed to cause early morning stiffness in rheumatoid arthritis patients. By attempting to synchronize the drug delivery with a biological cycle it is believed that low doses may be used to achieve desired results. However, this system does not overcome the limitations of delayed release systems described above.

Although it is possible to meet the requirements of chronopharmacology and pulse a medication with pills, this requires an enormous amount of discipline by the patient to comply with the treatment regiment, see for example, U.S. Pat. No. 6,214,379, which is incorporated herein by reference. As illustrated earlier, to achieve optimal results, many patients may need to wake up during the night to take their medication. Hence, what is needed is a non-invasive, reliable means of delivering drugs compounds in precisely timed and measured doses-without the inconvenience and hazard of injection, yet with improved performance as compared to orally delivered drugs.

Addressing patient compliance (taking the proper dosages at the prescribed times) is another critical problem facing caregivers and pharmaceutical firms alike. Studies show that only about half of patients take medications at the times and in the dosages directed by their physician. It is reported that each year, 125,000 deaths and up to 20% of all hospital and nursing home admissions result from patient noncompliance. It is estimated that non-compliance results in additional healthcare costs in excess of $100 billion per year in United States. These figures are even more pronounced for the elderly.

An individual's failure to comply with a dosing regimen, e.g. failure to take one or more doses of a drug or taking too many doses, will have an adverse impact upon the success of the regimen. Individuals may fail to comply with their drug-dosing regimen for a number of reasons. For example, drug-dosing regimens, such as every 4 hours, i.e., 8-12-4-8 involve a rigid dosing schedule that may be incompatible with an individual's personal schedule. Such a rigid dosing schedule when combined with normal human traits such as forgetfulness or denial of a medical condition, as well as a busy life, represent substantial obstacles to compliance with a drug dosing regimen. Accordingly, such rigid dosing regimens often result in the failure by an individual to take one or more doses at the prescribed time. This has an adverse impact on the levels of the therapeutic substance at the active site and consequently on the overall efficacy of the therapeutic substance.

Hence, a need exists for systems and methods that increase patient compliance for administration of a variety of nutraceuticals and/or active substance (including, e.g., drugs). Also, there remains a need for an improved patch-based (or membrane-based) delivery system for a nutraceutical and/or active substance that is able to administrate the delivery of a nutraceutical and/or active substance to a subject over a period of time in a controllable way. It is a preferable for such a system or device to administrate the delivery of the nutraceutical and/or or active substance in a pulsatile and scheduled manner, pursuant to a pre-programmed dosage delivery regimen, meaning dosage sizes and times can be automatically varied according to such pre-programming.

In addition to disease conditions, there are other conditions which also may benefit from a new controlled delivery methodology. For example, longevity is defined as long life or the length of a person's life (life expectancy). Reflections on longevity have usually gone beyond acknowledging the basic shortness of human life and have included thinking about methods to extend life.

Life extension refers to an increase in maximum or average lifespan, especially in humans, by slowing down or reversing the processes of aging. Average lifespan is determined by vulnerability to accidents and age-related afflictions such as cancer or cardiovascular disease. Good diet, exercise and avoidance of hazards such as smoking and excessive eating of sugar-containing foods can achieve extension of the average lifespan. Maximum lifespan is determined by the rate of aging for a species inherent in its genetic code. Currently, the only widely recognized method of extending maximum lifespan is by calorie restriction with adequate nutrient supplementation. Theoretically, extension of maximum lifespan can be achieved by reducing the rate of aging damage, by periodic replacement of damaged tissues, or by molecular repair or (rejuvenation) of deteriorated cells and tissues.

Similarly, obesity is a disease that affects nearly one-third of the adult American population (approximately 60 million). The number of overweight and obese Americans has continued to increase since 1960, a trend that is not slowing down. Today, 64.5 percent of adult Americans (about 127 million) are categorized as being overweight or obese. Each year, obesity causes at least 300,000 excess deaths in the U.S., and healthcare costs of American adults with obesity amount to approximately $100 billion.

SUMMARY OF THE INVENTION

The invention relates to drugs, pharmaceuticals, nutraceuticals and other bioactive substances are delivered transdermally into a body in a manner that is synchronized with biological processes and/or biological rhythms so as to improve performance of the substance in the body. The invention also relates to overcoming active agent tolerance, which may be experienced from continuous administration, improve patient compliance, and in some cases reducing the amount of drug needed per dose due to advantages of biosynchronization.

The present invention describes a method for promoting good health and treating a wide variety of conditions treating obesity, excess weight gain, and weight management Alzheimer's disease (AD) treating difficult and delayed waking in the morning Parkinson's disease (PD) treating attention deficit disorder (ADD) and attention deficit-hyperactivity disorder (ADHD) smoking and nicotine addiction in humans anti-aging and life extension therapy for humans and mammals. This method involves treating non-insulin-dependent diabetes mellitus (NIDDM), hyperglycemia and other glucose disorders in humans involving synchronizing and tailoring the administration of a wide variety of substances and drug compounds with the body's natural circadian rhythms, or more notably a user's typical nicotine craving cycles in order to alleviate a myriad of symptoms of excess weight and obesity, conditions, for longevity, life extension or minimizing the aging process in humans, of morning drowsiness and to counteract symptoms when they are likely to be at their worst, to counteract symptoms of nicotine withdrawal and craving associated with cessation of tobacco or nicotine use, by use of an automated and pre-programmed device. This invention relates to programmable transdermal delivery system for delivering a stimulant through the skin for short periods of time, in order to extend and improve alertness, while at the same time allowing for easy device removal and termination of drug delivery. The invention further relates to the field of chronobiology in that the invention systems can be designed to modulate active agent delivery in accordance with biological rhythms. Drugs, pharmaceuticals, and other bioactive substances are delivered transdermally into a body, in a temporal manner, that is increasingly incremental, decreasingly incremental or a mixture of the two so as to purposefully modulate the active substance in the body. This system can utilize a pump or pressurized reservoir, and/or a system for removing depleted carrier solution, or other modulated dispensing actuator, in conjunction with porous membranes or micro-fabricated structures commonly referred to as micro-channels, with micro-needles, light, heat, iontophoresis, electroporation, sonophoresis and dermal abrasion (together referred to as mechanical permeation enhancement) or a wide range of chemical permeation enhancers and/or a wide range of nano-structures and substances known as nanotechnology or any combination of these techniques.

More specifically, these methods synchronize and tailor drug administration to the human body's circadian rhythms or to deliver varying dosages at varying times. This ensures that peak concentrations of nutraceuticals, drugs and/or chemical substances (collectively herein "active substance") are present in the bloodstream to offset peak disease symptoms arising from variances and fluctuation in the body's natural circadian rhythms.

Further, this method ensures that less of a active substance is in the bloodstream when disease symptoms and conditions are at their lowest. Negative side effects can be minimized, while at the same time active substance efficacy is enhanced by the dosing regimen.

Embodiments of the present invention provide for a active substance-reservoir/patch based transdermal delivery device to administer the delivery of a active substance to a patch or other drug reservoir adjacent to the membrane or in close proximity to the skin for transdermal absorption that absorbs or is filled with the substance (the administration reservoir) over a period of time or from time to time in a controllable and/or automated and programmable way. Significantly, these transdermal delivery devices include a reusable, active portion that includes a control and display unit and an active dispensing mechanism, e.g., a micropump that is in some embodiments a specially configured peristaltic pump, a pressurized reservoir, a piezo electric pump, osmotic pump, infusion pump, syringe pump or other actuator.

Further, the transdermal delivery devices include a detachable and disposable passive portion that includes a drug reservoir that is separated from the administration reservoir and holds the active substance until the micropump or other actuator places the drug into the administration reservoir for transdermal absorption and a coupling mechanism/assembly for mating with the active dispensing mechanism, e.g., when the active dispensing mechanism is a peristaltic pump the coupling mechanism may include one or more elongate feed chambers (e.g., flexible tubes) that are connected to the active substance reservoir and, in many cases, to the administration reservoir adjacent the membrane or skin or other material in contact with the skin. The coupling mechanism may be defined in part by the outer surfaces of a housing for the passive portion, and these surfaces may include grooves or guides for receiving and supporting the active dispensing mechanism. In some cases, the outer surfaces of the housing define an arcuate surface upon which the feed chamber or tube is disposed such that the shoes or other portions of the peristaltic pump can compress the tube to move liquid from the dispensing reservoir to the administration reservoir near the semipermeable membrane or patch.

In addition, in the context of automated transdermal pulsatile active substance delivery, starting dosing or bringing the nutraceutical, drug or other active compound (collectively herein "active substance") into contact with the skin may be only one part of the necessary methodology. The other part of the methodology may be to stop dosing or to stop permeation of the active substance through the skin. Stopping dosing automatically is extremely useful in certain situations to start and stop dosing so as to achieve programmed pulsatile active substance delivery. The present invention not only has dosing or delivering methodologies, but also methodologies to stop dosing or delivering in a controlled manner.

More specifically, in certain embodiments where the stoppage of permeation or dosing is desired, the active compound or solvent is removed from the administration reservoir to stop dosing and/or decrease or end active substance permeation through the skin. In this embodiment, a active substance and/or solvent removal means is introduced (solvent/nutraceutical/drug removal means). In this situation, either the above mentioned micropump or actuator (which may move gas or air) or a second micropump or actuator (which may move gas or air) will act to remove, and/or flush the active substance formulation or residual active substance formulation/and or solvent from the administration reservoir into either into a waste reservoir or other area for evaporation or other removal. The first or second micropump or actuator, as applicable, may flush the administration reservoir with air, gas, inactive solution and/or a combination of these. A heating element may also be present to either aid in evaporation, if applicable, or to assist in permeation.

The inventive system or device allows for pulsatile transdermal active substance delivery, and the administration of differing sized dosages at different times of the day automatically, pursuant to a pre-programmed dosage profile (e.g., a program stored in memory accessed by the control unit). This system or device can be most advantageous when the pre-set or programmed active substance delivery profile corresponds to desired peaks and troughs in disease symptoms based on chronobiology and a person's circadian rhythms. This system or device can also be highly advantageous in addiction management when programmed to coincide with a person's peak addiction cravings. This system or device can also be highly advantageous when patient compliance with a particular delivery regimen is a desired effect so that a person, whether forgetful, elderly, children, mentally impaired desires to ensure correct active substance delivery compliance. This device can also be highly advantageous when a person or physician a doctor wants to have a active substance administered in differing dosages while asleep automatically without the need to wake up, or if the active substance being used is a stimulant and the person does not want any active substance released at night thereby causing sleep disturbances, but does want the device to administer active substance shortly before waking so that therapeutically effective blood plasma concentrations of the active substance are present upon waking.

According to some embodiments of the present invention, the device comprises a control and display unit, a dispensing mechanism, e.g., a pump, pressurized reservoir or other actuator, a active substance reservoir, an administration element, and/or a solvent/nutraceutical/drug removal means (e.g., a desiccant or evaporative means), and/or a vapor removal element, when applicable, to the embodiment a waste reservoir, and/or an additional micropump or actuator. Embodiments of the invention may include one or more of the following features. The pump may be a peristaltic pump that includes a micromotor, a roller, a mounting plate, a tubing, and a housing. As discussed above, the peristaltic pump is separated into two parts; the first part comprises the motor on the mounting plate and the roller (e.g., provided in the reusable portion of the device) and the second part includes the tubing and the housing (e.g., provided in the detachable and disposable passive portion of the device). The micromotor and the roller are mounted in the device with the control unit. The speed of the micromotor is controlled by the control unit, so that the turning speed of the roller is controlled which, in turn, controls the flow rate from the dispensing reservoir to the administration reservoir. The tubing and the housing are detachable from the device.

Embodiments of the invention may include one or more of the following features. The tubing and the housing of the peristaltic pump and the dispensing or active substance reservoir are combined together, resulting in one, interconnected disposable and replaceable dosing element. In other words, this disposable dosing element (or detachable and disposable passive portion) is a replaceable dosing capsule, which can be used for one or multiple dosings. This disposable dosing capsule can be "snapped" into place prior to substance administration by the patient or other health worker, and, after the active substance reservoir is exhausted, the disposable dosing element is "popped" out to be disposed, and a fresh disposable dosing element is then "snapped" back into the device. The tubing is provided inside the body of the capsule in some embodiments. One end of the tubing is connected to the active substance or dispensing reservoir while the other end of the tube is a fluidic adapter or distributor near the administration reservoir or area near the patch or membrane. In certain embodiments, the waste reservoir, desiccant chamber capturing vapors evaporated from the nutraceutical/drug/solvent, tubing and analogous components of the second micro pump or actuator as the first pump mentioned above, a gas/air cartridge and the administration reservoir may also be part of this snapped on or snapped off portion or may be disposable pursuant to another means. Further, embodiments of the invention may include one or more of the following features. The disposable dose capsule, the administration element, and a nutraceutical/drug/solvent removal element are connected and packed together as a disposable package, whenever the dosage is needed to applied to skin, the whole disposable package is changed and replaced into the device.

More particularly, an apparatus is provided for selectively delivering a liquid, powder, or temporarily free-flowing solution (e.g., a active substance formulation or the like). The apparatus includes an active assembly with a controller and a power source (e.g., a battery). The apparatus further includes a passive assembly configured for mechanically coupling and decoupling with the active assembly. The passive assembly includes a active substance reservoir containing the active substance formulation to be delivered. The apparatus further includes a micropump/actuator combination that acts as the dispensing mechanism with an active portion in the active assembly that provides a motive force to draw or otherwise move the active substance formulation from the active substance reservoir onto or into the administration reservoir. The micropump/actuator or dispensing mechanism includes a passive portion provided in the detachable passive assembly so as to be proximate to the active portion of the micropump/actuator. The passive portion defines a feed or delivery chamber through which the active substance formulation flows from the active substance reservoir when the motive force is applied to the passive portion. In some embodiments, the micropump/actuator includes a peristaltic pump with the active portion being made up of: a motor powered by the power source and operated by the controller to control the motor speed and its time of operation; a roller with rotatably mounted shoes; a shaft contacting the roller and driven by the motor; and a mounting plate supporting the motor. The passive portion, in turn, includes a housing with a guide slot or recessed surface for receiving the mounting plate and roller so as to position one or more of the shoes in contact with an outer surface of the feed chamber, which in some embodiments is a length of compressible tubing. The guide slot in these cases may include a curved surface and the tubing is positioned between the roller/shoes and the curved surface such that the motive force includes using the shoes to sequentially compress the tubing.

The passive assembly may further include an administration assembly including an administration reservoir connected to the tubing to receive the active substance formulation and a membrane adjacent to the administration reservoir that is permeable to an active or effective substance in the active substance formulation, but not or less permeable to a solvent portion of the liquid. In certain embodiments, an absorbent sheet (e.g., blotting paper or the like) may be provided in the administration reservoir so as to distribute the received liquid in a relatively uniform manner over the surface of the membrane. In other embodiments, instead of an absorbent sheet, the administration reservoir may be or include a rigid or flexible, permanent or disposable substrate with a plurality of ducts, conduits or culverts that contain internal passageways for movement of the active substance formulation and have either a series of openings or a single opening mounted on the membrane or skin or otherwise adjacent to the membrane or skin to allow the active substance formulation to be absorbed or otherwise transferred or to move from the substrate ducts to the membrane or skin for transdermal absorption. In this manner, the ducts, conduits, or culverts or in this substrate can be filled by the micropump/actuator with active substance formulation originating in the active substance reservoir. Then, these ducts, conduit, or culverts can be flushed either by the first micropump actuator or a second micropump/actuator into a waste reservoir or flushed into an area for evaporation to begin and stop dosing in an accurate fashion. Yet further, a heat element may be provided in the administration assembly near the administration reservoir to raise the temperature 3 to 10 degrees Celsius over a dermal temperature to enhance transdermal permeation and/or diffusion and/or movement of the active substance formulation through the substrate and in some cases to increase evaporation when it is desired to dry the reservoir (or absorbent sheet). In the latter instance, the heating element may be configured with a plurality of flow paths for vapor or evaporated portions of the liquid (such as solvent vapor) that facilitates relatively uniform or at least in a well distributed flow, away from the reservoir.

The invention may employ internally or externally a wide range of chemical permeation enhancers such as azones, oleic acid, ethanol, amino acids, oleyl alcohol, long chain fatty acids, propylene glycol, polyethylene glycol, isopropanol, ethoxydiglycol, sodium xylene sulfonate, N-methylpyrrolidone, laurocapram, alkanecarboxylic acids, dimethylsulfoxide, polar lipids, N-methyl-2-pyrrolidone, anionic, cationic and non-ionic surfactants, terpenes, piperine and piperine derivatives, isopropyl myristate, isopropyl palmitate and the like, which increase the permeability of the skin to the active material and permit the active material to penetrate through the skin. Pharmaceutically acceptable compositions may be combined with one or more agents including, but not limited to, alcohols, moisturizers, humectants, oils, emulsifiers, thickeners, thinners, surface-active agents, fragrances, preservatives, antioxidants, vitamins, or minerals.

For example, when administering a an active compound pursuant to a chronopharmacological dosage profile as set forth herein, using a programmed, transdermal, pulsatile drug delivery device, a pharmaceutically acceptable composition of an active material may be combined with either mechanical skin penetration enhancers including, but not limited to, micro-fabricated structures commonly referred to as Micro-needles, heat, or sonophoresis, or a wide range of chemicals.

Additional advantages and novel features of this invention shall be set forth in part in the description that follows, and in part will become apparent to those skilled in the art upon examination of the following specification or may be learned by the practice of the invention.

DETAILED DESCRIPTION OF PREFERRED EMBODIMENTS

Figure 1:
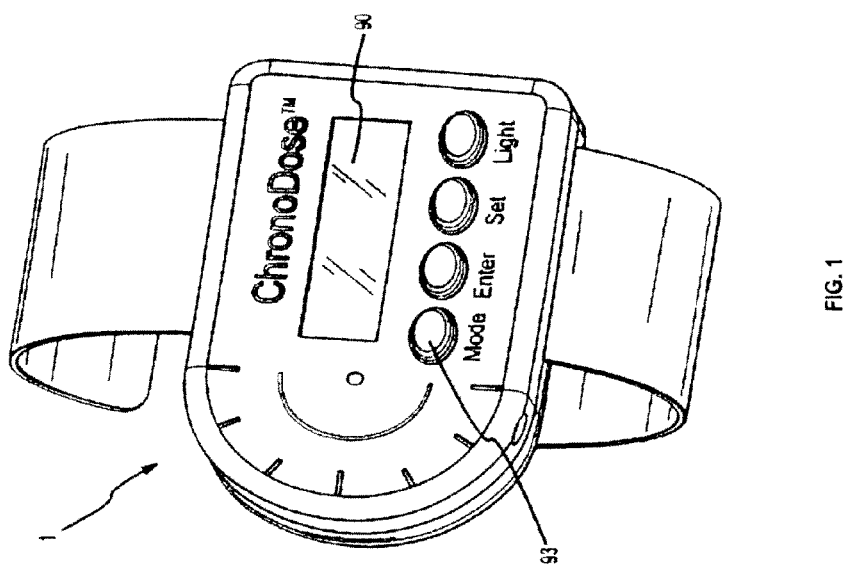
FIG. 1 is a perspective view of an exemplary portable transdermal nutraceutical, drug or active substance (collectively herein "active substance") delivery device or assembly of the present invention.

Biological rhythms are periodic fluctuations in biological characteristics over time, which also include circadian as well as seasonal variations. The reality of circadian rhythms in animals including humans is well known (Halberg et al. J. Exp. Ther. Oncol. 3 (5) 223-260 (2003), Redfern et al. Chronobiology International 11 (4) 253-265 (1994)).

Circadian (approximately 24-hour) rhythms include the production of biological molecules such as endorphins, gonadotropin releasing hormone (GnRH), cortisol and adrenaline. These regulate the body's temperature and heart rate, changes in characteristics of blood, such as stickiness, and behaviors such as wakefulness, sleep and periods of activity.

Some of the rhythms that affect our bodies include:
ultradian, which are cycles shorter than a day (for example, the milliseconds it takes for a neuron to fire, or a 90-minute sleep cycle)
circadian, which last about 24 hours (such as sleeping and waking patterns)
infradian, referring to cycles longer than 24 hours (e.g., monthly menstruation)
seasonal, such as seasonal affective disorder (SAD), which causes depression in susceptible people during the short days of winter.

Research demonstrates that certain disease symptoms follow a daily pattern, with peak symptoms at certain times of the day. It has been widely acknowledged that hormones, neurotransmitters and other intra-body compounds are released in different amounts at different times of the day pursuant to daily patterns. It is believed that the failure of current transdermal systems to synchronize active substance administration with the body's natural rhythms often lead to (i) severe side effects, including debilitating sleep disorders (in the context of night-time nicotine administration, for example), (ii) ever increasing tolerance (in the case of nitroglycerin and other pharmaceuticals for example), (iii) more expensive therapies, due to the fact that more of a compound is needed because the daily body rhythm is ignored and time based dosing is not implemented.

In addition, many addictions follow a daily pattern consistent with one's circadian rhythms. For example, according to studies performed, immediately upon waking, smokers have peak nicotine cravings. These peak cravings return after each meal, due to the interplay of serotonin release as a trained response to the culmination of a meal. The present invention precisely times the administration of active substances so that they reach peak levels when symptoms are likely to be at their worst, and efficacy is greatly improved.

The present invention involves precisely timing the administration of active substances so that they reach peak levels in synchronization with times when symptoms are likely to be at their worst, or times at which the active substances are believed to be more effective in the body and/or better tolerated by the patient. The present invention is described in terms of a particular example of a active substances delivery system that provides automated and precise control over dosing, with single-dose capability, (once while people sleep) or capability to administer separate and varying-sized doses many times throughout a multiple day period. The present invention also relates to the administration of different, distinct, active substances and dosages at different times of the day. The particular implementation is consistent with a commercial development of a miniaturized, automated and programmable non-invasive active substances delivery system called the ChronoDose™ system being developed by the assignee of the present invention. The system enables controlling of the amount of active substances exposed to the skin in a controlled time dependent way according to a programmed administration schedule that implements a desired dosage profile. In this manner the present invention enables one to precisely control and vary the time of active substances release and the amount of each dose, pursuant to an easily set pre-programmed dosage profile. Research demonstrates that for certain symptoms, conditions and diseases, active substances effects can be optimized when administered in a defined (and often varying) dosage at predefined times. This is known as Chronopharmacology (Reinberg, A. E., Concepts of Circadian Chronopharmacology, In "Temporal Control of Drug Delivery" edited by Hrushesky, W. J. M., et al, Annal NY Academy of Science, New York. Volume 618 102-115 (1991), Lemmer, B. Pharmacol Res. 33(2) 107-15 (1996)).

To illustrate the importance of Chronopharmacology consider the following facts:

Asthma attacks are 100 times more likely between 4:00 and 6:00 AM.

Heart attacks and strokes are most likely to occur around 6:00 AM.

Variant Angina attacks occur 30 times more often in the middle of the night between 2:00 AM and 4:00 AM.

Smokers experience the highest cravings immediately upon waking up.

Lethargy and difficulty getting out of bed is highest immediately upon waking up early in the morning.

Cold and flu symptoms peak during nighttime and early morning hours, when cold medications are wearing off Chronopharmacokinetics is defined as the predictable changes observed in the plasma levels of drugs and in the parameters used to characterize the pharmacokinetics of a drug. Studies on animals and humans indicate that the $C_{max}$, $T_{max}$, AUC and half-life often vary as a function of the hour of administration of the drug. Table 1 presents a list of medications for which temporal changes in pharmacokinetics have been documented. See, Labrecque, G., et al. Chronopharmacokinetics, Pharmaceutical News, 4 (2) 17-21 (1997).

TABLE 1

Drugs with documents time-dependent changes in pharmacokinetics

| CLASSES OF DRUGS | SPECIFIC MEDICATIONS |
| --- | --- |
| Analgesic and NSAID | aspirin, sodium salicylate, acetaminophen, ketoprofene, phenyl butazone, indomethacin |
| CNS Drugs | hexabarbitol, carbamazepine, clorazepate, diazepam, triazolam, lorazepam, midazolam, amitryptiline, sodium valproate |
| Cardiovascular Drugs | atenolol, metoprolol, lidocaine, dipyridamole, digoxine |
| Anti-asthmatic Drugs | aminophylline, theophyline, terbutaline |
| Antibiotic | ampicillin, erythromicin, griseofulvin, cefoxizime |
| Anti-cancer Agents | Cisplatin |

We have carefully identified specific active substances and diseases because they have the following attributes: (i) Chronopharmacology is critical to optimized dosing but is not being implemented because no automated transdermal system exists, and (ii) these active substances are preferably transdermally absorbed passively (i.e., without the need for external modulation or pre-treatment such as sonophoresis, iontophoresis, electrophoresis, electroporation, or other permeation enhancement.

TABLE 2

Examples of Disease States for ChronoDose ™ Application

| THERAPEUTIC AREA | DISEASE OR CONDITION | CHRONO-PHARMACOLOGY RATIONALE |
|---|---|---|
| Cancer | Various forms | Chemotherapy may be more effective and less toxic if drugs are administered at carefully selected times that take advantage of tumor cell cycle times while less toxic to normal tissue. |
| Cardiovascular | Angina | Angina (variant) attacks occur 30 times more often between 2:00 a.m. and 4:00 a.m. → Larger doses of Nitroglycerin early in the morning |
| | Heart Attacks and Strokes | Heart Attacks are most likely between Strokes 6:00 a.m. and Noon. → Cardiovascular active drugs before waking. |
| | Hypercholesterolemia | A circadian rhythm occurs during hepatic cholesterol synthesis, which is generally higher during the night than during daylight. Studies with HMG CoA reductase inhibitors suggest that evening dosing is more effective than morning dosing. → Simvastatin in evening and during night. |
| | Hypertension | Automatically and precisely release clonidine or other hypertension drugs in peak amounts to offset the peak symptoms associated with the dangerous morning symptoms. → Clinidine, Captopril or other medication in the morning. |
| CNS Degenerative Disorders | Parkinson's Disease | Automated dosing for patient compliance → Selegiline, Benztropine, Apomorphine |
| | Alzheimer's Disease | Automated dosing for patient compliance → Rivastigmine, Memantine |
| Diabets | Diabetes (Type II) | Automated dosing for elderly patient compliance. Oral medication is poorly absorbed. → Miglitol before meals. Glibenclamide |
| Epilepsy | Epileptic seizure | Epileptic seizures are most likely between 6:00 a.m. and 7:00 a.m. → Gabapentan or other Epileptic drugs before waking up |
| Pulmonary | Asthma | Asthma attacks are 100 times more likely between 4:00 a.m. and 6:00 a.m. Adrenaline and Cortisol are virtually absent at night. → Albuterol or Tulobuterol in early morning. |
| Pain | Acute Pain | Neurological pain is worst between 3:00 a.m. and 8:00 a.m. → Fentanyl in the middle of night. |
| | Migraine Headaches and/or Cluster headaches | Migraine headaches usually begin and occur between 8:00 a.m. and 10:00 a.m. Cluster headaches start earlier, around 4:00 a.m. → Zolmitriptan or dihydroergotamine in the middle of night. |
| Mental Health | Depression | Selegiline at night can create sleeping disorders (nightmares), but depression symptoms are high immediately upon waking up → Selegiline before waking up |
| Inflammation | Rheumatoid Arthritis, Osteoarthritis | Worst upon awakening. Cortisol and anti-inflammatory hormones are very low at night → Indomethacin or Valdecoxib before waking up. |
| Women's Health | Tocolytic Therapy | Programmed-in-time administration of tocolytic medication relative to the circadian rhythm in uterine contractility to avert preterm labor and birth. → Nifedipine, Terbutaline or Ritodrine synchronized with uterine contractions. |
| OTC | Smoking Cessation | Nicotine at night creates sleeping disorders (nightmares), but cravings are the highest immediately upon waking → Nicotine before waking up. |
| | Circadian rhythm sleep disorders and Morning Lethargy | Adrenaline is lowest in the morning, making early morning waking uncomfortable and difficult for many people. → OTC Stimulant before waking |
| | Insomnia | Some sleep medications induce drowsiness but do not provide for continuous sleep in sensitive patients. → Pulsatile and low dose delivery of sleep medication will provide continuous sleep. |

TABLE 2-continued

Examples of Disease States for ChronoDose ™ Application

| THERAPEUTIC AREA | DISEASE OR CONDITION | CHRONO-PHARMACOLOGY RATIONALE |
|---|---|---|
| | Peptic Ulcer Disease | Gastric acid secretion increases in late afternoon and early night. Also, partial nocturnal resistance to $H_2$-blockade has been noted. → $H_2$-blockers (ranitidine, cimetidine, famotidine, roxatidine, nizatidine) during the night. Drugs other than $H_2$-blockers or antibiotics during the night. |
| | Jet lag Shift work | Melatonin can be used to reset circadian Shift work rhythms. |
| | Colds and Flu | Heaviest symptoms overnight and in the morning. → Cold/Flu medicine during the night. Triprolidine, Doxylamine |
| | Supplements/weight loss | Vitamins and Supplements are best administered in low doses over the course of the day to be most effective. |

The construction and use of transdermal patches for the delivery of pharmaceutical agents is known. See, for example, U.S. Pat. No. 5,370,635, the disclosure of which is incorporated herein by reference. Such patches may be constructed using a saturated or unsaturated media, pressurized reservoirs, or unpressurized reservoirs with micropumps for continuous, pulsatile, or on-demand delivery of an active material.

Device

The present invention is generally directed to a portable active substance delivery device that can controllably deliver a particular dose accurately and in a timed manner. The devices of the invention are typically configured with a reusable portion and a disposable portion. The reusable portion typically includes the display and control components such as a microprocessor, memory, interfaces, and power source and also includes the active portion of a dispensing mechanism (e.g., active portion of a micropump). The disposable portion can be selectively coupled or attached to the reusable portion and includes the passive portion of the dispensing mechanism (e.g., a micropump housing and feed or delivery chamber/tubing) as well as the active substance or dispensing reservoir and also the administration assembly that may include an administration reservoir, a diffusion membrane, and a solvent removal element. In this manner, the present invention addresses problems with a membrane having a decreasing diffusivity that may be caused by saturation with solvent, the contact surface becoming dirty or clogged, or other factors. The device also facilitates the reuse of more expensive components such as the microprocessor, memory components, a liquid crystal display (LCD) or other display, and active pump portions. These and other unique features of the invention will become apparent in the following description.

FIG. 1 illustrates one embodiment of a portable active substance delivery device or assembly 1 of the present invention. The device 1 is shown to generally take the form of a wrist watch for easy attachment to a patient's arm or wrist to place an administration element and more specifically a diffusion membrane for transdermal delivery (or, in some cases, a needle for subcutaneous delivery), e.g., an administration assembly that can be removed from the reusable portion of the device 1 shown in FIG. 1 is provided on the underside or reverse side of the device 1. The device 1 includes a display 90 to allow a patient or user of the device 1 to obtain a status of a dosing regimen, e.g., to know whether the device 1 actively dosing, when a next dose may be administered, how many doses remain for the device based on the particular disposable dosing element, or the like. An input area or keyboard/keypad 93 is provided to allow the user to alter the display 90 and otherwise interact with the device 1.

Figure 2:
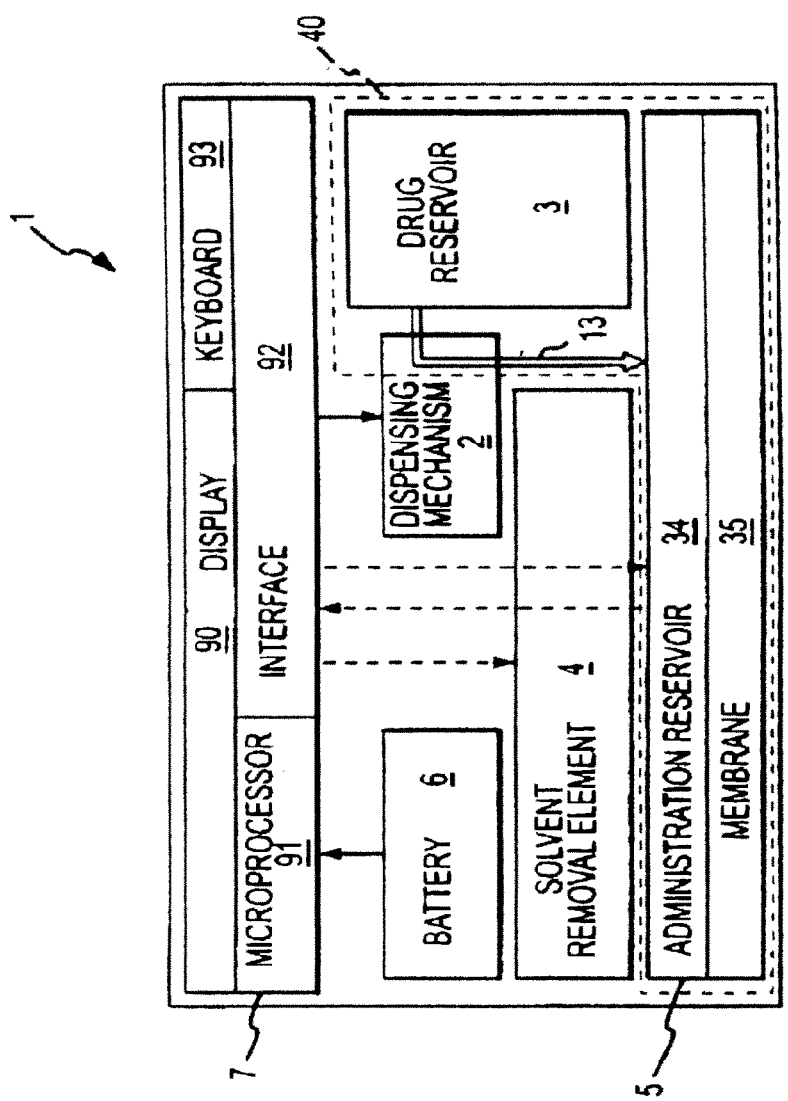
FIG. 2 is a block diagram of the active substance delivery device of FIG. 1 showing in block form representative components of a portable device for transdermal active substance delivery.

FIG. 2 illustrates in block form the components of the device 1 in one embodiment of the invention. The portable device 1 as shown is configured for transdermal active substance delivery and includes a control and display unit 7, a dispensing mechanism 2, a active substance reservoir 3, an administration element 5, a solvent removal element 4, and a battery 6. A liquid is typically provided in the active substance reservoir 3 for dispensing via feed chamber or delivery tube 13. The liquid includes a sufficient or predetermined amount of one or more active substances dissolved or dispersed at an appropriate concentration in a formulation that contains a solvent (or more volatile liquid) or a mixture of solvent along with the active substances. For example, the solvent may include one or more generally regarded as safe (GRAS) agents such as water, ethanol and other low molecular weight alcohols, acetone, ethyl acetate, volatile oils or the like. If appropriate, other excipients may be provided in the reservoir 3 such as tissue permeation promoter (enhancers), thickening substances, solubilizers, buffers, chemical stabilizers, preservatives, moisturizers, humectants, emulsifiers, thinners, surface-active agents, fragrances, or the like.

The invention can also contain agents known to accelerate the release of the active substance onto the body surface or through the skin in the active substance formulation or adjacent to the skin. This class of agents includes those with diverse mechanisms of action including those which have the function of improving the solubility and diffusivity of the active substance and which improve percutaneous absorption. For example, by changing the stratum corneum's (skin) ability to retain moisture, softening the skin, improving the skin's permeability, acting as penetration assistants or hair-follicle openers or changing the state of the skin including the boundary layer. Some of these agents have more than one mechanism of action and can, in addition, enhance the efficacy of the active substance.

Some examples of these permeation enhancers are glycerol, ethanol, isopropanol and other low molecular weight alcohols and glycols such as diethylene glycol, propylene glycol or polyethylene glycol which enhance compound solubility, oils such as olive oil, squalene or lanolin which enhance active substance diffusibility, urea and urea derivatives such as allantoin which affect the ability of keratin to retain moisture, polar solvents such as dimethyldecylphosphoxide, methyloctylsulfoxide, dimethyllaurylamide, dodecylpyrrolidone, isosorbitol, dimethyl-acetonide, dimethylsulfoxide, decylmethylsulfoxide and dimethylformamide which affect keratin permeability, salicylic acid which softens the keratin, amino acids which are penetration assistants, benzyl nicotinate which is a hair follicle opener.

Additional chemical permeation enhancers such as oleic acid, amino acids, oleyl alcohol, long chain fatty acids, ethoxydiglycol, sodium xylene sulfonate, ethanol, N-methylpyrrolidone, laurocapram, alkanecarboxylic acids, polar lipids, N-methyl-2-pyrrolidone, and the like, which increase the permeability of the skin to the active material and permit the active material to penetrate through the skin and into the bloodstream are also included. Included also are cationic, anionic and non-ionic surfactants and higher molecular weight aliphatic surfactants such as lauryl sulfate salts which change the surface state of the skin and active substance administered, concomitantly which have good percutaneous absorption.

Other agents include carvone and other azones, lactic acid, linoleic and ascorbic acids, terpenes such as limonene, panthenol, butylated hydroxytoluene, propyl oleate and propyl or isopropyl myristates as well as tetrahydropiperine and analogs and derivatives thereof, including dihydropiperine. Additional, penetration enhancement as described by U.S. Pat. Nos. 6,849,645, 6,019,997; 5,601,839; 5,834,010; 5,472,946; 5,262,165 and 5,149,719 are incorporated herein by reference.

A wide variety of active substances can be delivered through transdermal systems so long as the active substance can be provided in a form that can cross the skin barrier, see for example U.S. Pat. No. 6,638,528, which is incorporated herein by reference. Examples of active substances are included in the application section below. However, other APIs include, but are not limited, to nicotine, steroid hormones, analgesics, antioxidants, vitamins, CNS drugs, cardiovascular drugs, anti-asthmatics, antibiotics, anti-cancer drugs, and the like and the invention is intended to cover any nutraceutical, drug or other substance for which it is desirable to provide to a patient or other body (animal or human) in a time and dose controlled manner.

The control and display unit 7 can be implemented, for example, by a microprocessor 91 with a LCD or other display 90 and a drive circuit and/or interface 92. The microprocessor 91 is programmed (with software, such as a dosing regimen routine or the like, in memory for example) as a programmable timer to send a control signal to the dispensing mechanism 2 through the drive circuit 92 at multiple timing points. Battery 6 provides power to the device 1. In a specific embodiment, the dispensing mechanism 2 is a two-part peristaltic micropump (e.g., a peristaltic pump with an active portion that is provided with reusable portion of device 1 and a passive portion that is provided with detachable and disposable portion 40) that delivers a active substance formulation from the active substance reservoir 3 to the administration element 5 at a certain flow rate and a certain duration that are defined by the microprocessor 91 of the control and display unit 7.

In some embodiments, the active substance reservoir 3 is in form of a collapsible balloon that contains active substance formulation. A flexible and collapsible reservoir 3 is preferable in the device 1 to avoid backpressures that may resist flow from the reservoir 3 if a more rigid-walled reservoir were utilized. The walls of the reservoir 3 are also preferably resist permeation, i.e., are non-permeable or relatively impermeable, of the solvent/nutraceutical/drug mixture or formulation and in this regard, the walls may be formed of Teflon™, a high molecular membrane, or other similar material.

The administration element 5 is typically provided in the disposable, detachable portion or unit 40 to allow it to be periodically replaced with a new element 5. This is useful for providing a new membrane to achieve a known diffusion rate and to provide a new administration reservoir (and any wicking material or the like provided in such an administration reservoir as discussed below). As shown, the administration element 5 includes an administration reservoir 34 and a diffusion membrane 35 (e.g., a membrane that allows a particular diffusion rate for the active substance in the liquid or mixture in the active substance reservoir 3 but is impermeable or much less permeable to the solvent).

One important aspect of the invention is the inclusion of material, such as blotting paper or sheet, in the reservoir 34 to uniformly distribute the formulation to the diffusion membrane both in volume (e.g., the liquid is relatively equally provided over the upper surface of the membrane rather than much more at the outlet of the feed or delivery chamber/tube 13) and at a relatively uniform rate. For example, in one embodiment, the administration element 5 includes an absorption sheet (e.g., blotting paper or the like to "wick" the liquid from chamber or tube 13 over the administration reservoir 34) and a membrane, which are laminated tightly together at their interface and typically to the edges of the frame of the element 5.

The particular film or membrane used for membrane 35 is not limiting and may include any conventional materials such as silicones and siloxanes, microporous polyethylene and/or microporous polypropylene, polyethylene co-vinyl acetate (EVA copolymer) ranging from 2% to 40% vinyl acetate content, polyurethane and the like.

An adhesive covering the perimeter or the entire skin adjacent area may include, but is not limited to, silicone, polyisobutylene (PIB), acrylic adhesives and other pressure sensitive adhesives (PSAs), as well as ethylcellulose, hydroxypropyl cellulose, poly (ethylene co-vinyl acetate) (EVA), polyvinyl pyrrolidone (PVP), poly(ethylene oxide) (PEO), poly (ethylene vinyl alcohol) (PVA), poly(acrylic acid) (PAA) and the like, which may be in a dry or wet form, crosslinked or not crosslinked, or any mixture to provide the composition in gel or hydrogel form or adhesive state. These may be dissolved in solvents such as water, ethanol, methylene chloride, ethyl acetate and the like and processed or applied as a hot melt.

A device-skin interface coupling media and/or control membrane or layer may further be provided of ethylcellulose, hydroxypropyl cellulose, poly(ethylene co-vinyl acetate) (EVA copolymer), polyvinyl pyrrolidone (PVP), poly(ethylene oxide) (PEO), poly(ethylene vinyl alcohol) (PVA), poly(acrylic acid) (PAA), silicones and siloxanes, polyisobutylene (PIB), hydrogels and the like.

Tubing or a feed chamber 13 is provided in the detachable and disposable unit 40 to connect the active substance reservoir 3 to the administration element 5 through passive portion of the dispensing mechanism 2. When the device 1 is positioned for use, the membrane 35 is preferably in tight contact with the skin using an adhesive and/or wristband. The device 1 then operates to provide even diffusion of the active substance over the active substance absorption surface area of the membrane 35. A solvent removal element 4 is typically provided in the device 1 (e.g., in the reusable portion as shown or in the disposable portion in some cases)

to control dosing by removing the solvent or fluid mixture. The element 4 may include desiccant, absorbent material, or other material to absorb evaporating solvent, with the element 4 being connected to the administration element such as by one or more tubes (not shown). A connection is shown between the interface or drive circuit 92 of control unit 7, and this may be used to sense the concentration of a active substance in the administration reservoir 34 and to control operation of the solvent removal element (e.g., in embodiments where active components are provided to further solvent removal as discussed below). In some embodiments, these connections may also be used to allow the control 7 to receive temperature signals from a sensor contacting or near the reservoir 34 and/or membrane 35.

In some preferred embodiments, the dispensing mechanism 2 is a micropump, e.g., positive displacement micropump. For example, the pump 2 may be a two part piezoelectric micropump in which the drive or active portion is provided in the reusable portion of the device 1 and the chamber 13 is provided in the disposable portion 40. In one preferred embodiment, the micropump is configured as a two-part peristaltic pump that can be provided as an active part and a passive part to allow the active part to be provided in the reusable portion of device 1 and the passive parts including the tube or feed chamber 13 and portions of the pump housing (including the compression surface) provided in the detachable and disposable portion 40.

The use of a peristaltic pump as the dispensing mechanism 2 provides significant advantages for a active substance delivery device according to the invention. These advantages include low risk of active substance formulation contamination as the active substance only contacts the tubing and not the drive components of the pump 2 and this tube 13 is disposed of with the disposable unit. The use of a peristaltic pump 2 also provides simple and cost-effective operation, accuracy of dosing, low maintenance, self-priming, and gentle pumping action, as well as the ability to pump liquid, mixed-phase and viscous fluids, and the elimination of the need to clean or flush the pump or tubing of substance residue, to ensure sterility of the device over period of time. One of the chief advantages of the peristaltic pump 2 for the active substance delivery device 1 is that the active substance formulation from the active substance reservoir 3 to the administration element 5 does not contact any internal parts. Seals and valves are not needed as in other pumps.

Various types of micropumps have been developed for delivering or dispensing a controlled flow of a liquid in a small, measurable (or known) quantity. In the field of drug delivery, it is recognized that supplying a drug in a correct temporal pattern is an important attribute of any drug delivery methodology. Controlled release drug delivery systems, such as those described herein, are intended to improve the response to a active substance and/or lessen side effects of that active substance. This is also important in the field of chronopharmacology, where biological rhythms are an important aspect of clinical pharmacology and are preferably taken into account when controlling a active substance delivery system (or selecting a dosing regimen).

There has been an extensive amount of research into the design of various micropumps. Currently, most micropumps are driven by a piezoelectric element bonded to a flexible membrane covering the pump chamber. Many research groups have developed various micropumps such as pumps with pumping pressures over 7 m of water and micropumps using nozzles and/or diffuser components, which even at miniature length scales results in accurate flow volume control and high reliability. Some of these micropumps are relatively low cost, high performance silicon micropumps for disposable active substance delivery systems (such as the micropump described in Maillefer, D., et al., "A High Performance Silicon Micropump for an Implantable Drug Delivery System," Technical Digest MEMS '99, pp. 541-46, 1999, which is incorporated herein by reference). Similarly, the piezoelectric diaphragm micropumps available from Star Micronics may be used in the dispensing mechanism of the invention, and generally include a diaphragm bonded to a piezo-ceramic element that mechanically vibrates to induce change of chamber volume and, thus, conveys fluid or gas through the pump chamber (which, in the embodiments described above, would be in the passive portion of the dispensing mechanism).

However, it should be noted that there might be some drawbacks to using piezoelectric materials to achieve a micropump (although they have been well developed where a pump element is oscillated by the application of electrical impulses on piezoelectric elements to create a pressure differential in a liquid). First, piezoelectric elements are formed from brittle crystal materials that are difficult and expensive to machine, particularly on small scales. Second, piezoelectric materials generally are not suitable for contacting liquids. Micropumps that exploit piezoelectric movement typically must be designed to insulate the piezoelectric material from contact with liquid. Third, even though the power consumption of the piezoelectric micropump is typically low, electrical circuitry with a high voltage supply is necessary to drive and control piezoelectric movement, which requires a certain voltage and current power supply to work. For portable devices and devices powered by a battery, this presents a challenge for using a piezoelectric pump in the dispensing mechanism.

In contrast, peristaltic pumps are desirable for use in the dispensing mechanism as they use a flexible tube that is compressed by a series of shoes on a roller to induce liquid flow. Such pumps provide a positive displacement and require little or no maintenance. A continuous tube that contains the fluid to be moved (such as in a cooling embodiment) or delivered sits between the shoes and a rigid wall (e.g., the curved surface provided the housing of the passive portion of the dispensing mechanism). The shoes pinch the tube against the wall as the roller is turned by an electric motor, which creates a positive pressure on the output side of the tube and a negative pressure on the input side. Peristaltic pumps are self-priming, and the only material in contact with the solution or liquid is the tube. Thus, a wide variety of fluid-compatible tube material can be selected to meet the life expectancy (e.g., the expected number of cycles and the like). There is a demand for a battery-driven or a low-voltage-driven micropump that is able to induce an amount of liquid flow. For life sciences, it is often preferable that the micropump be relatively inexpensive and disposable.

The pump tube is typically a consumable part and may be frequently changed to avoid any possible contamination. Given the small size of the micropump (e.g., several millimeters in its physical dimension and several micrometers to hundreds of micrometers on the tube dimension), changing such tubes may be difficult. Hence, the desirability to provide a detachable, disposable passive portion as discussed.

Figure 3:
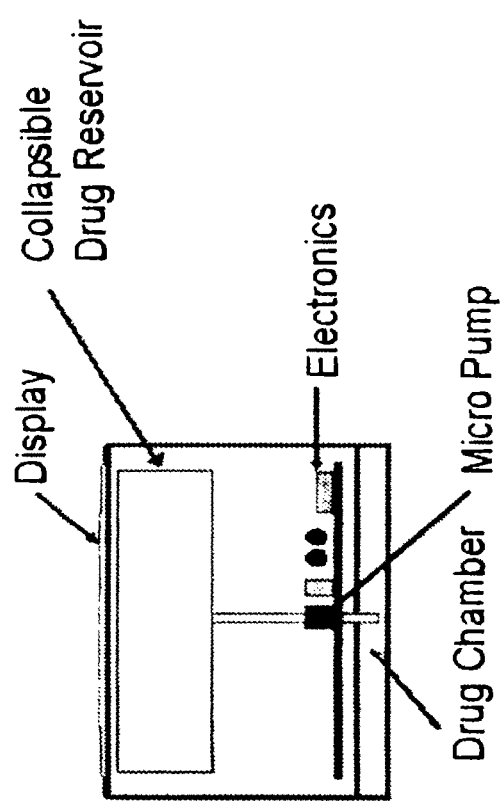
FIG. 3 is a schematic illustration of a active substance delivery device in accordance with the present invention. Alternatively, permeation through the skin may be assisted by pretreatment with and/or using micro-fabricated structures commonly referred to as micro-channels, micro-needles, heating devices, iontophoretic devices, or sonophoretic devices that are separate or attached to this device.

An exemplary implementation (shown in FIG. 3) comprises a collapsible active substance reservoir, an expandable waste reservoir, a micro-pump, electronics for automation, a display, and a highly permeable membrane. Further, a heating element or a gas or air blowing apparatus may be used to assist evaporation of liquids into the waste reservoir or the environment. An exemplary system is described in a United Kingdom patent entitled Transdermal Drug Delivery and Method filed on Sep. 13, 2004, Application No. PCT/IB2004/002947, which is incorporated herein by reference. The active substance reservoir will contain between about 0.4 ml and 4 ml of active substance formulation. A tiny, miniaturized pump is activated at pre-programmed times and releases a predefined amount of active substance formulation into the active substance chamber, where the formulation comes into contact with diffusion matrix. This diffusional matrix is in intimate contact with a highly permeable membrane. This membrane rests on the skin, and provides for even diffusion of the active substance over the device's active substance absorption surface area. This membrane works effectively with, and can be coated with, an adhesive, hydrogel or polymer substance, which allows for rapid transport kinetics. In operation, when the administration of the active substance needs to be discontinued, the remaining active substance formulation is either removed or evaporated from the membrane area via a waste chamber containing a desiccant, some other hydrophilic substance, or the device is taken off. Further, to achieve chronopharmacological active substance delivery for active substance that may not passively pass through the skin adequately, the above described device may use permeation enhancers whereby permeation through the skin is assisted, such as mechanical permeation enhancers that include micro-fabricated structures commonly referred to as micro-needles, light, or heat, or iontophoresis, electroporation, sonophoresis, or a wide range of chemical permeation enhancers.

Figure 4:
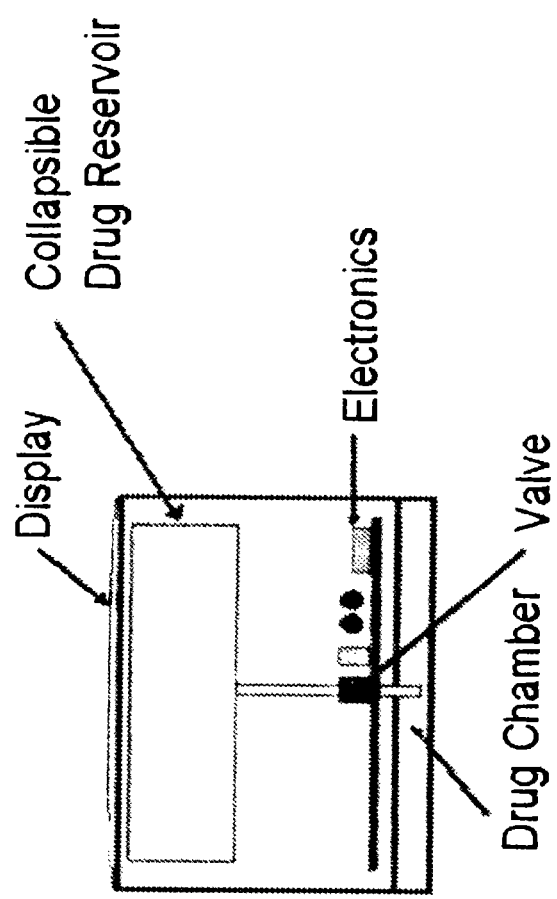
FIG. 4 is a schematic illustration of an alternative active substance delivery device in accordance with the present invention. Alternatively, permeation through the skin may be assisted by pretreatment with and/or using micro-fabricated structures commonly referred to as micro-channels and micro-needles, heating devices, iontophoretic devices, or sonophoretic devices that are separate or attached to this device.

In an implementation shown in FIG. 4, a pressurized active substance reservoir is used which minimizes or eliminates need for a micropump. Electronics control a valve that allows controlled quantities of the active substance to be applied to the active substance chamber where the formulation comes into contact with highly permeable membrane. Further, to achieve chronopharmacological active substance delivery for active substance that may not passively pass through the skin adequately, the above described device may use permeation enhancers whereby permeation through the skin is assisted, such as mechanical permeation enhancers that include micro-fabricated structures commonly referred to as micro-needles, light, or heat, or iontophoresis, electroporation, electrophoresis, sonophoresis (collectively referred to herein as the Mechanical Permeation Enhancers) or a wide range of chemical permeation enhancers.

The design of the present invention minimizes or eliminates the need for cleaning the peristaltic pump of the device. Another main practical advantage of this design is to avoid shelf-time problems of the device. Our embodiment separates the peristaltic pump into two parts, the active and passive parts, in order to retain the expensive active part of the peristaltic pump in the device and combine the passive part with the active substance reservoir.

A typical reservoir may provide active substance volumes that can be applied for multiple days (such as for 3 or more days), and controlled transdermal release of an active material such as a active substance can be timed and dosages selected to better match a body's rhythms to enhance chronopharmacological efficacy.

In a particular application the replaceable reservoir can include a description of an administration schedule that can be used to manually or automatically program device with an administration schedule. For example, a written schedule can be printed on or affixed to the reservoir or electrically programmed using volatile or non-volatile memory. In this manner, a dosing profile can be prescribed and filled by a pharmacy in much the same manner as a conventional active substance prescription is handled today.

Specifically, the co-pending and published U.S. patent application Ser. No. 11/162,525, entitled "Biosynchronous Transdermal Drug Delivery" filed Sep. 13, 2005, which is incorporated herein in its entirety by reference, describes the use of specific dosing regimens to select dosing (e.g., flow rates to the administration element) and also the timing of such dosages to enhance the effectiveness of the particular active substance (e.g., treat heart attack and stroke in early morning hours, treat arthritis prior to a patient awakening, and the like). This references teaching is incorporated for use in configuring the dosing regimen and otherwise for controlling operation of the processor 91 and other processors for operating the dispensing mechanism 2 (its flow rate and timing/duration of operation) and solvent removal components.

Figure 5B:
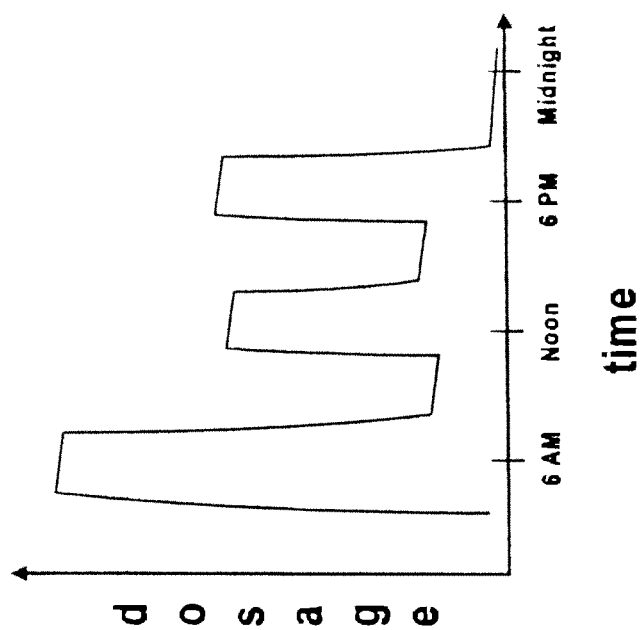
FIGS. 5A-5B illustrate comparative active substance release profiles demonstrating operation of the present invention.
Figure 5A:
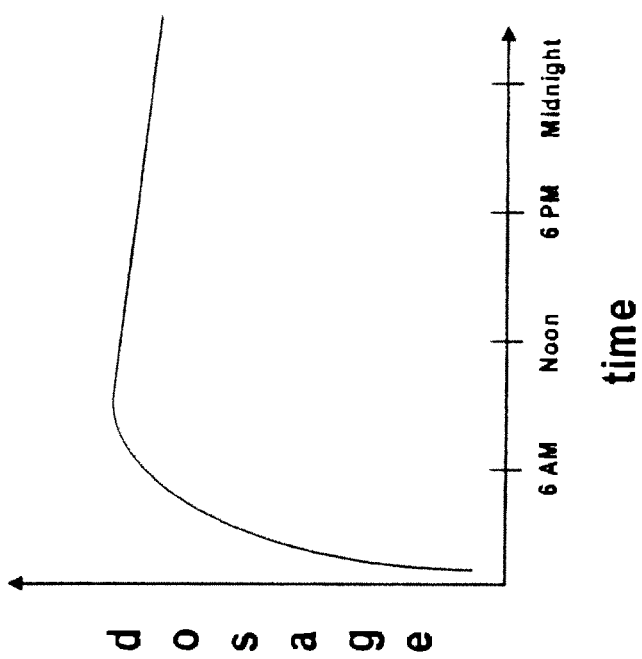

The present invention represents the first true non-invasive chronopharmacological active substance delivery device. While current transdermal applications are restricted to the dosage profile shown in FIG. 5a, the automated implementation of the present invention can be programmed for a variety of active substance delivery patterns to achieve customized patient dosing regiments for optimal therapy (FIG. 5b).

The following examples are set forth to describe the invention in greater detail. They are intended to illustrate, not to limit, the invention.

Example 1

In Vitro Evaluation of Skin Permeability

Figure 6:
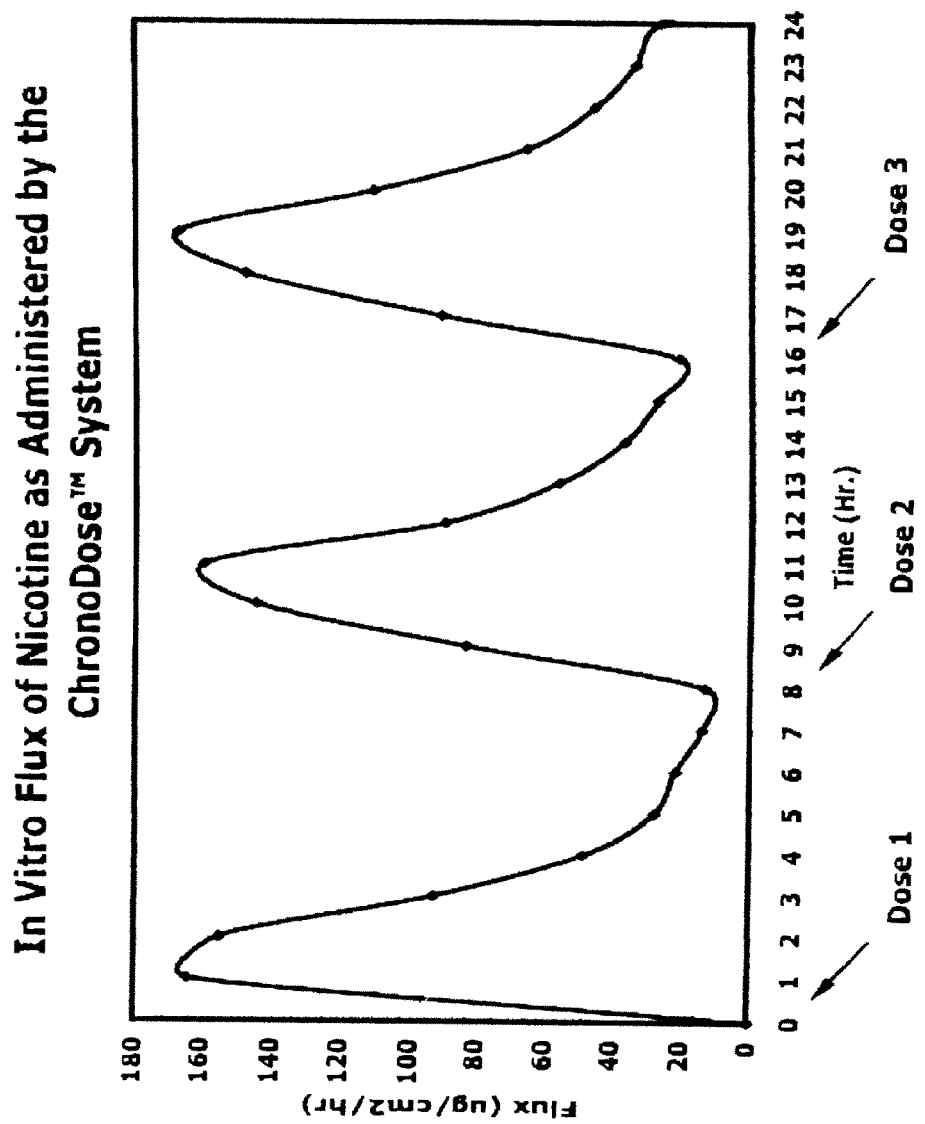
FIG. 6 shows the flux of a model drug compound (nicotine) permeated through skin in an in vitro test using a method of the present invention.

FIG. 6 shows in vitro flux results of a model compound (nicotine) delivery through human cadaver skin (dermatomed to 0.5 mm) by the ChronoDose™ prototype programmed and automatically operated via software and laptop computer. The area of skin permeation was 10 $cm^2$. A 100 mg/ml nicotine formulation in ethanol/water 1/1 was dispensed at 0, 1, 8, 9, 16 and 17 hours into the experiment. Each time, 200 µl of formulation was dispensed on a 10 $cm^2$ surface area of interface of diffusion, separated from the skin by the EVA membrane. Using proprietary software, the prototype was triggered by a laptop computer. Additionally, the dose quantity was strictly controlled and monitored. Drug flux samples were obtained using a flow-through Franz cell permeation system with samples collected every 15 minutes. Hourly time point samples were analyzed and recorded. Samples were analyzed by UV/Vis spectrophotometry.

The results demonstrate that three cycles of on/off delivery were achieved with this protocol for both drug reservoir concentrations within 24 hours corresponding to three drug delivery pulses. The maximum transdermal flux value reached under these in vitro conditions was 160 $ng/cm^2/hr$ and was comparable for all three cycles demonstrating a good reproducibility of the process.

Example 2

Clinical Study

Figure 7:
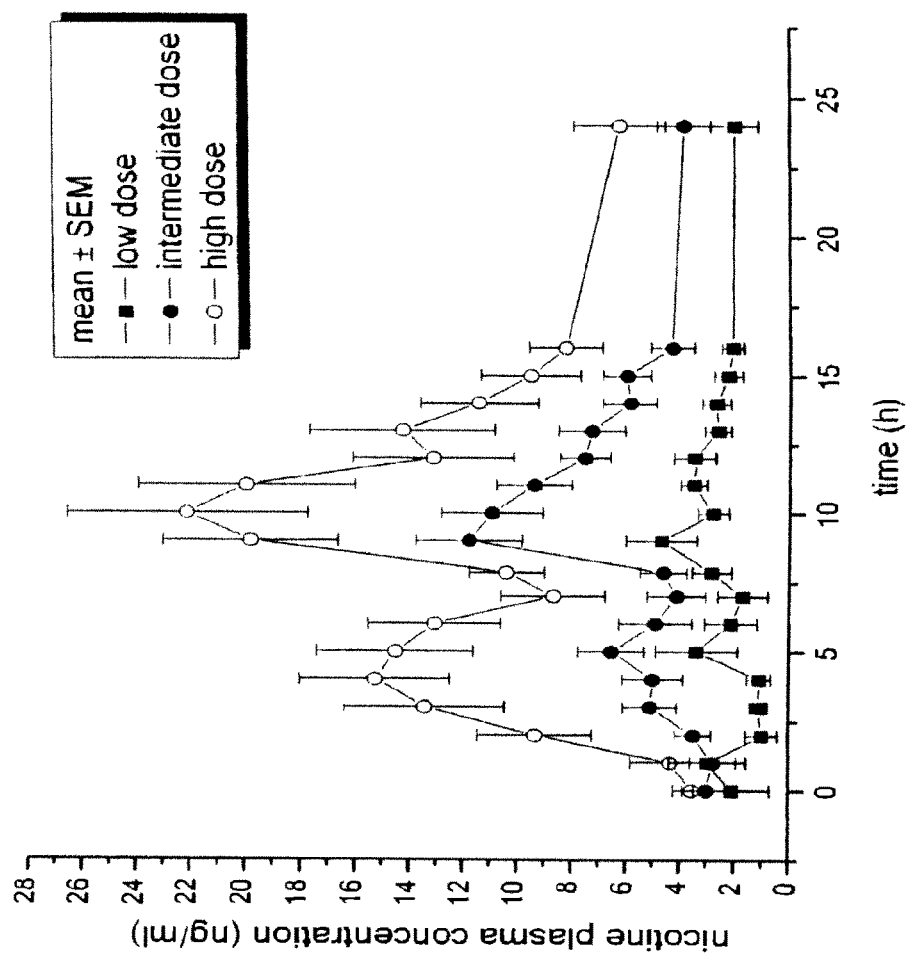
FIG. 7 shows the blood plasma concentration and test results of a model drug compound (nicotine) tested on 12 human subjects.

The device, described herein, was tested on 12 healthy male volunteers for an open, three-periods, single center, dose-escalation study using nicotine as the model compound. FIG. 7 shows test result on 12 human subjects. The dose escalation trial showed statistically significant modulation and control of the dosing profiles. Using low, medium and high concentrations, for 16 hours, the model drug permeated each subject's skin on multiple occasions, resulting in clear and distinct peaks and troughs of therapeutically effective and well-targeted blood plasma concentration levels.

Although the invention has been described and illustrated with a certain degree of particularity, it is understood that the present disclosure has been made only by way of example, and that numerous changes in the combination and arrangement of parts can be resorted to by those skilled in the art without departing from the spirit and scope of the invention, as hereinafter claimed. For example, the devices may also utilize piezoelectric or thermal droplet jet technology, see for example U.S. Pat. No. 6,723,077, the disclosure of which is incorporated herein by reference as described, as well as components other than heating elements to enhance drug diffusion such as components to implement iontophoresis, sonophoresis, and/or mechanical or chemical permeation enhancers.

In using this system, the present invention can preprogram the times and amount of each dosage by precisely controlling the amount of active substance exposed to the skin during each dosing. This feature is advantageous when a active substance is best administered during sleep, e.g., 1 to 2 hours before waking up. The present invention precisely counteracts peak disease symptoms and increase patient compliance.

There are many advantages for a controlled transdermal release of an active material such as a active substance. As used herein, the term 'controlled' or 'sustained' release of an active material includes continuous or discontinuous, linear or non-linear release of the active material according to a programmed schedule. Among the advantages of controlled release are the convenience of a single application for the patient, avoidance of peaks and valleys in systemic concentration which can be associated with repeated injections, the potential to reduce the overall dosage of the active material, lower body stress, and the potential to enhance the pharmacological effects of the active material. A lower, sustained dose can also prevent adverse effects that are occasionally observed with infusion therapy. In addition to significantly reducing the cost of care, controlled release active substance therapy can free the patient from repeated treatment or hospitalization, thus offering the patient greater flexibility and improving patient compliance.

A controlled release formulation of certain active substances also provides an opportunity to use the active substance in a manner not previously exploited or considered. The present invention is particularly advantageous when (i) known chronopharmacological information indicates that a active substance's effects can be optimized when administered in a defined dosage at a predefined time or times, and/or (ii) patient compliance with the dosing regimen is greatly increased due to automation, i.e. doses are required at inopportune times, i.e. at night while sleeping. For example, the drug delivery regimen of the present invention is administered to treat a condition selected from the group consisting of vitamin and/or mineral deficiency, Cancer, Addiction, Arthritis, Parkinson's Disease, Attention Deficit Disorder, Cardiovascular Disorder, Cold/Flu Symptoms, Pain, Childhood Bronchial Asthma, Peptic Ulcer, Post-operative Recuperation, and so forth as shown below.

Application—Nutraceuticals

The term "nutraceutical" was coined from "nutrition" and "pharmaceutical" in 1989 by Stephen DeFelice, Md., founder and chairman of the Foundation for Innovation in Medicine (FIM), Cranford, N.J. According to DeFelice, nutraceutical can be defined as, "a food (or part of a food) that provides medical or health benefits, including the prevention and/or treatment of a disease." However, the term nutraceutical as commonly used in marketing has no regulatory definition.

A nutraceutical is any substance that may be considered a food or part of a food and provides medical or health benefits, including the prevention and treatment of disease. Such products may range from isolated nutrients, dietary supplements and diets to genetically engineered "designer" foods, herbal products and processed foods such as cereals, soups and beverages.

Substances and/or their derivatives which may be used in the present invention include but are not limited to:

Stimulants:
Adrenergic stimulants such as: adrenaline, ephedrine and ephedrine derivatives, and dopamine
Methylxanthines such as: caffeine, theobromine, theophyline and their derivatives.
Ampakines such as: CX-516 (Ampalex), CX546, CX614 and CX717.
Other stimulants, anorexigens and anorectics such as cocaine, etc.
Pharmaceuticals such as cannabinoid type 1 (CBl) receptor antagonists (rimonabant, Acomplia™), humoral feedback signals leptin, ghrelin, nesfatin-1, or their re-uptake inhibitors, agonists or antagonists, appetite-regulating hormones such as peptide YY 3-36 and the like.

Nutritional Agents, Such as:
Minerals and Metals: i.e. boron, calcium, magnesium, chromium, selenium, zinc, etc.
Vitamins: Vitamin A (Retinoids (include: retinol, retinal, retinoic acid, 3-dehydroretinol and its derivatives); Vitamin B1 (Thiamine); Vitamin B2 (Riboflavin); Vitamin B3 (Niacin); Vitamin B5 (Pantothenic acid); Vitamin B6 (Pyridoxine); Vitamin B7 (Biotin); Vitamin B9 (Folic acid); Vitamin B12 (Cyanocobalamin); Vitamin C (Ascorbic acid); Vitamin D2-D4 (Lumisterol, Ergocalciferol, Cholecalciferol, Dihydrotachysterol, 7-Dehydrocholesterol); Vitamin E (Tocopherol, Tocotrienol) and Vitamin K (Naphthoquinone).
Amino Acids: Isoleucine, Alanine, Leucine, Asparagine, Lysine, Aspartate, Methionine, Cysteine, Phenylalanine, Glutamate, Threonine, Glutamine, Tryptophan, Glycine, Valine, Proline, Arginine, Serine, Histidine and Tyrosine.
Aside from the twenty standard amino acids and the two special amino acids, selenocysteine and pyrrolysine, there are a vast number of "nonstandard amino acids." Examples of nonstandard amino acids include the sulfur-containing taurine and n-acetylcysteine and the neurotransmitters GABA and dopamine Other examples are Carnosine (beta-alanyl-L-histidine), lanthionine, 2-Aminoisobutyric acid, and dehydroalanine, ornithine and citrulline.
Coenzymes: Coenzyme A, Coenzyme B12, Coenzyme Q, NAD, FAD, ATP, molybdopterin, etc.
Antioxidants such as Glutathione, Lutein, alpha-lipoic acid, polyphenols-including Pycnogenol (pine bark antioxidant), Grape seed extract, superoxide dismutase (SOD, EC 1.15.1.1), epicathechin, proanthocyanidins, sulfoxides, etc.
Botanicals, phytochemicals, phytonutrients, plant extracts, herbs, naturopathic, homeopathic drugs and substances, nutraceticals, cosmeceuticals, Ayuervedic xtracts, tissue extractions, antioxidants and the like. These include but are not limited to: Guarana and Brown Seaweed, or Fucus Vesiculosis, 5 HTP, yerba mate, flaxseed oil, L-caritine, Synephrine (oxedrine; Sympatol), *Coleus forskohlii* (forskohlin), diiodotyrosine, chromium poly-nicotinate, garlic extract, yeast extract, fatty acids, omega-3 fish oil, kava and kavalactones, Aniracetam, Bromocriptine, Carnosine, Centrophenoxine, Deprenyl, Gerovital-H3, Hydergine, Idebenone, Melatonin, Piracetam, Pramiracetam, Pyritinol, Resveratrol, Vinpocetine and Vitamin C, thymus, yohimbine, *Morinda citrifolia* (Noni, containing Proxeronine, Proxeronase, Xeronine, Damnacanthal and Scopoletin), etc.

Steroids and Steroid Precursors:

Some of the common categories of steroids include:

Anabolic steroids are a class of steroids that interact with androgen receptors to increase muscle and bone synthesis. There are natural and synthetic anabolic steroids. These are the "steroids" used by athletes to increase performance Corticosteroids include glucocorticoid and mineralocorticoids:

Glucocorticoids regulate many aspects of metabolism and immune function, and are often prescribed by doctors to reduce inflammatory conditions like asthma and arthritis.

Mineralocorticoids corticosteroids that help maintain blood volume and control renal excretion of electrolytes.

Sex steroids are a subset of sex hormones that produce sex differences or support reproduction. They include androgens, estrogens, and progestagens.

Phytosterols-steroids naturally occurring in plants.

Ergosterols-steroids occurring in fungi. This includes some Vitamin D supplements.

Examples include but are not limited to androgens, estrogens, and progestational agents, hydrocortisone, hydrocorticosterone acetate, cortisone acetate, dexamethasone and its derivatives such as betamethasone, triamcinolone, methyltestosterone, 17-.beta.-estradiol, ethinyl estradiol, ethinyl estradiol 3-methyl ether, prednisolone, 17-.beta.-hydroxyprogesterone acetate, 19-nor-progesterone, norgestrel, norethindrone, norethisterone, norethiederone, progesterone, norgesterone, norethynodrel, dehydroepiandrosterone (DHEA) and the like.

Nutritional Supplements such as Resveratrol, Dimethlyglycine (DMG), 5 Hydroxy L-tryptophan (5-HTP), Inositol hexaphosphate (IP6), S-adenosylmethionine (SAMe), Glucosamine sulfate or N.Acetyl glucosamine, Choline, inositol and melatonin, creatine, pyruvate, beta-hydroxy beta-methylbutyrate (HMB), ginseng, etc.

Natural Hormones (bio-identicals) such as black cohosh (*Cimicifuga racemosa*) root and rhizome extract (Remifemin™), extracts from soy beans or the wild Mexican yam, etc.

Ayuervedic herb extracts: Adhatoda; *A. vasica*, Arjun; *Teminalia arjuna*, Asafoetida; *Ferula asafetida*, Ashwaganda; *Withania sominifera*, Asparagus; *A. racemosa*, Bacopa; *B. monerii*, Crataeva; *C. nurvala*, Emblica; *E. ribes*, Momordica; *M. charantia*, Myrrh; *Commiphora mukul* and *C. myrrha*, Saraca; *S. asoka*, Tinospora; *T. cordifolia*.

Physiological metabolites, catabolites or other physiological active ingredient or precursors of all of the above or derivatives of all of the above thereof, as well as all other nutraceuticals, cosmeceuticals, naturopathic substances, homeopathic drugs, Ayuervedic extracts, botanical and dietary supplements having same or different physiological activity as those cited above, may be used within the scope of this invention.

Chronotherapeutic Rationale:

Nutraceutical is a portmanteau of "nutritional" and "pharmaceutical" and refers to foods thought to have a beneficial effect on human health. It can also refer to individual chemicals which are present in common foods (and therefore may be delivered in a non-drug form). Many such nutraceuticals are phytonutrients.

Figure 8:
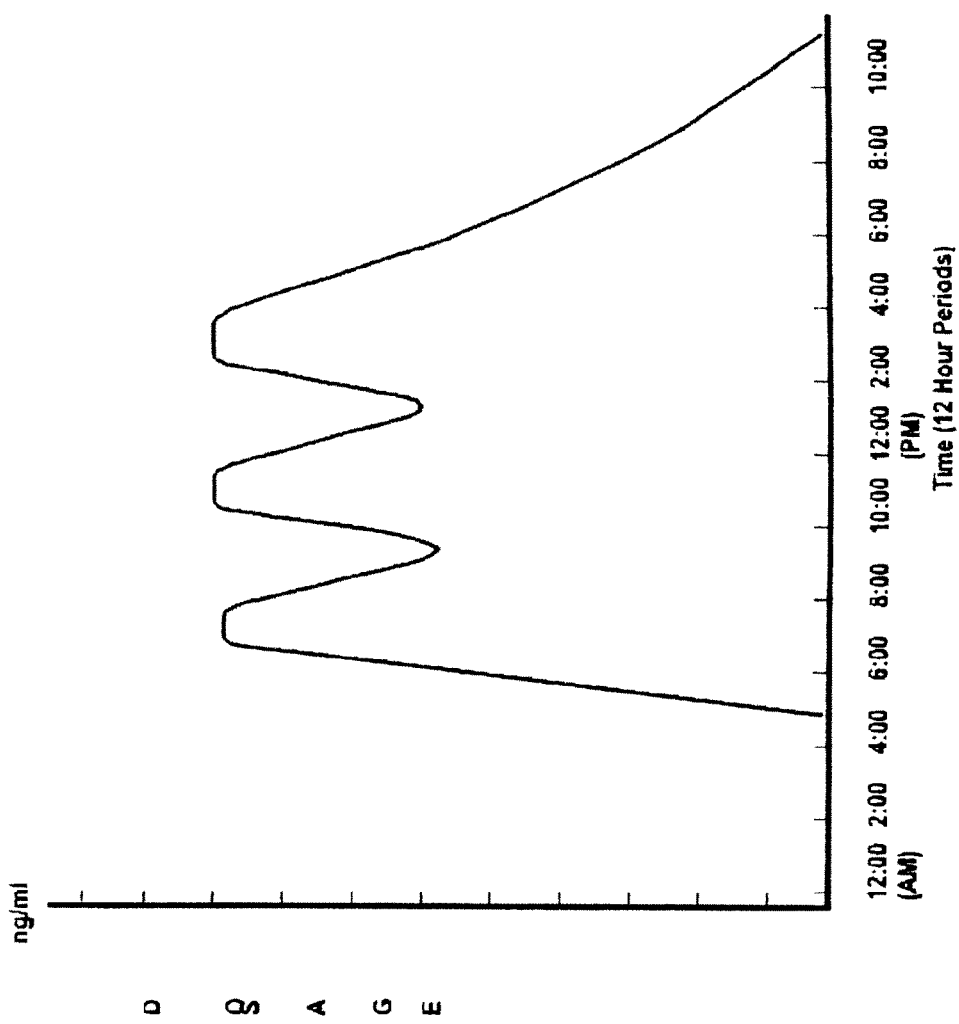
FIG. 8 shows an exemplary administration profile for an automatically delivered delivery system before meals for nutraceuticals and for anti-aging and weight-loss formulations.
Figure 9:
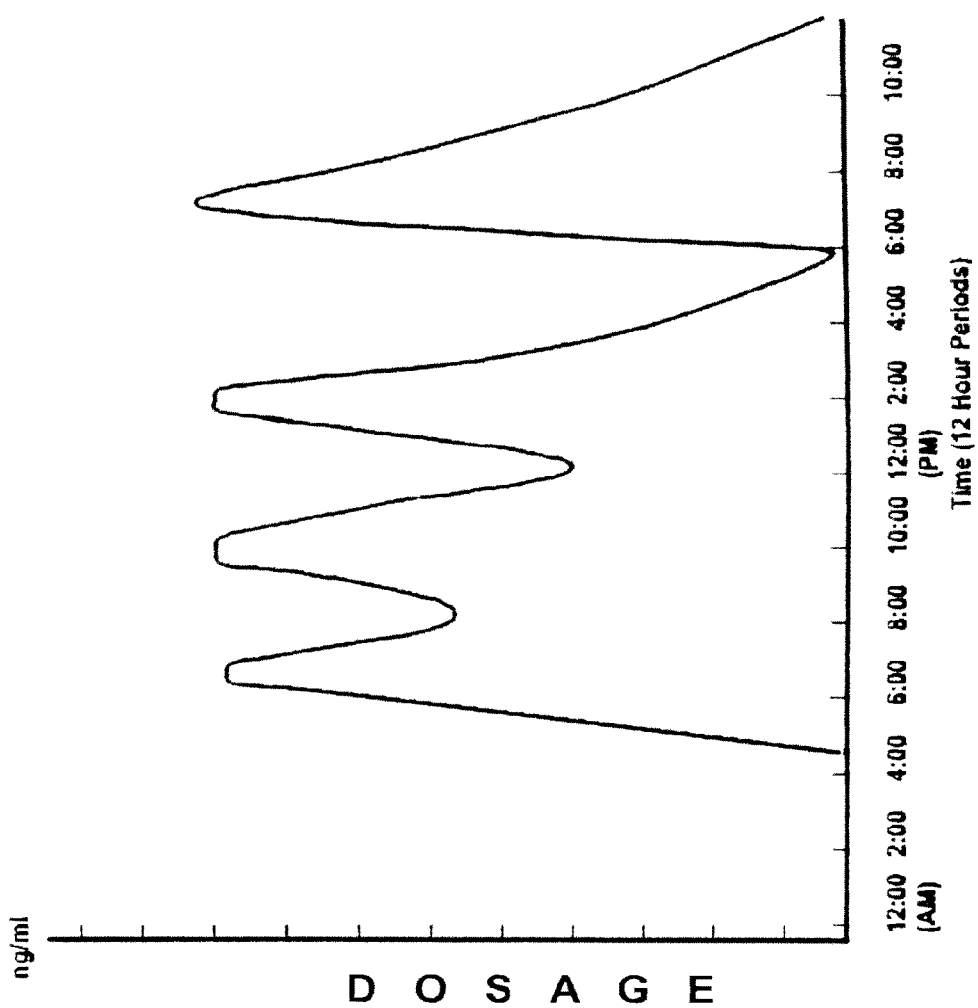
FIG. 9 shows an exemplary administration profile for an automatically delivered delivery system after meals for nutraceuticals and for anti-aging and weight-loss formulations.
Figure 10:
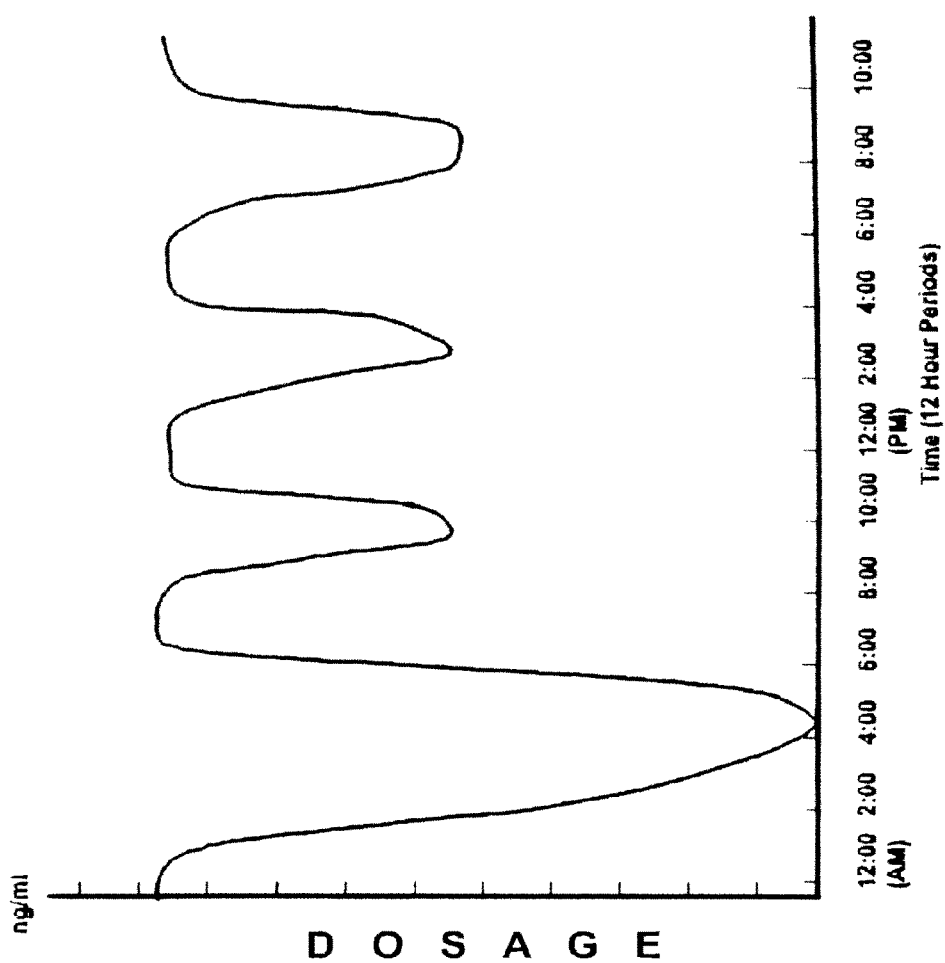
FIG. 10 shows an exemplary administration profile for an automatically delivered delivery system for 4 doses for nutraceuticals and for anti-aging and weight-loss formulations.

The nutraceutical implementation of the present invention allows individuals, while asleep, to have an over-the-counter (OTC) or prescription nutraceutical automatically administered during a 1-2 hour pre-wake-up period and periodically throughout the day, for example, before or after meals. FIGS. 8, 9 and 10 illustrate exemplary nutraceutical administration profiles showing a blood plasma level in nanograms per milliliter on the vertical axis, with time on the horizontal axis. Active ingredient concentrations will reach peak levels immediately prior to having to wake and around meal times. Any customized profile for any active ingredient may, of course, be preprogrammed into the device.

Dosing could be optimized using the ChronoDose™ system. For example, pulsatile delivery could have blood plasma concentrations (BPC) similar to the profile set forth below within the following ranges at the following times:

Peak 1 (Highest)
5:30 am-7:30 am: BPC should be in the highest therapeutic range.

Peak 2 (Highest)
10:30 am-12:30 pm: BPC should be in the highest therapeutic range.

Peak 3 (Highest)
3:30 pm-5:30 pm: BPC should be in the highest therapeutic range.

The time/dose chart should appear as shown in FIG. 8.

As an additional example, pulsatile delivery could have blood plasma concentrations (BPC) similar to the profile set forth below within the following ranges at the following times:

Peak 1 (Highest)
5:30 am-7:00 am: BPC should be in the highest therapeutic range.

Peak 2 (Highest)
9:00 am-11:00 am: BPC should be in the highest therapeutic range.

Peak 3 (Highest)
1:00 pm-3:00 pm: BPC should be in the highest therapeutic range.

Peak 4 (Highest)
7:00 pm-9:00 pm: BPC should be in the highest therapeutic range.

The time/dose chart should appear as shown in FIG. 9.

Still, an additional example, pulsatile delivery could have blood plasma concentrations (BPC) similar to the profile set forth below within the following ranges at the following times:

Peak 1 (Highest)
5:30 am-9:00 am: BPC should be in the highest therapeutic range.

Peak 2 (Highest)
11:30 am-3:00 pm: BPC should be in the highest therapeutic range.

Peak 3 (Highest)
5:30 pm-8:00 pm: BPC should be in the highest therapeutic range.

Peak 4 (Highest)
10:30 pm-12:00 am: BPC should be in the highest therapeutic range.

The time/dose chart should appear as shown in FIG. 10.

Application—Longevity

Life extension refers to an increase in maximum or average lifespan, especially in humans, by slowing down or reversing the processes of aging. Extension of an average lifespan can be achieved through good diet, exercise and avoidance of hazards such as smoking and excessive eating of sugar-containing foods. Theoretically, extension of maximum lifespan can be achieved by reducing the rate of aging damage, by periodic replacement of damaged tissues, or by molecular repair or (rejuvenation) of deteriorated cells and tissues. Much of anti-aging medicine has been concerned with the use of nutritional supplements to extend lifespan. The idea that antioxidant supplements, such as Vitamin C, Vitamin E, lipoic acid and N-acetylcysteine, might extend human life stems from the free radical theory of aging. Pulsatile transdermal Glutathione transdermal systems also a powerful anti-aging compound and is the subject of this invention.

Diabetes resembles accelerated aging and is associated with cross-linking of proteins by sugars, more specifically monosaccharides. Some believe that anti-glycating supplements (supplements that reduce the protein cross-linking by monosaccharides), such as carnosine, pyridoxamine, benfotiamine and lysine, might reduce aging.

Hormone replacement therapy-which aims at restoring youthful levels of growth hormone, testosterone, estrogen, progesterone, melatonin, DHEA and thyroid (all of which decline with age)—has also been tried as means of reducing the effects of aging. Other less popular hormones but which might also be useful are oxytocin, insulin, human chorionic gonadotropin (hCG), erythropoietin (EPO), and others. Resveratrol is a sirtuin stimulant proposed to extend life in mammals in a similar manner to that claimed for calorie restriction in simple model organisms such as nematodes.

Some supplements have been shown to be of benefit against some aging-related disease conditions, or have extended average lifespan. Calorie restriction and supplementation with the minerals selenium, chromium and zinc have been shown to extend maximum lifespan in mice.

Moreover, many of the compounds, chemicals, formulations and substances identified above under the heading "Application—Nutraceutricals" are applicable for longevity and anti-aging uses. Dosing regimens shown in FIGS. 8, 9 and 10 and described above, are also applicable to therapies utilized for increased longevity.

Application—Obesity, Weight-Loss and Weight Management

The prevalence of overweight and obesity is increasing worldwide at an alarming rate in both developing and developed countries. Environmental and behavioral changes brought about by economic development, modernization, and urbanization have been linked to the rise in global obesity. Obesity is increasing in children and adults, and true health consequences may become fully apparent in the near future.

About 100 million adults in the United States are overweight or obese. The medical problems caused by overweight and obesity can be serious and often life-threatening, and include diabetes, shortness of breath, gallbladder disease, hypertension, elevated blood cholesterol levels, cancer, arthritis, other orthopedic problems, reflux esophagitis (heartburn), snoring, sleep apnea, menstrual irregularities, infertility and heart trouble. Moreover, obesity and overweightness substantially increase the risk of morbidity from hypertension, dyslipidemia, type 2 diabetes, coronary heart disease, stroke, gallbladder disease, osteoarthritis and endometrial, breast, prostate, and colon cancers. Higher body weights are also associated with increases in all-cause mortality. Most or all of these problems are relieved or improved by permanent significant weight loss. Longevity is likewise significantly increased by permanent significant weight loss.

Weight loss of about 10 percent of body weight is proven to benefit health by reducing many obesity-related risk factors. Recommendations for treatment are now focusing on 10 percent weight loss to help patients with long-term maintenance of weight loss. Weight loss treatments vary depending, at least in part, on the degree of weight loss one is attempting to achieve in a subject as well as on the severity of overweight or obesity exhibited by the subject. For example, treatments such as low-fat diet and/or regular exercise are often adequate in cases where a subject is only mildly overweight. Such treatments can be enhanced by controlled use of over-the-counter appetite suppressants including caffeine, ephedrine and phenylpropanolamine (Acutrim™, Dexatrim™). Moreover, prescription medications including amphetamine, diethylpropion (Tenuate™), mazindol (Mazanor™, Sanorex™) phentermine (Fastin™, Ionamin™), phenmetrazine (Preludin™) phendimetrazine (Bontrol™, Plegine™ Adipost™, Dital™, Dyrexan™, Melfiat™, Prelu-2™, Rexigen Forte™), benzphetamine (Didrex™) and fluoxetine (Prozac™) are often used in the treatment of seriously overweight and/or obese subjects or patients.

The present invention may be used to treat, cure, prevent, control or alleviate a wide range of conditions and symptoms. In the present invention, the drug delivery regimen is administered to treat conditions associated with obesity, excess weight and weight management. Many of the compounds, chemicals, formulations and substances identified above under the heading "Application—Nutraceutricals" are applicable for treating obesity and for weight-loss and weight management. Dosing regimens shown in FIGS. 8, 9 and 10 and described above, are also applicable to therapies utilized for treating obesity and for weight-loss and weight management.

Application—Fatigue Management

Human fatigue is now recognized around the world as being the main cause of accidents in the transport industry. It is increasingly being recognized as a safety issue of the highest priority. The issue of fatigue in the workplace in all modes of transportation and even beyond transportation is something that is exploding as a priority issue across the industrialized world.

It is also an occupational health and safety issue, a commercial issue, a public safety issue and, at times, an environmental issue. With the 24/7 global economies, many people are having to continually shift and adjust to different daily schedules. Shift workers, as well as corporate executives, money managers and all types of business personnel must modify their schedules too. Individuals and organizations that fail to manage human fatigue sensibly, risk having or creating accidents with a broad range of damaging and enduring consequences.

In the same regard, modern warfare has become a long-range, 24/7 affair, and the physiological realities of sleep, fatigue, and circadian rhythms often get in the way of optimal performance "Go pills" pills are used as a "fatigue management tool" to help pilots stay alert through long missions.

In the early eighties, the Department of Defense developed go pills for the Air Force. Go pills are essentially amphetamine in the form of a pill. The Air Force wanted a drug to keep their bomber pilots alert and awake when they were on long missions. These missions can take over 24 hours and requires several delicate mid-air refueling operations. Despite their grandeur, air force pilots are fallible and they were falling asleep on these missions. Hence the development of go pills.

When fatigue closes in and all other tools in the fatigue management program have been exhausted, many pilots reach for the "go pill" to help them get home safely. Formally known as the amphetamine Dexedrine®, "go pills" are prescribed to pilots in very low doses to take the edge off fatigue. "Go pills" are only authorized for single-seat aircraft missions of more than eight hours, and dual-place aircraft missions of more than 12 hours. The 10-milligram "go pill" has the stimulating effect of three or four cups of coffee.

Once the mission has been completed, counteracting "no-go pills" prescription sedatives are used to help the pilots sleep after an extended mission and go-pill use.

No go pills are for after flying to induce sleep and re-adjust the sleeping schedule. It is recommended that pilots not fly for 12 to 16 hours after taking them. However, often less than 12 hours later, they are usually sent on their next mission In another scenario, a mission may be amended or aborted. Here, a backup mission crew may be instructed to take the "go pills" in preparation of a nighttime sortie. However at some point the mission plans get changed. In this scenario, the pilot has already taken the stimulant.

In this case, the pilot having already taken the stimulant, must wait 10-12 hours for the "Go pill" to clear his system or take a "no-go pill" to sleep. Additionally, the quality of sleep with these medications in the blood stream may not be the most restful and the pilot may not be in an optimum alert state upon awakening. In both cases, the pilot's circadian rhythm has been disrupted leaving him less ready for the next mission.

The current invention can be useful to Army, Navy, Air force and Marine as well as all service personnel that must work extended hours with the possibility of command changes. Shift workers, traveling executives and other business personnel can also benefit from the flexibility that this drug delivery device offers.

The current invention offers an alternative and automatic dosing regimen for stimulants as well as reducing the need for a follow-up depressant to induce sleep. The stimulant may be dosed-increasingly incremental, decreasingly incremental or a mixture of the two so as to purposefully modulate the active substance in the body and allow for schedule adjustments.

Example—Dextroamphetamine

In this example, dextroamphetamine is dosed in ever increasing amounts until the therapeutic dose equivalent is attained. By dosing in this fashion, the doses are incremental and additive. If the need arises to stop the dosing, due to a change in scheduling, the ChronoDose™ may be removed. By using this regimen, less dextroamphetamine will be in the user's system and allow for faster drug clearance.

Figure 15:
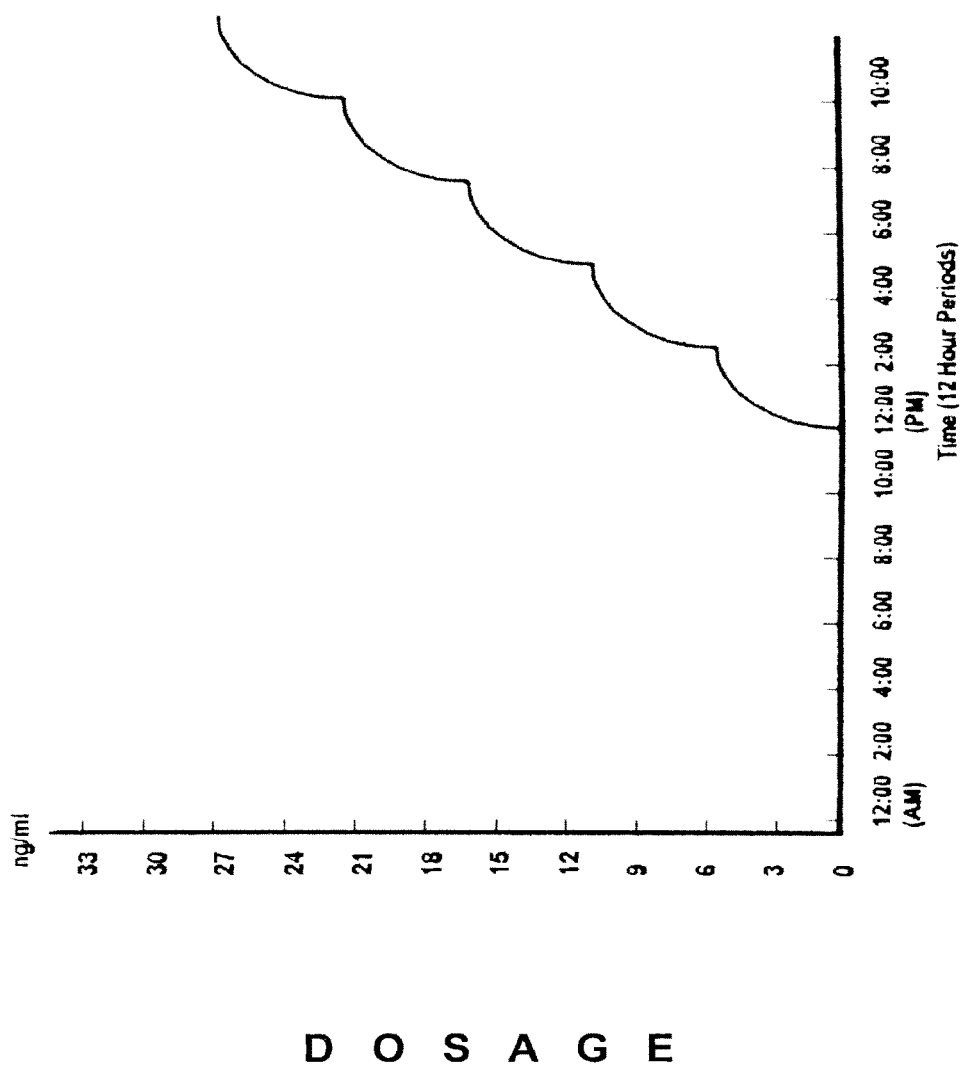
FIG. 15 shows an exemplary administration profile for an automatically delivered delivery system for dextroamphetamine.

The blood plasma concentration time/dose chart for dextroamphetamine should appear as shown in FIG. 15.

Example—Ephedrine

Ephedrine (EPH) is a sympathomimetic amine similar in structure to the synthetic derivatives amphetamine and methamphetamine Ephedrine is commonly used as a stimulant, appetite suppressant, concentration aid, decongestant and to treat hypotension associated with regional anaesthesia. Chemically, it is an alkaloid derived from various plants in the genus *Ephedra* (family Ephedraceae).

Figure 16:
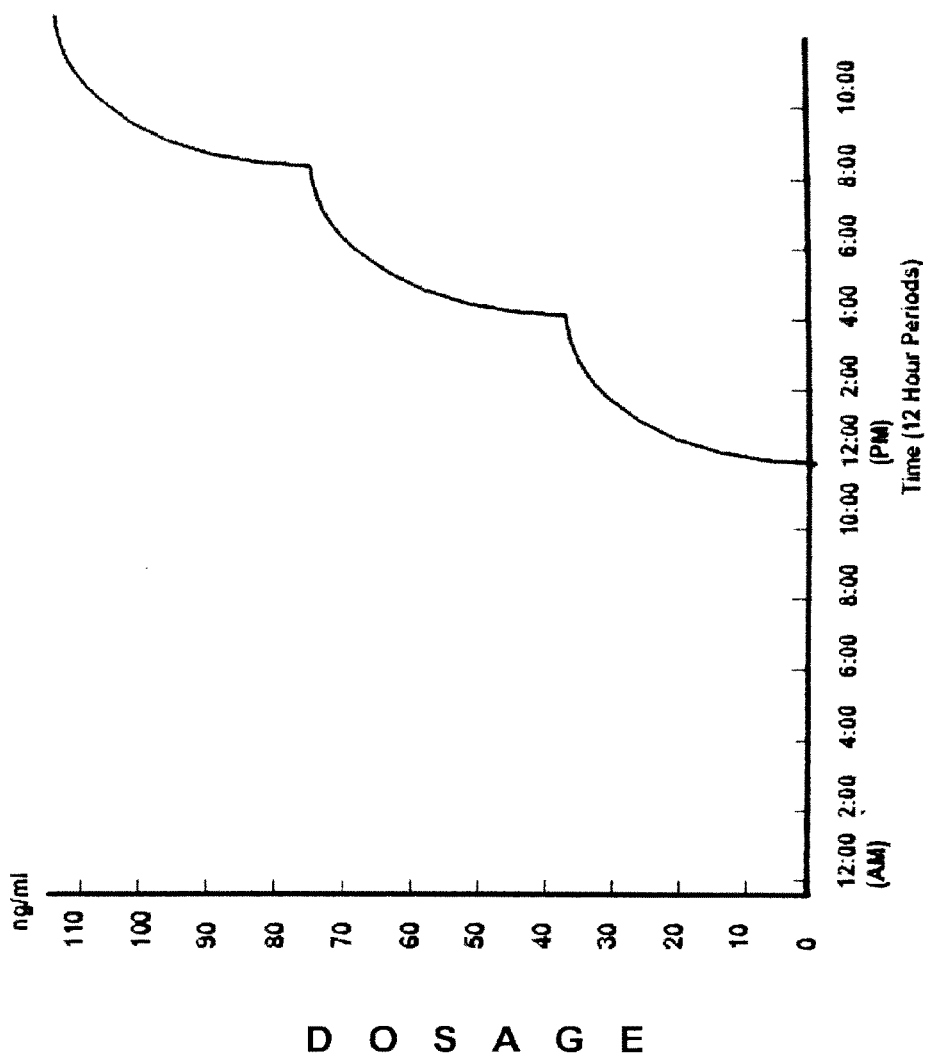
FIG. 16 shows an exemplary administration profile for ephedrine delivered automatically according to the present invention.

The blood plasma concentration time/dose chart for ephedrine should appear as shown in FIG. 16.

Example—Adrafinil (Olmifon), Modafinil (Provigil)

Modafinil has reportedly been investigated by the United States military for use by its soldiers. One study on helicopter pilots suggested that 600 mg of modafinil given in three doses can be used to keep pilots alert with only 8 hours of sleep in an 88 hour period. Another study on fighter pilots showed that 300 mg modafinil given in three divided 100-mg doses sustained the flight control accuracy of sleep-deprived F-117 pilots to within about 27 percent of baseline levels.

Adrafinil, an earlier compound relative to modafinil, has a half-life of about 60 minutes and a time to peak concentration of about 60 minutes. By taking advantage of the rapid pharmacokinetics, repetitive doses could be given and the user could stop the doses when necessary.

Figure 17:
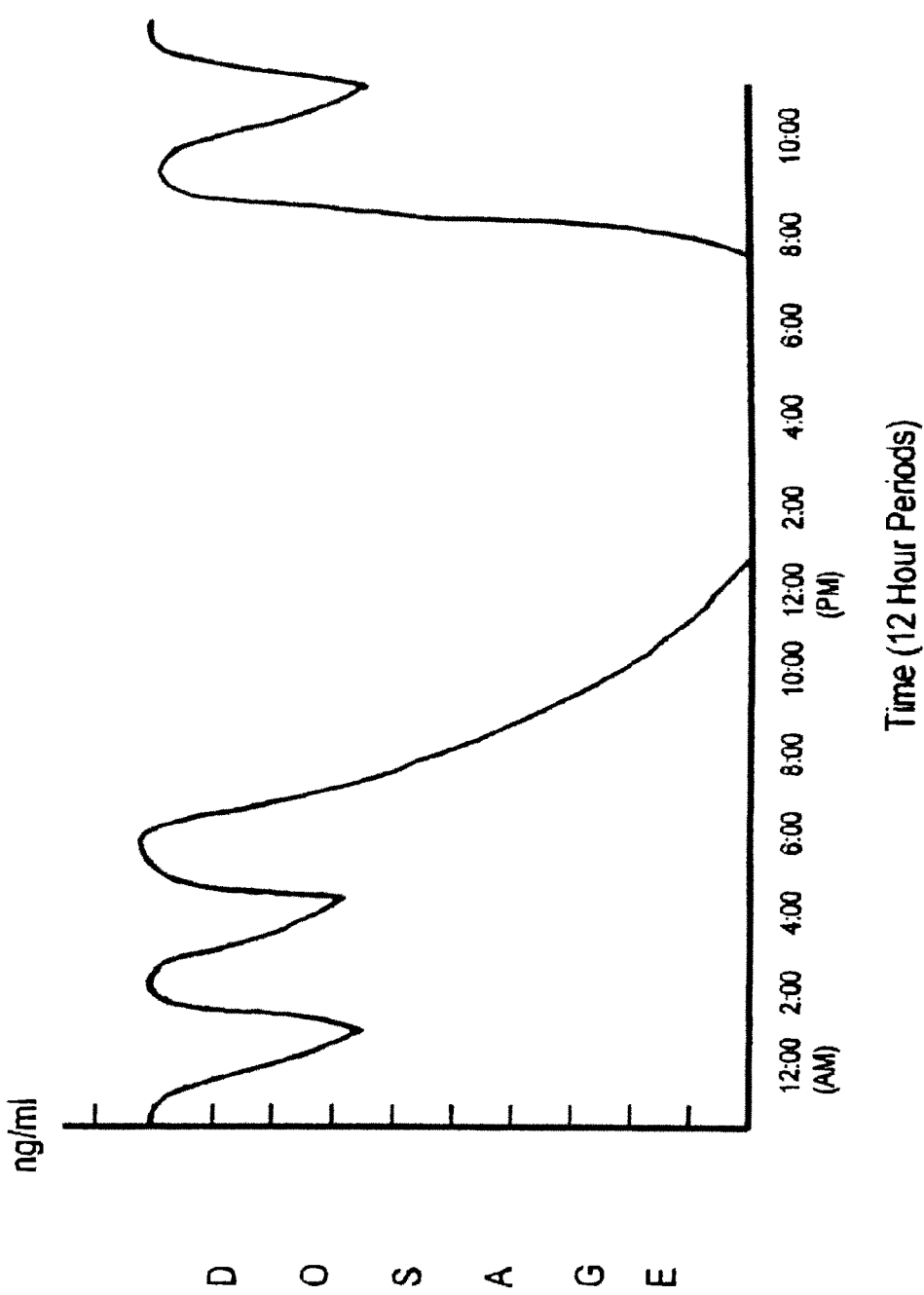
FIG. 17 shows an exemplary administration profile for adrifinal delivered automatically according to the present invention.

The time/dose chart for adrafinil should appear as shown in FIG. 17.

Example—Ampakine CX717

CX717 is an ampakine compound created by Dr. Gary Lynch at UCI in 1993 and further developed by Cortex Pharmaceuticals, an Irvine Calif. company created to explore possible applications. It affects the neurotransmitter glutamate, improving cognitive functioning and memory.

In 2005 The U.S. Food and Drug Administration (FDA) accepted Cortex Pharmaceuticals' IND (Investigational New Drug) application to initiate pilot Phase II clinical trials in the United States. Also, in 2005, the United States Department of Defense funded a study to look into CX717 and the physiological effects of sleepiness.

The study found that rhesus monkeys performed faster and better after receiving the drug, and it counteracted the effects of sleep deprivation. However, a 2006 study funded by DARPA found that CX717 did not improve cognitive performance in humans subjected to simulated night shift work.

The chemical structure of CX717 has not yet been revealed by Cortex Pharmaceuticals, but is presumably similar to earlier compounds in the series as shown below. It is very unusual for research on a compound to be released in scientific journals without disclosing exactly what the compound consists of, but this information is likely to have been kept confidential for reasons of intellectual property, and also because the research on CX717 was partially funded by DARPA, the United States Defense Advanced Research Projects Agency.

Figure 18:
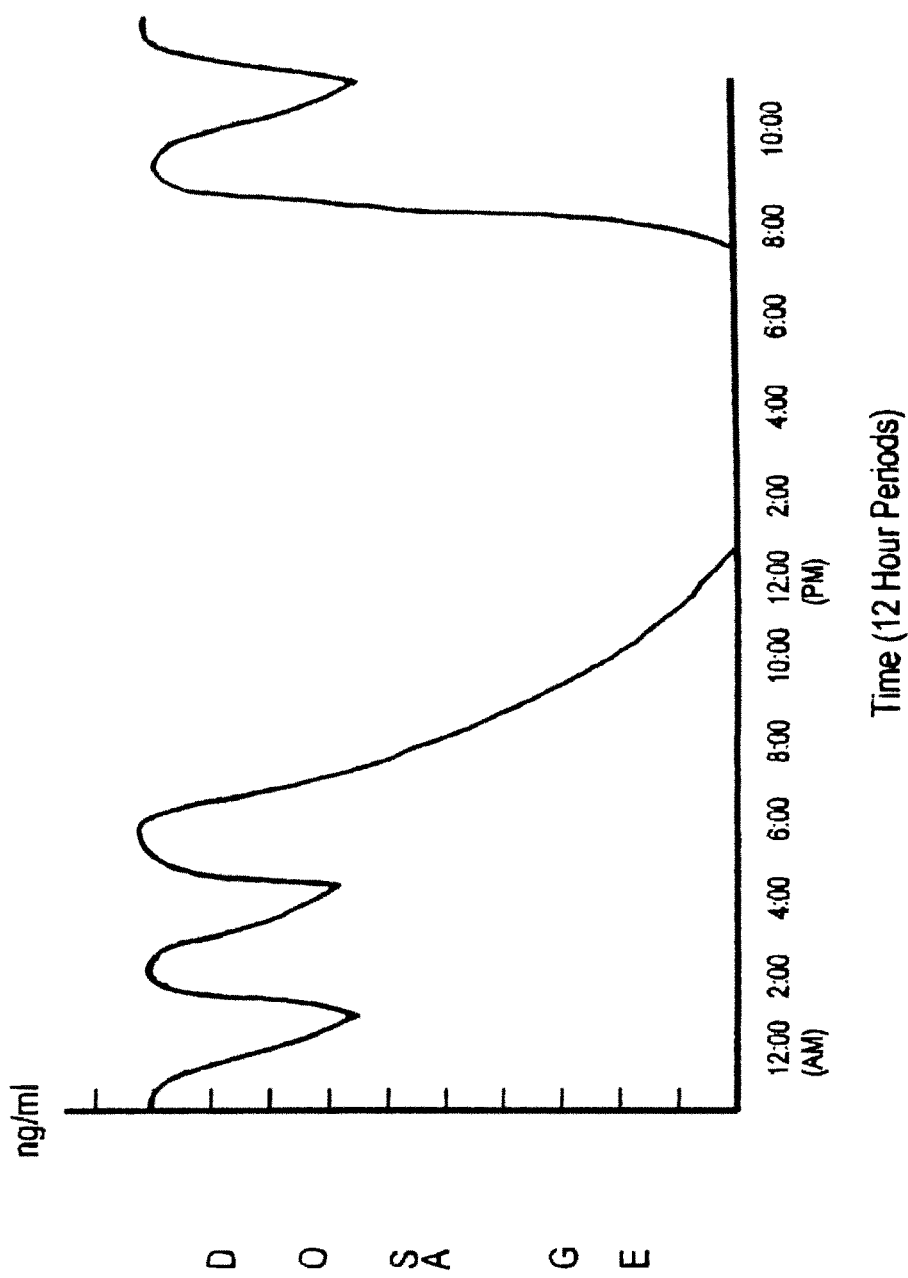
FIG. 18 shows an exemplary administration profile for ampakine delivered automatically according to the present invention.

The time/dose chart for ampakine should appear as shown in FIG. 18.

Application—Glucose Control

Diabetes Mellitus is the most common of the serious metabolic diseases affecting humans. It has been estimated that there are over 200 million people that have diabetes in the world.

Metabolically, diabetes is characterized by an inappropriate elevation of blood glucose levels. In Type I Diabetes Mellitus, this is due to an absence of insulin in the individual. In Type II Diabetes Mellitus, although there is circulating insulin, its signal is not efficiently transduced via the insulin receptor, giving rise to insulin resistance, where the body responds less and less well to a given amount of insulin. Insulin is a peptide hormone, which is produced by the Langerhorn islets in the pancreas. Insulin triggers increased glucose utilization, protein synthesis, and the formation and storage of neutral lipids. The present invention focuses on Type II Diabetes Mellitus, or non-insulin-dependent diabetes.

Non-insulin dependent diabetes mellitus of type II (NIDDM) is known to be a frequent metabolic disease and the main cause of hyperglycemia. In recent years, diabetes mellitus of type II has been proved to be a heterogeneous disease, with complex, unclarified metabolic aspects, which disease is characterized by three main metabolic abnormalities contributing to hyperglycemia: the partial or complete decrease in insulin secretion, the resistance of the peripheral tissues to insulin and the increased hepatic production of glucose in fasting conditions.

Diabetes Mellitus is also characterized by long-term complications involving the eyes, nerves, kidneys and blood vessels. These diabetic complications include premature atherosclerosis, intercapillary glomerulosclerosis, retinopathy and neuropathy. The major cause of morbidity and mortality among diabetics is coronary heart disease.

The primary goal in the treatment of diabetes is to maintain blood glucose levels as close to normal as possible. For Type II diabetics, the first line of therapy for maintaining blood glucose level is modification of diet and lifestyle. The diabetic diet features restrictions on fat content and an increased intake of dietary fiber.

Regular exercise is also emphasized to decrease weight and reduce the degree of insulin resistance. If diet and lifestyle modifications fail to control glucose levels, oral hypoglycemic therapy or insulin therapy is required to control glucose levels and thus minimize complications related to the disease.

The term antihyperglycemic drugs as used in this specification refers to drugs that are useful in controlling or managing noninsulin-dependent diabetes mellitus (NIDDM).

At present, the two main families of hypoglycemic agents available are sulfonylureas and biguanides. The use of sulfonylureas and biguanides in monotherapy, in most cases, allows to obtain an effective glycometabolic control for some years, if an appropriate diet and behavioural regimen are kept.

Medications for noninsulin-dependent diabetes mellitus (NIDDM) that may be used in the present invention include:

Biguanides such as Buformin, Metformin and Phenformin
Sulfonylureas: Chlorpropamide, Glibenclamide (Glyburide®), Gliclazide, Glimepiride, Glipizide, Gliquidone, Tolazamide, Tolbutamide, Acetohexamide, 1-Butyl-3-metanilylurea, Carbutamide, Glibomuride, Glisoxepid, Glybuthiazol, Glybuzole, Glyhexamide, Glymidine, Glypinamide, Phenbutamide, and Tolcyclamide;
Alpha-glucosidase inhibitor: Acarbose
Thiazolidinediones (TZD): Pioglitazone, Rosiglitazone (Avandia®), Troglitazone
Meglitinides: Nateglinide, Repaglinide
Dipeptidyl peptidase-4 (DPP-4) inhibitors: Sitagliptin, Vildagliptin and Galvus® (vildagliptin, formerly LAF237)
Other glycemia regulators such as Glibomuride, Repaglinide, Miglitol, Calcium Mesoxalate and Diazoxide Example—Glibenclamide (Glyburide®)

Glibenclamide is a potent oral sulphonylurea hypoglycemic agent. It lowers blood glucose concentration in diabetic and non-diabetic patients by stimulating the release of insulin from the pancreas, which requires functioning beta cells. It acts in concert with glucose (improved sensitivity of beta cells to physiological glucose stimulus) and leads to an insulin secretion in the rhythm of meals. Other mechanisms of the hypoglycemic action associated with short-term therapy appear to include reduction of basal hepatic glucose production and enhancement of peripheral insulin action at post-receptor sites.

According to Mutalik, S, and N. Udupa, N. (2004), glibenclamide transdermal patches successfully prevented severe hypoglycemia in the initial hours, which is the major side effect associated with oral route. The patches maintained similar effect during long-term treatment also. The transdermal systems produced better improvement with all the tested biochemical parameters compared to oral administration. They produced improved repair of the tissues after diabetes induced tissue injury and exhibited negligible skin irritation.

By automatically administering three times a day and transdermally, where first pass metabolism is reduced, glibenclamide can be a useful medication for the treatment of hyperglycemia. Dosing could be optimized using the ChronoDose™ system. For example, pulsatile delivery should have blood plasma concentrations (BPC) as set forth below within the following ranges at the following times:

Peak 1 (Highest)
7:30 am-10:00 am: BPC should be in the highest therapeutic range of from 90 to 110 ng/ml.
Peak 2 (Highest)
1:00 pm-3:30 pm: BPC should be in the highest therapeutic range of from 90 to 110 ng/ml.
Peak 3 (Highest)
6:30 pm-9:00 pm: BPC should be in the highest therapeutic range of from 90 to 110 ng/ml.

Figure 11:
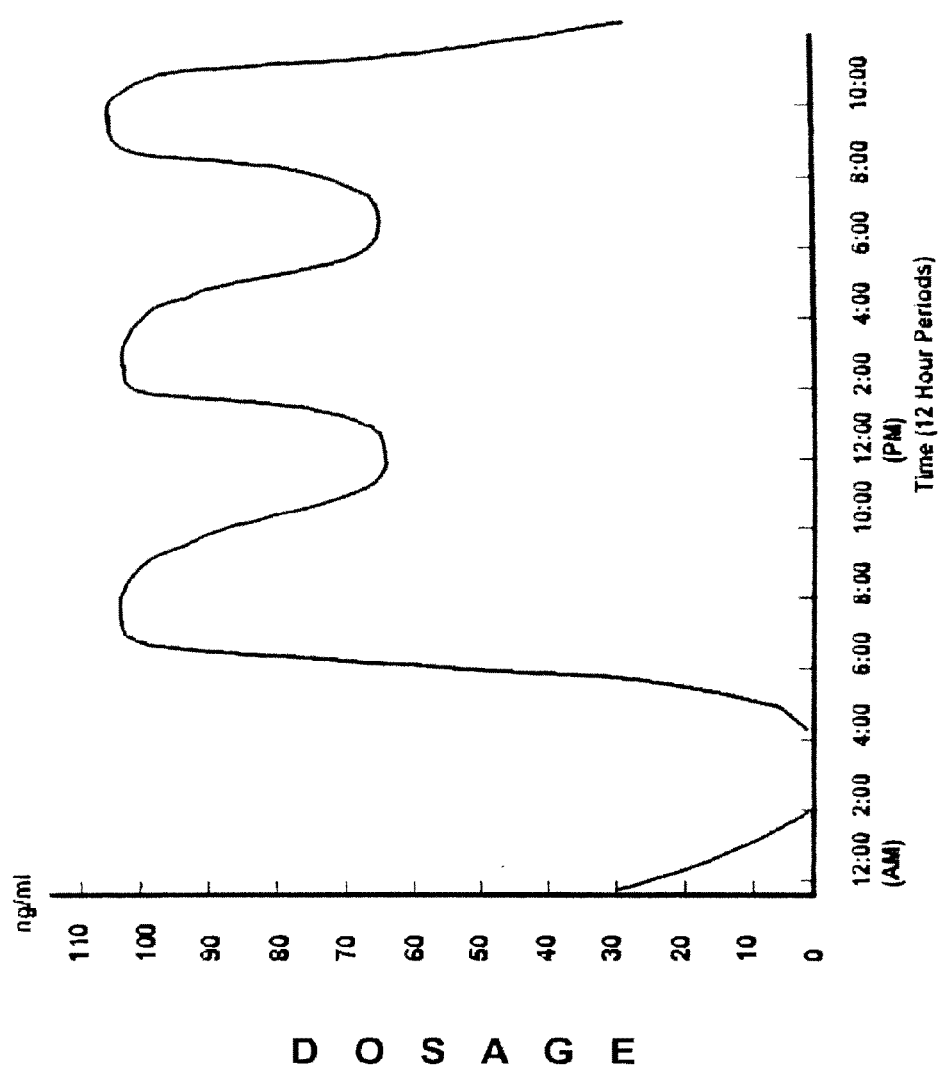
FIG. 11 shows an exemplary administration profile for an automatically delivered glibenclamide delivery system.

The time/dose chart should appear as shown in FIG. 11.

Example—Glipizide (Glucotrol®)

Glipizide is an oral medium-to-long acting anti-diabetic drug from the sulfonylurea class. The mechanism of action is produced by blocking potassium K+ channels in the beta cells of the Islets of Langerhans. By partially blocking the K+ channels, there is an increase in the time the cell spends in the calcium release stage of cell signaling leading to an increase in calcium. The increase in calcium will initiate more insulin release from each beta cell.

According to Mutalik, S, and N. Udupa, N. (2006), glipizide transdermal systems produced better improvement with respect to hypoglycemic activity, glucose tolerance and tested biochemical, histopathological and pharmacokinetic parameters all compared with oral administration and exhibited negligible skin irritation. The transdermal systems successfully prevented severe hypoglycemia in the initial hours and it was also effective for chronic application.

By automatically administering three times a day and transdermally, where first pass metabolism is reduced, glipizide can be a useful medication for the treatment of hyperglycemia. Dosing could be optimized using the ™ system. For example, pulsatile delivery should have blood plasma concentrations (BPC) as set forth below within the following ranges at the following times:

Peak 1 (Highest)
7:30 am-10:00 am: BPC should be in the highest therapeutic range of from 350 to 450 ng/ml.

Peak 2 (Highest)

1:00 pm-3:30 pm: BPC should be in the highest therapeutic range of from 350 to 450 ng/ml.

Peak 3 (Highest)

6:30 pm-9:00 pm: BPC should be in the highest therapeutic range of from 350 to 450 ng/ml.

Figure 12:
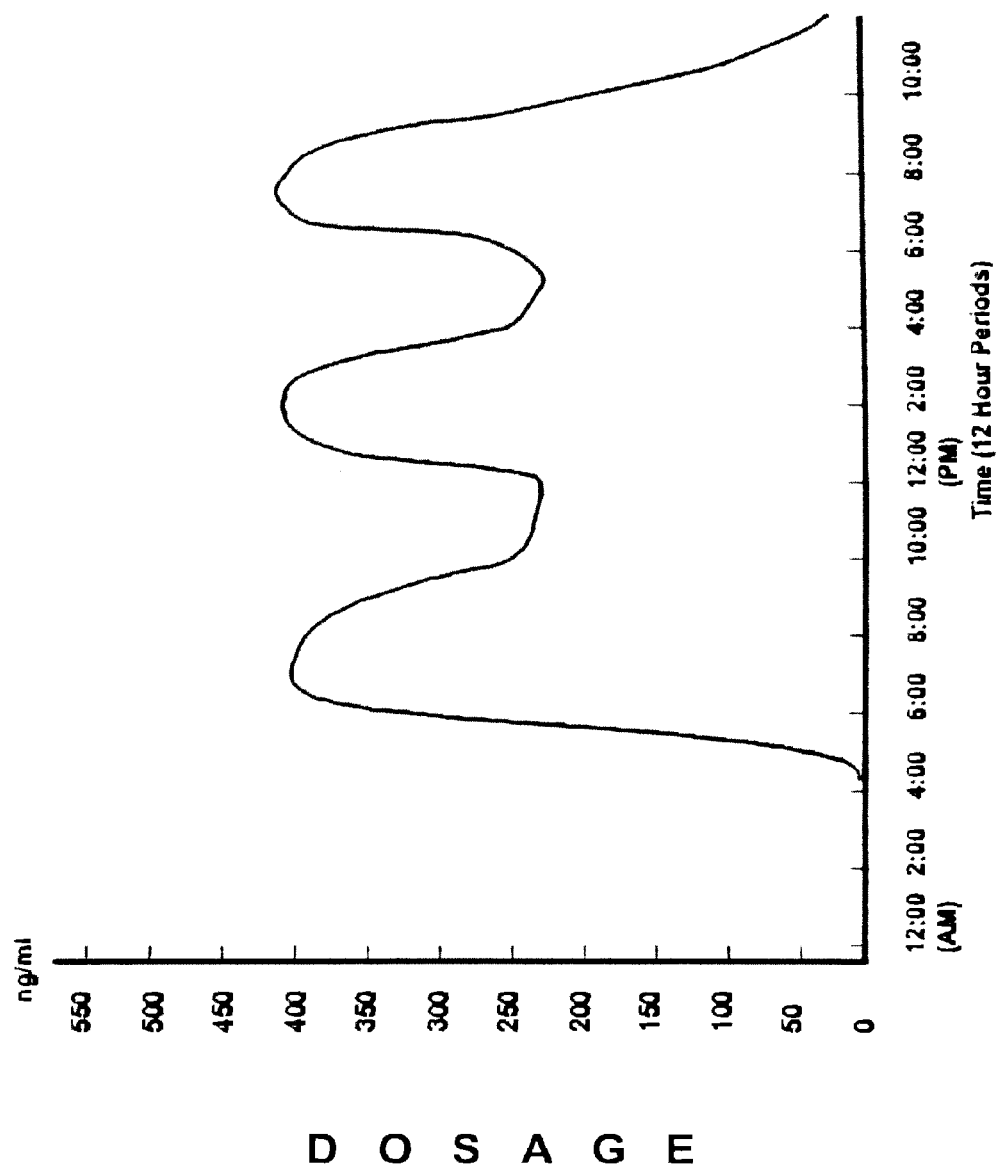
FIG. 12 shows an exemplary administration profile for an automatically delivered glipizide delivery system.

The time/dose chart should appear as shown in FIG. 12.

Example—Rosiglitazone (Avandia®)

Rosiglitazone is an oral antidiabetic agent which acts primarily by increasing insulin sensitivity. It is used in the management of type 2 diabetes mellitus (also known as non-insulin-dependent diabetes mellitus (NIDDM) or adult-onset diabetes). Rosiglitazone improves glycemic control while reducing circulating insulin levels. Pharmacological studies in animal models indicate that rosiglitazone improves sensitivity to insulin in muscle and adipose tissue and inhibits hepatic gluconeogenesis. Rosiglitazone is not chemically or functionally related to the sulfonylureas, the biguanides, or the alpha-glucosidase inhibitors.

By automatically administering three times a day and transdermally, where first pass metabolism is reduced, rosiglitazone can be a useful medication for the treatment of hyperglycemia. Dosing could be optimized using the ChronoDose™ system. For example, pulsatile delivery should have blood plasma concentrations (BPC) as set forth below within the following ranges at the following times:

Peak 1 (Highest)

7:30 am-10:00 am: BPC should be in the highest therapeutic range from 500 to 700 ng/ml.

Peak 2 (Highest)

1:00 pm-3:30 pm: BPC should be in the highest therapeutic range from 500 to 700 ng/ml.

Peak 3 (Highest)

6:30 pm-9:00 pm: BPC should be in the highest therapeutic range from 500 to 700 ng/ml.

Figure 13:
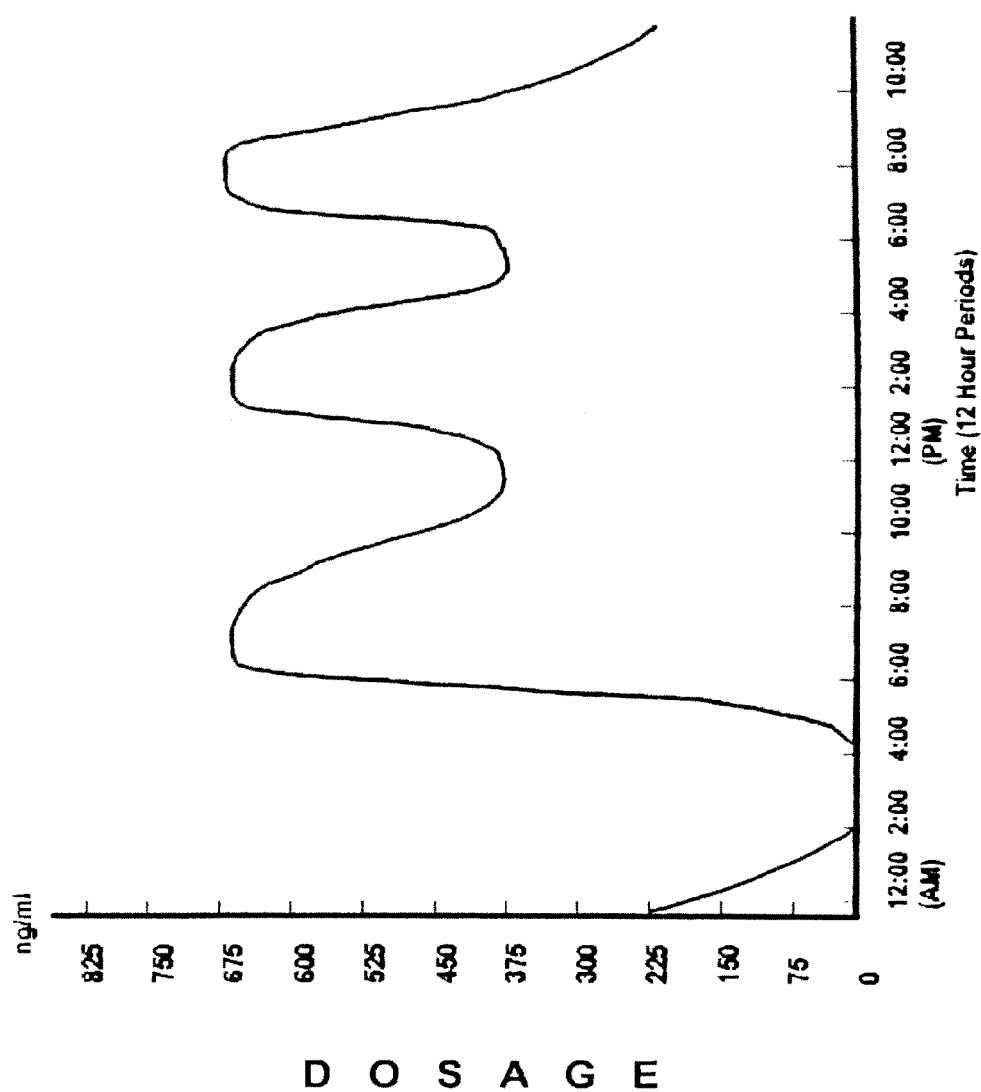
FIG. 13 shows an exemplary administration profile for an automatically delivered rosiglitazone delivery system.

The time/dose chart should appear as shown in FIG. 13.

Example—Metformin

Metformin is an oral medication that lowers blood glucose (sugar) and is used for treating type 2 diabetes. Metformin acts by increasing the sensitivity of liver, muscle, fat, and other tissues to the uptake and effects of insulin. These actions lower the level of sugar in the blood. Unlike glucose-lowering drugs of the sulfonylurea class, e.g. glyburide (Micronase; Diabeta) or glipizide (Glucotrol), metformin does not increase the concentration of insulin in the blood and, therefore, does not cause excessively low blood glucose levels (hypoglycemia) when used alone. In scientific studies, metformin reduced the complications of diabetes such as heart disease, blindness and kidney disease.

By automatically administering three times a day and transdermally, where first pass metabolism is reduced, metformin can be a useful medication for the treatment of hyperglycemia. Dosing could be optimized using the ChronoDose™ system. For example, pulsatile delivery should have blood plasma concentrations (BPC) as set forth below within the following ranges at the following times:

Peak 1 (Highest)

7:30 am-10:00 am: BPC should be in the highest therapeutic range of from 1000 to 1600 ng/ml.

Peak 2 (Highest)

1:00 pm-3:30 pm: BPC should be in the highest therapeutic range of from 1000 to 1600 ng/ml.

Peak 3 (Highest)

6:30 pm-9:00 pm: BPC should be in the highest therapeutic range of 1000 to 1600 ng/ml.

Figure 14:
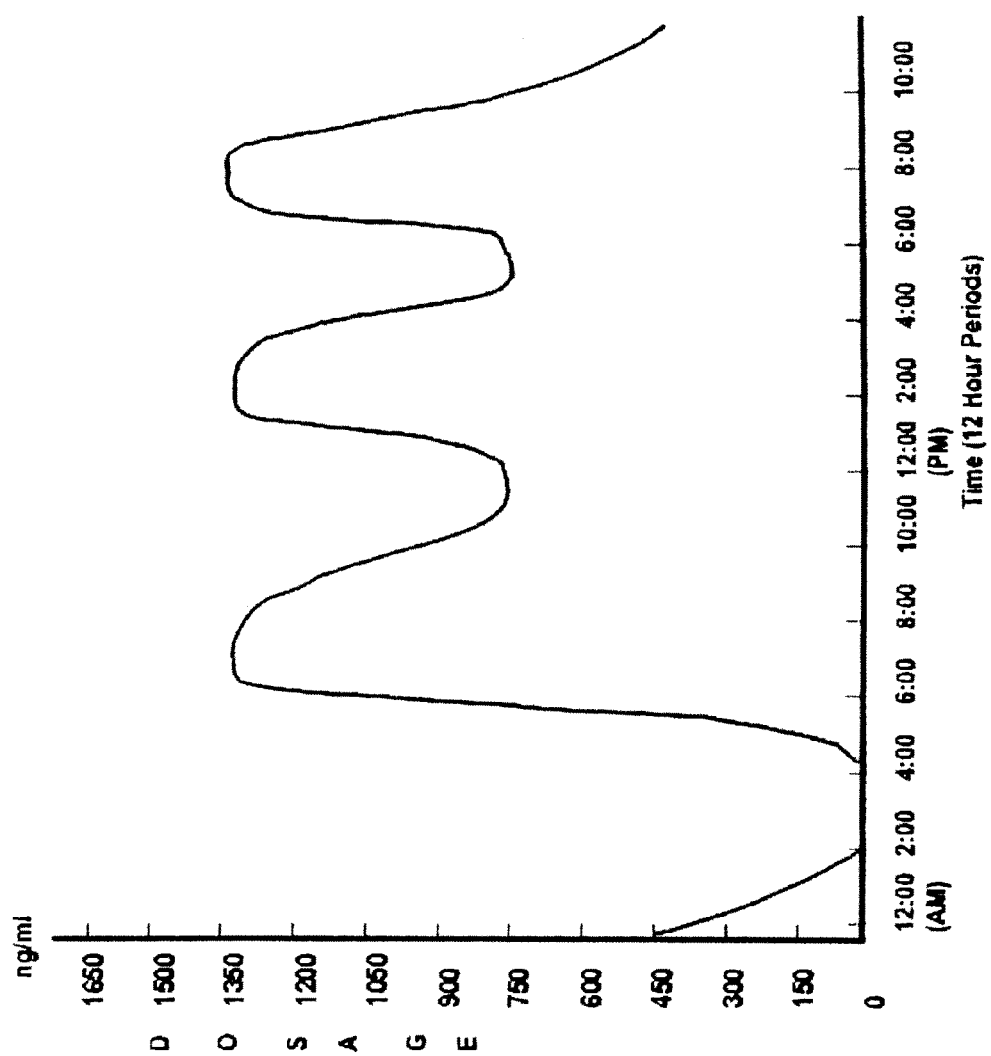
FIG. 14 shows an exemplary administration profile for an automatically delivered metformin delivery system.

The time/dose chart should appear as shown in FIG. 14.

Application—Alzheimer's Disease

In the present invention, the drug delivery regimen is administered to treat the condition of Alzheimer's disease (AD). Alzheimer's disease is an irreversible, progressive disorder in which brain cells (neurons) deteriorate, resulting in the loss of cognitive functions, primarily memory, judgment and reasoning, movement coordination, and pattern recognition. In advanced stages of the disease, all memory and mental functioning may be lost.

The condition predominantly affects the cerebral cortex and hippocampus, which lose mass and shrink (atrophy) as the disease advances.

The two most significant physical findings in the cells of brains affected by Alzheimer's disease are neuritic plaques and neurofibrillary tangles. Another significant factor in AD is the greatly reduced presence of acetylcholine in the cerebral cortex. Acetylcholine is necessary for cognitive function.

While some neuritic plaques, or patches, are commonly found in brains of elderly people, they appear in excessive numbers in the cerebral cortex of Alzheimer's disease patients. A protein called beta amyloid occupies the center of these plaques. Surrounding the protein are fragments of deteriorating neurons, especially those that produce acetylcholine (ACh), a neurotransmitter essential for processing memory and learning. Neurotransmitters are chemicals that transport information or signals between neurons.

Neurofibrillary tangles (NFTs) are twisted remnants of a protein called tau, which is found inside brain cells and is essential for maintaining proper cell structure and function. An abnormality in the tau protein disrupts normal cell activity.

As people grow old, their need for medications increases dramatically because of the higher incidence of chronic pain, diabetes mellitus, cardiovascular and neurological diseases in the elderly population. Furthermore, the elderly require special consideration with respect to drug delivery, drug interactions and adherence. In particular, patients with chronic neurological diseases often require multiple administration of drugs during the day to maintain constant plasma medication levels, which in turn increases the likelihood of poor adherence.

Upon waking, Alzheimer's disease patients can take pills or put on a patch. However, there is a 3-4 hour lag period before current medications reach peak blood concentrations when a pill or tablet is taken. Transdermal systems deliver drugs through the skin, while pills go to the stomach. Bypassing the stomach, medicine delivered via patches may help avoid gastrointestinal side effects such as nausea and vomiting. Patches may also be simpler to use than pills. Patients don't have to remember when to take their pills, which may be particularly helpful with Alzheimer's disease, since Alzheimer's affects the brain and memory. Patients wearing patches also don't have to swallow pills, a task that's difficult for some patients.

Originally created to help treat glaucoma, cholinesterase inhibitors (AChE1s) eventually became the earliest medications in the treatment of mild to moderate Alzheimer's disease. Cholinesterase inhibitors work by increasing the concentration of a chemical messenger in the brain known as acetylcholine. Acetylcholine is important in memory, thinking and other cognitive skills. Cholinesterase inhibitors are designed to keep amounts of this chemical high, even though the cells that transmit them continue to degenerate.

There is no cure for AD and no way to slow the progression of the disease. For some people in the early or middle stages of AD, medication such as tacrine (Cognex®) may alleviate some cognitive symptoms. Donepezil (Aricept®), rivastigmine (Exelon®), and galantamine (Reminyl®) may keep some symptoms from becoming worse for a limited time. A fifth drug, memantine (Namenda®), was recently approved for use in the United States.

Combining memantine with other AD drugs may be more effective than any single therapy. One controlled clinical trial found that patients receiving donepezil plus memantine had better cognition and other functions than patients receiving donepezil alone. Also, other medications may help control behavioral symptoms such as sleeplessness, agitation, wandering, anxiety, and depression.

The acetylcholinesterase inhibitors donepezil, rivastigmine and galantamine improve cognitive performance in manifest dementia. However, these substances also influence the quality of sleep, and particularly the quality and amount of dreams.

Example—Tacrine (Cognex®)

Tacrine is the prototypical cholinesterase inhibitor for the treatment of Alzheimer's disease. Studies have found that it may have a small beneficial effect on cognition and other clinical measures, though adequate study data is limited and the clinical relevance of these findings is unclear.

The use of tacrine is limited by poor oral bioavailability, the necessity for four-times daily dosing, and considerable adverse drug reactions (including nausea, diarrhea, urinary incontinence and hepatotoxicity) such that few patients could tolerate therapeutic doses.

By automatically administering three times a day and transdermally, where first pass metabolism is reduced, tacrine can be a useful medication for the treatment of Alzheimer's disease. Dosing could be optimized using the ChronoDose™ system. For example, pulsatile delivery should have blood plasma concentrations (BPC) as set forth below within the following ranges at the following times:

Peak 1 (Highest)
7:30 am-10:00 am: BPC should be in the highest therapeutic range of from 2.5 to 10 ng/ml.
Peak 2 (Highest)
1:00 pm-3:30 pm: BPC should be in the highest therapeutic range of from 2.5 to 10 ng/ml.
Peak 3 (Medium)
6:30 pm-9:00 pm: BPC should be in the medium therapeutic range of from 1.5 to 7.0 ng/ml.

Figure 19:
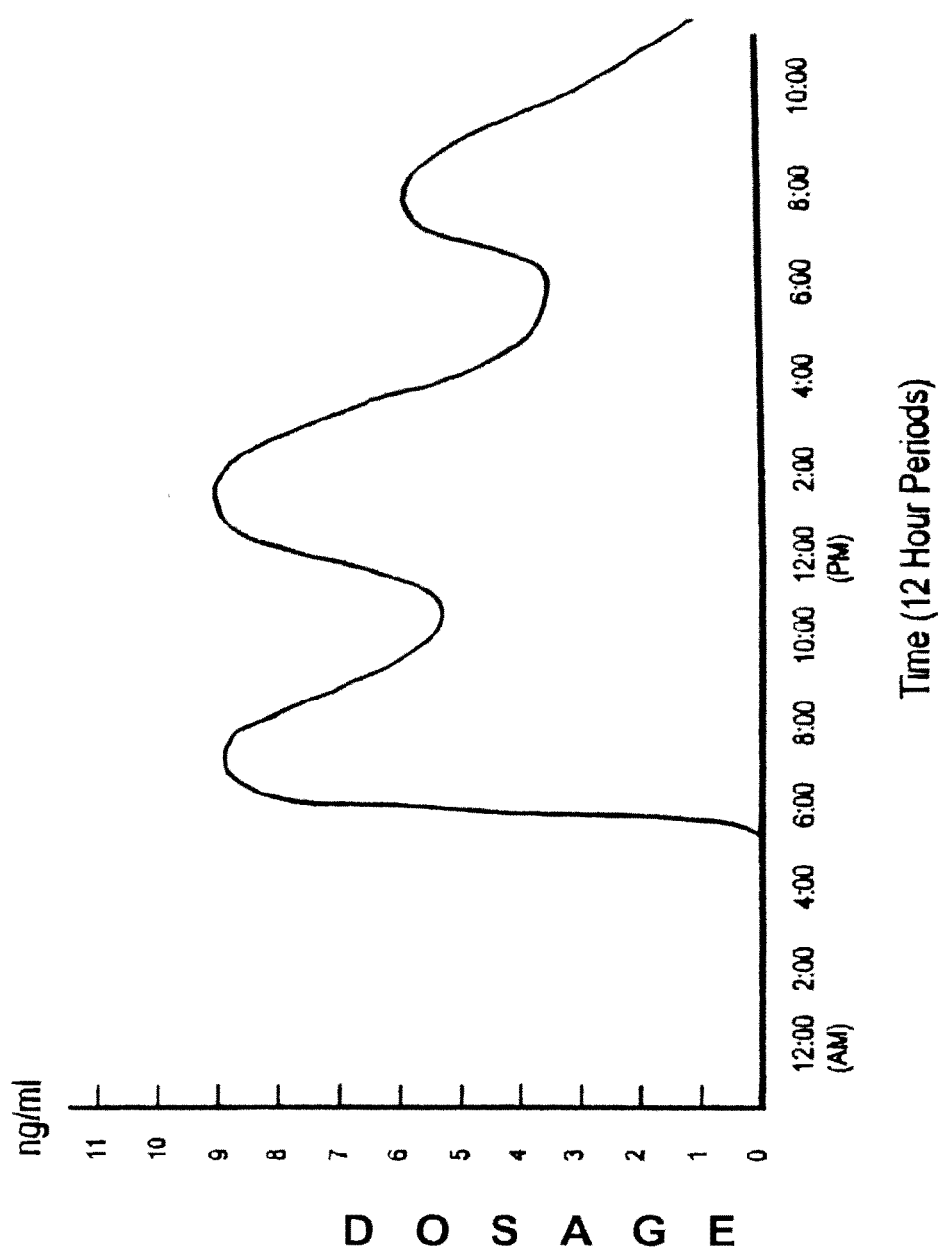
FIG. 19 shows an exemplary administration profile for tacrine delivered automatically according to the present invention.

The time/dose chart should appear as shown in FIG. 19.

Example—Donepezil (Aricept®)

A recent study (Brunner et. al, 2005) investigated the influence of the time point of donepezil intake on the occurrence of nightmares. A clear-cut relationship between the occurrence of nightmares and an evening dose of donepezil in eight patients with AD was observed. None of the patients reported nightmares when donepezil was taken in the morning. This suggests that the activation of the visual association cortex during REM sleep is enhanced by donepezil, a mechanism most likely facilitating the development of nightmares in patients with AD.

Therefore, morning dosing as well as customized dose amounts could be optimized using the ChronoDose™ system. For example, pulsatile delivery should have blood plasma concentrations (BPC) as set forth below within the following ranges at the following times:

Peak 1 (Highest)
7:00 am-9:00 am: BPC should be in the highest therapeutic range of from 15 to 30 ng/ml.
Peak 2 (Optional)
5:00 pm-7:00 pm: BPC should be in the medium to low therapeutic range of from 5 to 10 ng/ml.

Figure 20:
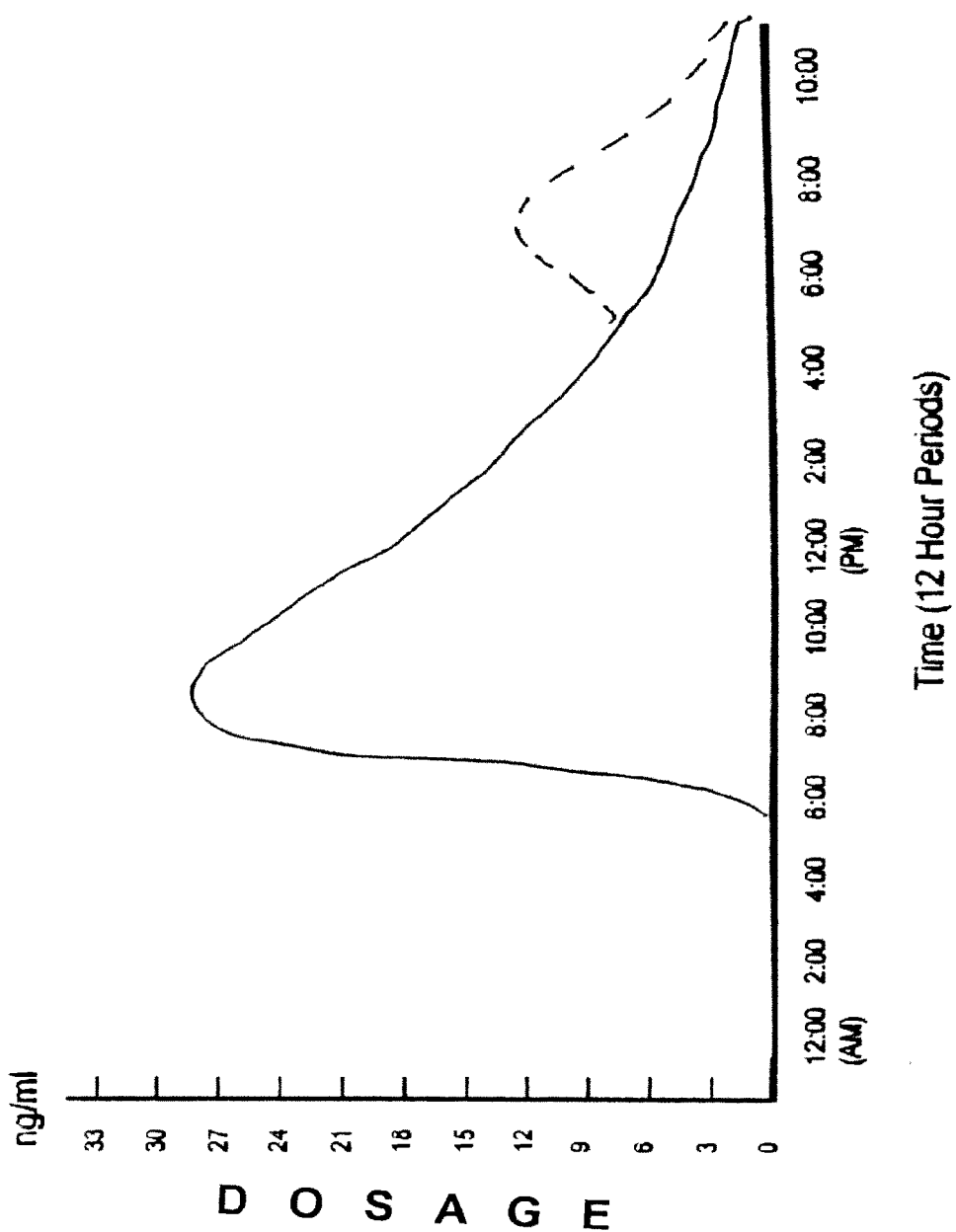
FIG. 20 shows an exemplary administration profile for donepezil delivered automatically according to the present invention.

The time/dose chart should appear as shown in FIG. 20.

Example—Rivastigmine (Exelon®)

Exelon™ (rivastigmine tartrate) is a reversible cholinesterase inhibitor and is known chemically as (S)—N-Ethyl-N-methyl-3-[1-(dimethylamino)ethyl]-phenyl carbamate hydrogen-(2R,3R)-tartrate. Rivastigmine tartrate is commonly referred to in the pharmacological literature as SDZ ENA 713 or ENA 713.

Pathological changes in Dementia of the Alzheimer type and Dementia associated with Parkinson's disease involve cholinergic neuronal pathways that project from the basal forebrain to the cerebral cortex and hippocampus. These pathways are thought to be intricately involved in memory, attention, learning, and other cognitive processes. While the precise mechanism of rivastigmine's action is unknown, it is postulated to exert its therapeutic effect by enhancing cholinergic function. This is accomplished by increasing the concentration of acetylcholine through reversible inhibition of its hydrolysis by cholinesterase.

The dosage of Exelon™ (rivastigmine tartrate) has been shown to be effective when given as twice-a-day dosing. Therefore, morning, as well as afternoon dosing and customized dose amounts could be optimized using the ChronoDose™ system. For example, pulsatile delivery should have blood plasma concentrations (BPC) as set forth below within the following ranges at the following times:

Peak 1 (Highest)
7:00 am-9:00 am: BPC should be in the highest therapeutic range of from 3.5 to 6 ng/ml.
Peak 2 (Medium)
5:00 pm-7:00 pm: BPC should be in the medium therapeutic range of from 2 to 4 ng/ml.

Figure 21:
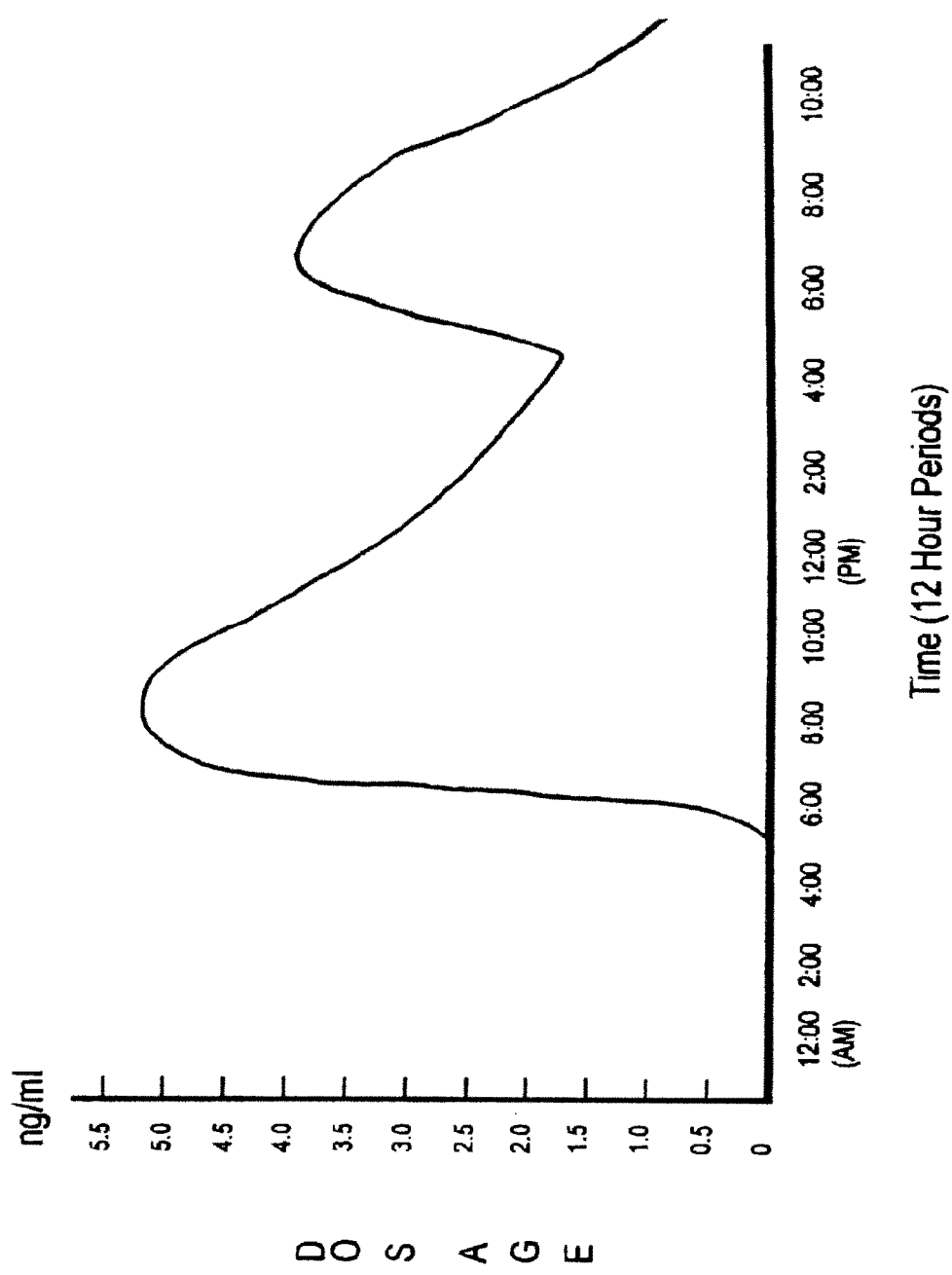
FIG. 21 shows an exemplary administration profile for rivastigmine delivered automatically according to the present invention.

The time/dose chart should appear as shown in FIG. 21.

Example—Galantamine (Razadyne®)

Galantamine, an alkaloid extracted from daffodil bulbs, is the fourth cholinesterase inhibitor approved for Alzheimer's disease (AD). Galantamine is a competitive and reversible cholinesterase inhibitor. It works by enhancing cholinergic function by increasing the concentration of acetylcholinesterase in the brain. Galantamine is a nicotinic modulator and works by slowing down or inhibiting acetylcholinesterase, which is the enzyme responsible for degrading the neurotransmitter acetylcholine Galantamine is usually taken twice a day, with the morning and evening meals. Therefore, morning, as well as afternoon dosing and customized dose amounts could be optimized using the ChronoDose™ system. For example, pulsatile delivery should have blood plasma concentrations (BPC) as set forth below within the following ranges at the following times:

Peak 1 (Highest)
7:00 am-9:00 am: BPC should be in the highest therapeutic range of from 10 to 60 ng/ml.

Peak 2 (Medium)

5:00 pm-7:00 pm: BPC should be in the medium therapeutic range of from 5 to 30 ng/ml.

Figure 22:
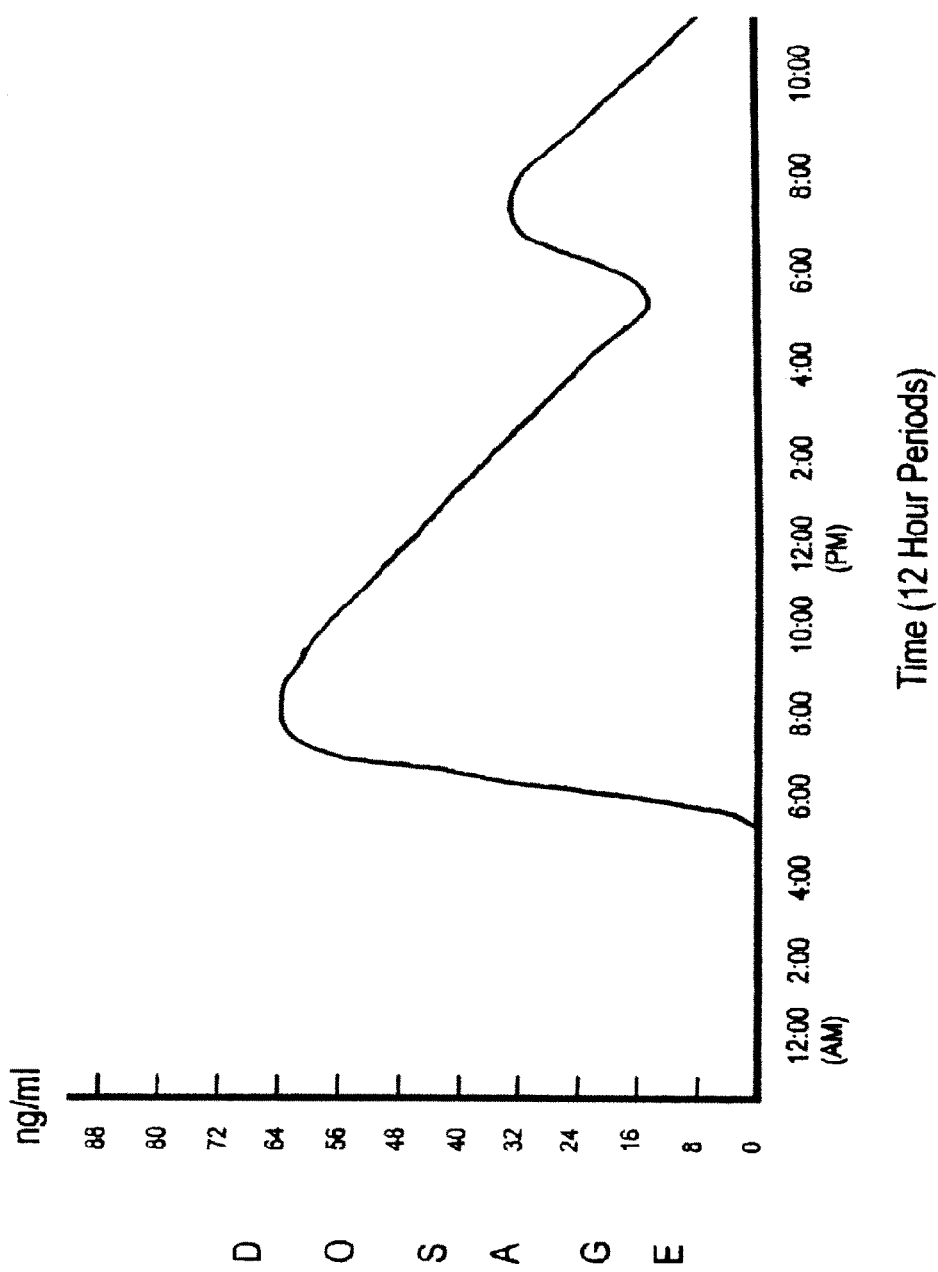
FIG. 22 shows an exemplary administration profile for galantamine delivered automatically according to the present invention.

The time/dose chart should appear as shown in FIG. 22.

Example—Memantine (Namenda®)

Memantine is usually taken twice a day, with the morning and evening meals. Therefore, morning, as well as afternoon dosing and customized dose amounts could be optimized using the ChronoDose™ system. For example, pulsatile delivery should have blood plasma concentrations (BPC) as set forth below within the following ranges at the following times:

Peak 1 (Highest)

7:00 am-9:00 am: BPC should be in the highest therapeutic range of from 25 to 100 ng/ml.

Peak 2 (Medium)

5:00 pm-7:00 pm: BPC should be in the medium therapeutic range of from 10 to 50 ng/ml.

Figure 23:
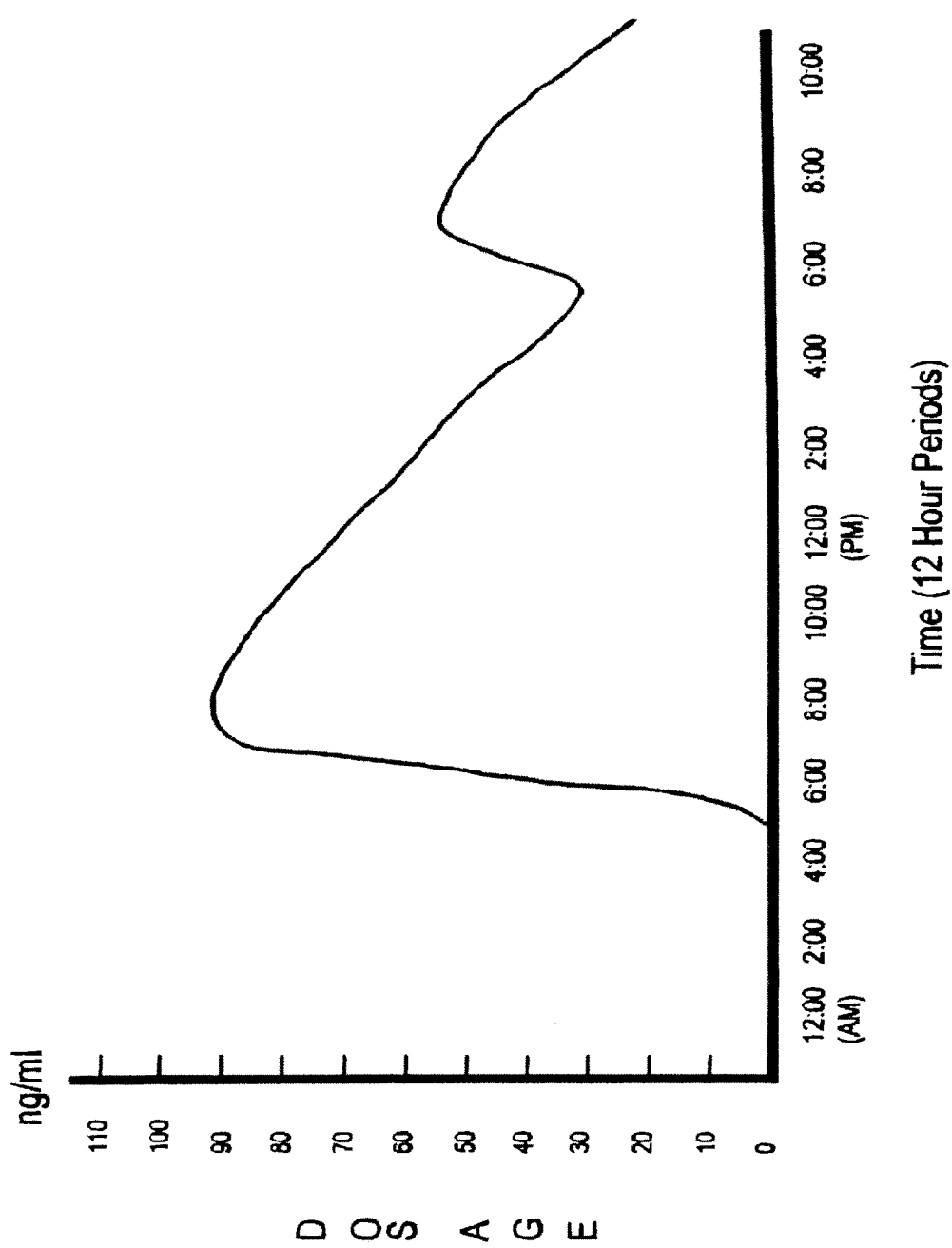
FIG. 23 shows an exemplary administration profile for memantine delivered automatically according to the present invention.

The time/dose chart should appear as shown in FIG. 23.

Application—Sleep Disorders

A contemplated consumer product is the ArisePatch™. Most people experience difficulty and discomfort when waking early in the morning. According to a 2002 National Sleep Foundation poll 49% of US adults age 18-29 have trouble waking in the morning and 41% of US adults age 30-64 have trouble waking in the morning. There are 165,000,000 adults in the US alone age 18-64; meaning approximately 74,250,000 US adults age 18-64 have trouble waking in the morning.

Adrenergic stimulants such as fenoterol, isoprenaline, orciprenaline, rimeterol, salbutamol, salmeterol, terbutaline, dobutamine, phenylephrine, phenylpropanolamine, pseudoephedrine may find particular utility in treating sleep disorders. Other stimulants which may find utility with the devices and methods of the present invention may include Cocaine, Dextroamphetamine (Dexedrine), Methamphetamine (Desoxyn), Methylphenidate (Ritalin), Phenmetrazine (Preludin), Biphetamine, Benzphetamine, Didrex, Chlorphentermine, Clortermine, Phendimetrazine tartrate (Plegine, Prelu 2), Norpseudoephedrine, Diethylpropion hydrochloride (Tenuate), Fencamfamin, Fenproporex, Phentermine (Fastin, Ionamin, Adipex), Mazindol (Sanorex, Mazanor), Mefenorex, Modafinil (Provigil), Pemoline (Cylert (No longer available in U.S.)), Pipradrol, Sibutramine (Meridia), Pyrovalerone, Diethylpropion, Fenproporex, Phentermine, Mazindol, Modafinil, Pemoline and Sibutramine.

Figure 40:
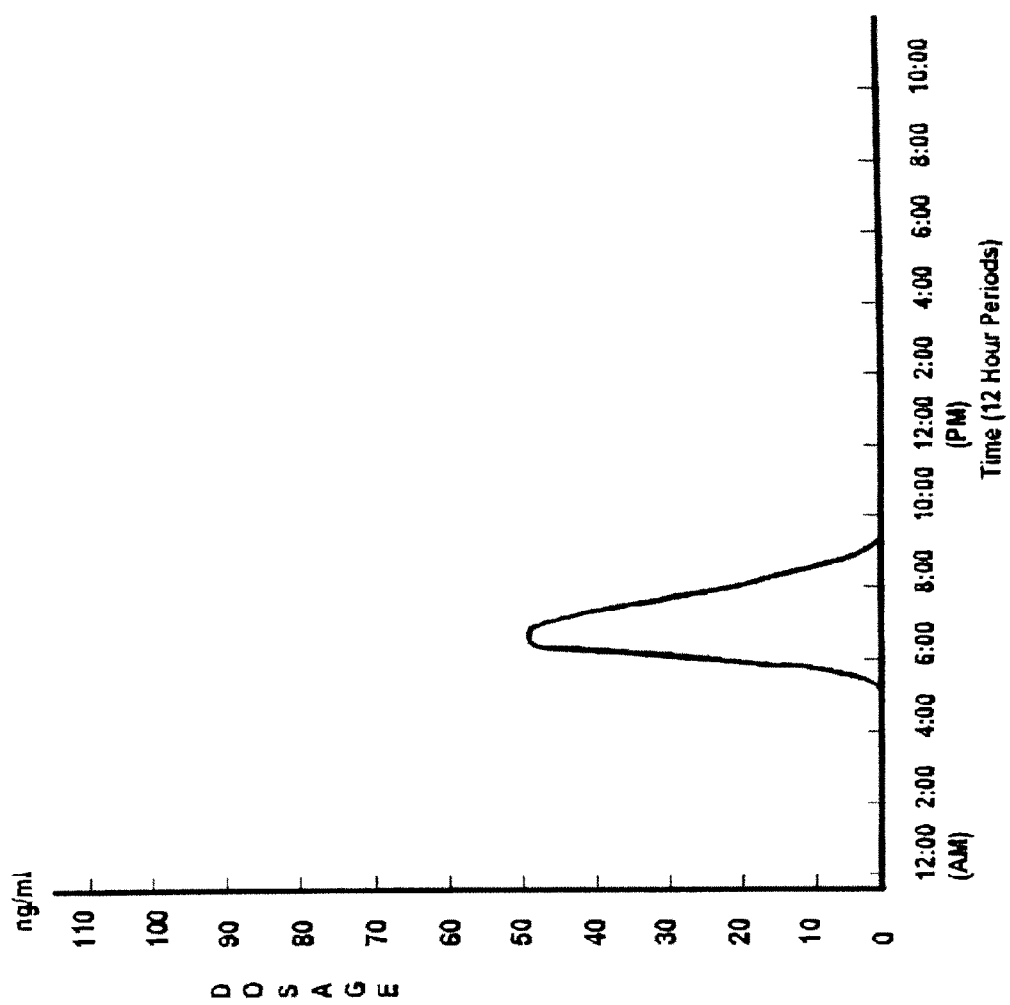
FIG. 40 shows an exemplary administration profile for a wake-up delivery system.

The ArisePatch implementation of the present invention allows individuals, while asleep, to have an over-the-counter (OTC) or prescription stimulant automatically administered during a 1-2 hour pre-wake-up period. FIG. 40 illustrates an exemplary stimulant administration profile showing a blood plasma level of ephedrine in nanograms per milliliter on the vertical axis, with time on the horizontal axis. Stimulant concentrations will reach peak levels immediately prior to having to wake Immediately upon waking up the individual will be alert and feel well rested. The ArisePatch™ will eliminate the typical discomfort or difficulty associated with getting up early. This functionality is attractive to employed people getting up for work to ensure punctuality, and just about anyone who wants to offset morning discomfort associated with a late night, jet lag, or sickness.

Application—Parkinson's Disease

The present invention may be used to treat, cure, prevent, control or alleviate a wide range of conditions and symptoms. In the present invention, the drug delivery regimen is administered to treat the condition of Parkinson's disease (PD).

Parkinson's disease (PD) belongs to a group of conditions called motor system disorders. Parkinson's disease occurs when a group of cells in an area of the brain called the substantia nigra begin to malfunction and die. These cells in the substantia nigra produce a chemical called dopamine Dopamine is a neurotransmitter, or chemical messenger, that sends information to the parts of the brain that control movement and coordination. The four primary symptoms of PD are tremor, or trembling in hands, arms, legs, jaw, and face; rigidity, or stiffness of the limbs and trunk; bradykinesia, or slowness of movement; and postural instability, or impaired balance and coordination. As these symptoms become more pronounced, patients may have difficulty walking, talking, or completing other simple tasks.

Medications for Parkinson's disease that may be used in the present invention include:

Dopamine precursors such as (Dopar®) and (Larodopa®).

Carbidopa such as (Lodosyn®).

Dopa decarboxylase inhibitors such as Carbidopa and Benserazide.

Mixtures.
  Levodopa/carbidopa mixtures such as (Sinemet®)
  Levodopa/carbidopa/entacapone mixtures such as (Stalevo®)
  Levodopa/benserazide mixtures such as (Madopar®) and (Prolopat).

Dopamine agonists include bromocriptine (Parlodel®), pergolide (Permax®), pramipexole (Mirapex®), rotigotine (Neupro®), dihydroergocryptine, ropinirole (Requip®), cabergoline (Cabaser®), apomorphine (Apokyn), lisuride (Revanil®) and piribedil.

Anticholinergics such as biperiden (Akineton®), diphenhydramine (Benadryl®), trihexyphenidyl (Artane®), benztropine mesylate (Cogentin®), procyclidine (Kemadrin®).

MAO-B inhibitors such as selegiline or deprenyl (Eldepryl®, Emsam® TTS), (Carbex®) and rasagiline (Azilect®).

COMT inhibitors such as entacapone (Comtan®) and tolcapone (Tasmar®).

Dopaminergic Agonists such as Amantadine (Symmetrel®)

Ampakines such as: CX-516 (Ampalex), CX546, CX614 and CX717.

Newer medications such as Istradefylline (KW-6002), S-(−)-2-(N-propyl-N-2-thienylethylamino)-5-hydroxytetralin (N-0923) and Sarizotan.

Other anti-Parkinson's medications such as of bornaprine, budipine, ethopropazine, lazabemide, memantine, modafinil, talampanel, altinicline, brasofensine, safinamide, droxidopa, piribedil, quinagolide, terguride, riluzole, talipexole, piroheptine, bifeprunox, spheramine, sumanirole, lisuride hydrogen maleateor, and orphenadrine.

Over-the-Counter Medications such as Coenzyme Q10 (CoQ-10), Vitamin E, Vitamin C, and glutathione.

Dopar® is a registered trademark of Proctor and Gamble

Larodopa® is a registered trademark of Roche (Can.)

Lodosyn® is a registered trademark of MERCK & CO., INC

Sinemet® is a registered trademark of Merck & Co., Inc. and is marketed by Du Pont Pharmaceuticals.

Stalevo® a registered trademark of Novartis Pharmaceuticals Corp.

Madopar® is a registered trademark of Hoffmann-La Roche Ltd.

Prolopa® is a registered trademark of Hoffmann-La Roche Ltd

Permax® is a registered trademark of Amarin Corporation

Parlodel is a registered trademark of Novartis Inc.

Mirapex® is a registered trademark of Pharmacia Corporation.

Requip® is a registered trademark of GlaxoSmithKline.

Cabaser® is a registered trademark of Pharmacia Australia Pty Limited

Apokyn® is a registered trademark of Vernalis Pharmaceuticals Inc.

Revanil® is a registered trademark of

Akineton® is a registered trademark of Knoll AG

Benadryl® is a registered trademark of Pfizer, Inc.

Artane® is a registered trademark of American Cyanamid Company, Lederle Laboratories Division.

Cogentin® is a registered trademark of Merck & Co., Inc.

Kemadrin® is a trademark of the GlaxoSmithKline group of companies.

Eldepryl® is a registered trademark of Somerset Pharmaceuticals, Inc.

Emsam® TTS is a registered trademark of Somerset Pharmaceuticals, Inc.

Carbex® is a registered trademark of Du Pont Pharmaceuticals.

Azilect® is a registered trademark of Teva Pharmaceutical Industries Ltd.

Comtan® is a registered trademark of Novartis AG

Tasmar® is a registered trademark of Hoffinann-La Roche Ltd.

Symmetrel® is a registered trademark of Endo Pharmaceuticals, Inc.

Neupro® is a registered trademark of Schwarz Pharma AG

Chronotherapeutic Rationale:

As people grow old, their need for medications increases dramatically because of the higher incidence of chronic pain, diabetes mellitus, cardiovascular and neurological diseases in the elderly population. Furthermore, the elderly require special consideration with respect to drug delivery, drug interactions and adherence. In particular, patients with chronic neurological diseases often require multiple administration of drugs during the day to maintain constant plasma medication levels, which in turn increases the likelihood of poor adherence. Consequently, several attempts have been made to develop pharmacological preparations that can achieve a constant rate of drug delivery. For example, transdermal lisuride and apomorphine have been shown to reduce motor fluctuations and duration of 'off' periods in advanced Parkinson's disease, while rotigotine allows significant down-titration of levodopa without severe adverse effects. Thus, parkinsonian patients with long-term levodopa syndrome or motor disorders during sleep could benefit from use of transdermal lisuride and apomorphine. Moreover, transdermal dopaminergic drugs, particularly rotigotine, seem the ideal treatment for patients experiencing restless legs syndrome or periodic limb movement disorder during sleep, disorders that are quite common in elderly people or in association with neurodegenerative diseases.

Parkinson's disease symptoms usually peak immediately upon waking. Most Parkinson's sufferers can barely move upon waking and are immobile due to the fact most medications for Parkinson's disease stop acting before awaking.

In addition, some Parkinson's medications have stimulant effects and cannot be administered during the sleep cycle. Upon waking, Parkinson's disease patients can take pills or put on a patch. However, there is a 4-hour lag period before current medications reach peak blood concentrations.

Clinical studies have shown that up to 82% of patients suffering with Parkinson's disease have difficulty swallowing and tend to dribble. Conventional selegiline tablets, syrups, and the like, still require the patient to attempt swallowing. Moreover, conventional tablets need to be administered with water, requiring another difficult swallowing act for such patients.

From a clinical perspective, it would be highly desirable to administer Parkinson's medication while enhancing the bioavailability of the active ingredient and avoiding first pass effect and its undesirable metabolites, hence affording a comparatively rapid onset and prolonged duration of effect as compared to conventional administration forms. Even more desirable would be the ability to administer Parkinson's medication in a dosage form that does not present difficulty in ingestion in those patients that have difficulty swallowing, can be handled easily, and affords assurance and greater predictability of its administration and effect.

Biosynchronous transdermal drug delivery administered by the ChronoDose™ system will automatically turn off drug delivery at night for sound sleep, and automatically turn on and release higher doses of medication prior to waking up.

Example—Selegiline (Eldepryl®, Emsam® TTS)

Sleep disturbances in Parkinson's disease patients reveal alterations of circadian rhythms. Autonomic dysfunction, described in Parkinson's disease, reveals numerous alterations in circadian regulations including loss of circadian rhythm of blood pressure, increased diurnal blood pressure variability, and postprandial hypotension. Many biologic indices such as cortisol, catecholamines, and melatonin are also altered. Circadian rhythms in dopaminergic systems as well as possible daily fluctuations in kinetics of drug treatments are likely involved in such variations.

Parkinson's disease is believed to be caused by a lack of dopamine in the brain. Selegiline is used as an adjunctive therapy with levodopa/carbidopa mixtures when there is a deterioration in the quality of response to levodopa/carbidopa therapy. Selegiline prevents the enzyme monoamine oxidase type B (MAO B) from breaking down dopamine in the brain. This allows dopamine to remain active in the brain for a longer period of time.

Thus, dosing could be optimized using the ChronoDose™ system. For example, pulsatile delivery should have blood plasma concentrations (BPC) as set forth below within the following ranges at the following times:

Peak 1 (Highest)

7:30 am-10:00 am: BPC should be in the highest therapeutic range of from 1.2 to 1.6 ng/ml.

Peak 2 (Highest)

1:00 pm-3:00 pm: BPC should be in the highest therapeutic range of from 1.2 to 1.6 ng/ml.

Figure 24:
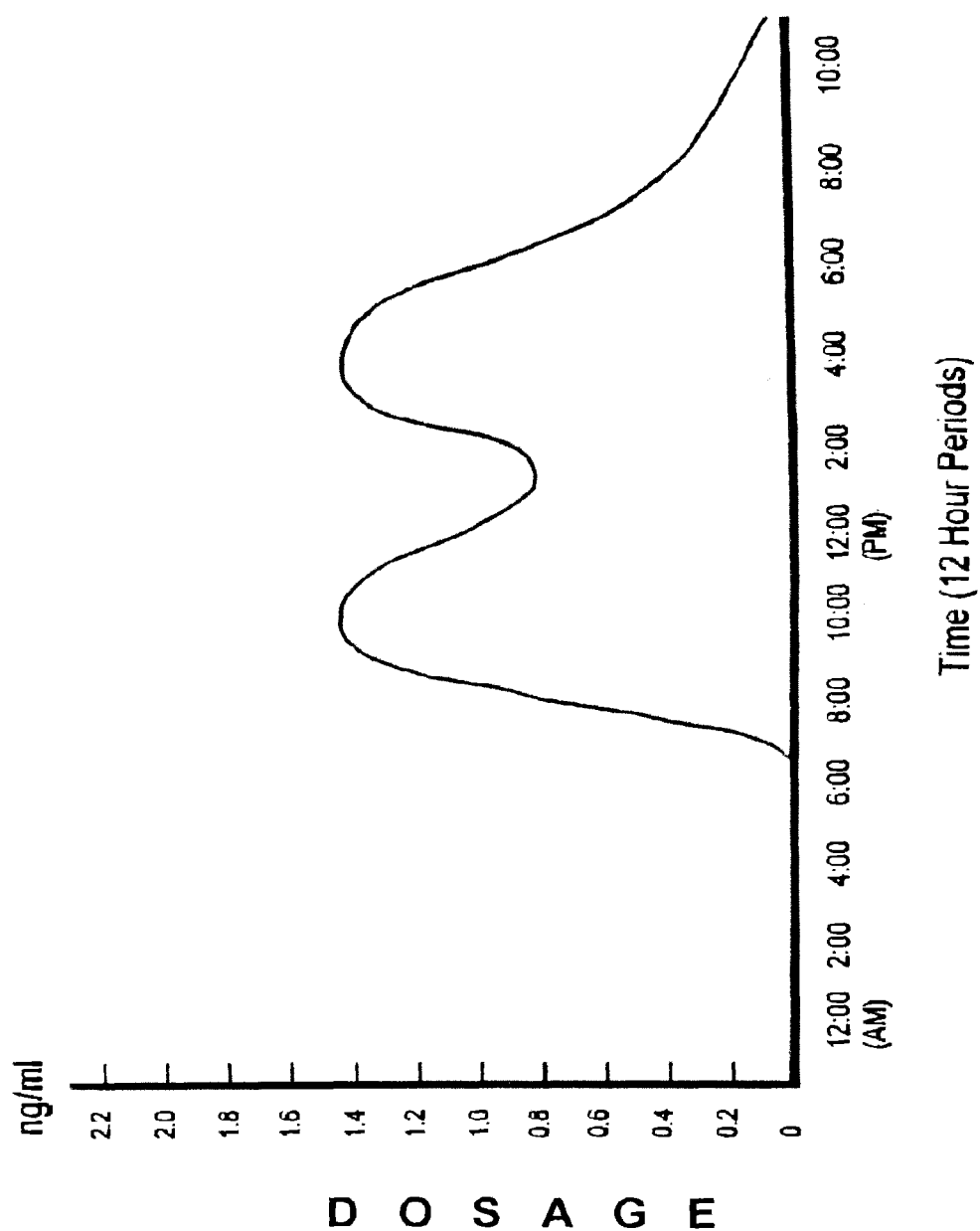
FIG. 24 shows an exemplary administration profile for selegiline delivered by a system of the present invention showing two doses.

The time/dose chart should appear as shown in FIG. 24.

Example—Ropinerole (Requip®)

Ropinerole stimulates dopamine production. However, one of the major side effects is sleepiness. Patients report falling asleep without any warning signs during activities of daily living, including operation of a motor vehicle, which sometimes resulted in accidents. Hallucinations and dizziness upon standing may also occur.

By taking advantage of the somnolence side effect of ropinerole, dosing could be optimized using the ChronoDose™ system. For example, pulsatile delivery should have blood plasma concentrations (BPC) as set forth below within the following ranges at the following times:

Peak 1 (Highest)

11:00 pm-5:00 am: BPC should be in the highest therapeutic range from 7.5 to 10.0 ng/ml.

Peak 2 (Medium)

6:00 am-1:00 pm: BPC should be in the medium therapeutic range of from 5.0 to 9.0 ng/ml.

Peak 3 (Lowest)

2:00 pm-8:00 pm: BPC should be in the lowest therapeutic range of from 4.0 to 5.5 ng/ml.

Figure 25:
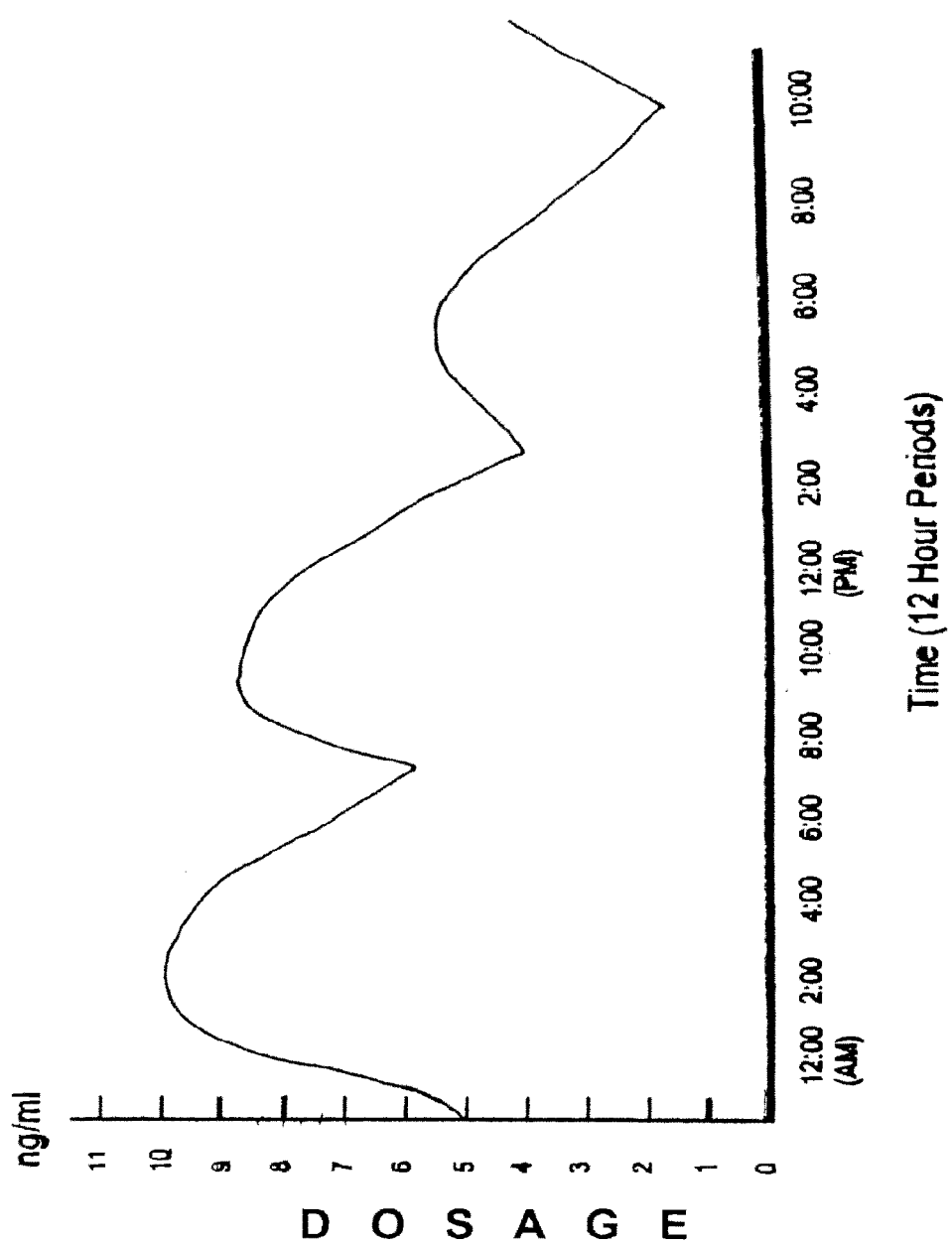
FIG. 25 shows an exemplary administration profile for ropinirole delivered by a system of the present invention showing three doses.

The time/dose chart should appear as shown in FIG. 25.

Example—Apomorphine (Apokyn®)

Apomorphine as a dopamine agonist appears to relieve the symptoms of parkinsonism for patients who experience severe motor fluctuations after chronic levodopa therapy. It has been approved for the acute, intermittent treatment of hypomobility, "off" episodes ("end-of-dose wearing off" and unpredictable "on/off" episodes) associated with advanced Parkinson's disease (Prod Info Apokyn™ 2004). In the past, apomorphine was not widely used because of tolerance issues (apomorphine has strong emetic and hypotensive effects), its short duration of action and the need for parenteral administration. However its rapid onset of action can be advantageous during "off" episodes and apomorphine may have a role in the treatment of patients not adequately treated with levodopa or other anti-parkinsonian medications (LeWitt, 2004). Apomorphine transdermal emulsion has been tested by Priano et al (2003).

Peak 1 (Highest)

1200 am-2:00 am: BPC should be in the highest therapeutic range of from 24 to 34 ng/ml.

Peak 2 (Highest)

5:00 am-7:00 am: BPC should be in the highest therapeutic range of from 24 to 34 ng/ml.

Figure 26:
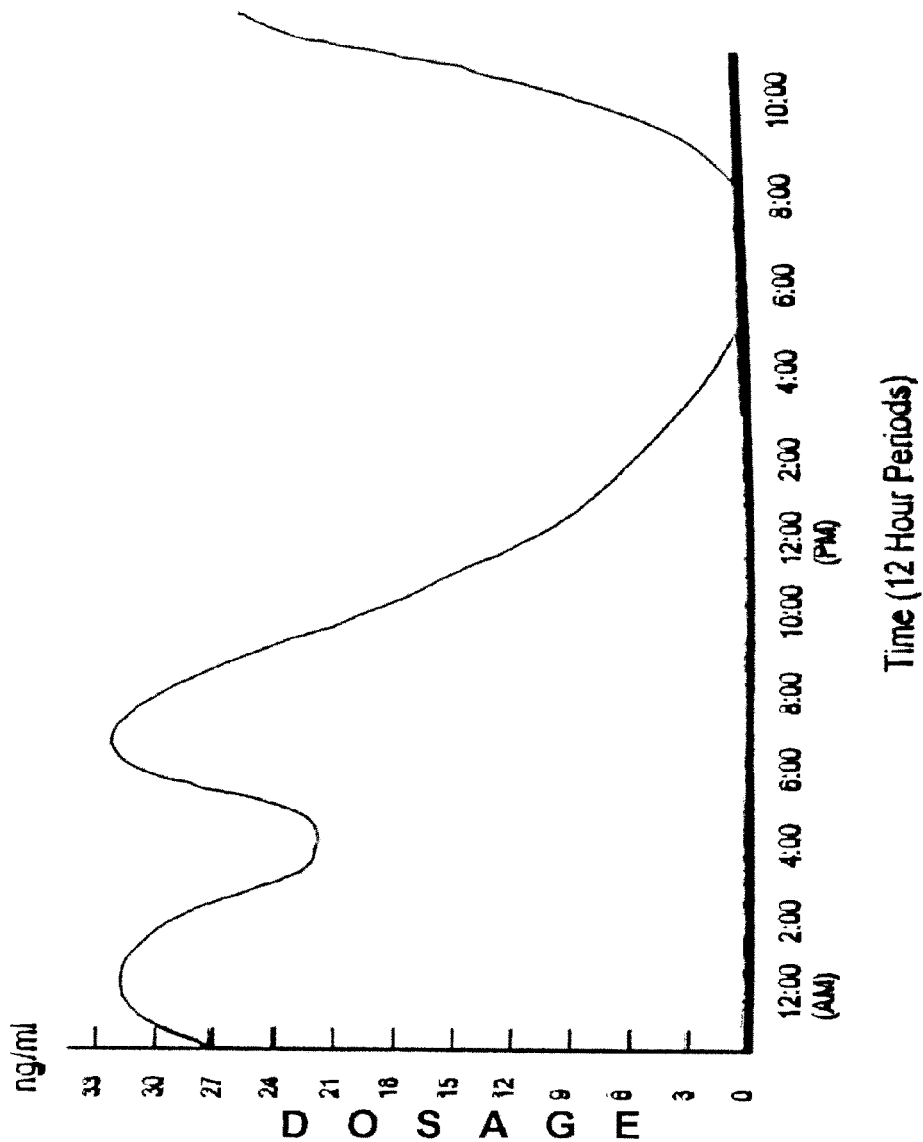
FIG. 26 shows an exemplary administration profile for apomorphine delivered by a system of the present invention showing two doses.

The time/dose chart should appear as shown in FIG. 26.

Example—Pramipexole (Mirapex®)

Even though Mirapex® stimulates dopamine production, one of the major side effects is sleepiness, which is why it is also used off-label for a variety of sleep disorders. Patients have reported falling asleep without any warning signs during activities of daily living, including operation of a motor vehicle, which sometimes resulted in accidents. Hallucinations and dizziness upon standing may also occur.

By taking advantage of the somnolence side effect of pramipexole, dosing could be optimized using the ChronoDose™ system, with a higher dose given at night. For example, pulsatile delivery should have blood plasma concentrations (BPC) as set forth below within the following ranges at the following times:

Peak 1 (Highest)

11:00 pm-5:00 am: BPC should be in the highest therapeutic range of from 1.2 to 2.1 ng/ml.

Peak 2 (Medium)

6:00 am-1:00 pm: BPC should be in the medium therapeutic range of from 1.0 to 1.6 ng/ml.

Peak 3 (Lowest)

2:00 pm-8:00 pm: BPC should be in the lowest therapeutic range of from 0.8 to 1.3 ng/ml.

Figure 27:
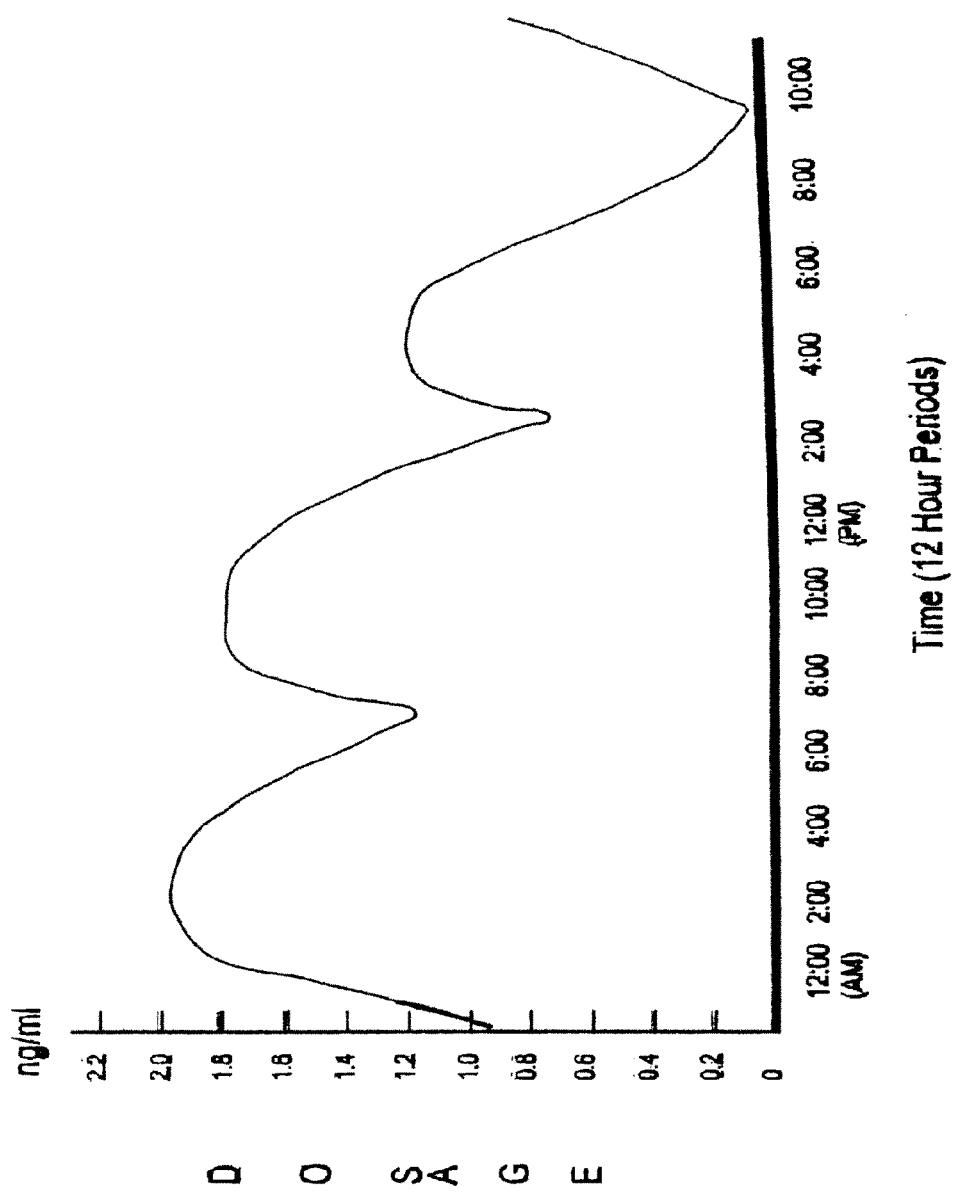
FIG. 27 shows an exemplary administration profile for pramipexole delivered by a system of the present invention showing three doses.

The time/dose chart should appear as shown in FIG. 27.

Example—Biperiden (Akineton®)

Biperiden is a weak peripheral anticholinergic agent. Parkinsonism is thought to result from an imbalance between the excitatory (cholinergic) and inhibitory (dopaminergic) systems in the corpus striatum. The mechanism of action of centrally active anticholinergic drugs such as biperiden is considered to relate to competitive antagonism of acetylcholine at cholinergic receptors in the corpus striatum, which then restores the balance. Biperiden is used as an adjunct in the therapy of all forms of parkinsonism (idiopathic, postencephalitic, arteriosclerotic), as well as for control of extrapyramidal disorders secondary to neuroleptic drug therapy (e.g., phenothiazines)

Biperiden (Akineton®) is usually prescribed to be taken three or four times a day. Thus, dosing could be optimized using the ChronoDose™ system. For example, pulsatile delivery should have blood plasma concentrations (BPC) as set forth below within the following ranges at the following times:

Peak 1 (Highest)

6:30 am-8:30 am: BPC should be in the highest therapeutic range of from 2.5 to 5.1 ng/ml.

Peak 2 (Highest)

1:30 pm-4:30 pm: BPC should be in the highest therapeutic range of from 2.5 to 5.1 ng/ml.

Peak 3 (Highest)

9:30 pm-12:30 am: BPC should be in the highest therapeutic range of from 2.5 to 5.1 ng/ml.

Figure 28:
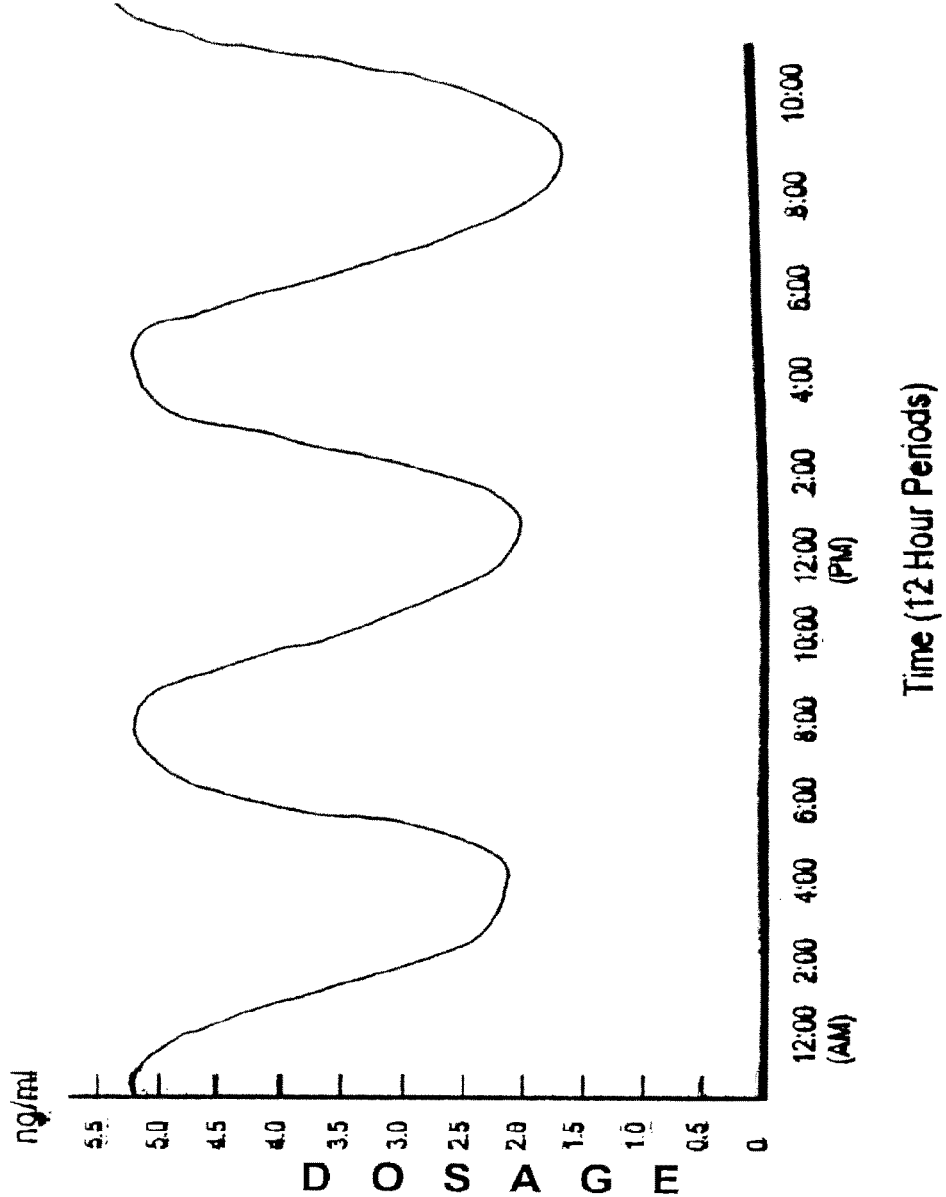
FIG. 28 shows an exemplary administration profile for biperiden delivered by a system of the present invention showing three doses.

The time/dose chart should appear as shown in FIG. 28.

Example—Bromocriptine (Parlodel®)

Bromocriptine mesylate mimics the action of dopamine by fitting into the dopamine pockets on the surface of the nerve cell that is receiving the dopamine message. One advantage of this substitution approach is that dyskinesias are less likely to occur. This is because the amount of dopamine is not actually being increased, as with Levodopa/carbidopa mixtures. Instead, bromocriptine acts as a substitute for dopamine. This makes it less likely for dyskinesias to occur since they are caused by too much dopamine in the brain.

Bromocriptine may cause some people to become drowsy, dizzy, or less alert than they are normally. By taking advantage of the somnolence side effect of bromocriptine, dosing could be optimized using the ChronoDose™ system, with a higher dose given at night. For example, pulsatile delivery should have blood plasma concentrations (BPC) as set forth below within the following ranges at the following times:

Peak 1 (Highest)

11:00 pm-5:00 am: BPC should be in the highest therapeutic range of from 0.70 to 1.0 ng/ml.

Peak 2 (Medium)

6:00 am-1:00 pm: BPC should be in the medium therapeutic range of from 0.85 to 0.45 ng/ml.

Peak 3 (Medium)

2:00 pm-8:00 pm: BPC should be in the medium therapeutic range of from 0.85 to 0.45 ng/ml.

Figure 29:
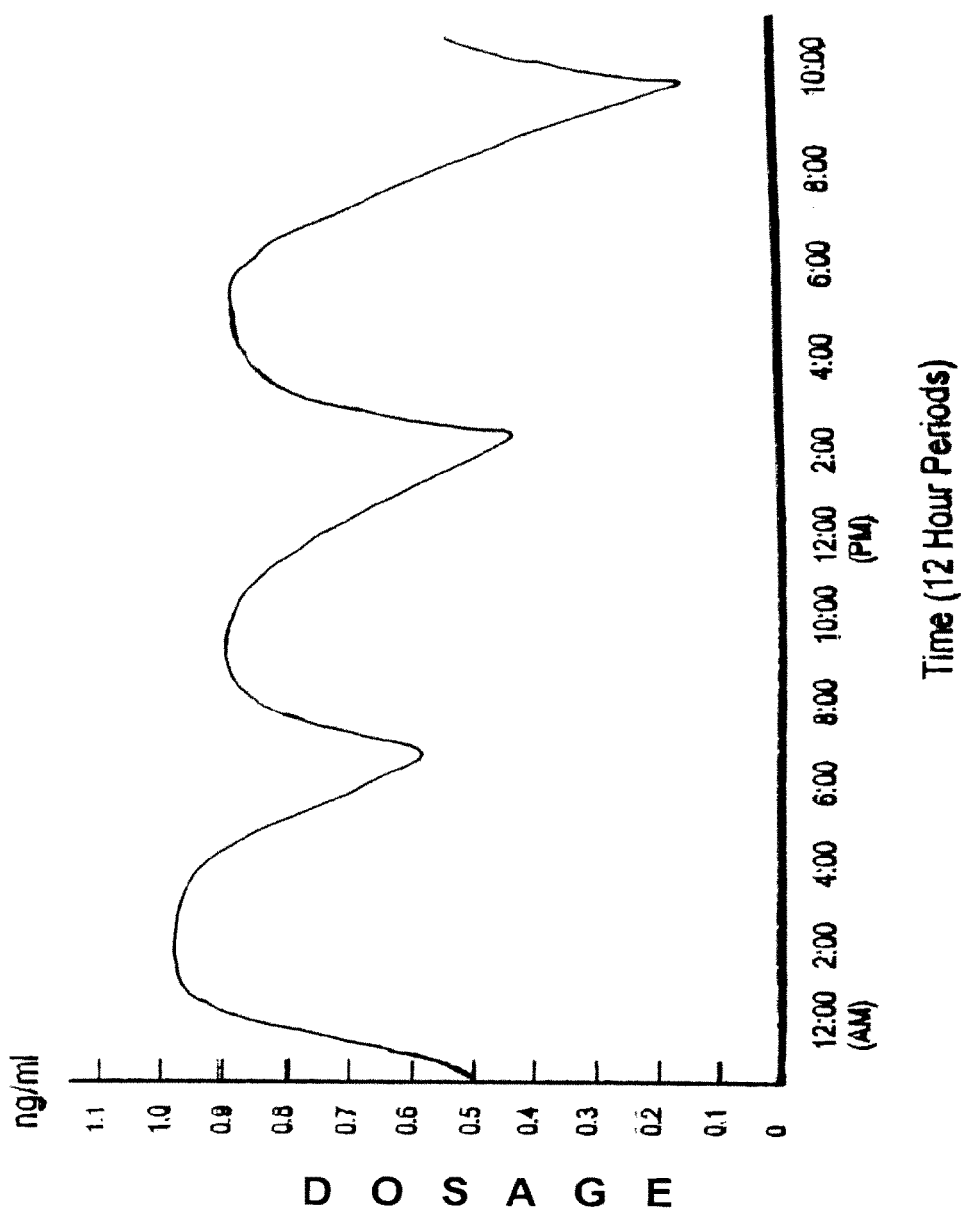
FIG. 29 shows an exemplary administration profile for bromocriptine delivered by a system of the present invention showing three doses.

The time/dose chart should appear as shown in FIG. 29.

Example—Levodopa (Larodopa®)

Within four to six years of treatment with levodopa, the effects of the drug in many patients begin to last for shorter periods of time (called the wearing off effect) and the following pattern may occur:

Patients may first notice slowness (bradykinesia) or tremor in the morning before the next dose is due.

Less commonly, some experience painful dystonia, muscle spasms that can cause sustained contortions of various parts of the body, particularly the neck, jaw, trunk, and eyes and possibly the feet.

Patients must increase the frequency of levodopa doses. This puts them at risk for dyskinesia (the inability to control muscles), which usually occurs when the drug level peaks. Dyskinesia can take many forms, most often uncontrolled flailing of the arms and legs or chorea, rapid and repetitive motions that can affect the limbs, face, tongue, mouth, and neck. Dyskinesia is not painful, but it is very distressing.

In some people, eventually L-dopa is effective only for one to two hours and most patients start to experience motor fluctuations. In about 15% to 20% of patients such fluctuations become extreme, a phenomenon known as the on-off effect, which consists of unpredictable, alternating periods of dyskinesia and immobility. Sometimes the symptoms switch back in forth within minutes or even seconds. The transition may follow such symptoms as intense anxiety, sweating, and rapid heartbeats. In order to reduce the effects of fluctuation and the wearing-off effect, it is important to maintain as consistent a level of dopamine as possible. Unfortunately, oral levodopa is poorly absorbed and may remain in the stomach a long time. Two strategies have been suggested to take care of these problems:

1. Taking multiple small doses on an empty stomach by crushing the pills and mixing them with a lot of liquid.
2. Taking the liquid form of levodopa/carbidopa mixtures, which may produce fewer fluctuations and a prolonged "on" time compared with the tablet.

Figure 30:
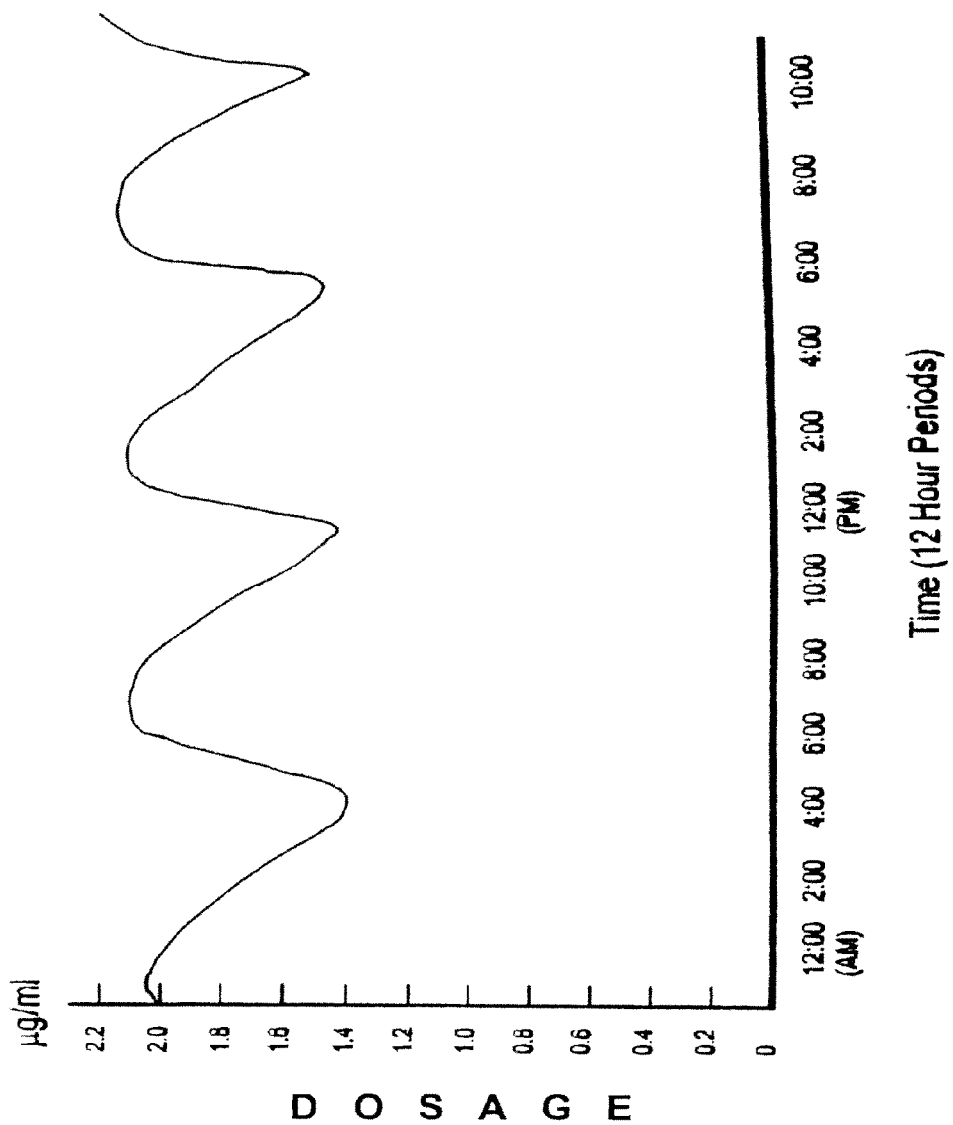
FIG. 30 shows an exemplary administration profile for levodopa delivered by a system of the present invention showing four doses.

Automated, periodic dosing by the ChronoDose™ system can address these immediate concerns. For example, pulsatile delivery should have blood plasma concentrations (BPC) as set forth below within the following ranges at the following times:

For 4 Doses
Peak 1 (Highest)
6:00 am to 8:00 am: BPC should be in the highest therapeutic range of 1.4 to 2.0 µg/ml.
Peak 2 (Highest)
3:00 pm to 5:00 pm: BPC should be in the highest therapeutic range of 1.4 to 2.0 µg/ml.
Peak 3 (Highest)
6:00 am to 8:00 am: BPC should be in the highest therapeutic range of 1.4 to 2.0 µg/ml.
Peak 4 (Highest)
3:00 pm to 5:00 pm: BPC should be in the highest therapeutic range of 1.4 to 2.0 µg/ml.
The time/dose chart should appear as shown in FIG. 30.

Figure 31:
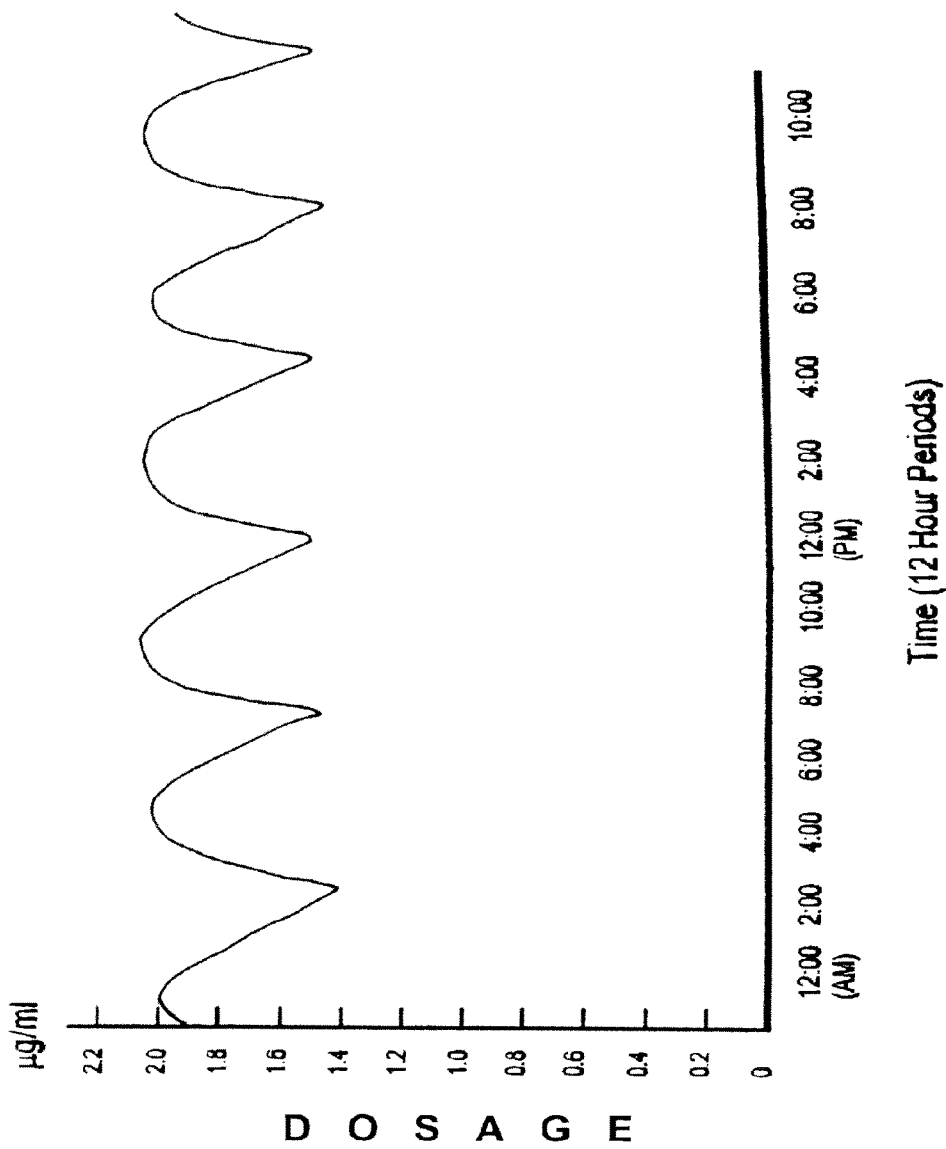
FIG. 31 shows an exemplary administration profile for levodopa delivered by a system of the present invention showing six doses.

For 6 Doses
Peak 1 (Highest)
6:00 am to 8:00 am: BPC should be in the highest therapeutic range of from 1.4 to 2.0
Peak 2 (Highest)
10:00 am to 12:00 pm: BPC should be in the highest therapeutic range of from 1.4 to 2.0
Peak 3 (Highest)
3:00 pm to 5:00 pm: BPC should be in the highest therapeutic range of from 1.4 to 2.0 µg/ml.
Peak 4 (Highest)
6:00 am to 8:00 am: BPC should be in the highest therapeutic range of from 1.4 to 2.0
Peak 5 (Highest)
10:00 am to 12:00 pm: BPC should be in the highest therapeutic range of from 1.4 to 2.0
Peak 6 (Highest)
3:00 pm to 5:00 pm: BPC should be in the highest therapeutic range of from 1.4 to 2.0 µg/ml.
The time/dose chart should appear as shown in FIG. 31.

Figure 32:
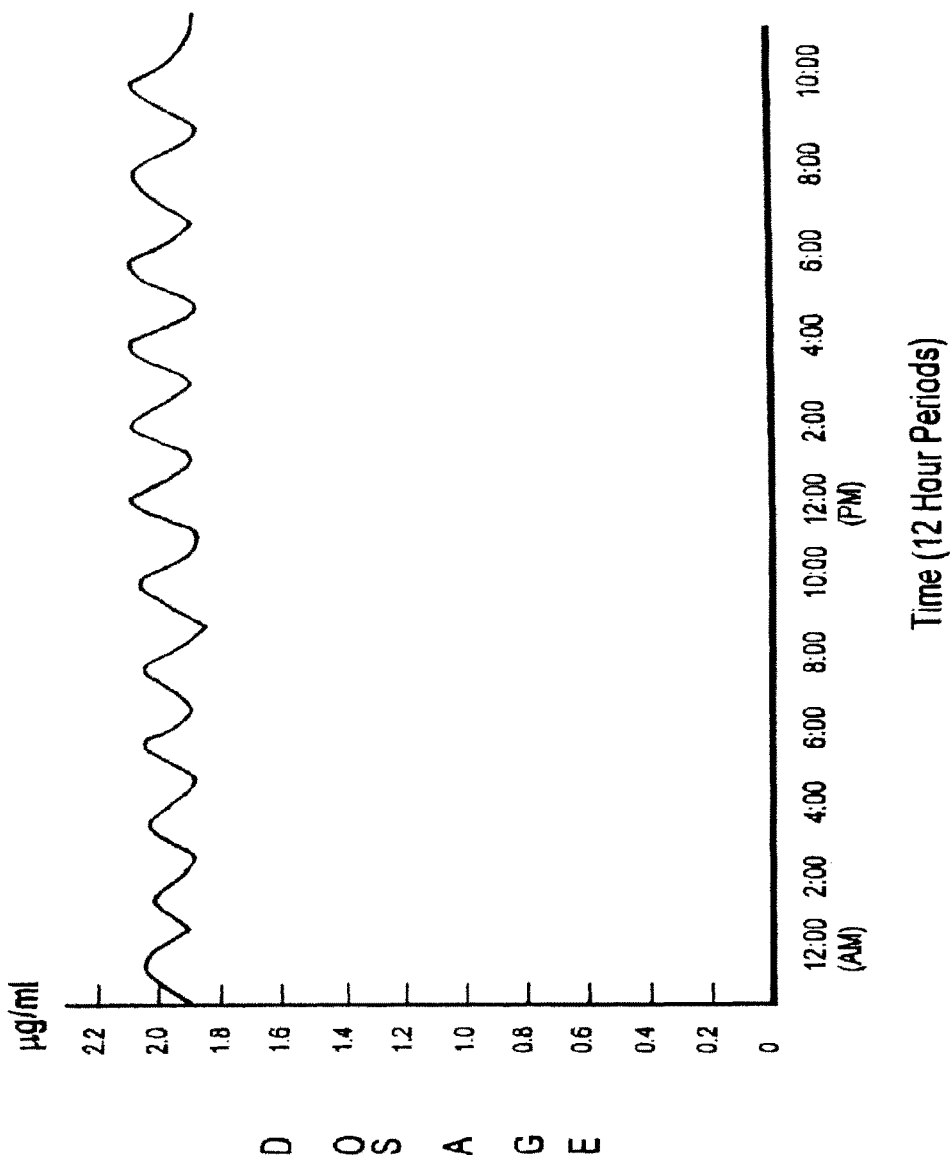
FIG. 32 shows an exemplary administration profile for levodopa delivered by a system of the present invention showing twelve doses.

For 12 Doses
All Peaks1 (Highest)
Every 2 Hrs.: BPC should be in the highest therapeutic range of from 1.4 to 2.0 µg/ml.
The time/dose chart should appear as shown in FIG. 32.

The examples above describe the multiple dosing regimens and plasma blood plasma concentration profiles for the major medications used for Parkinson's disease and serve as models for automated dosing by the ChronoDose™ system. Other medications for Parkinson's disease, as described above, can be dosed in similar fashion and are included herein.

Application—Attention Deficient Disorder (ADD) and/or Attention Deficit-Hyperactivity Disorder (ADHD)

The present invention may be used to treat, cure, prevent, control or alleviate a wide range of conditions and symptoms. In the present invention, the drug delivery regimen is administered to treat the condition of Attention Deficit Disorder (ADD) and/or and attention deficit-hyperactivity disorder (ADHD).

Most tragic are circumstances where children have died of heart failure during recess and periods of physical activity. A device is urgently needed that can turn off during periods of physical activity (recess, after school sports). The transdermal delivery techniques of the present invention allow for programming to increase safety by decreasing blood plasma concentrations of ADD/ADHD medicaments during periods of physical activity so as to decrease adverse side effects of drugs which may contribute to overexertion of the heart.

Medications for attention deficit disorder (ADD) and attention deficit-hyperactivity disorder (ADHD) which may be used in the present invention include:

Stimulants such as methylphenidate (Ritalin®), dextro-amphetamine sulfate
(Dexedrine®) and dextro-amphetamine sulfate with other amphetamine mixture (Adderall®),
Non-stimulants such as atomoxetine (Strattera®)
Antidepressants such as imipramine, desipramine and nortriptyline.
SSRIs such as bupropion HCl (Wellbutrin@ and Zybani®).
Pemoline (Cylert®—not commonly used anymore due to liver damage)
Ampakines such as: CX-516 (Ampalex), CX546, CX614 and CX717.
Newer norepinephrine-selective-uptake inhibitors may be useful in this disorder.

A list of less often prescribed medicines sometimes used together with psychotropics include: citalopram (Celexa®), Clonidine (Catapres®, Dixarit®, Catapres-TTS®), methylphenidate (Concerta®), valproic acid (Depakote®), paroxetine (Paxil®), fluoxetine (Prozac®), risperidone (Risperidal®), carbamazepine (Tegretol®), guanfacine hydrochloride (Tenex®), and sertraline (Zoloft®).

Additional medications used for ADD/ADHD include: dextro-methylphenidate (Focalin®), imipramine (Tofranil®), methylphenidate (Metadate®), methylphenidate HCl (Methylin ER®), desipramine (Norpramine®), nortriptyline (Pamelor®), modafinil (Provigil®) and dextroamphetamine (DextroStat®).

Ritalin® is a registered trademark of Novartis Pharmaceuticals

Adderall® is a registered trademark of Shire US Inc.

Dexedrine® is a registered trademark of GlaxoSmithKline

Strattera® is a registered trademark of Eli Lilly and Company

Wellbutrin® is a registered trademark of GlaxoSmithKline

Zyban® is a registered trademark of GlaxoSmithKline

Cylert® is a registered trademark of Abbott Laboratories

Celexa® is a registered trademark of Forest Pharmaceuticals

Catapres®, Dixarit®, Catapres-TTS® are registered trademarks of Boehringer Ingelheim Concerta® is a registered trademark of ALZA DepaKote® is a registered trademark of Abbott Laboratories Paxel® is a registered trademark of GlaxoSmithKline Prozac® is a registered trademark of Eli Lilly and Company Zoloft® is a registered trademark of Pfizer Inc.

Resperidal® is a registered trademark of Janssen

Tegretol® is a registered trademark of Novartis Pharmaceuticals

Tenex® is a registered trademark of A.H. Robins

Focalin® is a registered trademark of Novartis Pharmaceuticals

Tofranil® is a registered trademark of Novartis Pharmaceuticals

Metadate® is a registered trademark of Celltech

Methylin® is a registered trademark of Mallinckrodt

Norpramine® is a registered trademark of Avenis Pharmaceuticals

Pamelor® is a registered trademark of Sandoz Pharmaceuticals

DextroStat® is a registered trademark of Shire

Provigil® is a registered trademark of Cephalon, Inc.

Example—Methylphenidate (Ritalin®)

Methylphenidate (Ritalin®) is indicated as an integral part of a total treatment program which typically includes other remedial measures (psychological, educational, social) for a stabilizing effect in children with a behavioral syndrome characterized by the following group of developmentally inappropriate symptoms: moderate-to-severe distractibility, short attention span, hyperactivity, emotional lability, and impulsivity.

Methylphenidate is usually administered in divided doses 2 or 3 times daily, preferably 30 to 45 minutes before meals. Patients who are unable to sleep if medication is taken late in the day should take the last dose before 6 p.m. Since the suggested first dose is early in the morning, it would be beneficial to automatically control the dosage.

Thus, dosing could be optimized using the ChronoDose™ system. For example, pulsatile delivery should have blood plasma concentrations (BPC) as set forth below within the following ranges at the following times:

For 2 doses
Peak 1 (Highest)
6:00 am-8:00 am: BPC should be in the highest therapeutic range of 8-25 ng/ml.
Peak 2 (Highest)
3:00 pm-5:00 pm: BPC should be in the highest therapeutic range of from 8 to 25 ng/ml.
For 3 Doses
Peak 1 (Highest)
6:00 am-8:00 am: BPC should be in the highest therapeutic range of 8-25 ng/ml.
Peak 2 (Highest)
10:00 am to 12:00 pm: BPC should be in the highest therapeutic range of 8-25 ng/ml.
Peak 3 (Highest)
3:00 pm-5:00 pm: BPC should be in the highest therapeutic range of from 8 to 25 ng/ml.

Figure 33:
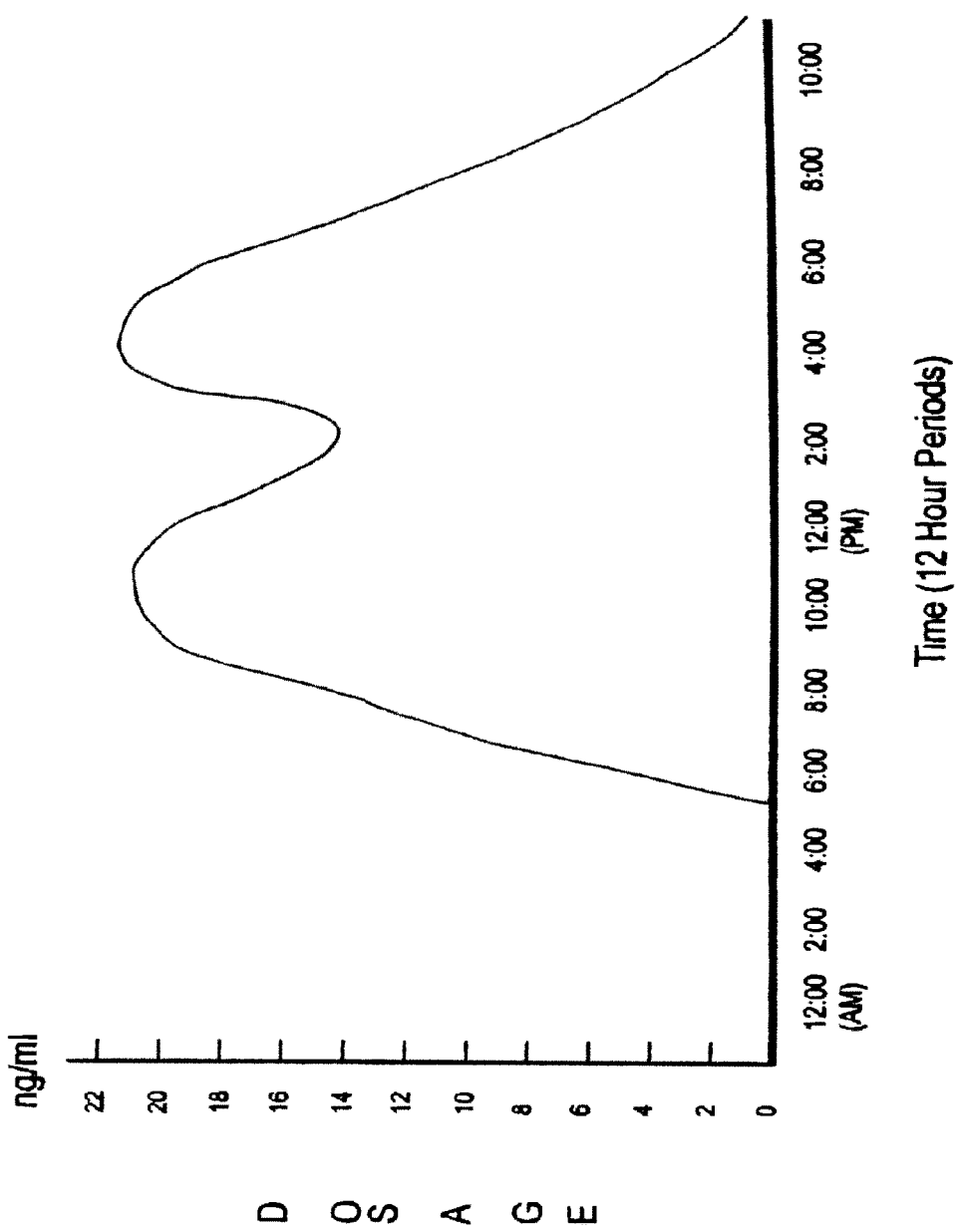
FIG. 33 shows an exemplary administration profile for methylphenidate (Ritaline®) delivered by a system of the present invention showing two doses.
Figure 34:
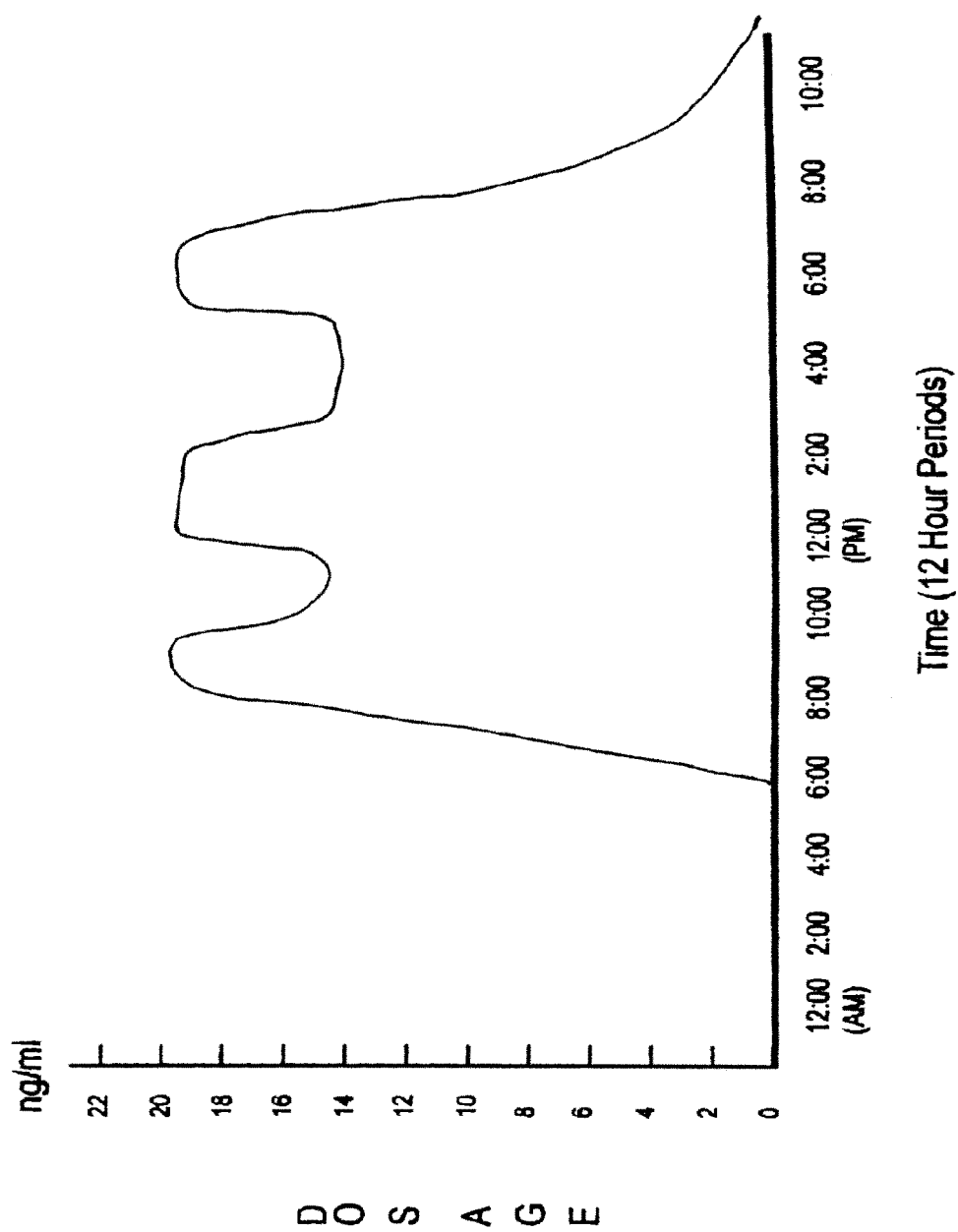
FIG. 34 shows an exemplary administration profile for methylphenidate (Ritaline®) delivered by a system of the present invention showing three doses.

The time/dose charts should appear as shown in FIGS. 33 and 34.

Example—Dextro-Amphetamine (Adderall®)

Dextro-amphetamine and dextro-amphetamine sulfate with other amphetamine complexes (Adderall®) is also prescribed as an integral part of a total treatment program which typically includes other remedial measures (psychological, educational, social) for a stabilizing effect in children with a behavioral syndrome characterized by the following group of developmentally inappropriate symptoms: moderate-to-severe distractibility, short attention span, hyperactivity, emotional lability, and impulsivity.

Dextro-amphetamine is usually administered as a single dose 1 or 2 times daily, preferably at 8:00 AM and 4:00 PM. Less overall side effects and dose equivalence were experienced with lower doses of Adderall®, when compared to higher doses of methylphenidate (1:2 ratio, Adderall® to Ritalin®). Since the suggested first dose is early in the morning, it would be beneficial to automatically control the dosage.

Thus, dosing could be optimized using the ChronoDose™ system. For example, pulsatile delivery should have blood plasma concentrations (BPC) as set forth below within the following ranges at the following times:
Peak 1 (Highest)
6:00 am-8:00 am: BPC should be in the highest therapeutic range of 8-15 ng/ml.
Peak 2 (Highest)
3:00 pm-5:00 pm: BPC should be in the highest therapeutic range of from 8 to 15 ng/ml.

Figure 35:
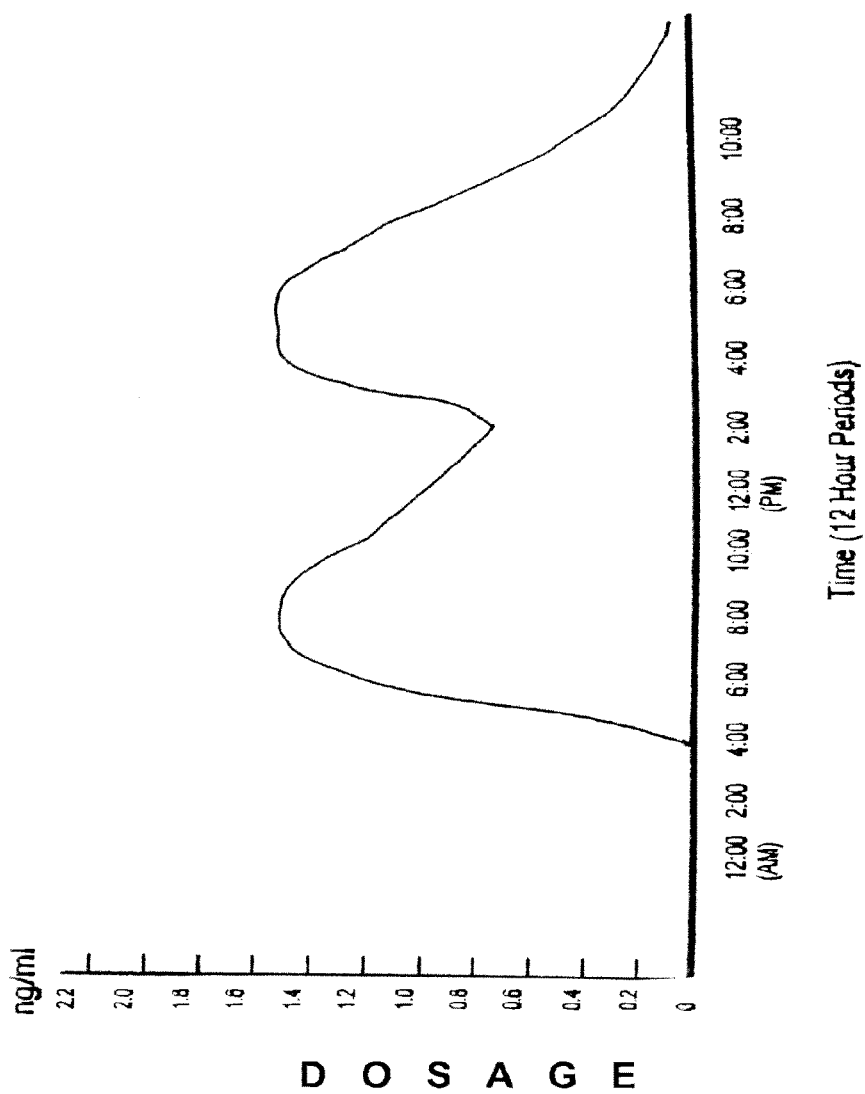
FIG. 35 shows an exemplary administration profile for dextro-amphetamine (Adderall®) delivered by a system of the present invention.

The time/dose chart should appear as shown in FIG. 35.

Example—Atomoxetine (Strattera®)

Studies of atomoxetine clearly demonstrate short-term efficacy relative to placebo in reducing both inattentive and hyperactive/impulsive ADHD symptoms and improving family and social functioning. A preliminary 9-week, open-label study, reported by Kratochvil and colleagues compared atomoxetine to a stimulant medication. Both atomoxetine and methylphenidate were associated with reductions in ADHD symptoms and improved global ratings in children aged 7 to 15, according to parent and clinician ratings. Atomoxetine (administered twice daily) and methylphenidate (administered either 2 or 3 times daily) were both well tolerated, with vomiting, insomnia, and weight loss reported more often for the group receiving atomoxetine.

Additionally, atomoxetine is prescribed using weight based dosing, usually 1.2 mg/kg/day to be taken twice a day. The peak plasma concentration occurs at 1-2 hrs. after dosing, with a half-life average of 3.12 hours.

Atomoxetine, with its different mechanism of action, is associated with a slightly different side-effect profile than stimulant medications, particularly increased somnolence and gastrointestinal symptoms in children. These side effects can be reduced or eliminated using a transdermal system. For individuals at risk of stimulant abuse, or who display stimulant-related side effects, which are not transitory, or insignificant (eg, severe stimulant-induced insomnia or tics), atomoxetine and other non-stimulants provide a welcome alternative.

The examples above describe the multiple dosing regimens and plasma blood plasma concentration profiles for the major ADD/ADHD medications and serve as models for automated dosing by the ChronoDose™ system. Other medications for ADD/ADHD, as described above, can be dosed in similar fashion and are included herein.

Application—Nicotine Addiction

Example—Smoking Cessation

The present invention may be used to treat, cure, prevent, control or alleviate a wide range of conditions and symptoms. In the present invention, the drug delivery regimen is administered to treat the condition of smoking and nicotine addiction.

Medications and substances for smoking cessation, which may be used in the present invention include:
Stimulants such as nicotine or nicotine analogs.
Anti-depressants such as Bupropion (Zyban®).
Partial nicotinic agonists such as Varenicline (Chantix®).
Anticholinergic drugs such as atropine and scopolamine
Other medications such as Rimonabant (a CB-1 receptor blocker), herbals, *plantago major*, botanicals, phytochemicals, phytonutrients, plant extracts, naturopathic, homeopathic drugs and substances, nutraceticals and others.

Example—Nicotine

Nicotine replacement has been the most frequently used therapy to support smokers in their effort to quit. Smokers report that the craving for a cigarette is greatest immediately upon waking in the morning. The time elapsed between wakening and the first cigarette is the best indicator of addiction. For most smokers this period of time is only a few minutes. Additionally, research has shown that nicotine transdermal delivery is influenced by chronopharmacokinetics. Nicotine patch design should compensate by decreasing the dose at night as well as increasing the dose in the morning and after meals (Gries et al., 1998).

Chronotherapeutic Rationale:

Current nicotine patches cause severe sleep disturbances by releasing nicotine steadily throughout the night to ensure sufficient morning nicotine levels to offset the strong morning craving. It is widely accepted that current nicotine patches have a detrimental and common side effect-sleeping disorders, and insomnia, including persistent nightmares. Therefore, users are often forced to remove the patch in the evening before they go to bed. This eliminates sleep disturbances, but results in nicotine levels that are insufficient to offset the strong morning craving. This is a major drawback to current nicotine patches and many users relapse, resulting in a less efficient smoking cessation therapy. Current patches present the user with a difficult decision, choosing between nightmares and relief from the strong morning cravings.

An exemplary product contemplated by the present invention is called Nicotine ChronoDose™ system. In accordance with the present invention, the system can begin to administer nicotine (or nicotine analogs or any other smoking cessation compound) automatically during a one-hour period immediately prior to waking. This will relieve the smoker's peak craving upon waking without causing nightmares and insomnia. We believe that this system clearly provides a superior method for smoking cessation.

A more advanced nicotine replacement system than that described above is worn for three days at a time and is programmed to release nicotine in a daily rhythmic pattern such as shown in FIG. 8 to offset peaks in a smoker's cravings. FIG. 8 illustrates an exemplary nicotine administration profile showing a blood plasma level of nicotine in nanograms per milliliter on the vertical axis, with time on the horizontal axis. This implementation will reduce nicotine dependency by administering pre-programmed levels of nicotine pursuant to typical smoking patterns. For instance many smokers report that cravings for a cigarette are greatest upon waking up, after lunch, mid afternoon, after dinner and before bedtime. This implementation of the present invention will automatically release larger doses of nicotine to offset peak cravings and no nicotine when cravings are typically at a minimum. The present invention may be delivered in a preprogrammed manner for each treatment regimen. The only involvement by the user will be the replacement of the 'reservoir' every three days, and the replacement of the platform housing as needed.

This implementation represents a tremendous move forward in nicotine replacement therapy, and is far superior to the old-technology systems that simply release the same amount of nicotine all day and night. With the present invention, one can systematically decrease a smoker's tolerance without increasing dependence (the result of a constant flow) and better wean a smoker off nicotine, as shown in FIGS. 9 and 10. This will allow the smoker to better 'tailor-down' and decrease the amount of nicotine he needs to quit. Modern smoking cessation is much more than nicotine replacement therapy. Programs also include weight control, diet and psychological support. The present invention fits well into these programs, since it addresses the key component of being able to quit smoking by efficiently countering the withdrawal symptoms while doing away with the negative side effects of current nicotine replacement therapy systems, namely sleep disturbance.

Figure 36:
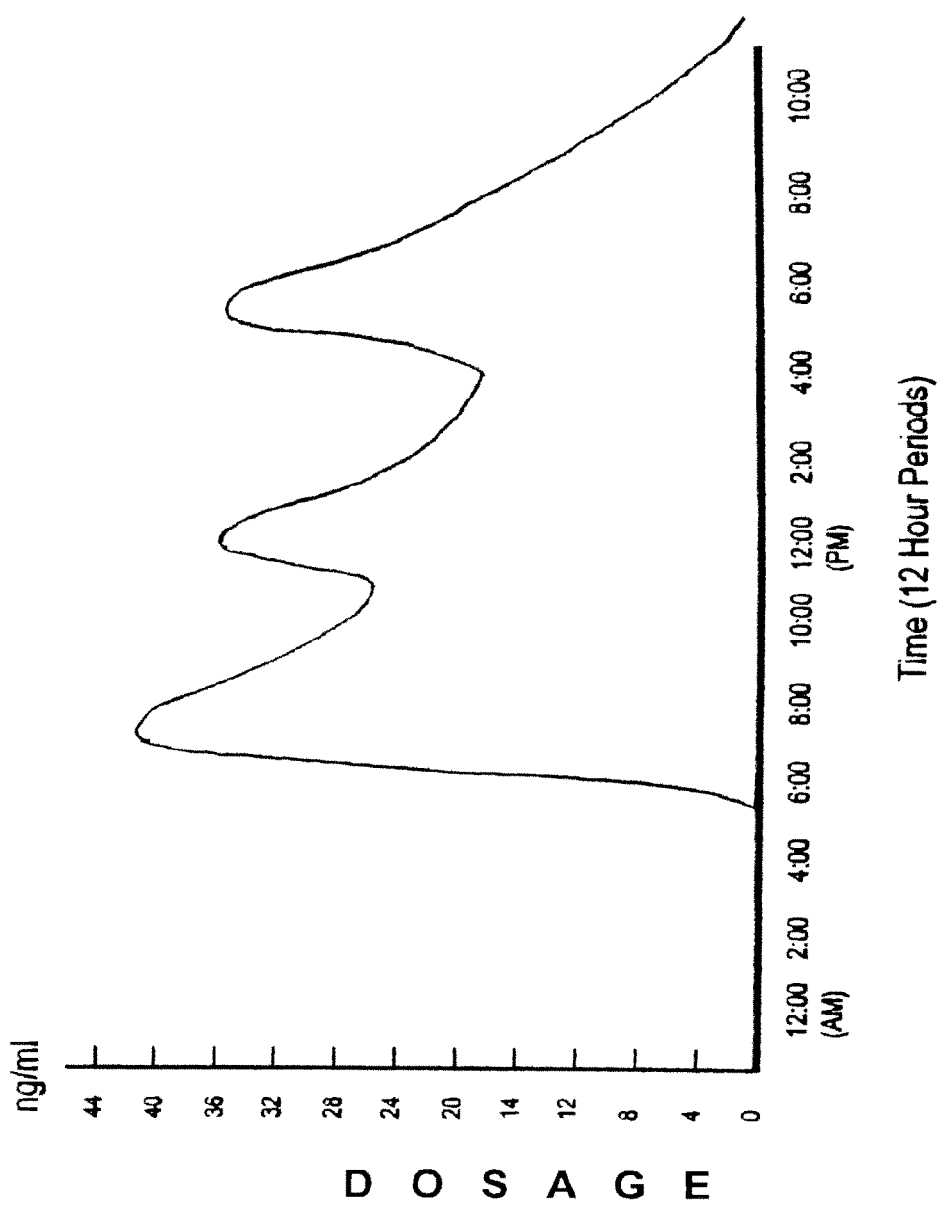
FIG. 36 shows an exemplary administration profile for full strength (Phase I) nicotine delivery system.

Thus, dosing could be optimized using the ChronoDose™ system. For example, pulsatile delivery should have blood plasma concentrations (BPC) as set forth below within the following ranges at the following times:

Phase I
Peak 1 (Highest)
6:00 am-10:00 am: BPC should be in the highest therapeutic range of from 44 to 24 ng/ml.
Peak 2 (Medium)
12:00 pm-2:00 pm: BPC should be in the medium therapeutic range of from 38 to 24 ng/ml.
Peak 3 (Lowest)
5:00 pm-7:00 pm: BPC should be in the medium therapeutic range of from 38 to 18 ng/ml.
The time/dose chart should appear as shown in FIG. 36.
Phase II
Peak 1 (Highest)
6:00 am-10:00 am: BPC should be in the highest therapeutic range of from 28 to 12 ng/ml.

Peak 2 (Medium)

12:00 pm-2:00 pm: BPC should be in the medium therapeutic range of from 23 to 12 ng/ml.

Peak 3 (Lowest)

5:00 pm-7:00 pm: BPC should be in the lowest therapeutic range of from 20 to 8 ng/ml.

Figure 37:
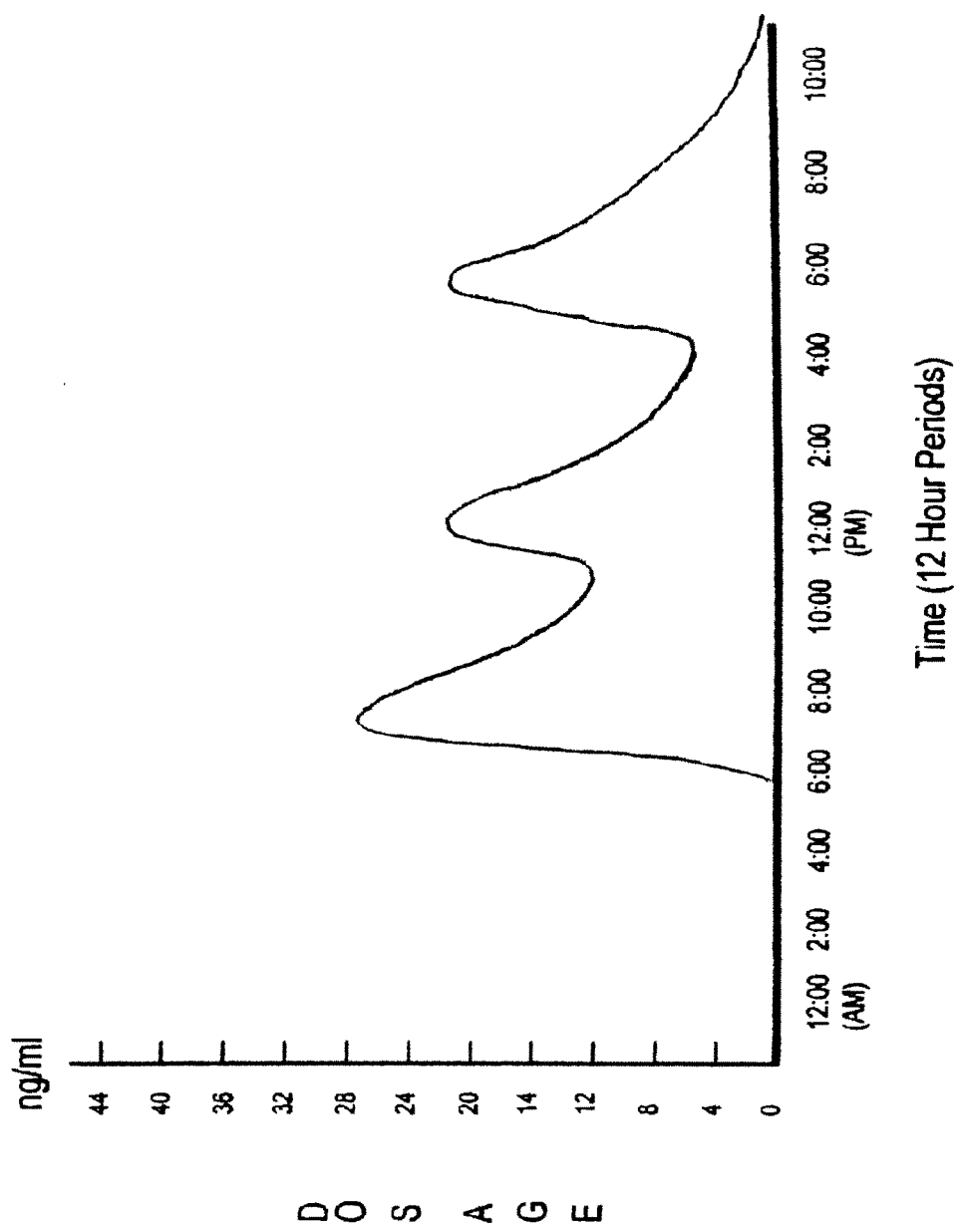
FIG. 37 shows an exemplary administration profile for reduced strength (Phase II) nicotine delivery system.

The time/dose chart should appear as shown in FIG. 37.

Phase III

Peak 1 (Highest)

6:00 am-10:00 am: BPC should be in the highest therapeutic range of from 18 to 8 ng/ml.

Peak 2 (Medium)

12:00 pm-2:00 pm: BPC should be in the medium therapeutic range of from 12 to 6 ng/ml.

Peak 3 (Lowest)

5:00 pm-7:00 pm: BPC should be in the lowest therapeutic range of from 10 to 4 ng/ml.

Figure 38:
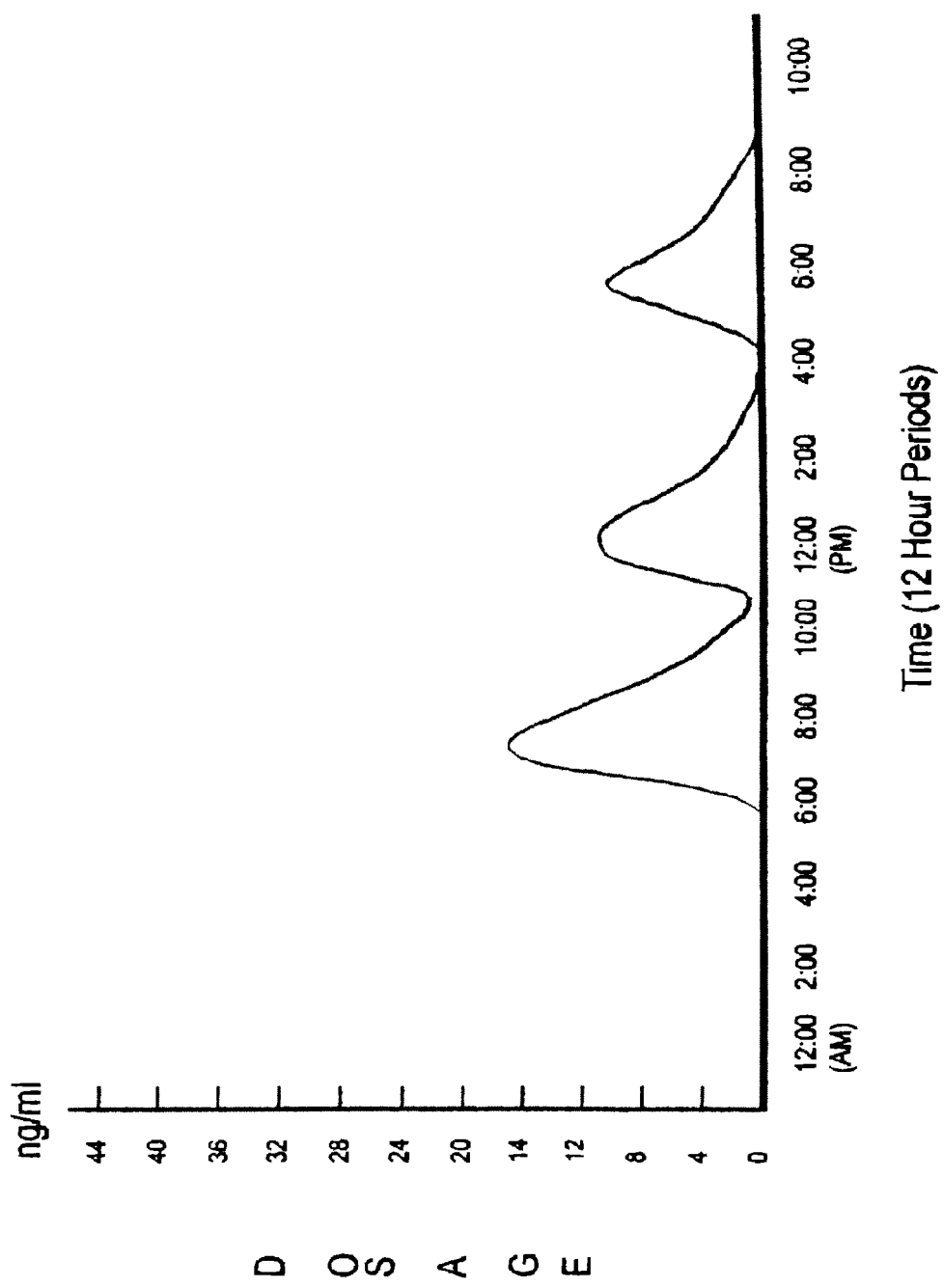
FIG. 38 shows an exemplary administration profile for minimal strength (Phase III) nicotine delivery system.

The time/dose chart should appear as shown in FIG. 38.

Example—Bupropion (Zyban®)

Bupropion (Zyban) is a prescription antidepressant in an extended-release form that reduces symptoms of nicotine withdrawal. It does not contain nicotine. This drug affects chemicals in the brain that are related to nicotine craving. It can be used alone or together with nicotine replacement. Some doctors may recommend combination drug therapy for heavily addicted smokers, such as using bupropion along with a nicotine replacement patch and/or a short acting from of nicotine replacement (such as gum or lozenges).

Thus, dosing could be optimized using the ChronoDose™ system. For example, pulsatile delivery should have blood plasma concentrations (BPC) as set forth below within the following ranges at the following times:

Peak 1 (Highest)

6:00 am-8:00 am: BPC should be in the highest therapeutic range of from 80 to 140 ng/ml.

Peak 2 (Highest)

2:00 pm-4:00 pm: BPC should be in the highest therapeutic range of from 80 to 140 ng/ml.

Peak 3 (Highest)

10:00 pm-12:00 am: BPC should be in the highest therapeutic range of from 80 to 140 ng/ml.

Figure 39:
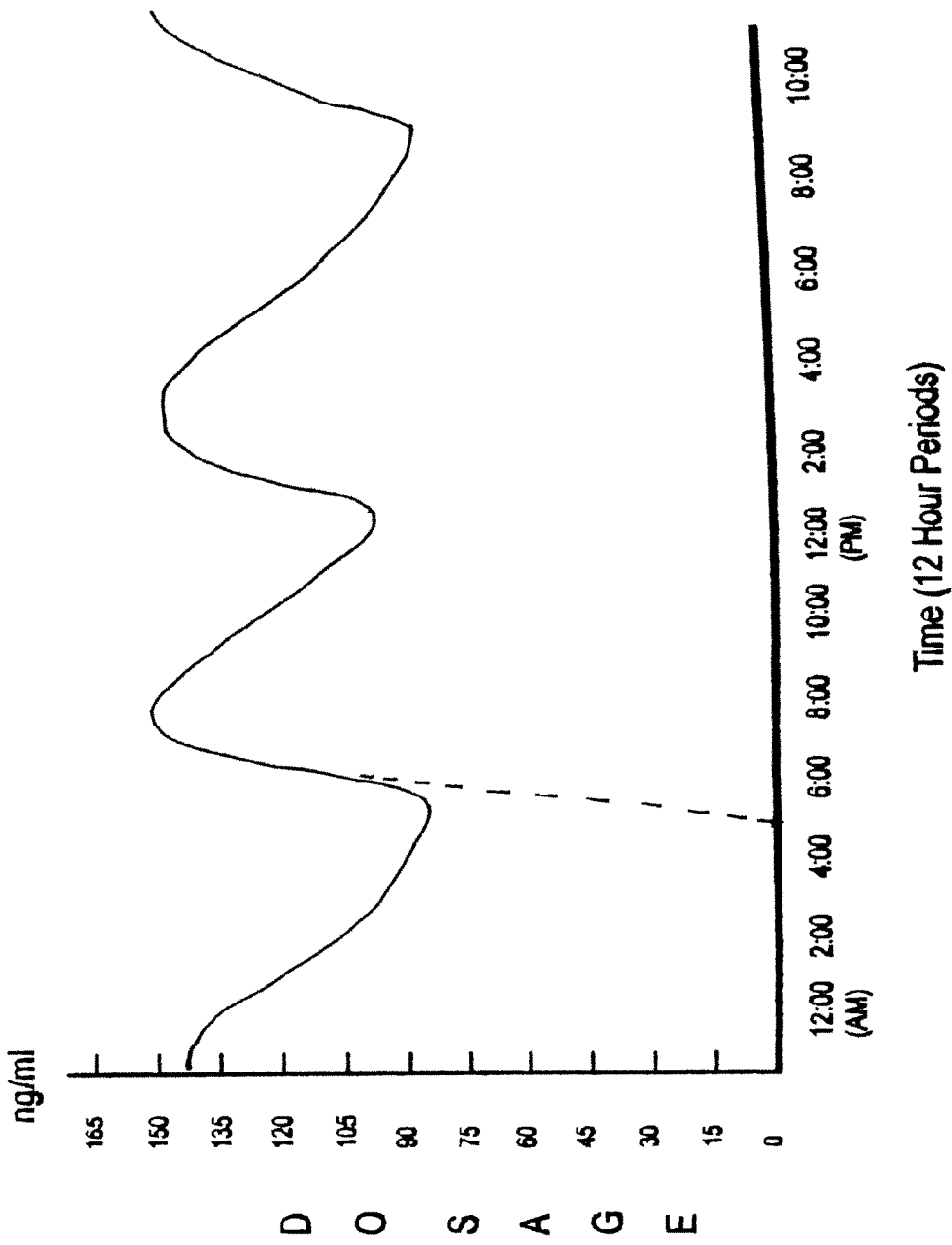
FIG. 39 shows an exemplary administration profile for a bupropion delivery system.

The time/dose chart should appear as shown in FIG. 39.

Example—Varenicline (Chantix®)

Varenicline (Chantix®) is a newer medicine developed specifically to help people stop smoking. It stimulates dopamine production as well as blocking nicotine receptors in the brain. It works by interfering with nicotine receptors in the brain, which has two effects. It lessens the pleasurable physical effects a person gets from smoking, as well as reducing the symptoms of nicotine withdrawal.

Several studies have shown varenicline can more than double the chances of quitting smoking. Some studies have also found it may be more effective than bupropion, at least in the short term. Reported side effects of varenicline, however, have included headaches, nausea, vomiting, trouble sleeping, unusual dreams, flatulence (gas), and changes in taste.

Other Medications:

Atropine and scopolamine combination therapy: Some smoking cessation clinics offer a program using shots of the anticholinergic drugs atropine and scopolamine to help reduce nicotine withdrawal symptoms. These drugs are more commonly prescribed for other reasons, such as digestive system problems, motion sickness, or Parkinson's disease.

For example, the drug delivery regimen of the present invention is administered to treat a condition selected from the group consisting of vitamin and/or mineral deficiency, Cancer, Addiction, Arthritis, Parkinson's Disease, Attention Deficit Disorder, Cardiovascular Disorder, Cold/Flu Symptoms, Pain, Childhood Bronchial Asthma, Peptic Ulcer, Post-operative Recuperation, and so forth as shown below.

Application—Angina

Example—Nitroglycerin

Research shows that variant angina occurs 30 times more often between 2:00 a.m. and 4:00 a.m. ('critical angina phase') than at any other time of the day. Nitroglycerin effectively combats angina attacks, if administered in optimal doses. Current nitroglycerin patches exist, but they can only release a constant amount of nitroglycerin steadily over time. Current patches cannot tailor the release of nitroglycerin to optimize treatment by releasing more nitroglycerine precisely during the critical angina phase to offset these peak symptoms.

In addition, nitroglycerine loses its effectiveness and requires higher and higher dosages when administered constantly. Our bodies become tolerant to it. Current systems cannot stop or decrease the release of nitroglycerine when disease symptoms are lowest. Thus, these current 'dumb' patches cannot offset the critical angina phase by releasing more of the drug, nor can they shut down or stop nitroglycerin administration when the body doesn't need it. It is a 'one dose fits all' type of scenario once each "dumb" patch is applied to the patient.

Chronotherapeutic Rationale:

The method in accordance with the present invention utilizes an automated transdermal system in order to transdermally administer more nitroglycerin during the critical angina phase to ensure adequate offset of these symptoms and less nitroglycerin when it is not needed so that no tolerance builds up. Our method utilizes a 'smart' patch medicine system at this time to offset these peak critical phases in the disease cycle arising due to the human body's circadian rhythm.

The pre-programmable automated transdermal system is worn around the wrist-like a watch (or the forearm arm or ankle) and releases nitroglycerin in optimal dosages at times that are optimally synchronized. This is pursuant to a pre-programmed and tailored dosage profile. Current nitroglycerin patches only have the capability to release a constant dose of nitroglycerin over a period of time. Current nitroglycerin patches simply cannot alter or vary dosages to increase dosages at different times of the day, and decrease dosages at other times of the day.

The nitroglycerin system in accordance with the present invention has three primary advantages over current nitroglycerin patches. First, the system automatically and precisely releases nitroglycerin in peak amounts to offset the peak symptoms of morning attacks occurring during the critical angina phase. Current nitroglycerin patches have release rates that stay constant and do not increase to offset critical phases, and do not decrease as symptoms decrease. Second, our system solves the tolerance issue by releasing less (or no) nitroglycerin in off-peak hours, and then releasing nitroglycerin at just the right time so that it is present during critical periods, without increasing tolerance. Third, our system accomplishes 1 and 2 above automatically, without the need for a patient to wake up to take a drug at this critical phase, which does away with the need for any increased patient compliance.

The nitroglycerin system represents an ideal delivery system for patients who use nitroglycerin regularly for the treatment and/or the prevention of heart attacks and strokes. Patient compliance regarding the timing and dose of heart attack medication is crucial. Patient non-compliance with physician's instructions for this is often a cause of re-hospitalization, according to the US Department of Health and Human Services. The system solves this problem, and will decrease the need for re-hospitalization by dramatically increasing patient compliance.

This system can be either an 'wear each night and remove in the morning' system, whereby it only releases nitroglycerin automatically to offset the critical angina phase in the morning, or a 'total solution' system, that is worn for a period of 24 hours to several days, and that administers nitroglycerin in tailored amounts and at tailored times as synchronized with the body's circadian rhythm (and conveniently taken off while showering or swimming)

The system is an innovative new drug therapy for angina. With the advantage of optimized and automated time and dose administration synchronized with a person's circadian rhythms, the system in accordance with the present invention ensures that nitroglycerin will circulate in the bloodstream exactly when the patient needs it, and without any build up tolerance. For these reasons, the present invention is superior to current steady release nitroglycerin patches. Our system's increased advantages are extremely relevant for those patients with moderate to severe angina.

Figure 41:
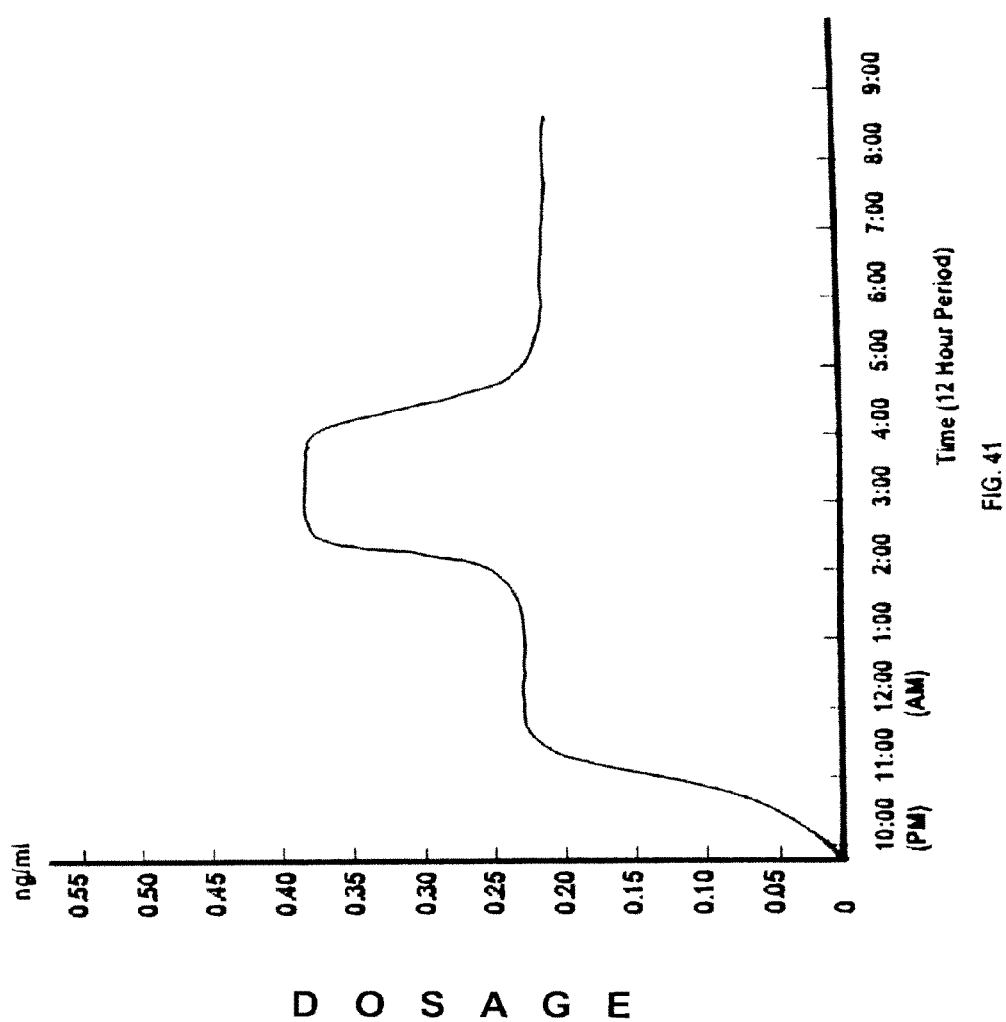
FIG. 41 shows an exemplary administration profile for a nitroglycerin delivery system tailored to treat variant angina attacks.

FIG. 41 shows an exemplary administration profile for a nitroglycerin delivery system tailored to treat variant angina attacks or angina pectoris. This type of angina attack has a peak frequency in many patients between the hours of 2:00 and 4:00 AM. This is a particularly difficult time to wake up to take a drug such as nitroglycerin. In accordance with the present invention an administration profile substantially like that shown in FIG. 41 is automatically administered. In FIG. 41 the vertical axis indicates blood plasma level in nanograms per milliliter, and the horizontal axis indicates time from 10:00 PM through the night to 8:00 AM.

Figure 42:
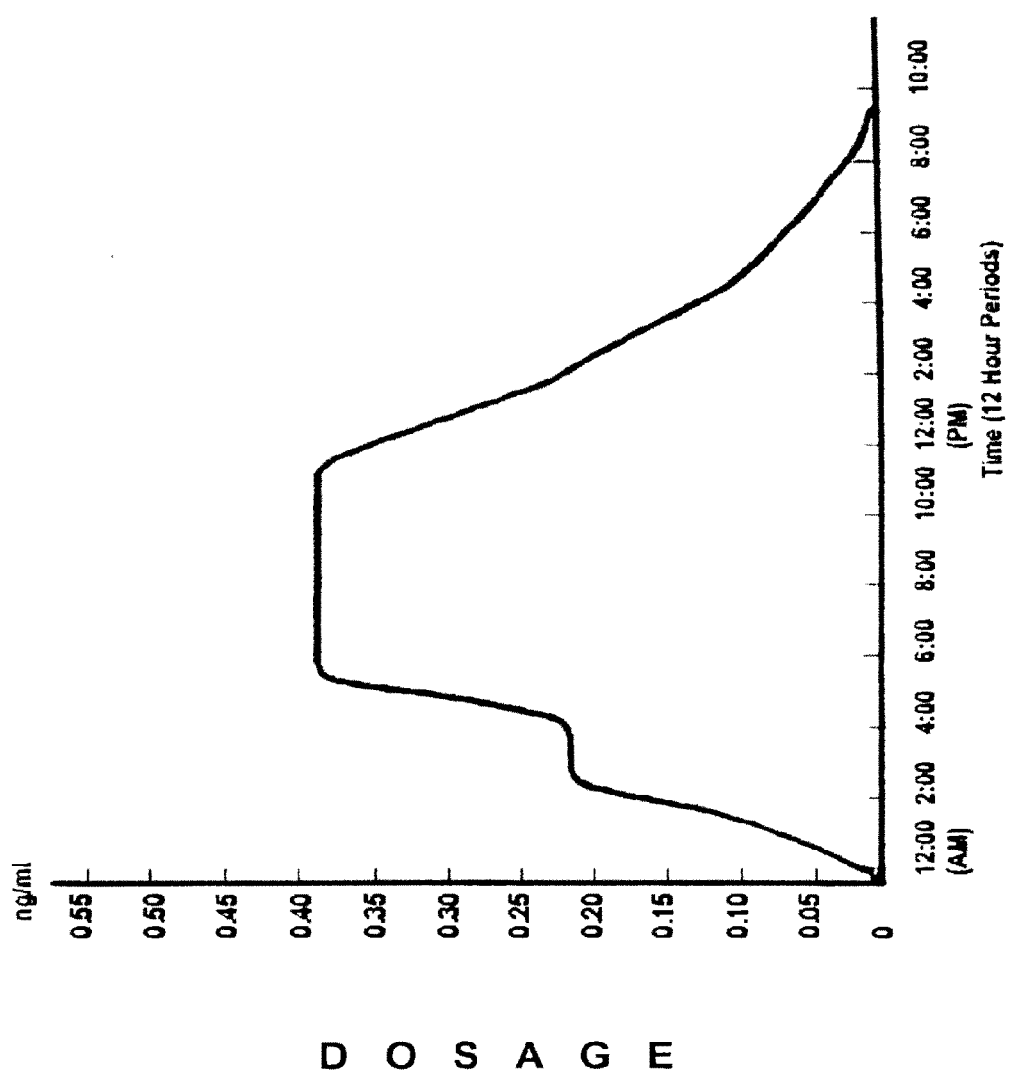
FIG. 42 illustrates an exemplary administration profile for a nitroglycerin delivery system tailored to treat stress-induced angina attack.

FIG. 42 illustrates an exemplary administration profile for a nitroglycerin delivery system tailored to treat stress-induced angina attack. In FIG. 42 the vertical axis indicates blood plasma level in nanograms per milliliter, and the horizontal axis indicates time from 12:00 AM through the day until about 4:00 PM. The administration profile shown in FIG. 42 provides a high blood plasma concentration throughout the waking hours of a day when stress is likely occur.

Application—Arthritis

Examples—Indomethacin, Valdecoxib

An automated, and programmed, pulsatile drug delivery regimen is desired to in order to increase drug concentrations automatically in the morning, just before a person awakes and the symptoms of arthritis are the worst. Later, towards mid-day, the drug concentration is also increased. Then in the evening, the drug dose is increased prior to bedtime.

Chronotherapeutic Rationale:

The most common forms, osteoarthritis and rheumatoid arthritis, both show distinctive circadian patterns of pain. While many people feel stiff for an hour or so after first getting up in the morning, people with osteoarthritis typically hurt most and have the most difficulty moving in the afternoon and evening. Those with rheumatoid arthritis almost always feel much worst in the morning. By dosing at night, early morning and mid-day, the benefits of non-steroidal anti-inflammatory drugs (NSAIDs) and cyclocoygenase-2 inhibitors (COX-2) can be maximized and side effects reduced.

Examples of medications for arthritis include:

Indomethacin (Indocin®)

Diclofinac (Voltarin® and Cataflam®)

Flurbiprofen (ANSAID®)

Celecoxib (Celebrex®)

Valdecoxib (Bextra®)

Acetomenophen (Tylenol®)

Oxaceprol

Example—Indomethacin (NSAID)

The primary adverse side effect of Indomethacin is gastrointestinal upset and bleeding.

Therefore a transdermal arthritis patch would be a beneficial dosage form as opposed to oral tablets and capsules. Additionally, studies using indomethacin showed better efficacy and patient compliance when dosed at night than when dosed at 8:00 am.

Theoretical unenhanced transdermal flux for indomethacin (Berner-Cooper predictive model) is 0.93 ug/cm2/hr.

Thus, dosing could be optimized using the ChronoDose™ system. For example, pulsatile delivery should have blood plasma concentrations (BPC) as set forth below within the following ranges at the following times:

Peak 1 (Highest)

5:00 am-9:00 am: BPC should be in the highest therapeutic range of 0.5-2.0 mcg/ml.

Peak 2 (Medium)

12:00 pm to 8:00 pm: BPC should be in the medium therapeutic range of 0.25-1.5 mcg/ml.

Peak 3 (Highest)

8:00 pm-11:00 pm: BPC should be in the highest therapeutic range of from 0.5 to 2.0 mcg/ml.

Figure 43:
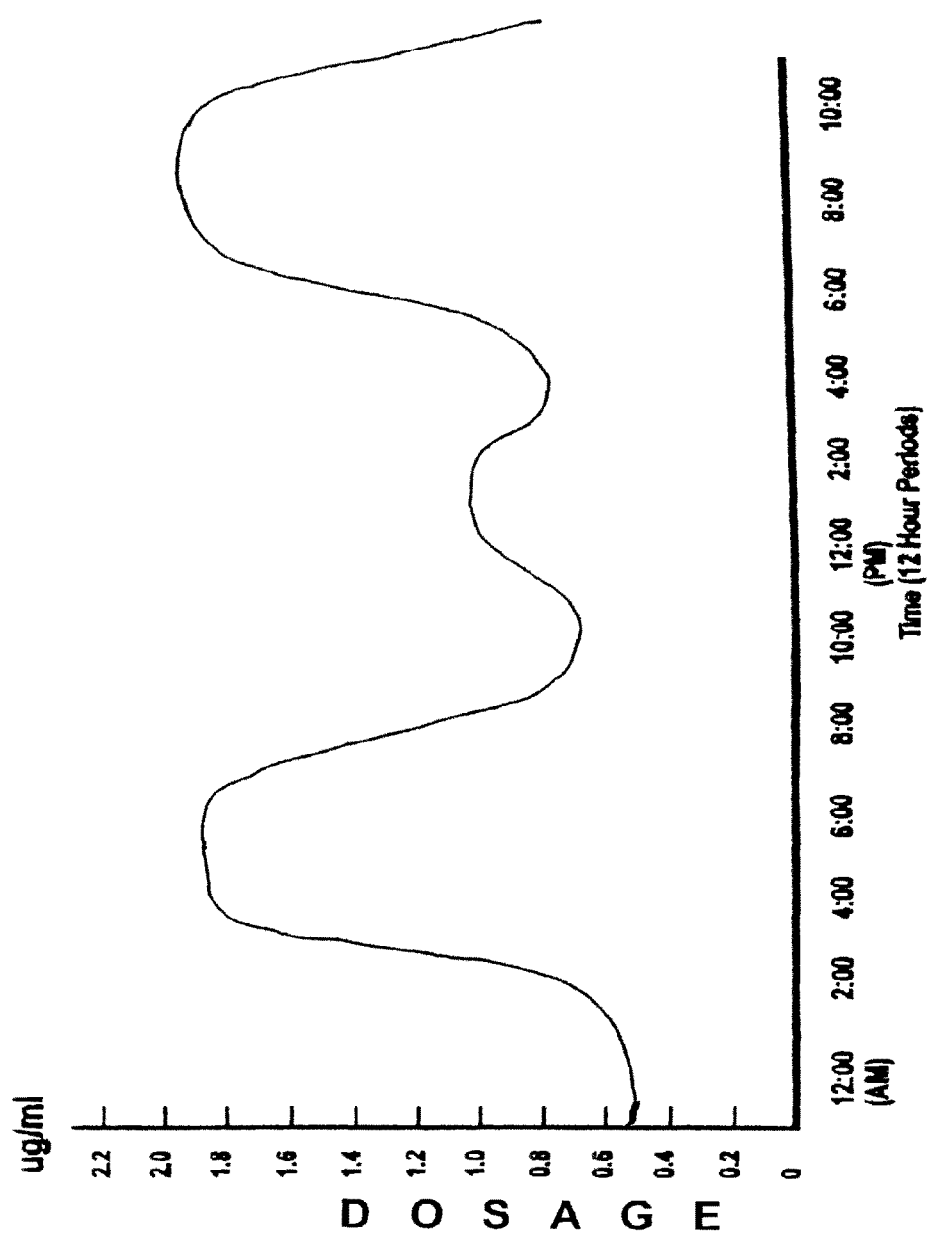
FIG. 43 illustrates an exemplary administration profile for an indomethacin delivery system tailored to arthritis.

The time/dose chart should appear as shown in FIG. 43.

Example—Valdecoxib (COX-2 Inhibitor)

Like indomethacin, the primary adverse side effect of COX-2 inhibitors is gastrointestinal upset and bleeding. Therefore a transdermal arthritis patch would be a beneficial dosage form as opposed to oral tablets and capsules. Lower blood plasma concentrations of COX-2 inhibitors delivered transdermally has been suggested as therapeutically equivalent to higher BPC obtained by oral dosing.

Thus, dosing could be optimized using the ChronoDose™ system. For example, pulsatile delivery should have blood plasma concentrations (BPC) as set forth below within the following ranges at the following times:

Peak 1 (Highest)

5:00 am-9:00 am: BPC should be in the highest therapeutic range of 50-175 ng/ml.

Peak 2 (Medium)

12:00 pm to 8:00 pm: BPC should be in the medium therapeutic range of 21-125 ng/ml.

Peak 3 (Highest)

8:00 pm-11:00 pm: BPC should be in the highest therapeutic range of from 50 to 175 ng/ml.

Figure 44:
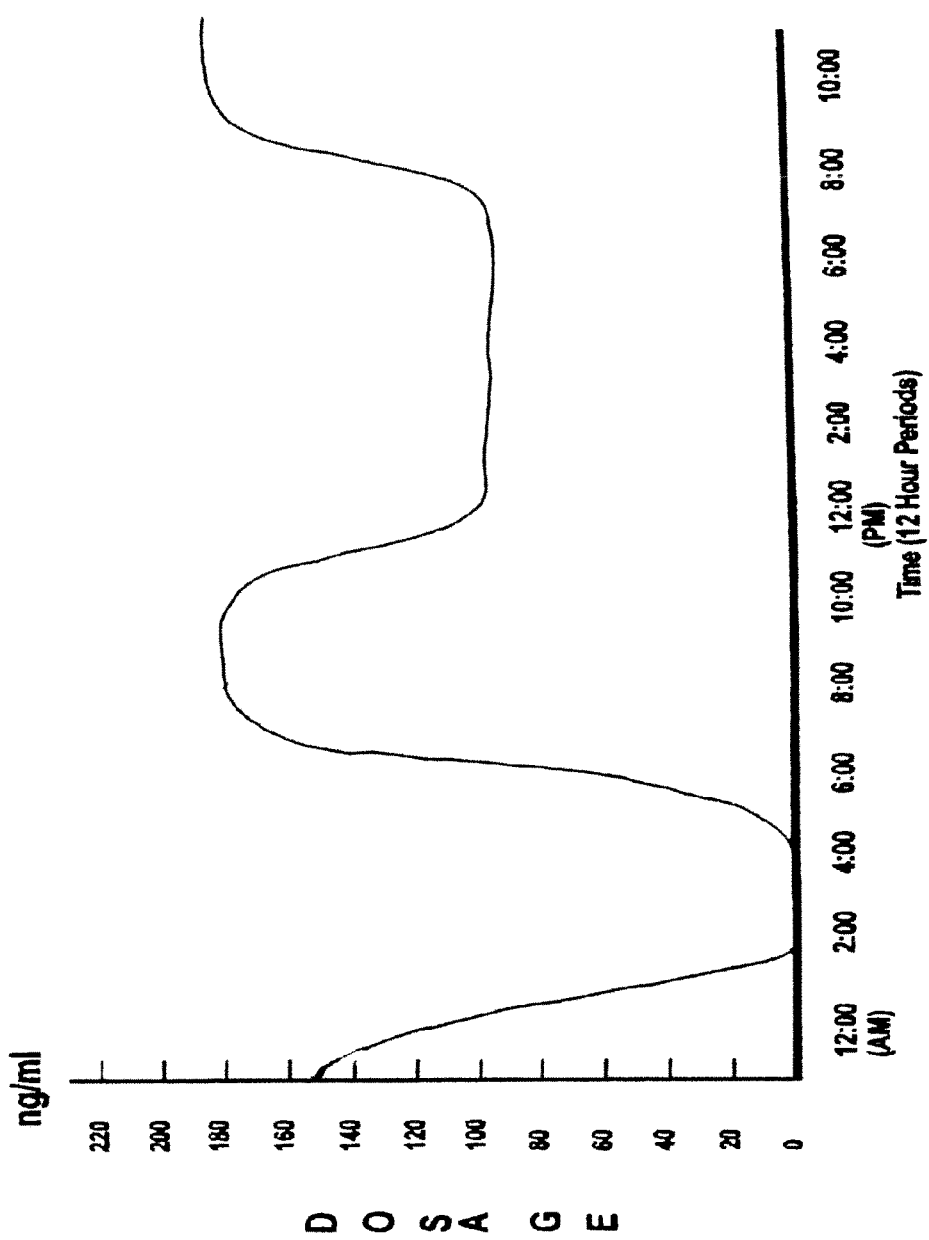
FIG. 44 illustrates an exemplary administration profile for a valdecoxib delivery system tailored to treat arthritis.

The time/dose chart should appear as shown in FIG. 44.

Application—Asthma

Example—Tulobuterol

The automated transdermal asthma system automatically administers a morning dose of albuterol, tulobuterol, salmeterol, beta 2 agonist or any other antiarrhythmic drug (an 'Asthma drug') to combat the peak symptom of morning asthma attacks known as the 'morning dip'.

Chronotherapeutic Rationale:

Asthma attacks occur 100 (one hundred) times more often between the hours 4 A.M. and 6 A.M., when most people are asleep. This is due to the early morning deterioration of respiratory function known as 'morning dip', which is the time of day that respiratory function is at its lowest. These early morning asthma attacks cause great distress to sufferers and care providers. The morning dip represents the dip in respiratory function at this time when asthma attacks are 100 times more likely to occur. Our system effectively combats the morning dip by releasing more Asthma drug at this time to offset this peak morning symptom. In other words, our 'smart' patch varies the level of drug in the bloodstream so that drug concentrations are highest when respiratory function is at its lowest.

Current 'dumb' asthma patches exist, but they can only release a constant amount of drug steadily over time. Current patches cannot tailor the release of drug to optimize treatment by releasing more drug precisely during the morning dip to offset these peak critical symptoms.

The Asthma system has two primary advantages over current patches. First, the system of the present invention utilizes its core competitive advantage to automatically and precisely release tulobuterol or other asthma drugs in peak amounts to offset the peak symptoms associated with the morning dip. Current patches have release rates that stay constant and do not increase to offset this peak critical phases, and do not decrease as symptoms decrease. Second, our system accomplishes 1 and 2 above automatically, without the need for a patient to wake up to take a drug at this critical phase, which does away with the need for any increased patient compliance.

The automated transdermal system for asthma is worn around the wrist like a watch (or the forearm arm or ankle) and releases albuterol or other asthma drugs in optimal dosages at times that are optimally synchronized, especially to offset the morning dip, pursuant to a pre-programmed and tailored dosage profile. Current Asthma patches only have the capability to release a constant dose over a period of time. Current Asthma patches simply cannot alter or vary dosages to increase dosages at different times of the day, and decrease dosages at other times of the day.

The system is an innovative new drug therapy for asthma. With its superior advantage of optimized and automated time and dose administration synchronized with our circadian rhythms, our system ensures that tulobuterol or another asthma drug will circulate in increased amounts in the bloodstream exactly when the patient needs it. For these reasons, our system is superior to current steady release patches. Our system's increased advantages are extremely relevant for those patients with moderate to severe asthma.

Figure 45:
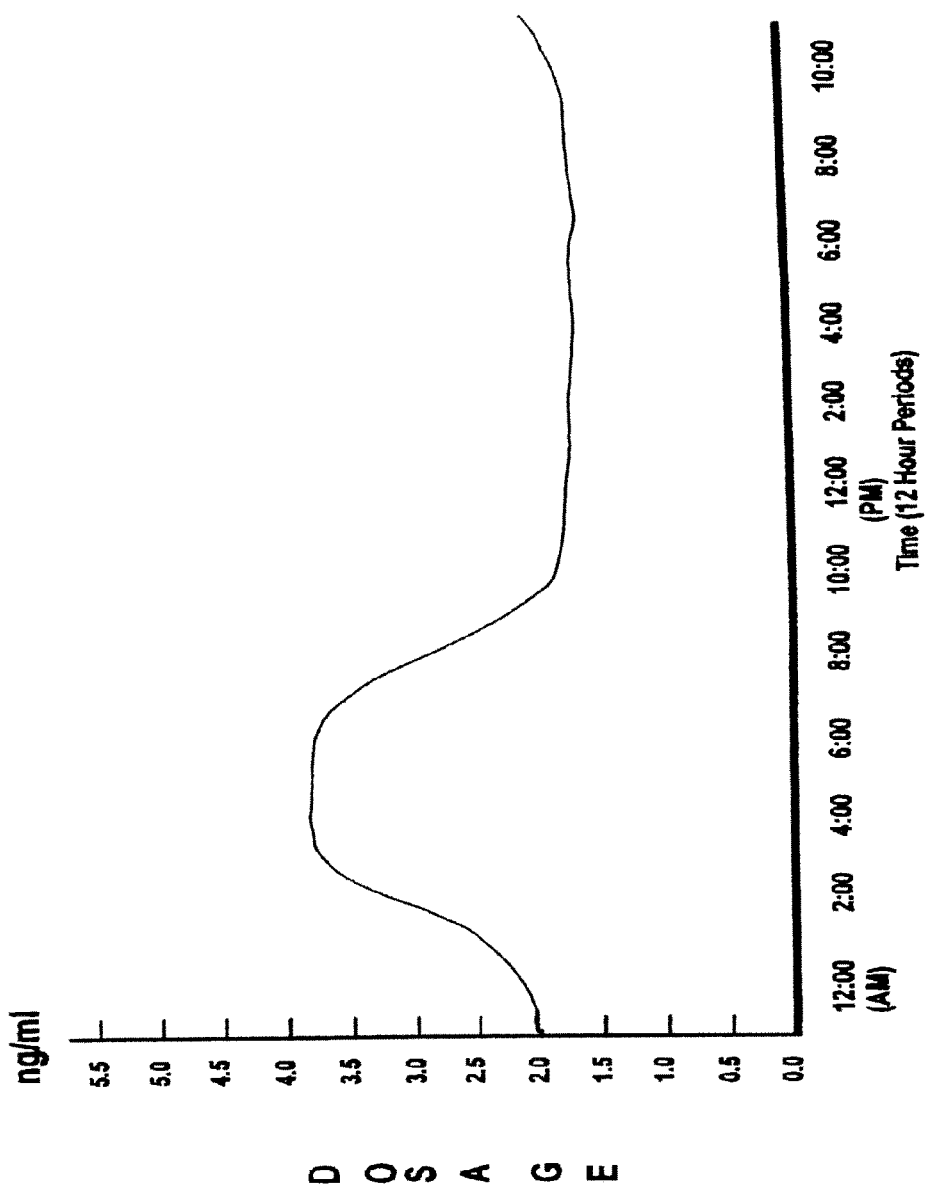
FIG. 45 illustrates an exemplary administration profile for a tulobuterol delivery system tailored to treat asthma.

The time/dose chart should appear as shown in FIG. 45.

Application—Hypertension

Example—Clonidine

Current clonidine patches release the drug consistently over time. It cannot release more of the drug when symptoms are worst. People die most when the symptoms peak. Having the advantage of administering more of the drug when a patient needs it the most can mean the difference between life and death, especially in patients with moderate to severe high blood pressure.

Chronotherapeutic Rationale:

The automated transdermal system for hypertension has two primary advantages over current patches. First, our system utilizes its core competitive advantage to automatically and precisely release clonidine or other hypertension drugs in peak amounts to offset the peak symptoms associated with the dangerous morning symptoms. Current hypertension patches have release rates that stay constant and do not increase to offset this peak critical phases, and do not decrease as symptoms decrease. Second, our system accomplishes 1 and 2 above automatically, without the need for a patient to wake up to take a drug at this critical phase, which does away with the need for any increased patient compliance. The clonidine automated transdermal system utilizes clonidine, (or another hypertension drug) an effective drug that combats high blood pressure.

Example

The clonidine automated transdermal drug delivery system has an automated morning release of Clonidine to combat the peak symptom of morning heart attacks. Blood pressure differs at different times of the day. Blood pressure surges upon waking, and is lower by 20 to 30 percent while sleeping. Our preprogrammed automatic transdermal system utilizes its core competitive advantage by releasing clonidine in a tailored fashion to counter high blood pressure when symptoms are highest, while releasing less clonidine when symptoms are less severe.

Figure 46:
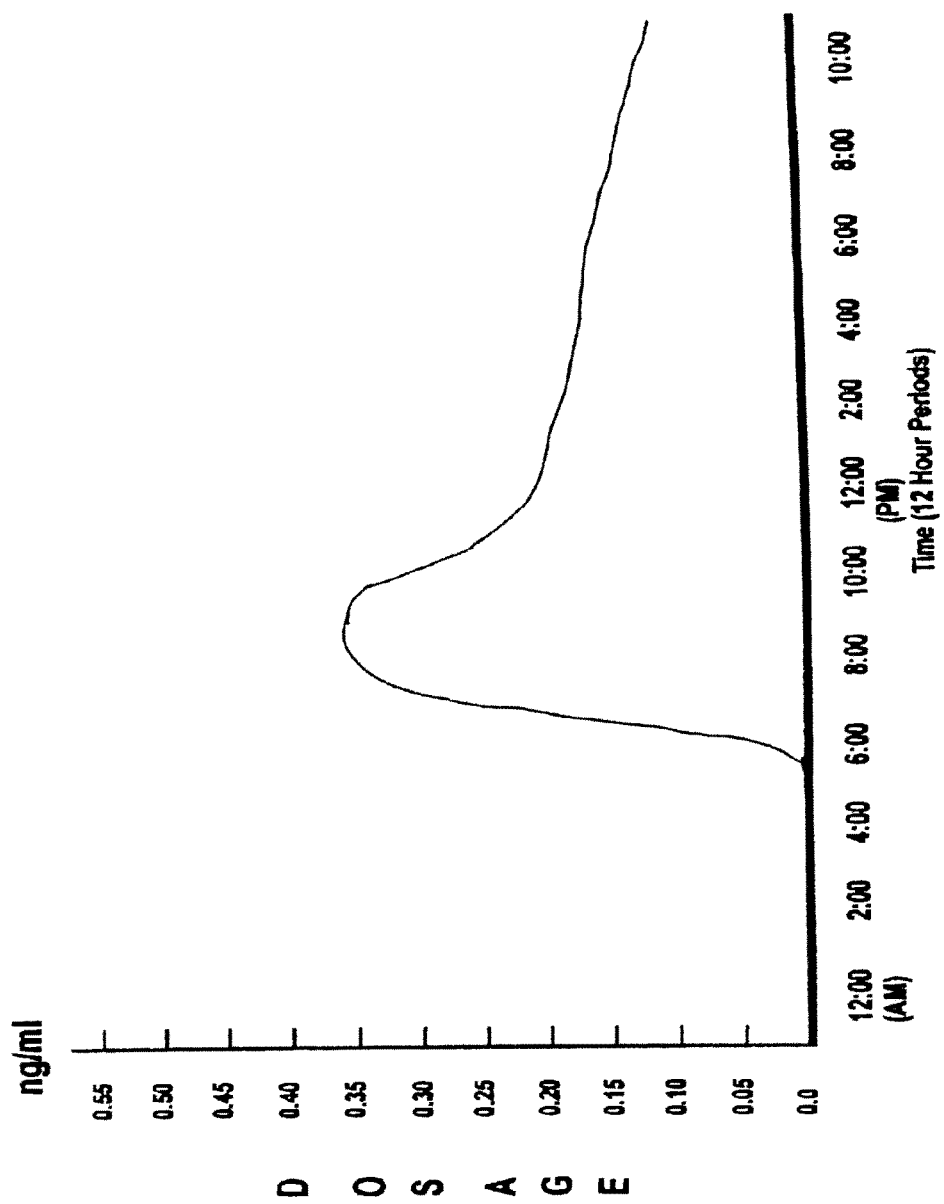
FIG. 46 illustrates an exemplary administration profile for a clonidine delivery system tailored to treat hypertension.

The time/dose chart should appear as shown in FIG. 46

Application—Depression

Example—Selegiline

Selegiline is an effective MAO inhibitor for the treatment of depression, Alzheimer's and Attention Deficit Disorder. Currently oral selegiline produces many undesirable side effects. A transdermal form of selegiline, EMSAM™, is currently being developed. However, it also produces sleep disturbances as well. It is believed that the system in accordance with the present invention would be superior to conventional selegiline product delivery systems.

Chronotherapeutic Rationale:

Primary negative side effects of the selegiline patches are abnormal dreams, insomnia, and difficulty sleeping. We believe that by specifically refraining from administering selegiline at night, and utilizing our system's core competitive advantage to turn it on an hour or so before waking, we can do away with this negative side effect and still offset the critical phase of morning symptoms of depression. It has been reported that patients have increased symptoms of depression upon waking if the critical amount of Selegiline is not circulating through their system.

The selegiline automated transdermal drug delivery system gives an automated morning release of selegiline to combat the peak symptom of morning depression without the side effect of sleep disturbances. The system in accordance with the present invention is applied before bed. It does not release the drug until one or two hours before morning, so symptom of morning depression would be corrected by our system without subjecting the patient to sleep disturbances.

Figure 47:
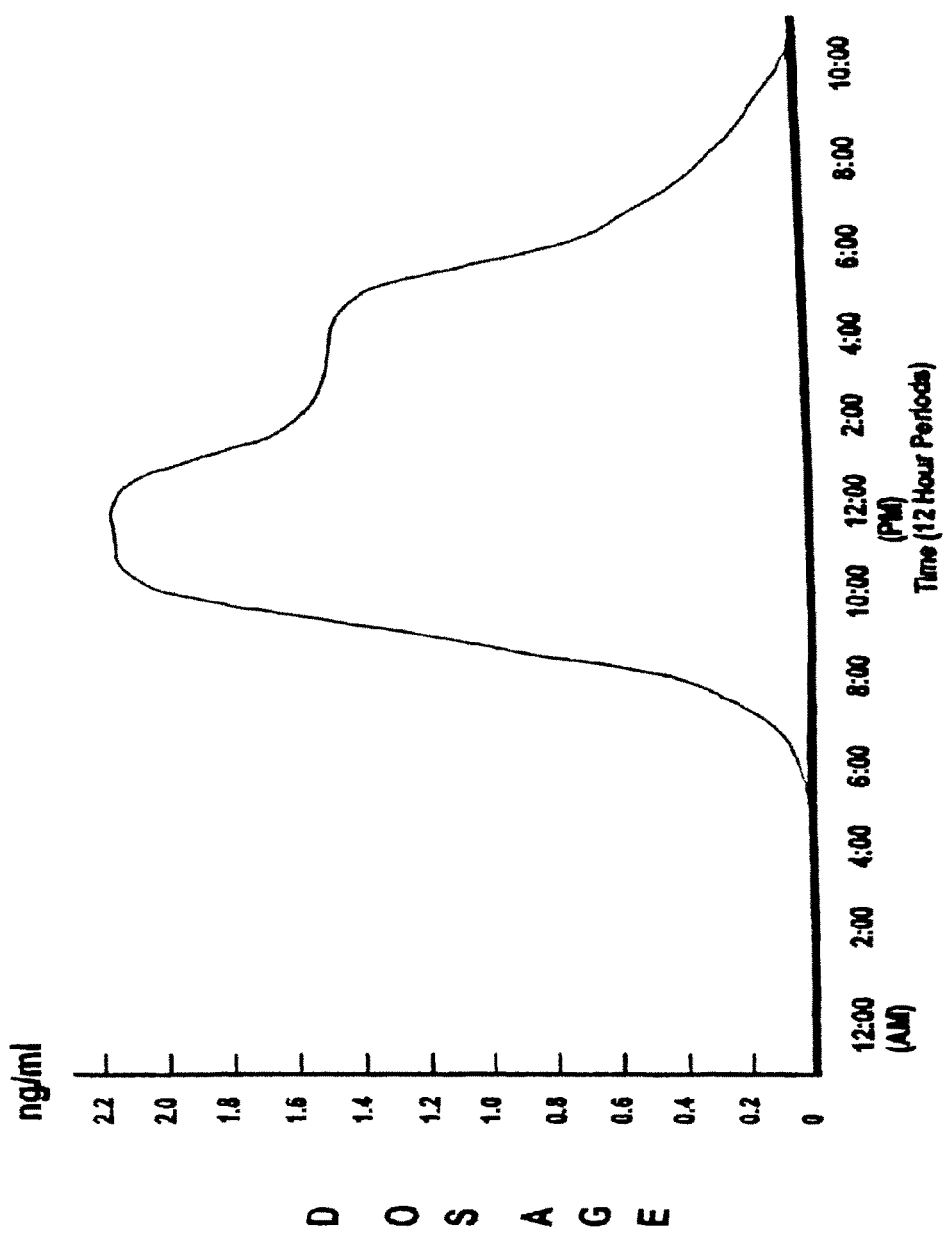
FIG. 47 illustrates an exemplary administration profile for a selegiline delivery system tailored to treat depression.

The time/dose chart should appear as shown in FIG. 47.

Application—Urinary Incontinence

Example—Oxybutynin

An automated, and programmed, pulsatile drug delivery regimen is desired to in order to increase drug concentrations automatically at night while asleep, and to decrease concentrations during the daytime work hours, and again to slightly increase drug concentrations after work and prior to bed.

Chronotherapeutic Rationale:

The primary adverse side effect of Oxybutynin is daytime sleepiness, daytime attention and cognitive deficits, drowsiness, dizzyness, blurred vision, (must use caution when driving, operating machinery, or performing other hazardous activities). Therefore, it seems that a dose in the lower end of the therapeutic range should be administered during the daytime, with a slightly larger dose administered after working hours, and with an even higher dose administered during the sleeping hours.

This would reduce the potentially serious adverse side effect of daytime drowsiness and daytime cognitive impairment. This dosing regimen would also give the user a higher dose at night, when one sleeps. At this time, increased drowsiness would be advantageous as well as providing a period of undisturbed sleep due to the inhibition of urge incontinence.

Medications for incontinence include:

Oxybutynin (Ditropan® and Oxytrol®)

Tolterodine (Detrol®)

Duloxetine (Yentreve®)

Example—Oxybutynin

The mean maximum blood plasma concentration following oral dosing with 5 mg oxybutynin or transdermally with 39 mg is 3 ng/mL. Blood plasma concentration between 1 and 3 ng/ml Theoretical unenhanced transdermal flux for oxybutynin (Berner-Cooper predictive model) is 10.98 ug/cm2/hr.

NOTE: Dose of current Oxytrol patches are 3.9 mg per day.

Thus, dosing could be optimized using the ChronoDose™ system. For example, pulsatile delivery should have blood plasma concentrations (BPC) as set forth below within the following ranges at the following times:

Peak 1 (Highest)

11:00 pm-7:00 am: BPC should be in the highest therapeutic range of 2.5-4.5 ng/ml.

Peak 2 (Low)

7:00 am to 5:00 pm: BPC should be in the lowest therapeutic range of 0.75-1.5 ng/ml.

Peak 3 (Medium)

5:00 pm-11:00 pm: BPC should be in the medium therapeutic range of from 1.5 to 2.5 ng/ml.

Figure 48:
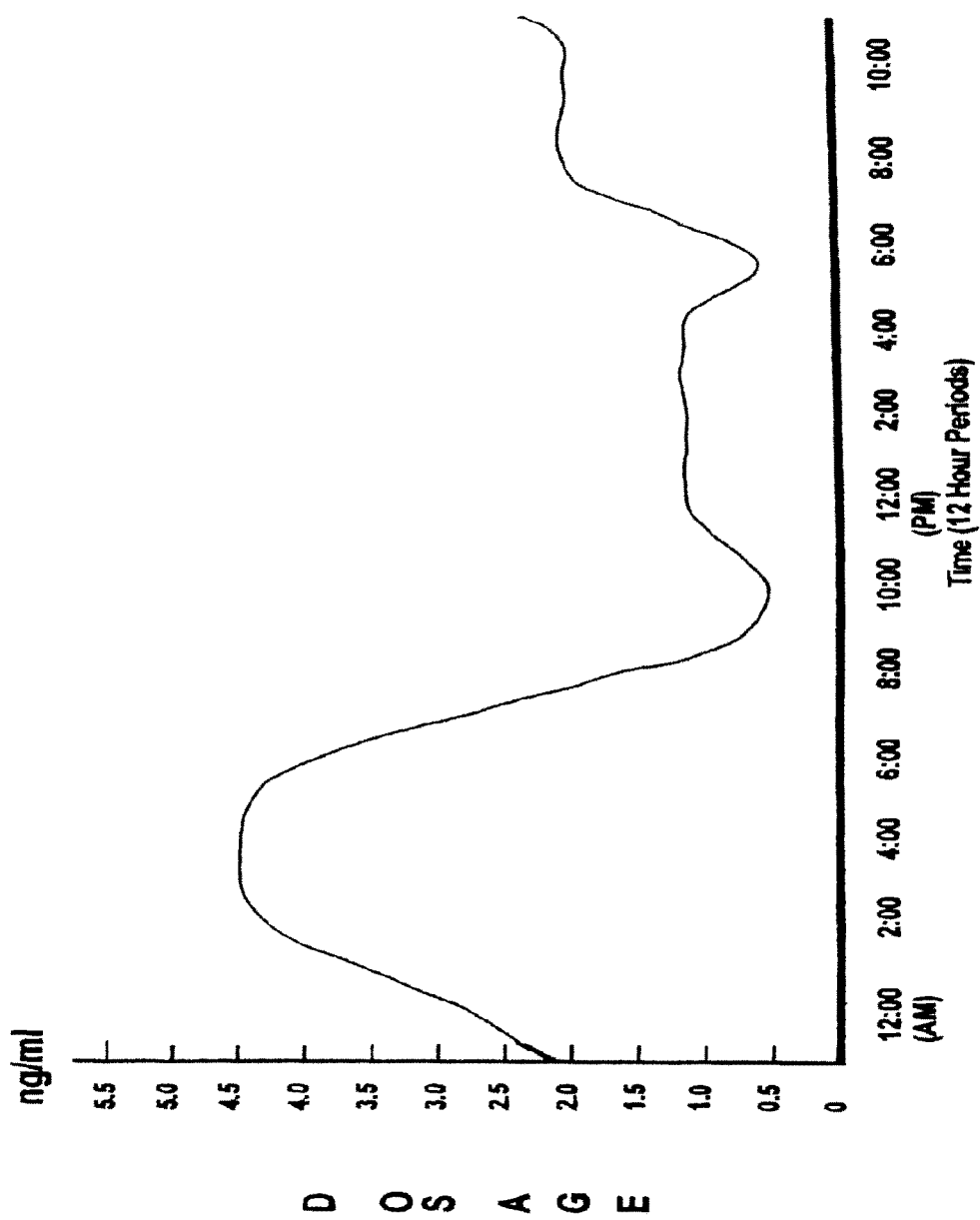
FIG. 48 illustrates an exemplary administration profile for an oxybutynin delivery system tailored to urinary incontinence.

The time/dose chart should appear as shown in FIG. 48.

Application—Headache and Migraine

Example—Zolmitriptan

An automated, and programmed, pulsatile drug delivery regimen is desired to in order to increase drug concentrations automatically in the evening to provide needed medication, in the very early morning (0200-0400) while asleep, and again later on (0800-1000) upon waking. Then, during the daytime work hours, decrease concentrations to allow for normal activities.

Chronotherapeutic Rationale:

Migraine, cluster and tension-type headaches may produce a headache that awakens an individual in the early morning hours (usually between 2 and 4 AM), or is present upon awakening. Those individuals with chronic tension-type headache are most likely to be awakened in the early morning hours due to headache. This headache also tends to be at its worst severity at that time of day. A variety of causes may account for this early-morning pattern to the headaches.

Additionally, primary headaches associated with late sleeping or weekends are caused by caffeine withdrawal. Sleeping in late delays morning caffeine intake, which often leads to withdrawal and migraine. Many people reduce their caffeine intake on weekends, which readily explains the weekend increase in migraine attacks. Fewer migraines occur on Mondays and Tuesdays than on other days of the week.

Medications for headache and migraine include:

Abortive Medications

Analgesics with caffeine such as Excedrin® Migraine (acetaminophen, aspirin and caffeine).

Analgesics with caffeine and barbiturates such as Fiorinal® (butalbital, aspirin and caffeine) and Fioricet® (butalbital, acetaminophen and caffeine).

Non steroidal antiinflammatory drugs (NSAIDs) such as Advil® (ibuprofen), and Aleve® (naproxen sodium).

Ergotamines such as Cafergot® (caffeine and ergotamine tartrate) and Migranal® (dihydroergotamine).

Triptans such as Zomig® (zolmitriptan), Maxalt® (rizatriptan), Imitrex® (sumatriptan), Frova® (frovatriptan), Axert® (almotriptan) and Amerge® (naratriptan).

Excedrin Migraine is a registered trademark of Bristol-Myers Squibb Company

Fiorinal and Fioricet are registered trademarks of Novartis Pharmaceuticals Corporation Advil is a registered trademark of Whitehall-Robbins Healthcare Aleve is a registered trademark of Bayer Corporation Cafergot and Migranal are registered trademarks of Novartis Pharmaceuticals Corporation Zomig is a registered trademark of AstraZeneca Maxalt is a registered trademark of Merck & Co., Inc.

Imitrex is a registered trademark of GlaxoSmithKline

Frova is a registered trademark of Elan Pharmaceuticals/UCB Pharma, Inc.

Axert is a registered trademark of Pharmacia

Amerge is a registered trademark of GlaxoSmithKline

Preventive Medications

Beta blockers such as Inderal® (propranolol)*, Blocadren® (timolol maleate)*, and metoprolol.

Calcium-channel blockers such as Cardizem® (diltiazem) and Procardia® (nifedipine).

Antidepressants such as Prozac® (fluoxetine), Paxil® (paroxetine) and Zoloft® (sertraline).

Anticonvulsants such as Depakote® (valproic acid or divalproex sodium).*

NSAIDs such as Orudis® (ketoprofen) and Aleve® (naproxen sodium).

Figure 49:
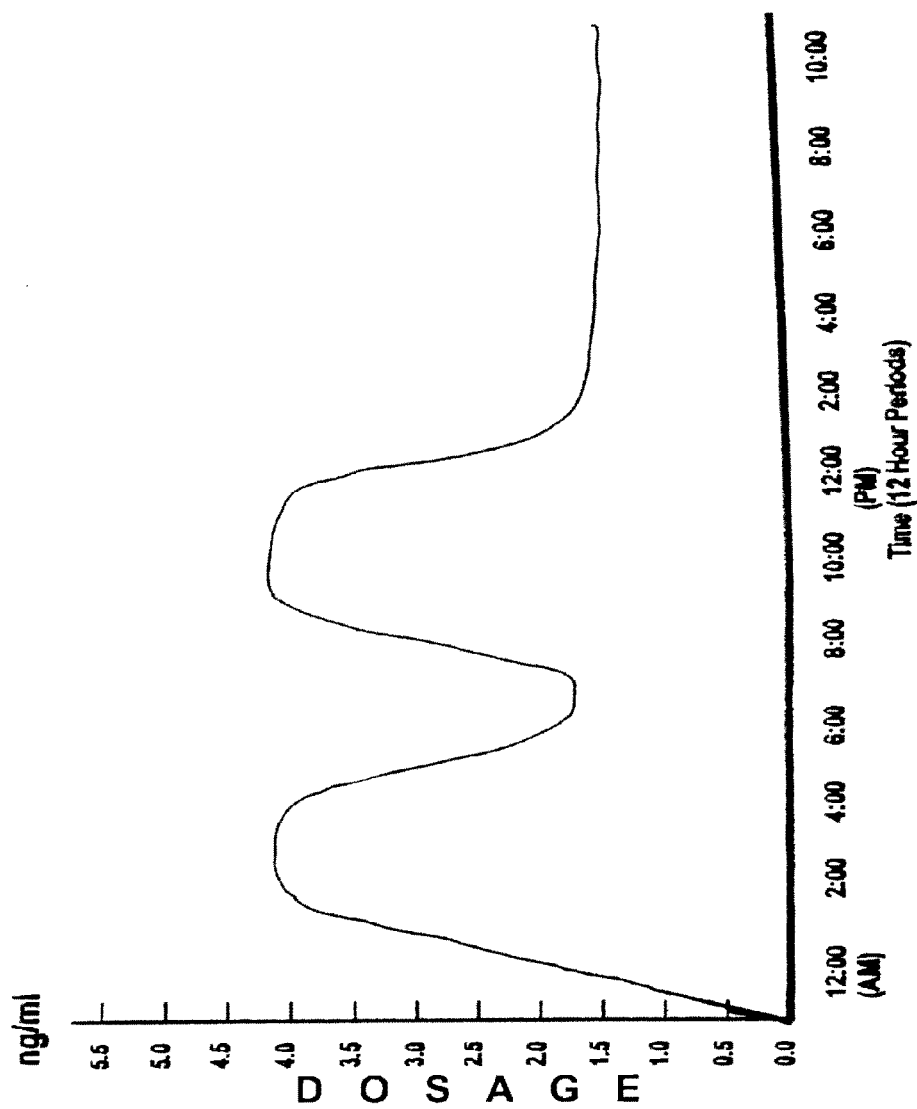
FIG. 49 illustrates an exemplary administration profile for a zolmitriptan delivery system tailored to treat migraine.

Inderal is a registered trademark of AstraZeneca
Blocadren is a registered trademark of Merck & Co, Inc.
Cardizem is a registered trademark of Aventis Pharmaceuticals
Procardia is a registered trademark of Pfizer Inc.
Prozac is a registered trademark of Eli Lilly and Company
Paxil is a registered trademark of GlaxoSmithKline
Zoloft is a registered trademark of Pfizer Inc.
Depakote is a registered trademark of Abbott Laboratories
Orudis is a registered trademark of Aventis Pharmaceuticals
Aleve is a registered trademark of Bayer Corporation Example—Zolmitriptan Blood plasma concentration between 1.0 and 5.0 ng/ml. Theoretical unenhanced transdermal flux for zolmitriptan (Berner-Cooper predictive model) is 6.02 ug/cm2/hr. Thus, dosing could be optimized using the ChronoDose™ system. For example, pulsatile delivery should have blood plasma concentrations (BPC) as set forth below within the following ranges at the following times:

Peak 1 (Highest)
2:00 am-4:00 am: BPC should be in the highest therapeutic range of 3.5-4.0 ng/ml.
Peak 2 (Highest)
8:00 am-10:00 am: BPC should be in the highest therapeutic range of 3.5-4.0 ng/ml.
Trough (Lowest)
12:00 pm to 12:00 am: BPC should be in the lowest therapeutic range of 1.0-3.0 ng/ml.
The time/dose chart should appear as shown in FIG. 49.
Applications—Diabetes Example—Miglitol An automated, and programmed, pulsatile drug delivery regimen is desired to in order to increase drug concentrations automatically in the morning (0800), midday (1200) and evening (1800) which coincide with mealtimes.

Miglitol is indicated as an adjunct to diet to improve glycemic control in patients with non-insulin-dependent diabetes mellitus (NIDDM) whose hyperglycemia cannot be managed with diet alone.

Theoretical unenhanced transdermal flux for miglitol (Berner-Cooper predictive model) is 49.24 ug/cm2/hr.

Figure 50:
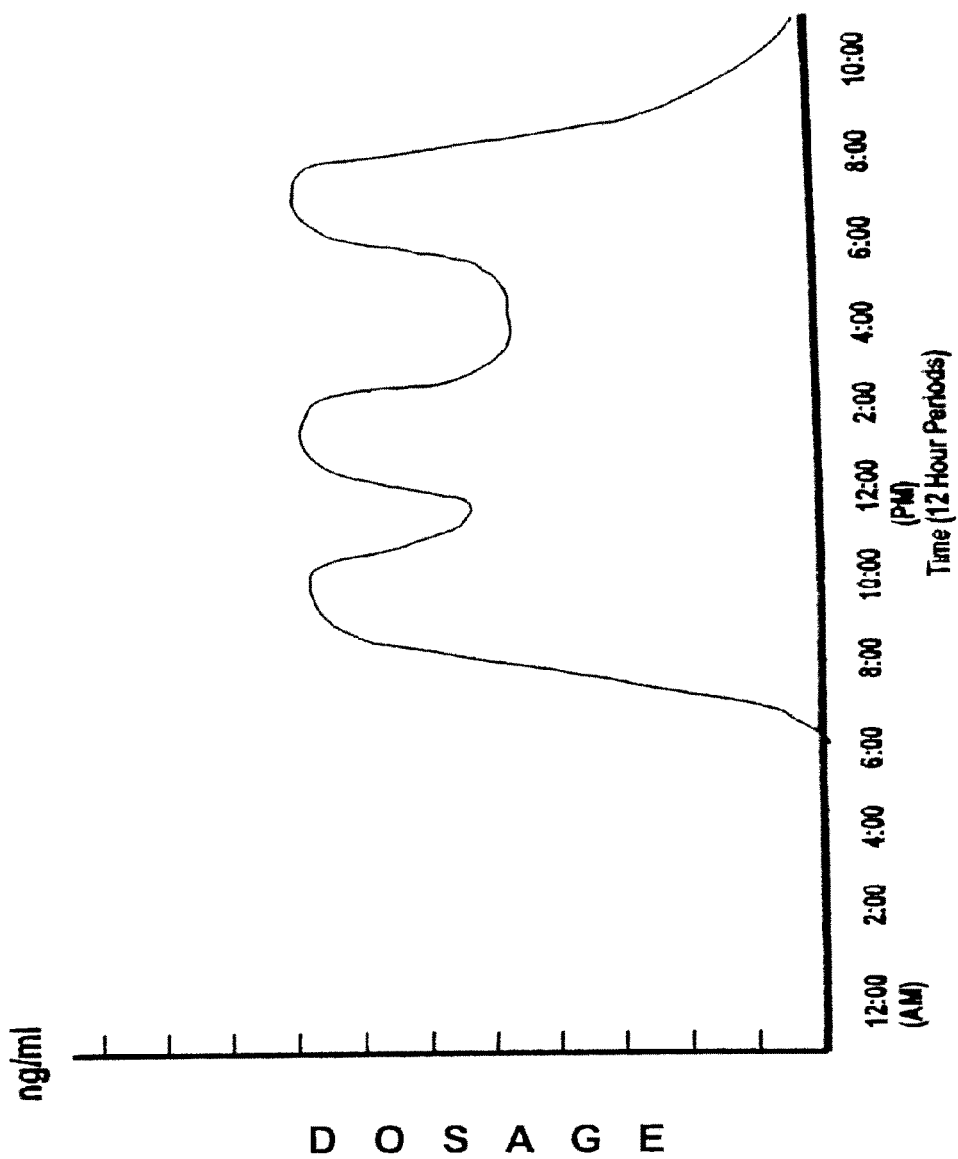
FIG. 50 illustrates an exemplary administration profile for a miglitol delivery system tailored to treat diabetes.

Thus, dosing could be optimized using the ChronoDose™ system. For example, pulsatile delivery should have blood plasma concentrations (BPC) as set forth below within the following ranges at the following times:

Peak 1 (Highest)
8:00 am-10:00 am: BPC should be in the highest therapeutic range.
Peak 2 (Highest)
12:00 am-2:00 pm: BPC should be in the highest therapeutic range.
Trough (Highest)
6:00 pm to 8:00 am: BPC should be in the highest therapeutic range.
The time/dose chart should appear as shown in FIG. 50.
Application—Pain Management Example—Fentanyl Many diseases and pain-causing situations (post-surgery, post trauma) have predictable pain patterns. For example, cortisol is virtually absent in the body overnight, and this is what fights inflammation. Thus, any pain resulting from inflammation (rheumatoid arthritis, post-surgical pain, post-traumatic pain, back pain, neurological pain) is most common in the early morning hours between 3:00 a.m. and 8:00 a.m. Migraine pain is worst around 6:00 a.m. Ankylosing spondylitis pain surges between 6:00 a.m. and 9:00 a.m. Osteoarthritis pain surges in mid-afternoon.

Pain varies tremendously from one patient to the next, and there are also some studies suggesting that the intensity of pain varies according to time of day. In human studies, pain induced experimentally was reported to be maximal in the morning, or in the afternoon or at night. A circadian pattern of pain has been seen in patients suffering from pain produced by different diseases. For instance, highest toothache intensity occurred in the morning, while biliary colic, migraine, and intractable pain were highest at night. Patients with rheumatoid arthritis reported peak pain early in the morning, while those with osteoarthritis of the knee indicated that the maximal pain occurred at the end of the day. The effectiveness of opioids appears also to vary according to time of day, but large differences in the time of peak and low effects were found. Peak pain intensity and narcotic demands occur early in the morning, or it can be at the end of the day. Pain is a complex phenomenon and specific to each clinical situation.

An automated, and programmed, pulsatile transdermal drug delivery regimen is needed to substantially increase blood plasma concentrations of Fentanyl or other pain medications, automatically between 3:00 am and 8:00 am, while people sleep, where pain results from inflammation, because cortisone, a key inflammation fighter, is lowest in the body at that time. Additionally, an automated, and programmed, pulsatile transdermal drug delivery regimen is needed to substantially increase blood plasma concentrations of Fentanyl or other pain medications automatically between 6:00 am and 9:00 am for Ankylosing spondylitis pain, and in mid-afternoon for Osteoarthritis pain.

Other pain medication includes: codeine, dihydrocodeine, hydrocodone or hydromorphone, Sufentanil, Nalbuphine, Buprenorphine, Hydromorphone and any type of opiate derivative.

These are exemplary choices for transdermal pain management since they are effective, there is considerable hepatic first pass effect and a short half life, and they are skin permeable.

Figure 51:
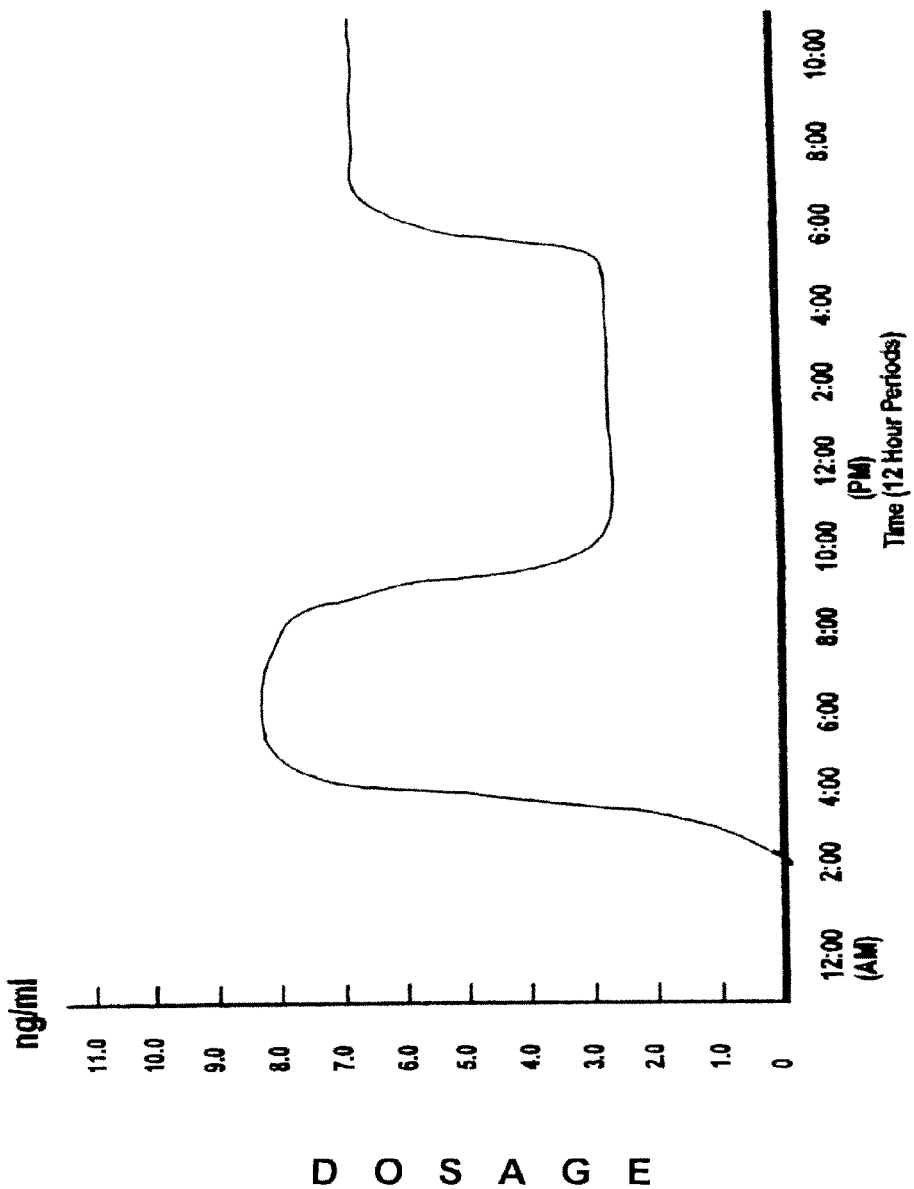
FIG. 51 illustrates an exemplary administration profile for a fentanyl delivery system tailored to treat pain.

For example, for pain that increases with inflammation, as in the situations noted above, our regimen would suggest automated and programmed, transdermal pulsatile delivery of fentanyl to reach blood plasma concentrations (BPC) as set forth below within the following ranges at the following times:

Peak 1 (Highest)
3:00 am-8:00 am: BPC of fentanyl should be in the highest therapeutic range of 2-8 ng/ml.
Peak 2 (Lowest)
8:00 am-5:00 pm: BPC should be in the lowest therapeutic range of 1-3 ng/m.
Peak 3 (Middle)
5:00 pm to 3:00 am: BPC should be in the a moderate therapeutic range of 2-5 g/ml.
The time/dose chart should appear as shown in FIG. 51.
Application—Cancer Cancer chronotherapy is attracting attention as a novel and logical therapy in which anti-cancer drugs are administered with optimal timing according to circadian rhythms of anti-cancer action and those of adverse effects on normal cells. Advances in chronobiology have identified the suprachiasmatic nucleus (SCN) as the center of biological rhythms and the area in which clock genes such as PER1, PER2, PER3, CLOCK, BMAL1, TIM, CRY1, CRY2, tau act to generate and coordinate biological rhythms. These findings have led to the development of chronotherapy. Clinically, patients with advanced gastrointestinal cancer have been treated by chrono-modulated chemotherapy with good response. For colorectal cancer patients with unresectable liver metastases, chronotherapy with g-OHP+5-FU+FA (folinic acid) has been reported to allow complete surgical resection of liver metastases, resulting in 39-50% 5-year survival.

The circadian timing of surgery, anticancer drugs, radiation therapy, and biologic agents can result in improved toxicity profiles, tumor control, and host survival. Optimally timed cancer chemotherapy with doxorubicin or pirarubicin (06:00 h) and cisplatin (18:00 h) enhanced the control of advanced ovarian cancer while minimizing side effects, and increased the response rate in metastatic endometrial cancer. Therapy of metastatic bladder cancer with doxorubicin-cisplatin was made more tolerable by this same circadian approach resulting in a 57% objective response rate. This optimally timed therapy is also effective in the adjuvant setting, decreasing the expected frequency of metastasis from locally advanced bladder cancer. Circadian fluorodeoxyuridine (FUDR) continuous infusion (70% of the daily dose given between 15:00 h and 21:00 h) has been shown effective for metastatic renal cell carcinoma resulting in 29% objective response and stable disease of more than 1 yr duration in the majority of patients. Toxicity is reduced markedly when FUDR infusion is modulated to circadian rhythms Chronotherapy has also been used to lower the amount of side effects from chemotherapy drugs. Over the years, doctors have realized that by giving two of these drugs, Adriamycin and cisplatin, in the morning and evening, respectively, side effects could be cut in half Thus, dosing could be optimized using the ChronoDose™ system. For example, pulsatile delivery should have blood plasma concentrations (BPC) as set forth for each specific medication.

Figure 52A:
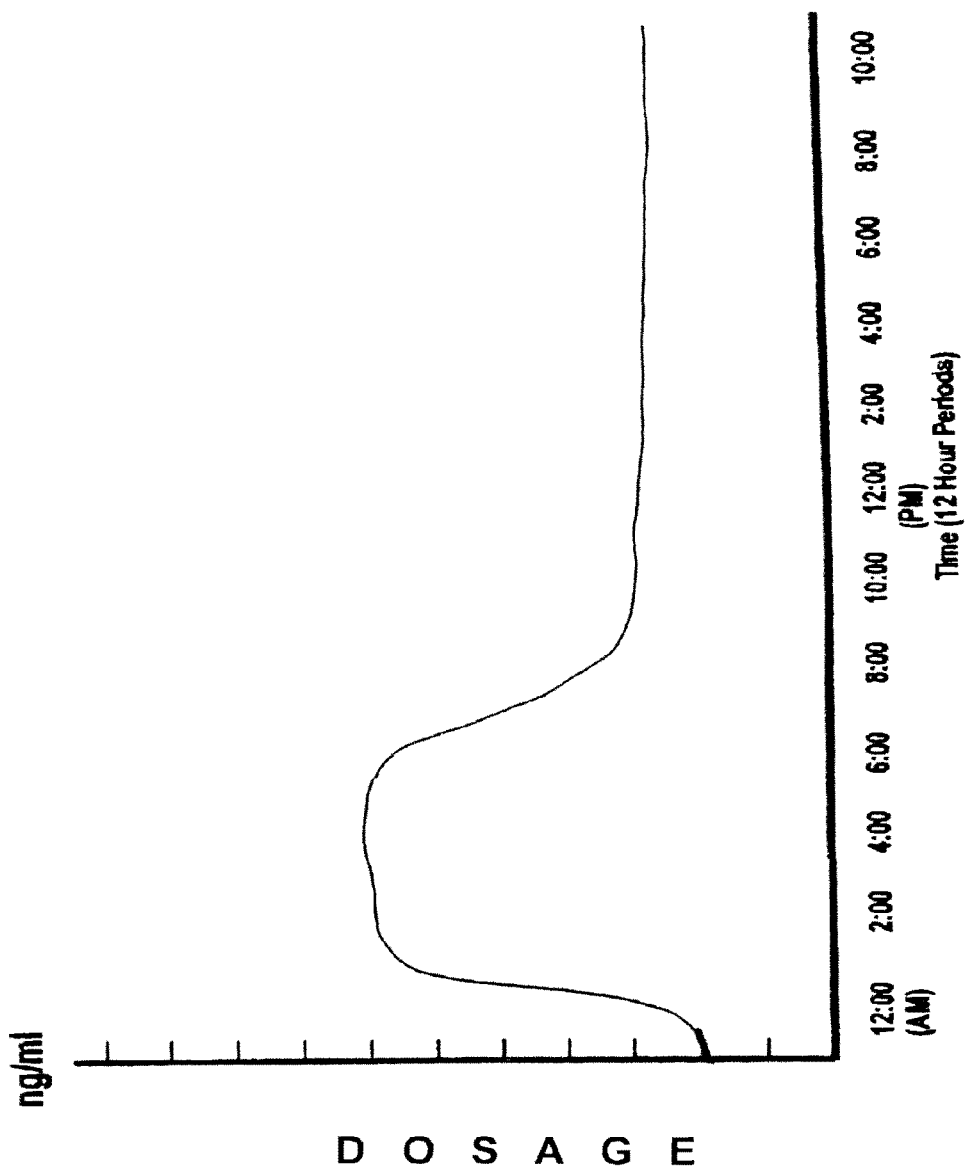
FIGS. 52A-52C illustrate an exemplary administration profile for 5-fluorouracil, doxorubicin and cisplatin delivery system tailored to treat cancer.
Figure 52B:
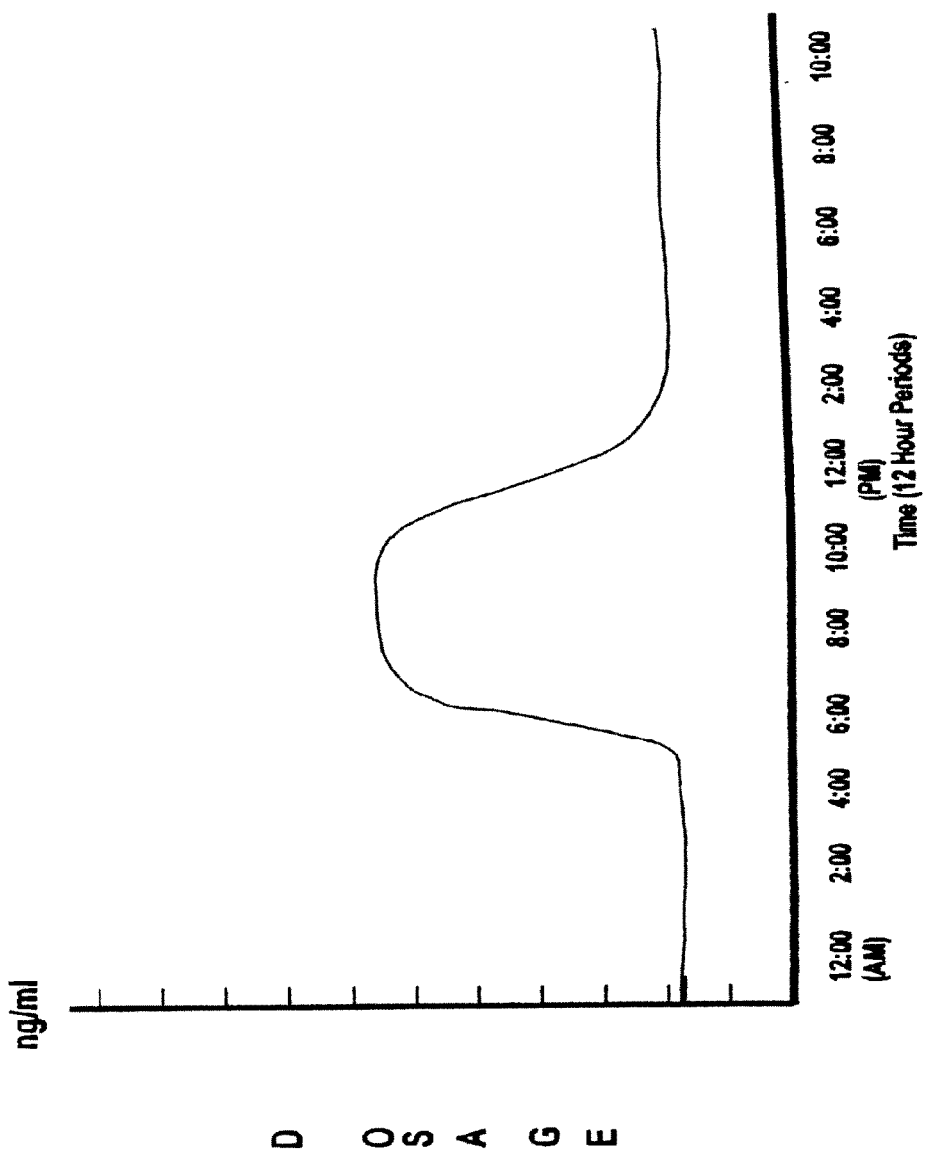
Figure 52C:
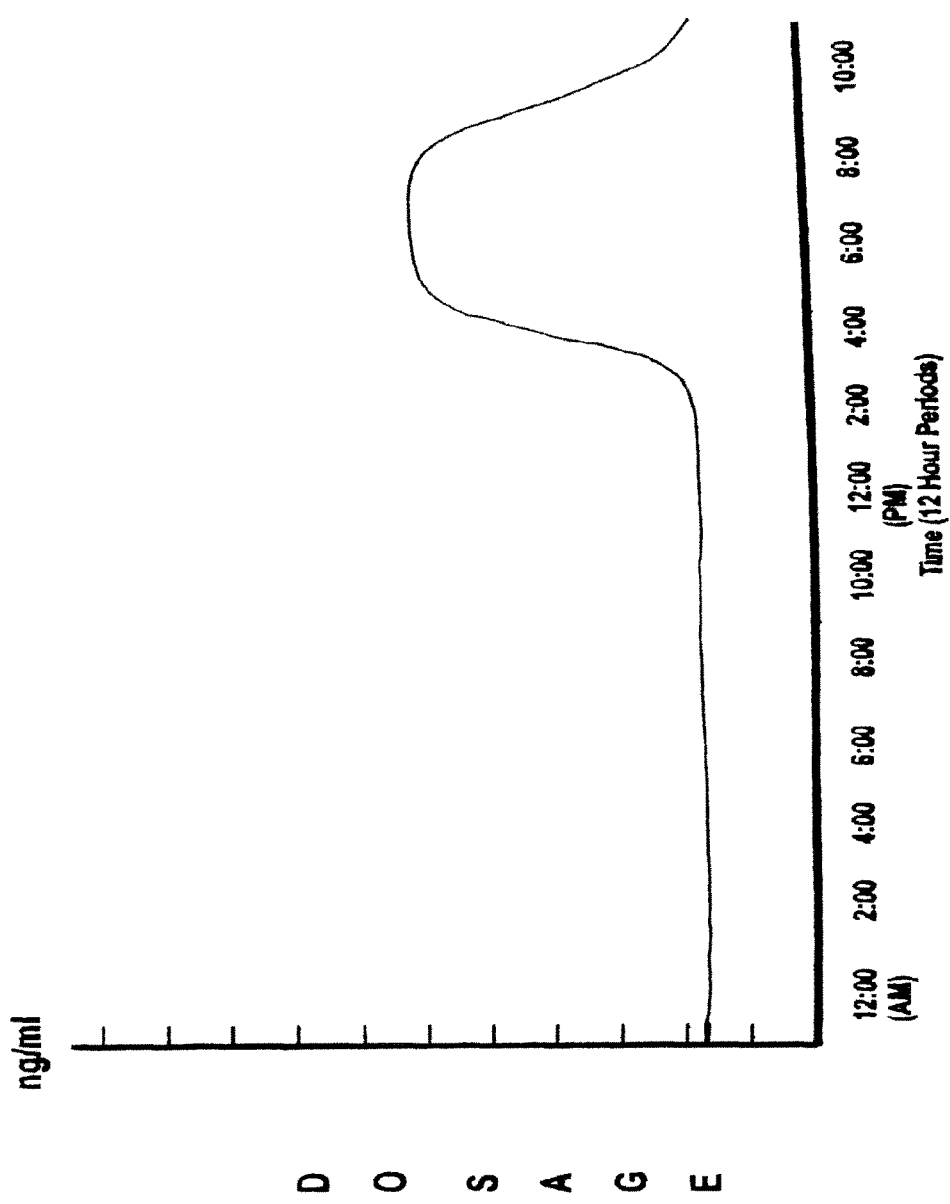

The time/dose charts should appear as shown in FIGS. 52 *a*, *b* and *c*.

Applications—Acquired Immune Deficiency Syndrome (AIDS/HIV)

Examples—Zidovudine, Didanosine

Currently available antiretroviral drug regimens are able to suppress HIV replication and allow CD4 recovery in the vast majority of patients with HIV infection. The challenge is to match each patient to the regimen that is most likely to durably suppress HIV replication enough to prevent resistance selection without causing treatment-limiting toxicities. It is also critical, but difficult, to know when to begin treatment relative to CD4 cell count and plasma viral load.

Adherence to antiretroviral therapy for the treatment of HIV infection and AIDS has become one of the most important clinical challenges among HIV health care providers and patients. Adherence to the prescribed regimen may predict which patients achieve undetectable viral loads. Unfortunately, non-adherence is common in antiretroviral therapy and has been associated with increases in viral load and the development of drug resistance. Efforts to maximize patient adherence are critical for suppressing HIV replication and preventing the transmission of drug-resistant virus.

Automated and programmed, transdermal pulsatile delivery of zidovudine to reach blood plasma concentrations (BPC) as set forth below within the following ranges at the following times:

Peak 1 (Highest)

5:00 am-9:00 am: BPC of zidovudine should be in the highest therapeutic range.

Peak 2 (Highest)

7:00 pm to 11:00 pm: BPC should be in the highest therapeutic range.

Theoretical unenhanced transdermal flux for zidovudine (Berner-Cooper predictive model) is 17.94 ug/cm2/hr.

Figure 53:
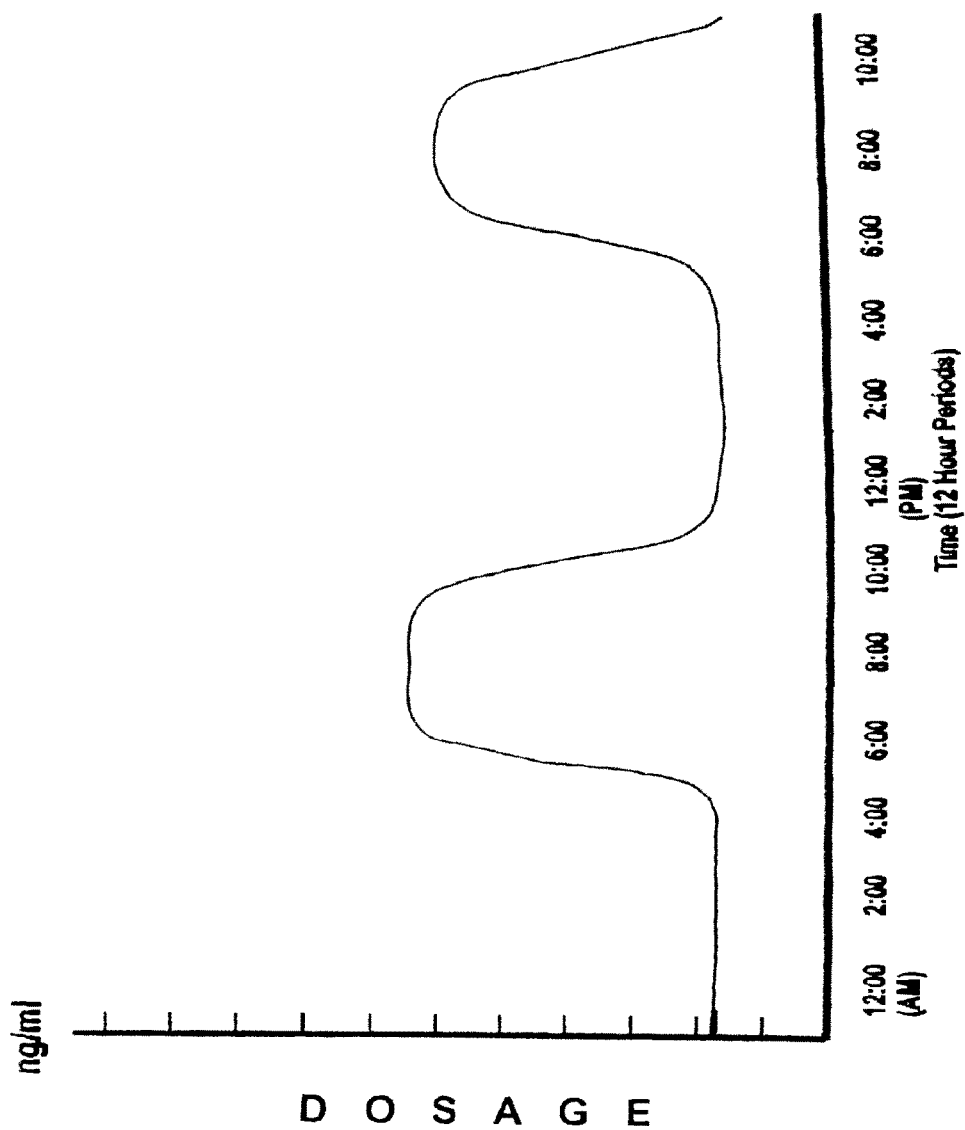
FIG. 53 illustrates an exemplary administration profile for a zidovudine delivery system tailored to treat AIDS.

The time/dose chart should appear as shown in FIG. 53.

Application—Epilepsy

Example—Gabapentan

In the majority of persons with the brain disorder epilepsy, seizures recur at predictable times of day. About half of those with epilepsy experience seizures mainly in waking hours. About one-quarter have them mainly in sleep. In the others, timing is less consistent; their seizures strike both day and night.

More than twenty anti-seizure medications (also called anticonvulsant or anti-epilepsy drugs) currently are available in the United States. Some are specifically designed not to interfere with the activity of other drugs, including birth control pills. They include gabapentin (Neurontin), lamotrigine (Lamictal), topiramate (Topamax), tiagabine (Gabatril), levetiracetam (Keppra), and oxcarbazepine (Trileptal).

None of the newer medications and only two of the older ones, valproate and phenyloin, have been studied with regard to how they work when taken at different times of the day or in different phases of the menstrual cycle. Whether the findings in valproate and phenyloin can be generalized to other anti-epilepsy drugs is not known; the results do raise issues, however, that urgently need further study. Studies of valproate show that people absorb it more slowly and less efficiently when they take it in the evening than in the morning. This finding is of concern because protection against seizures usually is needed most in NREM sleep, the state that dominates the first half of a night's sleep.

Automated and programmed, transdermal pulsatile delivery of gabapentan to reach blood plasma concentrations (BPC) as set forth below within the following ranges at the following times:

Peak 1 (Highest)

5:00 am-9:00 am: BPC of gabapentan should be in the highest therapeutic range.

Peak 2 (Highest)

7:00 pm to 11:00 pm: BPC should be in the highest therapeutic range.

Figure 54:
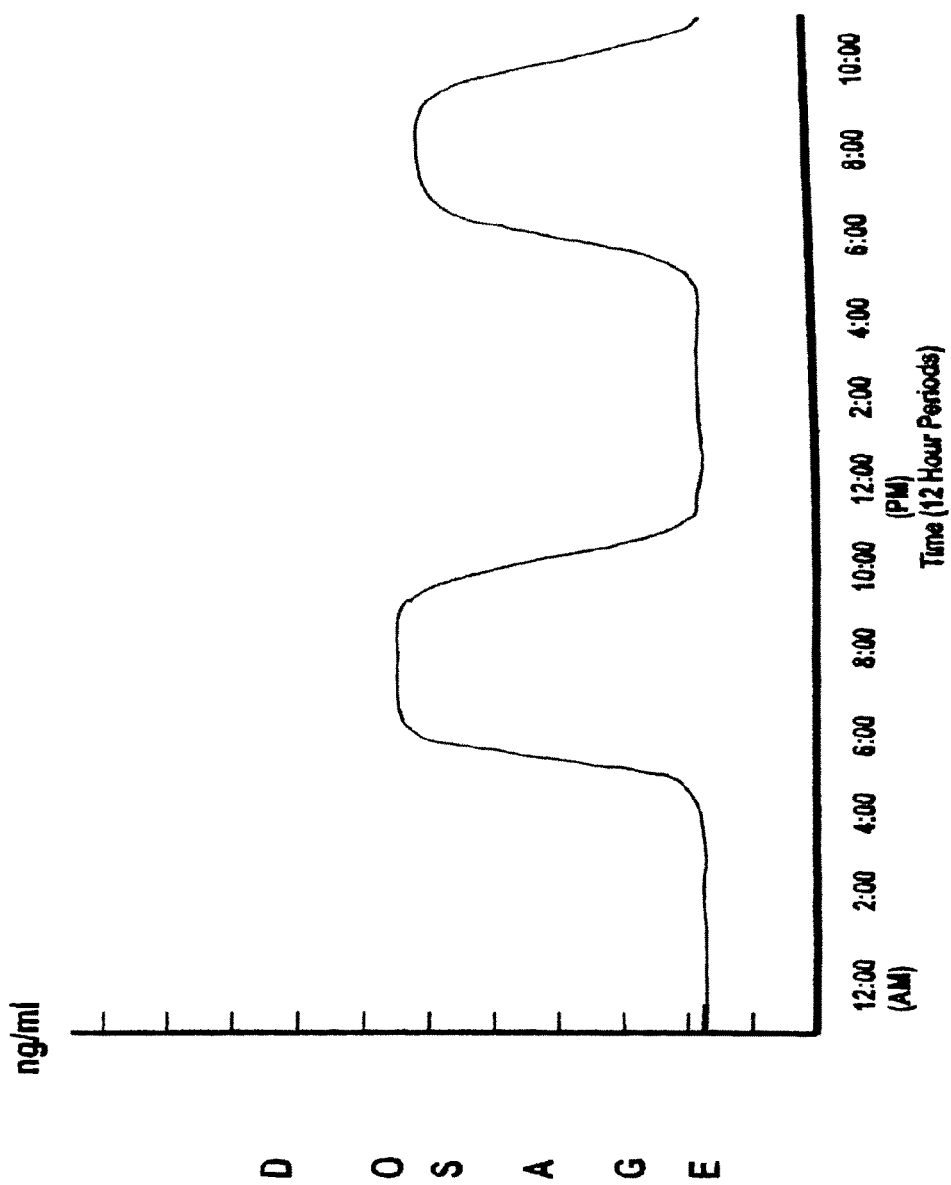
FIG. 54 illustrates an exemplary administration profile for a gabapentin delivery system tailored to epilepsy.

The time/dose chart should appear as shown in FIG. 54.

Applications—Cold and Flu Treatment

Example—Triprolidine

Cold and flu symptoms are worst from midnight until the early morning because the concentration of cortisol is lowest at that time. Current nighttime cold and flu medication end up losing efficacy by early morning when cold and flu symptoms are highest. Therefore people suffering from a cold or flu are often unpleasantly awoken by an increase in symptoms, cutting sleep short. Set and put on before bedtime, the present invention will automatically deliver a larger dose of medication and immuno-boosters in the early morning hours to more effectively combat the peak cold and flu symptoms that occur in the morning.

This implementation uses prescription or OTC cold medicine alone or optionally in combination with certain transdermally efficacious vitamins and immune system boosters to provide a total solution to cold and flu ailments. This is the first cold therapy that combines OTC medicine with supplemental immuno-boosters in a comprehensive and automated manner In a particular application, the Cold and Flu automated transdermal drug delivery system utilizes OTC cold medicine, Vitamin C, *Echinacea*, and Zinc to provide a total solution to cold and flu ailments, and all while a person sleeps. The Cold/Flu system releases these combination of compounds every 2 hours throughout the night, with a higher dosage of compounds being released in the morning to combat these proven middle of the night and early morning symptoms, which are the worst of the day. Users will experience less severe cold and flu symptoms during the morning hours, will not have their sleep cycle cut short, and will wake up feeling symptom-free.

Figure 55:
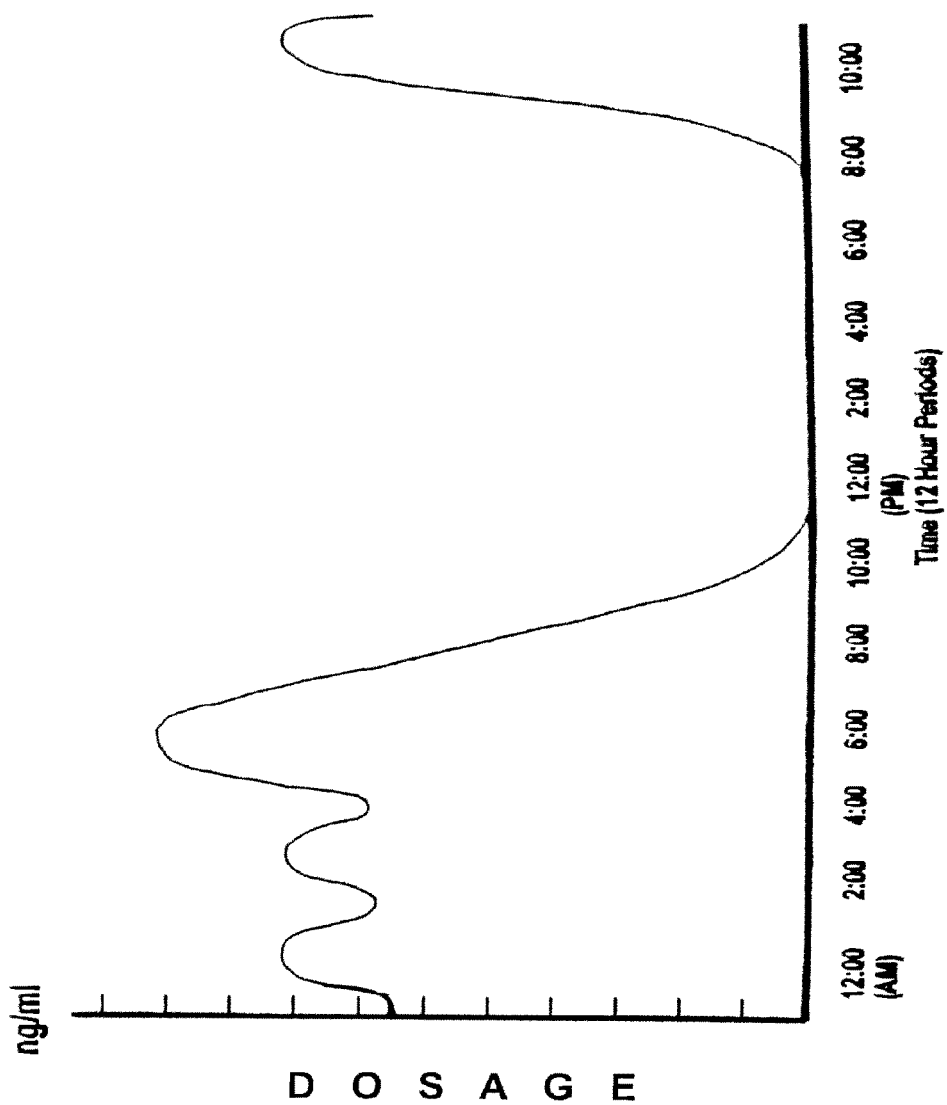
FIG. 55 illustrates an exemplary administration profile for a triprolidine delivery system tailored to treat colds and flu.

The time/dose chart should appear as shown in FIG. 55.

In General

Accordingly, a preferred method of the present invention for delivering an active agent such as a nutraceutical to a human or animal includes the steps of providing a transdermal drug delivery device coupled to the human or animal, the delivery device having a source of the bioactive agent, a programmable microprocessor timing mechanism, and a mechanism for causing the bioactive agent to be delivered transdermally in response to the timing mechanism; and timing routines implemented by the timing mechanism, wherein the timing routines are selected to deliver the bioactive agent at a time, rate, sequence and/or cycle that is synchronized with a biological rhythm of the human or animal.

The method contemplates the administration of differing sized dosages at different times of the day and/or night are automatically dispensed, pursuant to a pre-programmed dosage profile.

The active agent may be selected from the group consisting of but not limited to: adrenergic stimulants such as: adrenaline, ephedrine and ephedrine derivatives, and dopamine; methylxanthines such as: caffeine, theobromine, theophyline and their derivatives; ampakines such as: CX-516 (Ampalex), CX546, CX614 and CX717; other stimulants, anorexigens and anorectics such as cocaine, etc.; pharmaceuticals such as cannabinoid type 1 (CB 1) receptor antagonists (rimonabant, Acomplia™) humoral feedback signals leptin, ghrelin, nesfatin-1, or their re-uptake inhibitors, agonists or antagonists, appetite-regulating hormones such as peptide YY 3-36 and the like; Nutritional agents, such as: Minerals and Metals: i.e. boron, calcium, magnesium, chromium, selenium, zinc, etc.; Vitamins: Vitamin A (Retinoids (include: retinol, retinal, retinoic acid, 3-dehydroretinol and its derivatives); Vitamin B1 (Thiamine); Vitamin B2 (Riboflavin); Vitamin B3 (Niacin); Vitamin B5 (Pantothenic acid); Vitamin B6 (Pyridoxine); Vitamin B7 (Biotin); Vitamin B9 (Folic acid); Vitamin B12 (Cyanocobalamin); Vitamin C (Ascorbic acid); Vitamin D2-D4 (Lumisterol, Ergocalciferol, Cholecalciferol, Dihydrotachysterol, 7-Dehydrocholesterol); Vitamin E (Tocopherol, Tocotrienol) and Vitamin K (Naphthoquinone); Amino Acids: Isoleucine, Alanine, Leucine, Asparagine, Lysine, Aspartate, Methionine, Cysteine, Phenylalanine, Glutamate, Threonine, Glutamine, Tryptophan, Glycine, Valine, Proline, Arginine, Serine, Histidine and Tyrosine; two special amino acids, selenocysteine and pyrrolysine and other "nonstandard amino acids" including the sulfur-containing taurine and n-acetylcysteine and the neurotransmitters GABA and dopamine; other examples such as Carnosine (beta-alanyl-L-histidine), lanthionine, 2-Aminoisobutyric acid, and dehydroalanine, ornithine and citrulline; Coenzymes: Coenzyme A, Coenzyme B12, Coenzyme Q, NAD, FAD, ATP, molybdopterin, etc.; Antioxidants such as Glutathione, Lutein, alpha-lipoic acid, polyphenols-including Pycnogenol (pine bark antioxidant), Grape seed extract, superoxide dismutase (SOD, EC 1.15.1.1), epicathechin, proanthocyanidins, sulfoxides, etc.; Botanicals, phytochemicals, phytonutrients, plant extracts, herbs, naturopathic, homeopathic drugs and substances, nutraceticals, cosmeceuticals, Ayuervedic xtracts, tissue extractions, antioxidants include but are not limited to: Guarana and Brown Seaweed, or Fucus Vesiculosis, 5 HTP, yerba mate, flaxseed oil, L-caritine, Synephrine (oxedrine; Sympatol), *Coleus forskohlii* (forskohlin), diiodotyrosine, chromium poly-nicotinate, garlic extract, yeast extract, fatty acids, omega-3 fish oil, kava and kavalactones, Aniracetam, Bromocriptine, Carnosine, Centrophenoxine, Deprenyl, Gerovital-H3, Hydergine, Idebenone, Melatonin, Piracetam, Pramiracetam, Pyritinol, Resveratrol, Vinpocetine and Vitamin C, thymus, yohimbine, *Morinda citrifolia* (Noni, containing Proxeronine, Proxeronase, Xeronine, Damnacanthal and Scopoletin), etc.; Steroids and steroid precursors: Anabolic steroids; Corticosteroids, including glucocorticoid and mineralocorticoids; Mineralocorticoids; Sex steroids including androgens, estrogens, and progestagens; Phytosterols; Ergosterols; Vitamin D supplements; progestational agents, hydrocortisone, hydrocorticosterone acetate, cortisone acetate, dexamethasone and its derivatives such as betamethasone, triamcinolone, methyltestosterone, 17-.beta.-estradiol, ethinyl estradiol, ethinyl estradiol 3-methyl ether, prednisolone, 17-.beta.-hydroxyprogesterone acetate, 19-norprogesterone, norgestrel, norethindrone, norethisterone, norethiederone, progesterone, norgesterone, norethynodrel, dehydroepiandrosterone (DHEA) and the like; Nutritional Supplements such as Resveratrol, Dimethlyglycine (DMG), 5 Hydroxy L-tryptophan (5-HTP), Inositol hexaphosphate (IP6), S-adenosylmethionine (SAMe), Glucosamine sulfate or N.Acetyl glucosamine, Choline, inositol and melatonin, creatine, pyruvate, beta-hydroxy beta-methylbutyrate (HMB), ginseng, etc.; Natural Hormones (bio-identicals) such as black cohosh (*Cimicifuga racemosa*) root and rhizome extract, extracts from soy beans or the wild Mexican yam, etc.; Ayuervedic herb extracts: Adhatoda; *A. vasica*, Arjun; *Teminalia arjuna*, Asafoetida; *Ferula asafetida*, Ashwaganda; *Withania sominifera*, Asparagus; *A. racemosa*, Bacopa; *B. monerii*, Crataeva; *C. nurvala*, Emblica; *E. ribes*, Momordica; *M. charantia*, Myrrh; *Commiphora mukul* and *C. myrrha*, Saraca; *S. asoka*, Tinospora; *T. cordifolia*; Physiological metabolites, catabolites or other physiological active ingredient or precursors of all of the above or derivatives of all of the above thereof, as well as all other nutraceuticals, cosmeceuticals, naturopathic substances, homeopathic drugs, Ayuervedic extracts, botanical and dietary supplements having same or different physiological activity as those cited above.

The method of the present invention contemplates that the timing routines may be selected to deliver the said active agent at times that are automatically administered during a 1-2 hour pre-wake-up period and two or three times periodically throughout the day At least one of the selected times corresponds to a time at which the human or animal regularly exercises or has a routine physical activity. The selected times may correspond to mealtimes or regular food intake.

The method contemplates timing routines are selected to deliver the drug at a time when the human or animal is expected to be asleep. Alternatively, the timing routines may decrease or terminate the dosage of drug delivered at a time when the human or animal is expected to be asleep, or may deliver the bioactive agent immediately before the human or animal wakes up.

Accordingly, a method of the present invention for delivering a drug to a human or animal comprises a programmable drug delivery device coupled to the human or animal comprising: a method for device attachment to the skin of a host; an interface for coupling to the skin of a host; a reservoir storing a quantity of an active composition; a delivery mechanism for modulating the quantity of the active composition supplied from the reservoir to the interface in response to a control signal; a timing mechanism coupled to the delivery mechanism and configured to generate the control signal according to a programmed administration schedule; a microprocessor controller and a power source.

The device of the present invention may utilize a pump or pressurized reservoir for modulating the quantity of the active composition and/or a system for removing depleted carrier solution, or other modulated dispensing actuators, such as piezoelectric droplet jet dispensers and thermal droplet jet dispensers.

The device may also utilize a pump or pressurized reservoir for modulating the quantity of the active composition and/or a system for removing depleted carrier solution, or other modulated dispensing actuators, such as piezoelectric droplet jet dispensers and thermal droplet jet dispensers in conjunction with porous membranes or micro-fabricated structures commonly referred to as micro-channels, with micro-needles, light, heat, iontophoresis, sonophoresis and dermal abrasion (together referred to as mechanical permeation enhancement) or a wide range of chemical permeation enhancers and/or a wide range of nano-structures and substances known as nanotechnology or any combination of these techniques.

Permeation through the skin may be assisted using one or more skin permeation technologies from the group comprising: micro-fabricated structures commonly referred to as micro-needles, sonophoresis, dermal abrasion, electroporation, nanoporation, piezoelectric droplet jet dispenser, thermal droplet jet dispenser, heat, light and chemical permeation enhancers and/or a wide range of nano-structures and substances known as nanotechnology or any combination of these techniques.

Permeation through the skin may be assisted using one or more skin permeation technologies and/or in tandem with skin permeation pre-treatment techniques from the group comprising: micro-fabricated structures commonly referred to as micro-needles, iontophoresis, sonophoresis, dermal abrasion, electroporation, nanoporation, piezoelectric droplet jet dispenser, thermal droplet jet dispenser, heat, light and chemical permeation enhancers and/or a wide range of nano-structures and substances known as nanotechnology or any combination of these techniques.

It is further contemplated that the micro-pump mechanism controls a rate at which the active composition is supplied in response to the control signal.

The valve mechanism may also be used to control a rate at which the active composition is supplied in response to the control signal.

The device of the present invention may also use a droplet jet dispenser controls a rate at which the active composition is supplied in response to the control signal.

A mechanism for removing the active composition from the interface in response to the control signal is also contemplated.

It is also contemplated that the delivery element further comprises an evaporation channel defining a flow path for evaporated portions of the solvent to flow away from the administration reservoir to be captured by the solvent removal element.

The device of the present invention may also include a mechanism for removing carrier materials from the interface, whereby the technique used is not limited by but includes stoppage of permeation or dosing by micropump or actuator (which may move gas or air) or a second micropump or actuator (which may move gas or air) and/or a heating element which may aid in evaporation of the carrier solvent.

The device of the present invention may employ a heat element may be provided in the administration assembly near the administration reservoir to raise the temperature 3 to 10 degrees Celsius over a dermal temperature to enhance transdermal permeation and/or diffusion and/or movement of the drug formulation through the substrate.

An administration assembly is also contemplated which includes an administration reservoir connected to the tubing to receive the drug formulation and a membrane adjacent to the administration reservoir that is permeable to an active or effective substance in the drug formulation, but not or less permeable to a solvent portion of the liquid.

The device of the present invention may also employ an absorbent material provided in the administration reservoir so as to distribute the received liquid in a relatively uniform manner over the surface of the membrane.

The administration reservoir may be or include a rigid or flexible, permanent or disposable substrate with a plurality of ducts, conduits or culverts that contain internal passageways for movement of the drug formulation and have either a series of openings or a single opening mounted on the membrane or skin or otherwise adjacent to the membrane or skin to allow the drug formulation to be absorbed or otherwise transferred or to move from the substrate ducts to the membrane or skin for transdermal absorption.

The device of the present invention may include a skin-interface membrane. A preferred skin-interface membrane may include, but is not limited to silicones and siloxanes, microporous polyethylene and/or microporous polypropylene, polyethylene co-vinyl acetate (EVA copolymer) ranging from 2% to 40% vinyl acetate content, polyurethane and the like.

The device may be attached to the skin with an adhesive, which may be from the group consisting of but not limited to silicones and siloxanes, polyisobutylene (PIB), acrylic adhesives and other pressure sensitive adhesives (PSAs), as well as ethylcellulose, hydroxypropyl cellulose, poly(ethylene co-vinyl acetate) (EVA), polyvinyl pyrrolidone (PVP), poly(ethylene oxide) (PEO), poly(ethylene vinyl alcohol) (PVA), poly(acrylic acid) (PAA) and the like, which may be in a dry or wet form, crosslinked or not crosslinked, or any mixture to provide the composition in gel or hydrogel form or adhesive state.

The method may include a skin-coupling medium selected from the group consisting of glycerol, ethylcellulose, hydroxypropyl cellulose, polycarbophil, poly(ethylene co-vinyl acetate) (EVA), polyvinyl pyrrolidone (PVP), poly (ethylene oxide) (PEO), poly (ethylene vinyl alcohol)

(PVA), poly(acrylic acid) (PAA), silicones and siloxanes, polyisobutylene (PIB) and the like, which may be in a dry or wet form, crosslinked or not crosslinked, or any mixture to provide the composition in gel or hydrogel form or adhesive state.

The techniques of the present invention may also employ a membrane that, when a programmable electronic current is added, becomes porous to allow drug to flow or diffuse onto the skin or diffusion area from the administration reservoir or other adjacent area containing medicament. Optionally, a pump or other actuator is used to place the drug onto the membrane. The actuator may itself be the application of the electronic current to the membrane to allow the medicament to move into the diffusion area. Note that this technique is distinct from iontophoresis which applies the electronic current to the skin itself to make the skin more porous. Rather, the contemplated embodiment will not place an electric current into the skin, but utilizes passive diffusion. The electric current is applied to the membrane that is part of the diffusion area or is in intimate contact with the skin or other membrane or above the skin to open and become porous to allow drug to diffuse passively (when the electric current is applied) and close when the electronic current is removed (to close the membrane, and become no porous) so as to stop drug delivery. Also optional are a disposable cassette, a desiccant and a drying mechanism.

The coupling medium may include at least one polymer selected from poly(ethylene oxide), polycarbophil, poly(amidoamines), poly(dimethylsiloxanes), poly(hydroxyethyl methacrylates), poly(N-isopropyl acrylamides), poly[1-vinyl-2-pyrrolidinone-co-(2-hydroxyethyl methacrylate)], poly(acrylamides), poly(glutamic acid), poly(aspartic acid), poly(acrylic acids), poly(methacrylic acids), poly(ethylene glycols), poly(ethylene glycol monomethacrylate), poly(methacryloyloxyethyl 5-amino salicylate), poly(methacrylic acid)-co-poly(ethylene glycol), poly(vinyl alcohols), and poly(vinyl-pyrrolidones), poly[methacrylic acid-co-polyethylene glycol monomethacrylate-co-methacryloyloxyethyl 5-amino salicylate], poly(-hydroxyethyl methacrylate-co-methyl methacrylate), poly(acrylamides), poly(aminoproly methacrylamides), poly(N-(3-aminopropyl)methacrylamide), and poly(N,N-dimethyl-2-aminoethyl methacrylate), or copolymers, block copolymers, graft copolymers, and heteropolymers thereof, or combinations thereof which may be in a dry or wet form, crosslinked or not crosslinked, or any mixture to provide the composition in gel or hydrogel form or adhesive state.

The active agent may be premixed in the drug formulation and contained in a single reservoir. Alternatively, the active agent and the vehicle are held separate and contained in separate reservoirs and are mixed or reacted in a micromixer, microreactor or other microfluidic device immediately prior to dosing.

Drug formulations may include a solvent, an emulsifier, a surfactant and/or a humectant, from the group consisting of water, ethanol, lactic acid, urea, alcohols, polyalcohols, ethyl acetate, acetone, glycerol, glycerols, polyglycerols, glycols, polyglycols, ethylene glycol, polyethylene glycol (PEG) and polyethylene oxide (PEO) and other polyethers, polysorbates, polycarbophil, dimethyl sulfoxide (DMSO), formamide and the like, anionic, cationic and non-ionic surfactants, and mixtures thereof The active agent may be contained in a formulation comprising an emulsion or microemulsion or an acceptable vehicle, which takes the form of a colloidal dispersion having an aqueous phase and a lipid phase.

The present methodology may employ internally or externally a wide range of chemical permeation enhancers. Such enhancers include but are not limited to glycerol, ethanol, isopropanol and other low molecular weight alcohols and glycols such as diethylene glycol, propylene glycol or polyethylene glycol, oils such as olive oil, squalene or lanolin, urea and urea derivatives such as allantoin, polar solvents such as dimethyldecylphosphoxide, methyloctylsulfoxide, dimethyllaurylamide, dodecylpyrrolidone, isosorbitol, dimethyl-acetonide, dimethylsulfoxide, decylmethylsulfoxide and dimethylformamide, salicylic acid, amino acids, benzyl nicotinate, oleic acid, oleyl alcohol, long chain fatty acids, isopropanol, ethoxydiglycol, sodium xylene sulfonate, N-methylpyrrolidone, laurocapram, alkanecarboxylic acids, dimethylsulfoxide, polar lipids, N-methyl-2-pyrrolidone, propyl and isopropyl myristate, propyl and isopropyl palmitate and the like, cationic, anionic and non-ionic surfactants and higher molecular weight aliphatic surfactants such as lauryl sulfate, polysorbates, other agents include carvone and other azones, lactic acid, linoleic and ascorbic acids, terpenes such as limonene, panthenol, butylated hydroxytoluene, propyl oleate as well as piperine and piperine derivatives, tetrahydropiperine and analogs and derivatives thereof, including dihydropiperine.

The present invention may also employ internally or externally a wide range of anti-irritants. Such anti-irritants include but are not limited to steroids, antioxidants, methylxanthines, catechins, phenols and polyphenols.

The present invention is particularly useful in applications in which it is necessary and/or desirable to start the administration of a nutraceutical, drug or other substance, stop the administration of a nutraceutical, drug or other substance, and/or increase/decrease the dosage of a nutraceutical, drug or other substance at a time when it is inconvenient or impossible for a patient to initiate the necessary actions. This is particularly useful for a wide variety of nutraceutical, drug or other substance administration applications that benefit when an administration is started, stopped, or changed while a person is sleeping. As research and knowledge of chronotherapy increases, it is contemplated that a wide variety of applications will be discovered in which benefit is realized by starting, stopping and/or changing the administration while a patient sleeps).

This invention also particularly provides that drugs having stimulating effects but or can speed up the metabolism or burn fat or increase mitochondrial activity or benefit the body in another manner the ADD or ADHD treatment drug is not delivered during the sleep cycle, but the automated device of which this invention relates turns on automatically prior to wake up so that therapeutically effective blood plasma concentrations of the drug ADD or ADHD treating compound in question are present immediately upon waking, thereby avoiding the stimulation effects of the drug during the night which can cause insomnia, but ensuring disease symptoms are countered by the drug upon waking. This invention also particularly provides that drugs having stimulating effects or can speed up the metabolism or burn fat or increase mitochondrial activity or benefit the body in another manner is not delivered during the sleep cycle, but the automated device of which this invention relates turns on automatically at opportune and advantageous times throughout the day to assist anti-aging effects.

In each of the examples, treatment is continued as needed to provide superior symptomatic relief, prevent exacerbation of symptoms, and/or prevent and/or delay progression of the disease state or condition in the patient, or until it is no longer well tolerated by the patient, or until a physician terminates treatment. For example, a physician may monitor one or more symptoms and/or serum levels of active material and/or metabolic by-product(s) in a patient being treated according to this invention and, upon observing attenuation of one or more symptoms for a period of time, conclude that the patient can sustain the positive effects of the above-described treatment without further administration for a period of time. When necessary, the patient may then return at a later point in time for additional treatment as needed.

As used herein, 'day' means a 24-hour period. Thus, for example, 'for at least three consecutive days' means for at least a 72-hour period. During or after the treatment, a physician may monitor one or more symptoms and/or serum levels in the patient and, upon observing an improvement in one or more of the parameters for a period of time, conclude that the patient can sustain the positive effects of the treatment without further administration of the active material for a period of time.

In order to use an active material for therapeutic treatment (including prophylactic treatment) of mammals including humans according to the methods of this invention, the active material is normally formulated in accordance with standard pharmaceutical practice as a pharmaceutical composition. According to this aspect of the invention there is provided a pharmaceutical composition comprising an active material in association with a pharmaceutically acceptable diluting substance or carrier, wherein the active material is present in an amount for effective treating or preventing a particular condition.

While individual needs may vary, determination of optimal ranges for effective amounts of an active ingredient (alone or in combination with other nutraceuticals, drugs or substances) within the ranges disclosed herein is within the expertise of those skilled in the art. Accordingly, 'effective amounts' of each component for purposes herein are determined by such considerations and are amounts that improve one or more active ingredient functions and/or ameliorate on or more deleterious conditions in patients and/or improve the quality of life in patients.

Pharmaceutical Kits

The present invention also provides pharmaceutical kits for treating a particular symptom, condition and/or disease and/or improving a particular biological function, comprising one or more containers comprising one or more active compositions in accordance with this invention. Such kits can also include additional nutraceuticals drugs or therapeutics for co-use with the active composition for treatment or prevention of a particular symptom, condition and/or disease and/or improving a particular biological function. In this embodiment, the active composition and the nutraceutical, drug or other substance can be formulated in admixture in one container, or can be contained in separate containers for simultaneous or separate administration. The kit can further comprise a device(s) for administering the compounds and/or compositions, such as device shown in FIG. 1, and written instructions in a form prescribed by a governmental agency regulating the manufacture, use or sale of pharmaceuticals or biological products, which instructions can also reflect approval by the agency of manufacture, use or sale for human administration.

Although the invention has been described and illustrated with a certain degree of particularity, it is understood that the present disclosure has been made only by way of example, and that numerous changes in the dosages, administration profiles, timing, as well as the combination and arrangement of parts can be resorted to by those skilled in the art without departing from the spirit and scope of the invention, as hereinafter claimed.

What is claimed is:

1. A method for treating a human with Parkinson's disease comprising:
    delivering an active pharmaceutical ingredient (API) for treating Parkinson's disease, symptoms associated with Parkinson's disease, or symptoms associated with treatments for Parkinson's disease dissolved in a solvent to a skin-interface membrane of a transdermal drug delivery device coupled to a skin of the human;
    absorbing the active pharmaceutical ingredient from the skin-interface membrane transdermally into the human; and
    moving solvent from the skin-interface membrane through an evaporation channel of the transdermal drug delivery device.

2. The method of claim 1, wherein the API comprises one or more of the following: dopamine precursors, dopa decarboxylase inhibitors, Levodopa/carbidopa mixtures, Levodopa/carbidopa/entacapone mixtures, Levodopa/benserazide mixtures, dopamine agonists, anticholinergics, MAO-B inhibitors, COMT inhibitors, dopaminergic agonists, Ampakines Istradefylline (KW-6002), S-(−)-2-(N-propyl-N-2-thienylethylamino)-5-hydroxytetralin (N-0923), Sarizotan, bornaprine, budipine, ethopropazine, lazabemide, memantine, modafinil, talampanel, altinicline, brasofensine, safinamide, droxidopa, quinagolide, terguride, riluzole, talipexole, piroheptine, bifeprunox, spheramine, sumanirole, lisuride hydrogen maleateor, and orphenadrine.

3. The method of claim 1, wherein the API comprises levodopa.

4. The method of claim 3, wherein the API includes a Levodopa/carbidopa mixture, Levodopa/carbidopa/entacapone mixture, or Levodopa/benserazide mixture.

5. The method of claim 1, wherein the API comprises one or more of the following: Carbidopa, bromocriptine, pergolide, pramipexole, rotigotine, ropinirole, cabergoline, apomorphine, lisuride, piribedil, selegiline, Amantadine, memantine, and safinamide.

6. The method of claim 1, wherein the method further includes moving solvent from the skin-interface membrane into a solvent removal element, and wherein the solvent removal element comprises a desiccant, absorbent material, or hydrophilic material.

7. The method of claim 1, wherein delivering the API dissolved in the solvent to the skin-interface membrane of the transdermal drug delivery device coupled to the human includes delivering the API at a time, rate, sequence and/or cycle that is synchronized with a biological rhythm of the human.

8. The method of claim 1, wherein delivering the API dissolved in the solvent to the skin-interface membrane of the transdermal drug delivery device coupled to the human includes delivering the API at a time, rate, sequence and/or cycle that is selected to reduce dyskinesia in the human.

9. The method of claim 1, further comprising: repeating the delivering, absorbing and moving steps to modulate and control dosing to create a consistently therapeutically effective blood plasma concentration of the active pharmaceutical ingredient in the human.

10. The method of claim 1, further comprising: repeating the delivering, absorbing and moving steps to modulate and control dosing to create a plurality of active pharmaceutical ingredient blood plasma concentration peaks and troughs in the human.

11. The method of claim 2, wherein the API further comprises levodopa.

12. The method of claim 10, wherein the API includes levodopa and the peaks and troughs of the blood plasma concentration of levodopa are between about 1.4 to about 2.0 µg/ml.

13. The method of claim 1, wherein the API is for a purpose of treating dyskinesia.

14. The method of claim 1, further comprising: removing the transdermal drug delivery device after contacting the skin for greater than 24 hours.

15. The method of claim 1, wherein delivering the API dissolved in the solvent to the skin-interface membrane of the transdermal drug delivery device coupled to the skin of the human is performed immediately before the human wakes up.

16. The method of claim 1, wherein the transdermal drug delivery device includes a reservoir with the API dissolved in the solvent and further comprising: moving a portion of the API dissolved in the solvent from the reservoir to the skin-interface membrane.

17. The method of claim 1, wherein delivering the API dissolved in the solvent to the skin-interface membrane of the transdermal drug delivery device coupled to the skin of the human begins during a one hour period immediately prior to the human's waking to transdermally administer the API to the human.

18. The method of claim 1, wherein the delivery step comprises delivering a first dosage of API to the human to raise the human's blood plasma concentration of API from a first level to a second level higher than the first level.

19. The method of claim 18 wherein the first dosage is delivered while the human is asleep.

20. The method of claim 18, wherein delivering the first dosage of API to the human is at a time around 7:30 a.m. to 10:00 a.m.

21. The method of claim 18, wherein delivering the first dosage of API to the human is at a time around 10:00 a.m. to 12:00 p.m.

22. The method of claim 18, wherein the delivery step further comprises reducing or stopping delivery of API to the human to reduce the human's blood plasma concentration of API from the second level to a third level lower than the second level, then delivering a second dosage of API to the human to increase the human's blood plasma concentration of API from the third level to a fourth level higher than the third level.

23. The method of claim 22, wherein the second dosage of API to the human is at a time around 1:00 p.m. to about 3:00 p.m.

24. The method of claim 22, wherein the second dosage of API to the human is at a time around 3:00 p.m. to about 5:00 p.m.

25. The method of claim 22, wherein the delivery step further comprises reducing or stopping delivery of API to the human to reduce the human's blood plasma concentration of API from the fourth level to a fifth level lower than the fourth level, then delivering a third dosage of API to the human to increase the human's blood plasma concentration of API from the fifth level to a sixth level higher than the fifth level.

26. The method of claim 25, wherein the third dosage of API to the human is at a time around 6:00 p.m. to about 8:00 p.m.

27. The method of claim 25, wherein the API comprises Levodopa.

* * * * *